US009475855B2

(12) United States Patent
Kitajewski et al.

(10) Patent No.: US 9,475,855 B2
(45) Date of Patent: Oct. 25, 2016

(54) HUMAN NOTCH3 BASED FUSION PROTEINS AS DECOY INHIBITORS OF NOTCH3 SIGNALING

(75) Inventors: Jan Kitajewski, Ridgewood, NJ (US); Carrie Shawber, Washington Township, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 383 days.

(21) Appl. No.: 13/060,254

(22) PCT Filed: Aug. 21, 2009

(86) PCT No.: PCT/US2009/004765
§ 371 (c)(1), (2), (4) Date: May 26, 2011

(87) PCT Pub. No.: WO2010/021729
PCT Pub. Date: Feb. 25, 2010

(65) Prior Publication Data

US 2011/0223183 A1 Sep. 15, 2011

Related U.S. Application Data

(60) Provisional application No. 61/189,930, filed on Aug. 22, 2008.

(51) Int. Cl.

| | |
|---|---|
| ***C07K 14/705*** | (2006.01) |
| ***C07K 14/71*** | (2006.01) |
| ***C07K 14/715*** | (2006.01) |
| ***C07K 16/46*** | (2006.01) |
| ***C07K 19/00*** | (2006.01) |
| ***C07K 14/485*** | (2006.01) |
| *A61K 38/17* | (2006.01) |
| *A61K 39/395* | (2006.01) |
| *A61K 39/00* | (2006.01) |

(52) U.S. Cl.
CPC .......... *C07K 14/485* (2013.01); *C07K 14/705* (2013.01); *A61K 38/177* (2013.01); *A61K 38/179* (2013.01); *A61K 38/1793* (2013.01); *A61K 39/395* (2013.01); *A61K 2039/505* (2013.01); *C07K 14/71* (2013.01); *C07K 14/715* (2013.01); *C07K 16/46* (2013.01); *C07K 2319/00* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,428,130 A | 6/1995 | Capon et al. | |
| 6,090,922 A | 7/2000 | Artavanis-Tsakonas et al. | |
| 6,379,925 B1 | 4/2002 | Kitajewski et al. | |
| 6,689,744 B2 | 2/2004 | Gao et al. | |
| 6,703,221 B1 | 3/2004 | Chan et al. | |
| 6,716,974 B1 | 4/2004 | Maciag et al. | |
| 7,662,919 B2 * | 2/2010 | Kitajewski et al. | 530/350 |
| 2003/0082651 A1 | 5/2003 | Gao et al. | |
| 2003/0186290 A1 | 10/2003 | Tournier-Lasserve et al. | |
| 2003/0194804 A1 | 10/2003 | Lamb et al. | |
| 2005/0261477 A1 | 11/2005 | Champion et al. | |
| 2006/0002924 A1 | 1/2006 | Bodmer et al. | |
| 2006/0030694 A1 | 2/2006 | Kitajewski et al. | |
| 2006/0134121 A1 | 6/2006 | Thurston et al. | |
| 2007/0104746 A1 | 5/2007 | Fujii et al. | |
| 2008/0118520 A1 | 5/2008 | Li et al. | |
| 2010/0273990 A1 | 10/2010 | Kitajewski | |
| 2011/0008342 A1 * | 1/2011 | Kitalewski et al. | 424/134.1 |

FOREIGN PATENT DOCUMENTS

| | | |
|---|---|---|
| WO | WO 03042246 | 5/2003 |
| WO | WO 03/087159 | 10/2003 |
| WO | WO 2004/024764 | 3/2004 |
| WO | WO 2005/111072 | 11/2005 |
| WO | WO 2006/047878 | 5/2006 |
| WO | WO 2008/051797 | 5/2008 |
| WO | WO-2008091641 A2 * | 7/2008 |
| WO | WO 2009/025867 | 2/2009 |

(Continued)

OTHER PUBLICATIONS

Shimizu et al. Mouse Jagged1 physically interacts with Notch2 and other notch receptors. J Biol Chem 274(46): 32961-32969, 1999.*
Rebay et al. Specific EGF repeats of Notch mediate interactions with delta and serrate: implications for Notch as a multifunctional receptor. Cell 67: 687-699, 1991.*
Bellavia et al. Notch3: from subtle structural differences to functional diversity. Oncogene 27: 5092-5098, 2008.*

(Continued)

*Primary Examiner* — Bridget E Bunner
(74) *Attorney, Agent, or Firm* — John P. White; Cooper & Dunham LLP

(57) ABSTRACT

This invention provides a fusion protein comprising a signal peptide, EGF repeats 1-X of the extracellular domain of human Notch3 receptor protein wherein X is any integer from 12 to 34, and an Fc portion of an antibody bound thereto. This invention also provides a method for treating a subject having a tumor, a method for inhibiting angiogenesis in a subject, a method for treating a subject having ovarian cancer, and a method for treating a subject having a metabolic disorder, comprising administering to the subject an amount of the above fusion protein effective to treat the subject. This invention further provides uses of the above fusion protein for the preparation of a pharmaceutical composition for the treatment of a subject having a tumor, for inhibiting angiogenesis in a subject, for treating a subject having ovarian cancer, and for treating a subject having a metabolic disorder.

4 Claims, 67 Drawing Sheets

(56) References Cited

FOREIGN PATENT DOCUMENTS

| | | |
|---|---|---|
| WO | WO 2010/021729 | 2/2010 |
| WO | WO 2013/052607 | 11/2013 |

OTHER PUBLICATIONS

Peters et al. CADASIL-associated Notch3 mutations have differential effects on both ligand binding and ligand-induced Notch3 receptor signaling through RBP-Jk. Exp Cell Res 299: 454-464, 2004.*

Lin et al. Targeting specific regions of the Notch3 ligand-binding domain induces apoptosis and inhibits tumor growth in lung cancer. Cancer Res 70(2): 632-638, 2010.*

Notification of Transmittal of the International Search Report and the Written Opinion of the International Searching Authority, or the Declaration, including an International Search Report and Written Opinion, mailed Mar. 10, 2010 in connection with PCT International Application No. PCT/US2009/004765, filed Aug. 21, 2009.

International Search Report issued Feb. 20, 2009 in connection with International Application No. PCT/US2008/10045.

Written Opinion of the International Searching Authority issued Feb. 20, 2009 in connection with International Application No. PCT/US2008/10045.

International Preliminary Report On Patentability issued Feb. 24, 2010 in connection with International Application No. PCT/US2008/10045.

Written Opinion issued Jun. 19, 2006 in connection with International Application No. PCT/US2005/13884.

International Search Report issued Jun. 19, 2006 in connection with PCT International Application No. PCT/US05/13884.

Written Opinion of the International Searching Authority issued Mar. 10, 2010 in connection with International Application No. PCT/US2009/04765.

International Preliminary Report on Patentability issued Feb. 22, 2011 in connection with International Application No. PCT/US2009/004765.

International Search Report issued Mar. 10, 2010 in connection with International Application No. PCT/US2009/04765.

Extended European Search Report and Opinion issued Dec. 23, 2011 in connection with European Application No. 08795559.7.

Examination Report issued Nov. 24, 2012 in connection with New Zealand Patent Application No. 583649, filed Aug. 22, 2008.

May 23, 2012 Response to Examination Report issued Nov. 24, 2012 in connection with New Zealand Patent Application No. 583649, filed Aug. 22, 2008.

Examination Report and Notice of Acceptance of Complete Specification issued Jun. 13, 2012 in connection with New Zealand Patent Application No. 583649.

Jul. 20, 2012 Response to Extended European Search Report and Opinion issued Dec. 23, 2011 in connection with European Application No. 08795559.7, filed Aug. 22, 200.

Notification of Defects issued Jan. 2, 2012 in connection with Israeli patent Application No. 204111, filed Aug. 22, 2008, including English translation thereof.

Jul. 1, 2012 Response to Notification of Defects issued Jan. 2, 2012 in connection with Israeli patent Application No. 204111, including English translation thereof.

Office Action issued Jun. 20, 2012 in connection with Chinese patent Application No. 200880112057.3 filed Aug. 22, 2008, including English language translation thereof.

Official Action issued Nov. 23, 2012 in connection with Russian patent Application No. 2010110812 filed Aug. 22, 2008, including English language translation thereof.

Singec et al. "The Leading Edge Of Stem Cell Therapeutics" Annu Rev Med 58:313-328, 2007.

De La Costa, Immunol Lett. Jan. 15, 2006;102(1 ):1-9 Epub Jul. 18, 2005.

Kojika et al. Exp Hematol 2001 29:1041-1052.

UniProt Protein NOTC4_HUMAN, pp. 1-14. Mar. 27, 2002.

Varnum-Finney et al. Blood, Mar. 1, 2003; 101(5):1784-9. Epub Oct. 31, 2002.

Examination Report issued May 3, 2011 in connection with New Zealand Patent Application No. 591492, filed Mar. 2, 2011.

Sep. 10, 2012 Response to Examination Report issued May 3, 2011 in connection with New Zealand Patent Application No. 591492, filed Mar. 2, 2011.

Examination Report and Notice of Acceptance of Complete Specification issued Oct. 1, 2012 in connection with New Zealand Patent Applicaiton No. 591492, filed Mar. 2, 2011.

International Search Report issued Jan. 18, 2013 in connection with PCT International Application No. PCT/US2012/058662.

Apr. 10, 2012 Office Action issued in connection with U.S. Appl. No. 12/657,573.

Oct. 4, 2012 Amendment in Response to Apr. 10, 2012 Office Action filed in connection with U.S. Appl. No. 12/657,573.

Mar. 18, 2013 Office Action issued in connection with U.S. Appl. No. 12/657,573.

Jun. 27, 2012 Office Action issued in connection with U.S. Appl. No. 12/733,329.

Dec. 27, 2012 Amendment in Response to Jun. 27, 2012 Office Action filed in connection with U.S. Appl. No. 12/733,329.

Mar. 11, 2013 Office Action issued in connection with U.S. Appl. No. 12/733,329.

Official Action issued in connection with Russian Patent Application No. 2011110741, May 7, 2013.

Supplementary European Search Report issued Dec. 19, 2012 in connection with European Patent Application No. EP 09 80 8518.

Dec. 25, 2012 Office Action issued in connection with Israeli Patent Application No. 211232.

Jun. 21, 2013 Office Action issued in connection with Chinese Patent Application No. 200880112057.3.

Jan. 30, 2013 Communication issued in connection with European Patent Application No. 08 795 559.7.

Aug. 8, 2013 Response to Jan. 30, 2013 Communication filed in connection with European Patent Application No. 08 795 559.7.

May 7, 2013 Office Action issued in connection with Japanese Patent Application No. 2010-521897.

May 25, 2012 Examination Report issued in connection with New Zealand Patent Application No. 600171.

Apr. 25, 2013 Office Action issued in connection with Russian Patent Application No. 2010110812.

Peppel et al. (1991) "A Tumor Necrosis Factor (TNF) Receptor-IgG Heavy Chain Chimeric Protein as a Bivalent Antagonist of TNF Activity" J. Exp. Med., 174:1483-1489.

Funahashi et al. (2008) "A Notch1 Ectodomain Construct Inhibits Endothelial Notch Signaling, Tumor Growth, and Angiogenesis" Cancer Res., 68:(12)4727-4735.

Ahmad et al. (2011) "Regulation of Ocular Angiogenesis by Notch Signaling . . . " Investigative Ophthalmology & Visual Science, 52:(6)2868-2878.

Jan. 31, 2013 Office Action issued in connection with Mexican Patent Application No. MX/a/2011/001805 including summary set forth in English language version.

Jun. 7, 2013 Response to Jan. 31, 2013 Office Action filed in connection with Mexican Patent Application No. MX/a/2011/001805 including English language version.

Mar. 28, 2013 Response to Sep. 13, 2012 Office Action filed in connection with Chinese Patent Application No. 2009801331210 including English language version.

Mar. 8, 2013 Response to Jun. 20, 2012 Office Action filed in connection with Chinese Patent Application No. 200880112057.3 including English language version.

Response to Nov. 23, 2012 Office Action filed in connection with Russian Patent Application No. 2010110812 including English language version.

Singec at al. "The Leading Edge of Stem Cell Therapeutics" Annu Rev Med 58:313-328.

Dec. 6, 2013 Examination Report issued in connection with New Zealand Patent Application No. 600171.

Nov. 6, 2013 Examination Report issued in connection with New Zealand Patent Application No. 618129.

(56) References Cited

OTHER PUBLICATIONS

Nov. 20, 2013 Response filed in connection with European Patent Application No. EP 09 80 8518.6.
Sep. 5, 2013 Response filed in connection with Chinese Patent Application No. 200880112057 including English language version.
Nov. 22, 2013 Response filed in connection with New Zealand Patent Application No. 600171.
Oct. 27, 2013 Response filed in connection with Israeli Patent Application No. 211232 including English language translation.
Jul. 9, 2013 Office Action issued in connection with Israeli Patent Application No. 211232 including English language translation.
Nov. 26, 2013 Response filed in connection with Indonesian Patent Application No. W-00 2011 01013 including English language translation.
Jul. 22, 2013 Office Action issued in connection with Indonesian Patent Application No. W-00 2011 01013 including English language translation.
Nov. 29, 2013 Office Action issued in connection with Filipino Patent Application No. 1/2010/500422.
Jan. 14, 2014 Notice of Acceptance issued in connection with Australian Patent Application No. 2008289462.
Jan. 20, 2014 Response filed in connection with Mexican Patent Application No. MX/a/2010/002053 including English language version.
Dec. 18, 2013 Response filed in connection with U.S. Appl. No. 12/657,573.
Jan. 3, 2014 Response filed in connection with Australian Patent Application No. 2008289462.
Jan. 10, 2014 Notice of Acceptance issued in connection with New Zealand Patent Application No. 600171.
Jan. 1, 2014 Response filed in connection with Israeli Patent Application No. 204111 including English language translation.
Jul. 9, 2013 Office Action issued in connection with Chinese Patent Application No. 200880112057.3 including English language translation.
Jan. 8, 2014 Office Action issued in connection with European Patent Application No. 09808518.6.
Jan. 8, 2014 Response to Office Action filed in connection with Mexican Patent Application No. MX/a/2011/001805 including English language version.
Dec. 13, 2013 Response to Office Action filed in connection with Chinese Patent Application No. 2009801331210 including English language version.
Oct. 22, 2014 Response, filed in connection with U.S. Appl. No. 12/657,573.
Oct. 29, 2014 Notice of Allowance, issued in connection with U.S. Appl. No. 12/657,573.
Oct. 30, 2014 Request For Continued Examination and Information Disclosure Statement filed in connection with U.S. Appl. No. 12/657,573.
Feb. 15, 2012 Office Action, issued in connection with U.S. Appl. No. 12/733,329.
Apr. 16, 2012 Response, filed in connection with U.S. Appl. No. 12/733,329.
Dec. 3, 2012 Examination Report No. 1, issued in connection with Australian Patent Application No. 2008289462.
Aug. 1, 2013 Examination Report No 2, issued in connection with Australian Patent Application No. 2008289462.
Oct. 3, 2013 Communication issued in connection with European Patent Application No. 08795559.7.
Letter describing Jan. 19, 2014 Notification of Defects in connection with Israeli Patent Application No. 204111.
Jul. 16, 2014 Response, filed in connection with Israeli Patent Application No. 204111, including English translation thereof.
English language translation of Aug. 25, 2014 Notice, issued in connection with Israeli Patent Application No. 204111.
Sep. 16, 2014 Response, filed in connection with Israeli Patent Application No. 220723, including English translation.
Aug. 28, 2014 Notice of Result of Examination as to Substance, issued in connection with Vietnamese Patent Application No. 2010-521897, including English language translation thereof.
Oct. 21, 2014 Response, filed in connection with Vietnamese Patent Application No. 2010-521897, including English language translation thereof.
Letter describing Apr. 9, 2014 Notification of Non-Substantive Defects issued in connection with Israeli Patent Application No. 211232.
Aug. 10, 2014 Response, filed in connection with Israeli Patent Application No. 211232, including English language translation thereof.
Oct. 15, 2014 Office Action, issued in connection with Malaysian Patent Application No. PI 2011000718.
Aug. 25, 2014 Response, filed in connection with Vietnamese Patent Application. No. 1-2011-00752.
Sep. 30, 2014 Examination Report No. 1, issued in connection with Australian Patent Application No. 2009283134.
Oct. 13, 2014 Official Action, issued in connection with Russian Patent Application No. 2011110741, including English language translation.
Oct. 8, 2014 Response, filed in connection with Chinese patent Application No. 200980133121.0, including English language translation of Observation Request.
Zlobin et al. (2000) Toward the rational design of cell fate modifiers: Notch signaling as a target for novel biopharmaceuticals. Current Pharmaceutical Technology, 1, pp. 83-106.
Nov. 18, 2014 Notice of Allowance, issued in connection with U.S. Appl. No. 12/657,573.
Nov. 19, 2014 Office Action, issued in connection with U.S. Appl. No. 12/733,329.
Jan. 6, 2015 Office Action, issued in connection with Japanese Patent Application No. 2011-523820, including English translation thereof.
Feb. 2, 2015 First Examination Report, issued in connection with New Zealand Patent Application No. 624091.
Jan. 4, 2015 First Examination Report, issued in connection with Chinese Patent Application No. 201830054960.5.
Jul. 16, 2014 Request for Re-examination, filed in connection with Chinese Patent Application No. 200680112057.3, including English language translation of Request for Re-examination Form.
Apr. 19, 2006 Office Action, issued in connection with U.S. Appl. No. 11/114,962.
Aug. 21, 2006 Response, filed in connection with U.S. Appl. No. 11/114,962.
Nov. 14, 2006 Office Action, issued in connection with U.S. Appl. No. 11/114,962.
May 14, 2007 Response, filed in connection with U.S. Appl. No. 11/114,962.
Aug. 21, 2007 Final Office Action, issued in connection with U.S. Appl. No. 11/114,962.
Feb. 21, 2008 Response, filed in connection with U.S. Appl. No. 11/114,962.
Mar. 24, 2008 Office Action, issued in connection with U.S. Appl. No. 11/114,962.
Sep. 24, 2008 Response, filed in connection with U.S. Appl. No. 11/114,962.
Jan. 23, 2009 Final Office Action issued in connection with U.S. Appl. No. 11/114,962.
Jun. 23, 2009 Response, filed in connection with U.S. Appl. No. 11/114,962.
Sep. 17, 2009 Notice of Allowance, issued in connection with U.S. Appl. No. 11/114,962.
Jan. 29, 2014 Office Action, issued in connection with U.S. Appl. No. 12/657,573.
Apr. 29, 2014 Response, issued in connection with U.S. Appl. No. 12/657,573.
Jun. 27, 2014 Office Action, issued in connection with U.S. Appl. No. 12/657,573.
Sep. 11, 2013 Response, filed in connection with U.S. Appl. No. 12/733,329.
Feb. 12, 2014 Response, filed in connection with European Patent Application No. 08795559.7.

(56) References Cited

OTHER PUBLICATIONS

Dec. 19, 2013 Response, filed in connection with New Zealand Patent Application No. 600171.
Mar. 28, 2014 Response, filed in connection with Filipino Patent Application No. 1-2010-500422.
Jan. 20, 2014 Office Action, issued in connection with Israeli Patent Application No. 220723, including English translation thereof.
Jan. 22, 2014 Office Action, issued in connection with Israeli Patent Application No. 220724, including English translation thereof.
Jun. 19, 2014 Response, filed in connection with Israeli Patent Application No. 220724, including English translation thereof.
Nov. 21, 2013 Office Action, issued in connection with Chinese Patent Application No. 200880112057.3, including English translation thereof.
Apr. 1, 2014 Decision of Rejection, issued in connection with Chinese Patent Application No. 200880112057.3.
Jun. 16, 2014 Office Action, issued in connection with Indian Patent Application No. 1626/CHENP/2010.
Sep. 13, 2012 Office Action, issued in connection with Chinese patent Application No. 200980133121.0, including English language translation thereof.
Jul. 29, 2013 Second Office Action, issued in connection with Chinese patent Application No. 200980133121.0, including English language translation thereof.
Dec. 13, 2013 Response filed in connection with Chinese Patent Application No. 200980133121.0.
Apr. 21, 2014 Third Office Action, issued in connection with Chinese patent Application No. 200980133121.0, including English language translation thereof.
May 7, 2013 Office Action, issued in connection with Russian Patent Application No. 2011110741, including English language translation.
Feb. 18, 2014 Official Action, issued in connection with Russian Patent Application No. 2011110741, inlcluding English language translation.
Aug. 13, 2014 Response, filed in connection with Russian Patnet Application No. 2011110741, including English language claims.
Jul. 24, 2014 Communication About Intention to Grant, issued in connection with European Patent Application No. 09808518.6.
May 16, 2014 Response, filed in connection with European Patent Application No. 09808518.6.
Feb. 4, 2014 Office Action issued in connection with Japanese Patent Application No. 2011-523820, including English translation thereof.
English language translation of Apr. 26, 2014 Office Action, issued in connection with Vietnamese Patent Application No. 1-2011-00752.
Feb. 3, 2014 Letter Describing Objections in First Office Action, issued in connection with Pakistani Patent Application No. 636/2012.
Jul. 16, 2014 Office Action, issued in connection with Indian Patent Application No. 1626/CHENP/2010.
English Language Tranlsation of Jun. 2, 2014 Notice, issued in connection with Vietnamese Patent Application No. 1-2014-01381.
Jul. 1, 2014 Response, filed in connection with Vietnamese Patent Application No. 1-2014-01381, including English language translation.
Jul. 21, 2014 Notice, issued in connection with Vietnamese Patent Application No. 1-2014-01381, including English language translation.
Shimizu et al., (2000) Physical interaction of Delta1, Jagged1, and Jagged2 with Notch1 and Notch3 receptors. Biochem Biophys Res Comm. 276:385-9.
Xu et al., (2005) Regions of *Drosophila* Notch that contribute to ligand binding and the modulatory influence of Fringe. J Biol. Chem. 280:30158-65.
Feb. 27, 2014 Response, filed in connection with Chinese Patent Application No. 200880112057.3 and concise explanation thereof.
Nov. 7, 2013 Response, filed in connection with Japanese Patent Application No. 2010-521897 and concise explanation thereof.
Jul. 1, 2014 Office Action, issued in connection with Japanese Patent Application No. 2010-521897 and English Translation thereof.
Mar. 28, 2013 Response to First Office Action, filed in connection with Chinese Patent Application No. 200980133121.0 and concise explanation thereof.
Apr. 29, 2014 Office Action, issued in connection with Mexican Patent Application No. MX/a/2010/002053 and English language summary thereof.
Jul. 11, 2014 Response, filed in connection with Mexican Patent Application No. MX/a/2010/002053 and concise explanation thereof.
Jun. 4, 2014 Response, filed in connection with Japanese Patent Application No. 2011-523820 and concise explanation thereof.
Oct. 1, 2014 Response, filed in connection with Japanese Patent Application No. 2010-521897 and concise explanation thereof.
Jan. 30, 2015 Office Action, issued in connection with Mexican Patent Application No. MX/a/2010/002053 and redacted English language summary thereof.
Office Action issued Sep. 13, 2012 in connection with Chinese patent Application No. 200980133121.0 filed Feb. 22, 2011, including English language translation *- thereof.
Office Action issued Sep. 13, 2012 in connection with Chinese patent Application No. 200980133121.0 filed Feb. 22, 2011, including English language translation thereof.

* cited by examiner

Activation of Notch signaling in HUVEC infected with adenoviral encoding VEGF-165

Figure 7
Notch ectodomain (Notch Decoy) inhibit activation of Notch signaling induced by VEGF stimulation in adenovirus-infected HUVEC
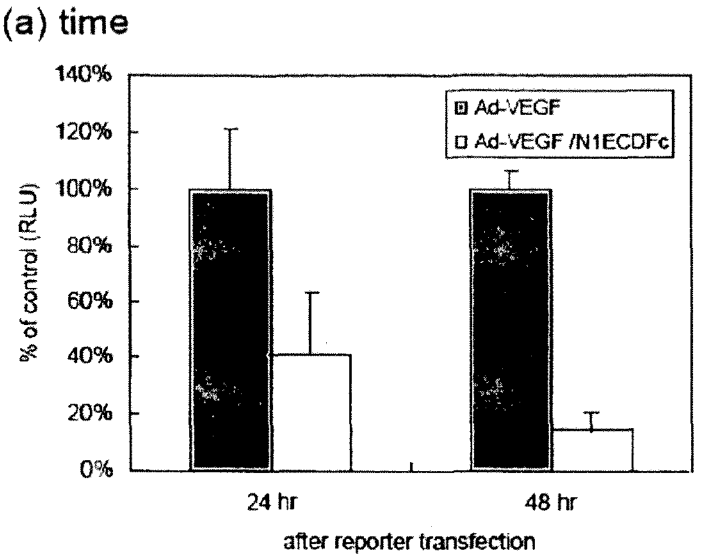
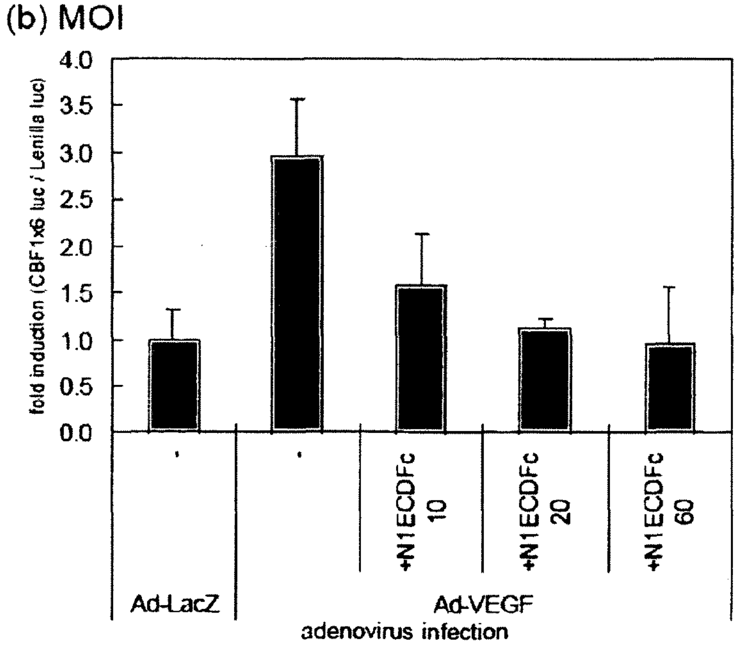

Figure 10

```
   1 mprllapllc ltllpalaar glrcsqpsgt clnggrceva ngteacvcsg afvgqrcqdp
  61 spclstpckn agtcyvvdhg givdyacscp lgfsgplclt planaclanp crnggtcdll
 121 tlteykcrcp pgwsgkscqq adpcasnpca nggqclpfes syicgcppgf hgptcrqdvn
 181 ecsqnpglcr hggtchneig syrcacrath tgphcelpyv pcspspcqng gtcrptgdtt
 241 hecaclpgfa gqnceenvdd cpgnnckngg acvdgvntyn crcppewtgq yctedvdecq
 301 lmpnacqnag tchnshggyn cvcvngwtge dcsdniddca saacfqgatc hdrvasfyce
 361 cphgrtgllc hlndacisnp cnegsncdtn pvngkaictc prgytgpacs qdvdecalga
 421 npcehagkcl ntlgsfecqc lqgytgprce idvnecisnp cqndatcldq igefqcicmp
 481 gyegvycein tdecasspcl hngrcvdkin eflcqcpkgf sghlcqydvd ecastpckng
 541 akcldgpnty tcvctegytg thcevdidec dpdpchiglc kdgvatftcl cqpgytghhc
 601 etninechsq pcrhggtcqd rdnyylclcl kgttgpncei nlddcasnpc dsgtcldkid
 661 gyecacepgy tgsmcnvnid ecagspchng gtcedgiagf tcrcpegyhd ptclsevnec
 721 nsnpcihgac rdglngykcd capgwsgtnc dinnnecesn pcvnggtckd mtsgyvctcr
 781 egfsgpncqt ninecasnpc lnqgtciddv agykcncplp ytgatcevvl apcatspckn
 841 sgvckesedy esfscvcptg wqgqtceidi necvkspcrh gascqntngs yrclcqagyt
 901 grncesdidd crpnpchngg sctdgvnaaf cdclpgfqga fceedineca tnpcqnganc
 961 tdcvdsytct cptgfngihc enntpdctes scfnggtcvd ginsftclcp pgftgsycqy
1021 dvnecdsrpc lhggtcqdsy gtykctcpqg ytglncqnlv rwcdsapckn ggkcwqtntq
1081 yhcecrsgwt gfncdvlsvs cevaaqkrgi dvtllcqhgg lcvdeedkhy chcqagytgs
1141 ycedevdecs pnpcqngatc tdylggfsck cvagyhgsnc seeineclsq pcqnggtcid
1201 ltntykcscp rgtqgvhcei nvddchppld pasrspkcfn ngtcvdqvgg ytctcppgfv
1261 gercegdvne clsnpcdprg tqncvqrvnd fhcecraght grrcesving crgkpcrngg
1321 vcavasntar gficrcparf egatcendar tcgslrclng gtcisgprsp tclclgsftg
1381 pecqfpassp cvgsnpcynq gtceptsesp fyrclcpakf ngllchildy sft 1433
```

LINKER SEQUENCE

DLGPG

Figure 11

```
   1 mpalrpaalr allwlwlcga gpahalqcrg gqepcvnegt cvtyhngtgy crcpegflge
  61 ycqhrdpcek nrcqnggtcv tqamlgkatc rcapgftged cqystshpcf vsrpcqnggt
 121 chmlswdtye ctcqvgftgk qcqwtdvcls hpcengstcs svanqfscrc pagitgqkcd
 181 adinecdipg rcqhggtcln lpgsyrcqcp qrftgqhcds pyvpcapspc vnggtcrqtg
 241 dftsechclp gfegsncern iddcpnhkcq nggvcvdgvn tyncrcppqw tgqfctedvd
 301 ecllqpnacq nggtctnrng gygcvcvngw sgddcsenid dcafasctpg stcidrvasf
 361 sclcpegkag llchlddaci snpchkgalc dtnplngqyi ctcpqaykga dctedvdeca
 421 mansnpceha gkcvntdgaf hceclkgyag prcemdinec hsdpcqndat cldkiggftc
 481 lcmpgfkgvh celevnecqs npcvnngqcv dkvnrfqclc ppgftgpvcq ididdcsstp
 541 clngakcidh pngyecqcat gftgtlcden idncdpdpch hgqcqdgids ytcicnpgym
 601 gaicsdqide cysspclndg rcidlvngyq cncqpgtsgl nceinfddca snpclhgacv
 661 dginryscvc spgftgqrcn ididecasnp crkdatcind vngfrcmcpe gphhpscysq
 721 vneclsspci hgnctgglsg ykclcdagwv gincevdkne clsnpcqngg tcnnlvngyr
 781 ctckkgfkgy ncqvnideca snpclnqgtc lddvsgytch cmlpytgknc qtvlapcspn
 841 pcenaavcke apnfesftcl capgwqgqrc tvdvdecvsk pcmnngichn tqgsymcecp
 901 pgfsgmdcee dindclanpc qnggscvdkv ntfsclclpg fvgdkcqtdm neclsepckn
 961 ggtcsdyvns ytctcpagfh gvhcennide ctesscfngg tcvdginsfs clcpvgftgp
1021 fclhdinecs snpclnsgtc vdglgtyrct cplgytgknc qtlvnlcsps pcknkgtcaq
1081 ekarprclcp pgwdgaycdv lnvsckaaal qkgvpvehlc qhsgicinag nthhcqcplg
1141 ytgsyceeql decasnpcqh gatcsdfigg yrcecvpgyq gvnceyevde cqnqpcqngg
1201 tcidlvnhfk cscppgtrgl lceeniddca gaphclnggq cvdriggysc rclpgfager
1261 cegdinecls npcssegsld ciqlknnyqc vcrsaftgrh cetfldvcpq kpclnggtca
1321 vasnvpdgfi crcppgfsga rcqsscgqvk crrgeqcvht asgphcfcpn hkdcesgcas
1381 npcqhggtcy pqrqppyysc rcsppfwgsh cesytapts 1419
```

LINKER SEQUENCE
DLGPG

Figure 12

```
   1 mglgargrrr rrrlmalppp pppmralpll lllaglgaaa ppcldgspca nggrcthqqp
  61 sleaaclclp gwvgercqle dpchsgpcag rgvcqssvva gtarfscrcl rgfqgpdcsq
 121 pdpcvsrpcv hgapcsvgpd grfacacppg yqgqscqsdi decrsgttcr hggtclntpg
 181 sfrcqcplgy tgllcenpvv pcapspcrng gtcrqssdvt ydcaclpgfe gqncevnvdd
 241 cpghrclngg tcvdgvntyn cqcppewtgq fctedvdecq lqpnachngg tcfnllgghs
 301 cvcvngwtge scsqniddca tavcfhgatc hdrvasfyca cpmgktgllc hlddacvsnp
 361 chedaicdtn pvsgraictc ppgftggacd qdvdecsiga npcehlgrcv ntqgsflcqc
 421 grgytgprce tdvneclsgp crnqatcldr igqftcicma gftgtycevd idecqsspcv
 481 nggvckdrvn gfsctcpsgf sgsmcqldvd ecastpcrng akcvdqpdgy ecrcaegfeg
 541 tlcernvddc spdpchhgrc vdgiasfsca capgytgirc esqvdecrsq pcryggkcld
 601 lvdkylcrcp pgttgvncev niddcasnpc tfgvcrdgin rydcvcqpgf tgplcnvein
 661 ecasspcgeg gscvdgengf hclcppgslp plclpanhpc ahkpcshgvc hdapggfrcv
 721 cepgwsgprc sqslapdace sqpcqaggtc tsdgigfrct capgfqghqc evlspctpsl
 781 cehgghcesd pdrltvcscp pgwqgprcqq dvdecagasp cgphgtctnl pgnfrcichr
 841 gytgpfcdqd iddcdpnpcl hggscqdgvg sfscscldgf agprcardvd eclsspcgpg
 901 tctdhvasft cacppgyggf hceidlpdcs psscfnggtc vdgvssfscl crpgytgthc
 961 qyeadpcfsr pclhggicnp thpgfectcr egftgsqcqn pvdwcsqapc qnggrcvqtg
1021 aycicppgws grlcdiqslp cteaaaqmgv rleqlcqegg kcidkgrshy cvcpegrtgs
1081 hcehevdpct aqpcqhggtc rgymggyvce cpagyagdsc ednidecasq pcqnggscid
1141 lvarylcscp pgtlgvlcei neddcdlgps ldsgvqclhn gtcvdlvggf rcncppgytg
1201 lhceadinec rpgachaaht rdclqdpggh frcvchpgft gprcqialsp cesqpcqhgg
1261 qcrhslgrgg gltftchcvp pfwglrcerv arscrelqcp vgipcqqtar gprcacppgl
1321 sgpscrvsra spsgatnasc asapclhggs clpvqsvpff rcvcapgwgg prcetpsaa 1379
```

Linker Sequence
No linker sequence

Figure 13

```
   1 mqpqllllll lplnfpvilt rellcggspe pcanggtclr lsrgqgicqc apgflgetcq
  61 fpdpcrdtql ckngqscqal lptppssrsp tspltphfsc tcpsgftgdr cqthleelcp
 121 psfcsngghc yvqasgrpqc scepgwtgeq cqlrdfcsan pcanggvcla typqiqcrcp
 181 pgfeghtcer dinecflepg pcpqgtschn tlgsyqclcp vgqegpqckl rkgacppgsc
 241 lnggtcqlvp eghstfhlcl cppgftgldc emnpddcvrh qcqngatcld gldtytclcp
 301 ktwkgwdcse dideceargp prcrnggtcq ntagsfhcvc vsgwggagce enlddcaaat
 361 capgstcidr vgsfsclcpp grtgllchle dmclsqpchv naqcstnplt gstlcicqpg
 421 ysgstchqdl decqmaqqgp spcehggsci ntpgsfnclc lpgytgsrce adhneclsqp
 481 chpgstcldl latfhclcpp glegrlceve vnectsnpcl nqaachdlln gfqclclpgf
 541 tgarcekdmd ecsstpcang grcrdqpgaf yceclpgfeg phcekevdec lsdpcpvgas
 601 cldlpgaffc lcrpgftgql cevplctpnm cqpgqqcqgq ehrapclcpd gspgcvpaed
 661 ncpchhghcq rslcvcdegw tgpecetelg gcistpcahg gtchpqpsgy nctcpagymg
 721 ltcseevtac hsgpclnggs csirpegysc tclpshtgrh cqtavdhcvs asclnggtcv
 781 nkpgtffclc atgfqglhce ektnpscads pcrnkatcqd tprgarclcs pgytgsscqt
 841 lidlcarkpc phtarclqsg psfqclclqg wtgalcdfpl scqkaamsqg ieisglcqng
 901 glcidtgssy fcrcppgfqg klcqdnvnpc epnpchhgst cvpqpsgyvc qcapgyegqn
 961 cskvldacqs qpchnhgtct srpggfhcac ppgfvglrce gdvdecldrp chpsgtaach
1021 slanafycqc lpghtgqrce vemdlcqsqp csnggsceit tgpppgftch cpkgfegptc
1081 shkalscgih hchngglclp spkpgspplc aclsgfggpd cltppappgc gppspclhng
1141 tctetpglgn pgfqctcppd spgprcqrpg 1170
```

LINKER SEQUENCE
DLGPG

Figure 14A

```
   1 atgacaggct tccagggctg ccaggccctg ctgcatctgg ccaaggccgt ggttcgcttg
  61 agatgctccc agccaagtgg gacctgcctg aatggaggga ggtgcgaagt ggccaacggc
 121 actgaagcct gtgtctgcag cggagcgttc gtgggccagc gatgccagga ccccagccct
 181 tgcctcagca caccatgtaa gaatgctgga acgtgctatg ttgtggacca tggcggcatc
 241 gtggactatg cctgcagttg cccccctgggt ttctctgggc ccctctgcct gacacctctg
 301 gccaatgcct gcctggccaa cccctgccgc aacgggggga cctgtgacct gctcactctc
 361 acagaataca agtgccggtg cccgccaggg tggtcaggaa agtcatgtca gcaagccgac
 421 ccctgtgcct ccaaccccctg tgccaatggt ggccagtgcc tgccctttga gtcttcatac
 481 atctgtggct gcccgcccgg cttccatggc cccacctgca gacaagatgt taacgagtgc
 541 agccagaacc ctgggttgtg ccgtcatggc ggcacgtgcc acaatgagat tggctcctat
 601 cgctgtgcct gccgtgccac ccacactggt ccccactgcg agctgcccta cgtgccctgc
 661 agcccctcac cctgccagaa cggaggcacc tgccgcccta cgggggacac cacccacgag
 721 tgtgcctgcc tgccaggctt tgctggacag aactgtgaag aaaatgtgga tgactgccca
 781 ggaaacaact gcaagaacgg gggtgcctgt gtggacggtg tgaataccta caattgccgc
 841 tgcccaccgg agtggacagg tcagtactgc acagaggatg tggacgagtg tcagctcatg
 901 cccaacgcct gccagaatgg cggaacctgc cacaactccc acggtggcta caactgcgtg
 961 tgtgtcaatg gctggactgg tgaggactgc agtgagaaca ttgatgactg tgccagtgcc
1021 gcctgttttc agggtgccac ctgccatgac cgtgtggctt ccttctactg cgagtgtcca
1081 catgggcgca caggcctgct gtgccacctg aacgatgcgt gtatcagcaa cccctgcaac
1141 gagggctcca actgcgacac caaccctgtc aacggcaagg ccatctgcac ttgcccctcg
1201 gggtacacgg ggccagcctg cagccaggac gtggatgagt gcgctctagg tgccaacccg
1261 tgtgagcacg cgggcaagtg cctcaacaca ctgggctctt tcgagtgtca gtgtctacag
1321 ggctacactg ggccccgctg tgagattgat gtcaacgagt gcatctccaa cccatgtcag
1381 aatgatgcca cgtgcctgga ccagattggg gagtttcagt gtatatgtat gccaggttat
1441 gagggtgtat actgtgagat caacacggac gagtgtgcca gcagcccctg tctacacaat
1501 ggccgctgcg tggacaagat caacgagttc ctgtgtcagt gtcccaaagg cttcagcggg
1561 cacctgtgcc agtatgacgt ggatgagtgc gccagcacac catgcaagaa cggcgccaag
1621 tgcctggatg gccccaacac ctacacctgc gtgtgcacag aaggttacac ggggacccac
1681 tgcgaggtgg acattgacga gtgtgaccct gacccctgtc actatggttt gtgcaaggat
1741 ggtgtggcca cctttacctg cctctgccag ccaggctaca caggccatca ctgtgagacc
1801 aacattaatg agtgtcacag ccagccgtgc cgccatggcg gcacctgcca ggaccgtgac
1861 aactactacc tctgcttatg cctcaagggg accacaggac ccaactgtga gatcaatctg
1921 gatgactgtg cgagcaaccc ctgtgactct ggcacgtgtc tggacaagat cgatggctac
1981 gagtgtgcgt gcgagccagg ctacacaggg agcatgtgta atgtcaacat tgacgaatgt
2041 gcgggcagcc cctgccacaa cgggggcacc tgtgaggatg gcatcgccgg cttcacttgc
2101 cgctgccccg agggctacca cgaccctacg tgcctgtctg aggtcaacga gtgcaacagt
2161 aacccctgca tccatggagc ttgccgggat ggcctcaatg gatacaaatg tgactgtgcc
2221 cctgggtgga gtgggacaaa ctgtgacatc aacaacaatg agtgtgagtc caaccccttgt
2281 gtcaacggtg gcacctgcaa agacatgacc agtggctacg tatgcacctg ccgagaaggc
2341 ttcagtggcc ctaactgcca gaccaacatt aacgaatgtg cttccaaccc ctgcctgaac
2401 cagggcacct gcattgatga tgtcgctggg tacaaatgca actgccctct gccctataca
2461 ggagccacat gtgaggtggt gttggcccca tgtgccacca gcccctgcaa aaacagtggg
2521 gtatgcaagg agtctgagga ctatgagagc ttttcctgtg tctgtcccac aggctggcaa
2581 ggtcaaacct gcgagatcga catcaatgag tgtgtgaaaa gcccgtgtcg ccatggtgcc
2641 tcttgccaga acaccaatgg cagctaccgc tgcctctgcc aggctggcta cacgggtcgc
2701 aactgcgaga gtgacatcga tgactgccga cccaacccat gtcacaacgg gggttcctgc
2761 actgacgggg tcaacgcggc cttctgcgac tgcctgcccg gcttccaggg tgccttctgt
2821 gaggaggaca tcaacgaatg cgccagcaat ccatgccaaa atggcgccaa ctgcactgac
2881 tgcgtggaca gctacacgtg cacctgcccc acgggcttca atggcatcca ttgcgagaac
2941 aacacacctg actgtaccga gagctcctgt ttcaatggtg gcacctgtgt ggatggtatc
3001 aactccttca cctgtctgtg cccacctggc ttcacgggca gctactgcca gtatgacgtc
3061 aatgagtgtg actcacggcc ctgtctgcat ggtggcacct gccaagacag ctatggtacc
3121 tataagtgta cctgcccaca gggctacact ggtctcaact gccagaacct tgtgcgctgg
3181 tgtgactcag ctccctgcaa gaatggcggc aagtgctggc agaccaacac acagtaccac
3241 tgcgagtgcc gcagcggctg gactggcttc aactgcgacg tgctcagtgt gtcctgcgag
```

Figure 14B

```
3301 gtggctgcac agaagcgagg catcgatgtc actctcctat gccagcacgg agggctctgt
3361 gtggatgagg aagacaagca ttactgccac tgccaggcag gatacacggg cagctactgt
3421 gaggacgagg tggacgagtg ctcacctaat ccctgccaga acggagccac ctgcactgac
3481 tatctcggtg gcttttcctg caagtgtgtg gctgggtacc atggctctaa ctgctctgag
3541 gagatcaacg agtgcctatc ccaaccctgc cagaatgggg gtacctgcat tgatctgacc
3601 aacacctaca agtgctcctg ccccagggc acacagggtg tacactgtga gatcaacgtc
3661 gatgactgcc atcctcccct agaccctgct tcccgaagcc ccaaatgctt caataatggc
3721 acctgcgtgg accaggtggg tggctatacc tgcacctgcc cgccaggctt cgtcggggag
3781 cggtgcgagg gcgatgtcaa tgagtgtctc tccaacccct gtgacccacg tggcacccag
3841 aactgcgtgc agcgtgttaa tgacttccac tgcgagtgcc gggctggcca cactggacgc
3901 cgctgtgagt cggtcattaa tggctgcagg ggcaaaccat gcaggaatgg aggtgtctgt
3961 gctgtggcct ccaacaccgc ccgtggattc atctgtaggt gccctgcggg cttcgagggt
4021 gccacttgtg aaaatgacgc ccgcacttgt ggcagtttgc gctgcctcaa cggtggtacg
4081 tgcatctcag gcccacgcag tcccacctgc ctatgcctgg gctccttcac tggccctgaa
4141 tgccagttcc cagccagcag cccctgtgtg ggtagcaacc cctgctacaa tcagggcacc
4201 tgtgagccca catccgagag ccctttctac cgctgtctat gccctgccaa attcaacggg
4261 ctgctgtgcc acatcctgga ctacagcttc aca 4293
```

Figure 15A

```
511 atgcccgctc tgcgtcccgc cgcgctgcgg
     541 gcgctgctgt ggctctggct gtgcggcgcg ggccccgcgc acgctttgca gtgtcgaggt
     601 ggtcaagagc cctgtgtaaa tgaggggacc tgtgttacct accacaacgg cacaggctac
     661 tgccgatgtc cagagggctt cttgggagaa tattgtcaac atcgagaccc ttgtgagaag
     721 aaccgctgtc agaatggtgg tacttgtgtg acgcaggcca tgttgggaaa agccacctgt
     781 cgatgtgctc cagggttcac aggggaggac tgccaatact cgacctctca cccctgtttt
     841 gtttcccgcc cctgtcagaa tggaggtacc tgccacatgc tcagctggga cacctatgag
     901 tgcacctgtc aagttggctt cacaggaaag cagtgtcagt ggacagatgt ctgtctgtct
     961 catccctgtg aaaatggaag cacctgtagc tctgtggcca accagttctc ctgcagatgt
    1021 cctgcaggca tcacaggcca gaagtgtgac gccgacatca atgaatgtga cattccagga
    1081 cgctgccaac atggtggcac ctgcctcaac cttcctgggt cctaccgatg ccaatgccct
    1141 cagcggttca caggccagca ctgtgacagc ccttacgtgc cctgtgcacc ctcaccctgc
    1201 gtcaatggag gcacctgccg tcagactgga gacttcactt ctgaatgcca ttgcctgcca
    1261 ggctttgaag ggagcaactg cgagcggaat atcgacgact gccctaacca caagtgtcag
    1321 aatggagggg tgtgtgtgga tggcgtcaat acttacaact gccgctgccc ccctcagtgg
    1381 actgggcagt tctgcacaga agacgtggat gagtgtctgc tgcagcccaa tgcttgtcag
    1441 aatggaggca cttgcaccaa ccgcaacgga ggctacggct gcgtgtgcgt gaacggctgg
    1501 agtggggatg actgcagcga gaacatcgat gactgtgcct tcgcttcctg cacgccaggc
    1561 tccacctgta ttgaccgtgt ggcctccttc tcctgccttt gtccagaggg aaaggcaggg
    1621 ctcctgtgtc atctggatga tgcctgtatc agcaaccctt gtcacaaggg ggcgctgtgt
    1681 gataccaacc ccctgaatgg gcagtacatt tgcacctgcc cacaggcgta caagggcgct
    1741 gactgcacag aagacgtgga tgagtgtgct atggccaaca gtaacccttg tgagcatgca
    1801 ggaaagtgtg tgaatacaga tggcgccttc cactgcgagt gtctgaaggg ctacgcaggg
    1861 cctcgctgtg agatggacat caacgagtgt cactcagacc cctgtcagaa cgacgccacc
    1921 tgcctggata agattggagg cttcacctgt ctctgcatgc cgggtttcaa aggtgtgcat
    1981 tgtgaactgg aggtgaatga atgccagagc aacccgtgtg taaacaatgg gcagtgtgtg
    2041 gacaaagtca atcgcttcca gtgtctgtgt ccccctggtt tcacaggacc agtgtgccag
    2101 atcgacattg acgactgctc cagtactccc tgcctgaatg gggccaagtg catcgatcac
    2161 ccgaatggct atgaatgcca gtgtgccaca ggattcactg gcacactgtg tgatgagaac
    2221 atcgacaact gtgacccgga tccttgccac catggccagt gccaggatgg gattgactcc
    2281 tacacctgca tctgcaaccc cgggtacatg ggagccatct gtagtgacca gattgatgaa
    2341 tgctacagca gcccctgcct gaatgatgga cgctgcatcg acctggtgaa cggctaccag
    2401 tgcaactgcc aaccgggtac ctcaggcctt aattgtgaaa ttaattttga tgactgtgcc
    2461 agcaacccct gtctgcacgg agcctgtgtg gacggcatca accgttacag ttgtgtgtgc
    2521 tctccgggat tcacagggca gaggtgcaac atagacattg atgagtgtgc ctccaacccc
    2581 tgtcgcaagg atgcgacgtg catcaatgac gtgaatggtt tccggtgtat gtgccctgag
    2641 ggaccacacc atcccagctg ctactcacag gtgaacgagt gtttgagcag tccctgcatc
    2701 catggaaact gtactggagg tctcagtggc tataagtgcc tctgcgatgc aggctgggtt
    2761 ggtatcaact gcgaagtgga caaaaatgag tgtctttcta acccgtgcca gaatggaggg
    2821 acatgtaata acctggtgaa tggctacagg tgtacatgca agaaggggtt caaaggctat
    2881 aactgccagg tgaacataga tgagtgtgcc tcgaacccgt gtctgaacca agggacctgc
    2941 ctcgatgacg tcagtggcta cacctgccac tgcatgctgc cttacacagg caagaattgt
    3001 caaacggtgt tggcgccctg ctcccctaac ccgtgtgaga acgctgcagt ttgtaaagag
    3061 gcacccaact ttgagagctt cacctgcctg tgtgcccctg gctggcaagg tcagcgctgt
    3121 acagttgacg ttgatgagtg tgtctccaag ccgtgtatga acaatggcat ctgccataat
    3181 actcagggca gctacatgtg cgagtgccct cccggcttca gtggtatgga ctgtgaggag
    3241 gacatcaatg actgccttgc caacccctgc cagaacggag gctcctgtgt ggacaaagtg
    3301 aacaccttct cctgcctgtg ccttcctggc ttcgtagggg acaagtgcca aacagacatg
    3361 aatgaatgtc tgagcgagcc ctgtaagaat gggggggacct gctctgacta cgtcaacagc
    3421 tacacctgca cgtgccctgc gggcttccat ggagtccact gtgaaaacaa catcgatgag
    3481 tgcactgaga gctcctgttt caatggcggc acgtgtgttg atgggatcaa ctctttctct
    3541 tgcttatgcc ctgtgggttt cactggtccc ttctgcctcc atgatatcaa tgagtgcagc
    3601 tctaacccgt gcctgaattc gggaacgtgt gttgatggcc tgggtaccta ccgatgcacc
    3661 tgtcccttgg gctacactgg gaaaaactgt cagaccctgg tgaacctctg cagcccctct
    3721 ccatgtaaaa acaaaggaac ttgtgctcag gaaaaggcaa ggccacgctg cctgtgtccg
    3781 cctggatggg atggcgcata ctgtgatgtg ctcaatgtgt cctgtaaggc ggcagccttg
```

Figure 15B

```
3841 cagaaaggag tacctgttga acacttgtgc cagcactcgg gtatctgtat caatgctggc
3901 aacacgcatc actgccagtg ccccctgggc tacacgggga gctactgcga ggaacagctt
3961 gacgagtgtg cgtccaatcc atgccagcat ggtgccacct gcagtgactt catcggagga
4021 tacagatgtg agtgtgttcc agggtatcag ggtgtcaact gtgagtatga agtggacgag
4081 tgccagaacc agccctgtca gaacggaggc acctgcatcg acctcgtgaa ccatttcaag
4141 tgctcgtgcc caccaggcac ccggggcctg ctttgtgaag agaacattga tgactgtgct
4201 ggggcccccc actgccttaa tggtggccag tgtgtggacc ggattggagg ctacagttgt
4261 cgctgtttgc ctggctttgc tggggagcgg tgtgaggggg acatcaatga atgcctgtcc
4321 aatccttgca gctcagaggg cagcctggac tgcattcagc tcaaaaataa ctaccagtgt
4381 gtctgccgca gcgccttcac aggccgacac tgcgaaacct tcctagatgt gtgtccccag
4441 aagccttgcc tgaatggagg gacttgtgct gtggctagca acgtgcctga tggcttcatt
4501 tgtcgttgtc ccccagggtt ctccggggca agatgccaga gcagctgtgg acaagtgaag
4561 tgcagaagag gggagcagtg tgtgcacacc gcctcgggac cccactgctt ctgcccgaac
4621 cacaaggact gcgagtcagg ttgcgctagt aacccctgcc agcacggagg cacctgctac
4681 cctcagcgcc agcctcctta ctactcttgc cgctgctccc caccgttctg ggcagccac
4741 tgcgagagct acacagcccc caccagc 4767
```

Figure 16A

```
  60                                                             a
  61 tggggctggg ggcccggggc cgccgccgcc gtcgtcgcct gatggccttg ccaccgccac
 121 caccgcccat gcgggcgctg cccctgctgc tgctgctagc ggggctgggg gctgcagcac
 181 ccccttgtct ggatggaagc ccatgtgcaa atggaggtcg gtgcacccac cagcagccct
 241 ccctggaggc tgcttgcctg tgcctgccag gctgggtggg tgagcggtgc cagctggaag
 301 acccttgcca ctcaggccct tgtgctggcc gaggcgtttg ccagagttca gtggtggcgg
 361 gcaccgcccg attctcctgt cgttgtctcc gtggcttcca aggcccagac tgctcccagc
 421 cagacccctg cgtcagcagg ccctgtgttc atggtgcccc ctgctcagtg ggccggatg
 481 gccgatttgc ctgtgcctgc ccacctggct accagggtca aagctgccaa agtgacatag
 541 atgagtgccg atctggtaca acttgccgtc atggtggtac ctgtctcaat acacctggat
 601 ccttccgctg ccagtgtcct cttggttata cagggctgct gtgtgagaac cccgtagtgc
 661 cctgtgcccc ttccccgtgt cgtaatggtg gcacctgtag gcagagcagt gatgtcacat
 721 atgactgtgc ttgccttcct ggcttcgagg gccagaactg tgaagtcaac gtggatgact
 781 gtcctggaca tcggtgtctc aatgggggaa cgtgtgtaga cggtgtcaat acttacaact
 841 gccagtgccc tccggagtgg acaggccagt tctgtacaga agatgtggat gagtgtcagc
 901 tgcagcccaa tgcctgccac aatgggggta cctgcttcaa cctactgggt ggccacagct
 961 gtgtatgtgt caatggctgg acgggtgaga gctgcagtca gaatatcgat gactgtgcta
1021 cagccgtgtg tttccatggg gccacctgcc atgaccgtgt ggcctctttc tactgtgcct
1081 gccctatggg gaagacaggc ctcttgtgtc atctggatga tgcatgtgtc agcaacccct
1141 gccatgagga tgctatctgt gacacaaacc ctgtgagtgg ccgggccatc tgcacctgcc
1201 cacctggctt cactggaggg gcatgtgacc aggatgtgga tgagtgctcg attggtgcca
1261 acccctgtga acatttgggt cggtgtgtga atacacaggg ctcattcttg tgccaatgtg
1321 gccgtggcta tactggacct cgctgtgaga ctgatgtcaa tgagtgtctc tccgggccct
1381 gccgcaacca ggccacgtgt cttgaccgaa ttggccagtt tacttgcatc tgcatggcag
1441 gcttcacagg gacctactgt gaggtggaca tcgacgaatg tcagagcagc ccatgtgtca
1501 atggtggtgt ctgcaaggac agagtcaatg gcttcagctg cacctgccca tcaggattca
1561 gtgggtccat gtgtcagctg gatgtggatg agtgtgcaag cactccctgc cggaatggtg
1621 ccaagtgtgt ggaccagcct gacggctatg agtgtcgctg tgcagagggc tttgagggca
1681 ctttgtgtga gcgaaacgtg gatgactgct ctccggatcc ctgccaccac gggcgctgtg
1741 tcgatggcat tgctagcttc tcgtgtgctt gtgccccagg ctatacgggc atacgctgtg
1801 agagccaggt ggatgagtgc cgcagccagc cctgtcgata tgggggcaaa tgtctagact
1861 tggtggacaa gtacctctgc cgttgtcctc ccggaaccac aggtgtgaac tgtgaagtca
1921 acattgatga ctgtgccagt aacccctgta cctttggagt ttgccgtgat ggcatcaacc
1981 gttatgactg tgtctgtcag cctggattca cagggcccct ctgcaacgtg gagatcaatg
2041 agtgtgcatc cagcccatgt ggagagggtg gctcctgtgt ggatggggaa aatggcttcc
2101 actgcctctg tccacctggc tccctgcctc cactttgcct acctgcgaac catccctgtg
2161 cccacaagcc ctgtagtcat ggagtctgcc atgatgcacc aggcgggttc cgctgtgttt
2221 gtgagcccgg gtggagtggc cctcgctgta gccagagcct ggctccagat gcctgtgagt
2281 cccagccctg ccaggctggt ggcacctgca ccagtgatgg aataggcttt cgctgcacct
2341 gtgcccctgg attccagggc catcagtgtg aggtgctgtc cccctgtact ccaagcctct
2401 gtgagcacgg aggccactgt gagtctgacc ctgaccggct gactgtctgt tcctgtcccc
2461 caggctggca aggcccacga tgccagcagg atgtggatga atgtgccggt gcctcaccct
2521 gcggccccca tggtacctgc accaacctgc cagggaattt caggtgcatc tgccacaggg
2581 gatacactgg cccccttctgt gatcaagaca ttgacgactg tgaccccaac ccgtgcctcc
2641 atggtggctc ctgccaggat ggcgtgggct ccttttcctg ttcttgcctc gacggctttg
2701 ctggtcctcg ctgtgcccga gatgtggacg aatgtctgag cagcccctgt ggccctggca
2761 cctgtactga tcacgtggcc tccttcacct gtgcctgtcc acctggttat ggaggcttcc
2821 actgtgagat tgacttgccg gactgcagcc ccagttcctg cttcaatgga gggacctgtg
2881 tggatggcgt gagctccttc agctgtctgt gtcgccccgg ctacacaggc acacactgcc
2941 aatacgaggc tgacccctgc ttttcccggc cctgtctgca cgggggcatc tgcaacccca
3001 cccacccagg atttgaatgc acctgccggg agggcttcac tgggagtcag tgtcagaacc
3061 cagtggactg gtgcagccag gcaccctgtc agaatggggg tcgctgtgtc cagactgggg
3121 cttactgcat ttgtccacct ggatggagtg gccgcctgtg cgacatacaa agcctgccct
3181 gcacggaggc cgcagcccag atgggggtga ggttggagca gctgtgtcag gaaggtggaa
3241 agtgcataga caagggccgc tcccactact gtgtgtgtcc agagggccgt acgggtagtc
3301 actgtgaaca cgaggtggat ccctgcacgg cccagccttg ccagcacggg ggcacttgcc
```

Figure 16B

```
3361 gtggttacat ggggggctat gtgtgtgagt gtccagctgg ctatgctggt gacagttgtg
3421 aggataatat agatgagtgt gcttcccagc cctgccagaa cggaggctcc tgtatcgatc
3481 ttgtggcccg ctatctctgt tcctgtcccc ctggcacact gggagttctc tgtgagatca
3541 atgaggacga ctgtgaccta ggcccatcct tggactcagg cgttcagtgc ctacacaatg
3601 gcacctgtgt ggacctggtg ggtggcttcc gctgtaactg tcccccagga tacacaggtc
3661 tgcactgtga ggcagacatc aatgagtgtc gcccgggtgc ctgccatgca gcgcatactc
3721 gggactgcct acaagatcca ggtgggcatt tccgctgcgt ctgccatcct ggcttcacag
3781 ggcctcgctg tcagattgct ctgtcccccct gtgagtccca gccatgtcag catggaggcc
3841 agtgccgtca cagcctaggc cgtggaggtg ggctgacctt cacctgtcac tgtgtcccgc
3901 cattctgggg tctgcgttgt gagcgggtgg cacgctcttg ccgagagctg cagtgcccag
3961 tgggtatccc atgccagcag acagcccgtg gaccacgctg cgcttgtcct ccggggctgt
4021 ccgggccctc ctgccgggtt tctagggcgt caccctcagg agctactaac gccagctgcg
4081 cctctgcccc ttgtctgcat gggggctcat gcctacctgt acagagtgtc cctttcttcc
4141 gctgtgtgtg cgctccgggc tggggcggcc cgcgttgtga gacccccttcc gcagcc 4196
```

Figure 17A 117 atgc
121 agccccagtt gctgctgctg ctgctcttgc cactcaattt ccctgtcatc ctgaccagag
181 agcttctgtg tggaggatcc ccagagccct gtgccaacgg aggcacctgc ctgaggctat
241 ctcagggaca agggatctgc cagtgtgccc ctggatttct gggtgagact tgccagtttc
301 ctgacccctg cagggatacc caactctgca agaatggtgg cagctgccaa gccctgctcc
361 ccacaccccc aagctcccgt agtcctactt ctccactgac ccctcacttc tcctgcacct
421 gcccctctgg cttcaccggt gatcgatgcc aaacccatct ggaagagctc tgtccacctt
481 ctttctgttc caacgggggt cactgctatg ttcaggcctc aggccgccca cagtgctcct
541 gcgagcctgg gtggacaggt gagcaatgcc agctccgaga cttctgctca gccaacccct
601 gtgccaacgg aggcgtgtgc ctggccacat acccccagat ccagtgccgc tgtccacctg
661 ggttcgaggg tcacacctgt gaacgcgaca tcaacgagtg cttcctggag ccgggaccct
721 gccctcaggg cacctcctgc cataacacct tgggttccta ccagtgtctc tgccctgtgg
781 ggcaggaagg tccccagtgc aagctcagga agggagcctg ccctcctgga agctgtctca
841 atgggggcac ctgccagctg gtcccagagg gacactccac ctttcatctc tgcctctgtc
901 ccccaggttt cacggggctg gactgtgaga tgaacccaga tgactgtgtc aggcaccagt
961 gtcagaacgg ggccacctgt ctggatgggc tggataccta cacctgcctc tgccccaaga
1021 catggaaggg ctgggactgc tctgaagata tagatgaatg tgaagcccgg ggtcccccctc
1081 gctgcaggaa cggtggcacc tgccagaaca cagctggcag ctttcactgt gtgtgcgtga
1141 gtggctgggg cggtgcaggt tgtgaggaga acctggatga ctgtgcagct gccacctgtg
1201 ccccgggatc cacctgcatc gaccgtgtgg gctctttctc ctgcctctgc ccacctggac
1261 gcacaggcct cctgtgccac ctggaagaca tgtgtttgag tcagccgtgc cacgtgaatg
1321 cccagtgcag caccaaccct ctgacaggct ccaccctctg catatgccag cctggctact
1381 caggatccac ctgtcaccaa gatctggatg agtgccaaat ggcccagcaa ggacccagtc
1441 cctgcgaaca tggcggctcc tgcatcaaca cccctggctc cttcaactgc ctctgcctgc
1501 ctggttacac gggctcccgc tgtgaagctg accacaatga gtgcctgtca cagccctgcc
1561 acccaggcag cacctgcctg gacctgcttg caaccttcca ctgcctctgc ccaccaggct
1621 tggaagggag gctctgtgag gtggaggtca atgagtgcac ctctaatccc tgcctgaacc
1681 aagctgcctg ccatgacctg ctcaacggct tccagtgcct ctgccttcct ggattcaccg
1741 gcgcccgatg tgagaaagac atggacgagt gtagcagcac cccctgtgcc aatgggggc
1801 gctgccgaga ccagcctgga gccttctact gcgagtgtct cccaggcttt gaagggccac
1861 actgtgagaa agaagtggac gaatgtctga gtgacccctg ccccgtggga gccagctgcc
1921 ttgatctccc cggagcattc ttctgcctct gccgtcctgg tttcacaggt caactttgtg
1981 aggttccctt gtgcaccccc aacatgtgcc aacctggaca gcaatgccaa ggtcaggaac
2041 acagagcccc ctgcctctgc cctgacggaa gtcctggctg tgttcctgcc gaggacaact
2101 gcccctgtca ccatggccat tgccagagat ccttgtgtgt gtgtgatgag ggctggactg
2161 gaccagaatg cgagacagaa ctgggtggct gcatctccac accctgtgcc catgggggga
2221 cctgccaccc acagccgtct ggctacaact gtacctgccc tgcaggctac atggggttga
2281 cctgtagtga ggaggtgaca gcttgtcact cagggccctg tctcaatggt ggctcttgca
2341 gcatccgtcc tgagggctat tcctgcacct gccttccaag tcacacaggt cgccactgcc
2401 agactgccgt ggaccactgt gtgtctgcct cgtgcctcaa tgggggtacc tgtgtgaaca
2461 agcctggcac tttcttctgc ctctgtgcca ctggcttcca ggggctgcac tgtgaggaga
2521 agactaaccc cagctgtgca gacagcccct gcaggaacaa ggcaacctgc caagacacac
2581 ctcgaggggc ccgctgcctc tgcagccctg gctatacagg aagcagctgc cagactctga
2641 tagacttgtg tgcccggaag ccctgtccac acactgctcg atgcctccag agtgggccct
2701 cgttccagtg cctgtgcctc cagggatgga caggggctct ctgtgacttc ccactgtcct
2761 gccagatggc cgcaatgagc caaggcatag agatctctgg cctgtgccag aatggaggcc
2821 tctgtattga cacgggctcc tcctatttct gccgctgccc tcctggattc caaggcaagt
2881 tatgccagga taatatgaac ccctgcgagc ccaatccctg ccatcacggg tctacctgtg
2941 tgcctcagcc cagtggctat gtctgccagt gtgccccagg ctatgaggga cagaactgct
3001 caaaagtact tgaagcttgt cagtcccagc cctgccacaa ccacggaacc tgtacctcca
3061 ggcctggagg cttccactgt gcctgccctc caggcttcgt gggactgcgc tgtgagggag
3121 atgtggatga gtgtctggac cggccctgtc acccctcggg cactgcagct tgccactctt
3181 tagccaacgc cttctactgc cagtgtctgc ctgggcacac aggccagcgg tgtgaggtgg
3241 agatggacct ctgtcagagc caaccctgct ccaatggagg atcctgtgag atcacaacag
3301 ggccaccccc tggcttcacc tgtcactgcc ccaagggttt tgaaggcccc acctgcagcc

Figure 17B

```
3361 acaaagccct ttcctgcggc atccatcact gccacaatgg aggcctatgt ctgccctccc
3421 ctaagccagg gtcaccacca ctctgtgcct gcctcagtgg ttttgggggc cctgactgtc
3481 tgacacctcc agctccaccg ggctgcggtc ccccctcacc ctgcctgcac aatggtacct
3541 gcactgagac ccctgggttg ggcaacccgg gctttcaatg cacctgccct cctgactctc
3601 cagggccccg gtgtcaaagg ccaggg 3626
```

Linker Sequence

```
GAT CTG GGC CCG GGC
 D   L   G   P   G
```

Figure 18A

```
   1 atgccgccgc tcctggcgcc cctgctctgc ctggcgctgc tgcccgcgct cgccgcacga
  61 ggcccgcgat gctcccagcc cggtgagacc tgcctgaatg gcgggaagtg tgaagcggcc
 121 aatggcacgg aggcctgcgt ctgtggcggg gccttcgtgg gcccgcgatg ccaggacccc
 181 aacccgtgcc tcagcacccc ctgcaagaac gccgggacat gccacgtggt ggaccgcaga
 241 ggcgtggcag actatgcctg cagctgtgcc ctgggcttct ctgggcccct ctgcctgaca
 301 cccctggaca atgcctgcct caccaacccc tgccgcaacg gggcacctg cgacctgctc
 361 acgctgacgg agtacaagtg ccgctgcccg cccggctggt cagggaaatc gtgccagcag
 421 gctgacccgt gcgcctccaa cccctgcgcc aacggtggcc agtgcctgcc cttcgaggcc
 481 tcctacatct gccactgccc acccagcttc catggcccca cctgccggca ggatgtcaac
 541 gagtgtggcc agaagcccgg gctttgccgc cacggaggca cctgccacaa cgaggtcggc
 601 tcctaccgct gcgtctgccg cgccacccac actggcccca actgcgagcg gccctacgtg
 661 ccctgcagcc cctcgccctg ccagaacggg ggcacctgcc gccccacggg cgacgtcacc
 721 cacgagtgtg cctgcctgcc aggcttcacc ggccagaact gtgaggaaaa tatcgacgat
 781 tgtccaggaa acaactgcaa gaacgggggt gcctgtgtgg acggcgtgaa cacctacaac
 841 tgccgctgcc cgccagagtg gacaggtcag tactgtaccg aggatgtgga cgagtgccag
 901 ctgatgccaa atgcctgcca gaacggcggg acctgccaca acacccacgg tggctacaac
 961 tgcgtgtgtg tcaacggctg gactggtgag gactgcagcg agaacattga tgactgtgcc
1021 agcgccgcct gcttccacgg cgccacctgc catgaccgtg tggcctcctt ctactgcgag
1081 tgtccccatg gccgcacagg tctgctgtgc cacctcaacg acgcatgcat cagcaacccc
1141 tgtaacgagg gctccaactg cgacaccaac cctgtcaatg gcaaggccat ctgcacctgc
1201 ccctcggggt acacgggccc ggcctgcagc caggacgtgg atgagtgctc gctgggtgcc
1261 aacccctgcg agcatgcggg caagtgcatc aacacgctgg gctccttcga gtgccagtgt
1321 ctgcagggct acacgggccc ccgatgcgag atcgacgtca acgagtgcgt ctcgaacccg
1381 tgccagaacg acgccacctg cctggaccag attggggagt tccagtgcat ctgcatgccc
1441 ggctacgagg gtgtgcactg cgaggtcaac acagacgagt gtgccagcag cccctgcctg
1501 cacaatggcc gctgcctgga caagatcaat gagttccagt gcgagtgccc cacgggcttc
1561 actgggcatc tgtgccagta cgatgtggac gagtgtgcca gcaccccctg caagaatggt
1621 gccaagtgcc tggacggacc caacacttac acctgtgtgt gcacggaagg gtacacgggg
1681 acgcactgcg aggtggacat cgatgagtgc gaccccgacc cctgccacta cggctcctgc
1741 aaggacggcg tcgccacctt cacctgcctc tgccgcccag gctacacggg ccaccactgc
1801 gagaccaaca tcaacgagtg ctccagccag ccctgccgcc acgggggcac ctgccaggac
1861 cgcgacaacg cctacctctg cttctgcctg aaggggacca caggacccaa ctgcgagatc
1921 aacctggatg actgtgccag cagcccctgc gactcgggca cctgtctgga caagatcgat
1981 ggctacgagt gtgcctgtga gccgggctac acagggagca tgtgtaacat caacatcgat
2041 gagtgtgcgg gcaacccctg ccacaacggg ggcacctgcg aggacggcat caatggcttc
2101 acctgccgct gccccgaggg ctaccacgac cccacctgcc tgtctgaggt caatgagtgc
2161 aacagcaacc cctgcgtcca cggggcctgc cgggacagcc tcaacgggta caagtgcgac
2221 tgtgaccctg ggtggagtgg gaccaactgt gacatcaaca acaatgagtg tgaatccaac
2281 ccttgtgtca acggcggcac ctgcaaagac atgaccagtg gctacgtgtg cacctgccgg
2341 gagggcttca gcggtcccaa ctgccagacc aacatcaacg agtgtgcgtc caacccatgt
2401 ctgaaccagg gcacgtgtat tgacgacgtt gccgggtaca agtgcaactg cctgctgccc
2461 tacacaggtg ccacgtgtga ggtggtgctg gccccgtgtg cccccagccc ctgcagaaac
2521 ggcggggagt gcaggcaatc cgaggactat gagagcttct cctgtgtctg ccccacgggc
2581 tggcaagcag ggcagacctg tgaggtcgac atcaacgagt gcgttctgag cccgtgccgg
2641 cacggcgcat cctgccagaa cacccacggc ggctaccgct gccactgcca ggccggctac
2701 agtgggcgca actgcgagac cgacatcgac gactgccggc ccaacccgtg tcacaacggg
2761 ggctcctgca cagacggcat caacacggcc ttctgcgact gcctgcccgg cttccggggc
2821 actttctgtg aggaggacat caacgagtgt gccagtgacc cctgccgcaa cggggccaac
2881 tgcacggact gcgtggacag ctacacgtgc acctgccccg caggcttcag cgggatccac
2941 tgtgagaaca acacgcctga ctgcacagag agctcctgct tcaacggtgg cacctgcgtg
3001 gacggcatca actcgttcac ctgcctgtgt ccacccggct tcacgggcag ctactgccag
3061 cacgatgtca atgagtgcga ctcacagccc tgcctgcatg gcggcacctg tcaggacggc
3121 tgcggctcct acaggtgcac ctgcccccag ggctacactg gccccaactg ccagaacctt
3181 gtgcactggt gtgactcctc gccctgcaag aacggcggca aatgctggca gacccacacc
3241 cagtaccgct gcgagtgccc cagcggctgg accggccttt actgcgacgt gcccagcgtg
3301 tcctgtgagg tggctgcgca gcgacaaggt gttgacgttg cccgcctgtg ccagcatgga
```

Figure 18B

```
3361 gggctctgtg tggacgcggg caacacgcac cactgccgct gccaggcggg ctacacaggc
3421 agctactgtg aggacctggt ggacgagtgc tcacccagcc cctgccagaa cggggccacc
3481 tgcacggact acctgggcgg ctactcctgc aagtgcgtgg ccggctacca cggggtgaac
3541 tgctctgagg agatcgacga gtgcctctcc cacccctgcc agaacggggg cacctgcctc
3601 gacctcccca acacctacaa gtgctcctgc ccacggggca ctcagggtgt gcactgtgag
3661 atcaacgtgg acgactgcaa tccccccgtt gaccccgtgt cccggagccc caagtgcttt
3721 aacaacggca cctgcgtgga ccaggtgggc ggctacagct gcacctgccc gccgggcttc
3781 gtgggtgagc gctgtgaggg ggatgtcaac gagtgcctgt ccaatccctg cgacgcccgt
3841 ggcacccaga actgcgtgca gcgcgtcaat gacttccact gcgagtgccg tgctggtcac
3901 accgggcgcc gctgcgagtc cgtcatcaat ggctgcaaag gcaagccctg caagaatggg
3961 ggcacctgcg ccgtggcctc caacaccgcc cgcgggttca tctgcaagtg ccctgcgggc
4021 ttcgagggcg ccacgtgtga gaatgacgct cgtacctgcg gcagcctgcg ctgcctcaac
4081 ggcggcacat gcatctccgg cccgcgcagc cccacctgcc tgtgcctggg ccccttcacg
4141 ggccccgaat gccagttccc ggccagcagc ccctgcctgg gcggcaaccc ctgctacaac
4201 caggggacct gtgagcccac atccgagagc cccttctacc gttgcctgtg ccccgccaaa
4261 ttcaacgggc tcttgtgcca catcctggac tacagcttc 4299
```

Figure 19A

```
   1 tcatctggaa ttatgcccgc cctgcgcccc gctctgctgt gggcgctgct ggcgctctgg
  61 ctgtgctgcg cggccccccgc gcatgcattg cagtgtcgag atggctatga accctgtgta
 121 aatgaaggaa tgtgtgttac ctaccacaat ggcacaggat actgcaaatg tccagaaggc
 181 ttcttggggg aatattgtca acatcgagac ccctgtgaga agaaccgctg ccagaatggt
 241 gggacttgtg tggcccaggc catgctgggg aaagccacgt gccgatgtgc ctcagggttt
 301 acaggagagg actgccagta ctcaacatct catccatgct ttgtgtctcg accctgcctg
 361 aatggcggca catgccatat gctcagccgg gatacctatg agtgcacctg tcaagtcggg
 421 tttacaggta aggagtgcca atggacggat gcctgcctgt ctcatccctg tgcaaatgga
 481 agtacctgta ccactgtggc caaccagttc tcctgcaaat gcctcacagg cttcacaggg
 541 cagaaatgtg agactgatgt caatgagtgt gacattccag gacactgcca gcatggtggc
 601 acctgcctca acctgcctgg ttcctaccag tgccagtgcc ctcagggctt cacaggccag
 661 tactgtgaca gcctgtatgt gccctgtgca ccctcacctt gtgtcaatgg aggcacctgt
 721 cggcagactg gtgacttcac ttttgagtgc aactgccttc caggttttga agggagcacc
 781 tgtgagagga atattgatga ctgccctaac cacaggtgtc agaatggagg ggtttgtgtg
 841 gatggggtca acacttacaa ctgccgctgt cccccacaat ggacaggaca gttctgcaca
 901 gaggatgtgg atgaatgcct gctgcagccc aatgcctgtc aaaatggggg cacctgtgcc
 961 aaccgcaatg gaggctatgg ctgtgtatgt gtcaacggct ggagtggaga tgactgcagt
1021 gagaacattg atgattgtgc cttcgcctcc tgtactccag gctccacctg catcgaccgt
1081 gtggcctcct tctcttgcat gtgcccagag gggaaggcag gtctcctgtg tcatctggat
1141 gatgcatgca tcagcaatcc ttgccacaag gggcactgt gtgacaccaa ccccctaaat
1201 gggcaatata tttgcacctg cccacaaggc tacaaagggg ctgactgcac agaagatgtg
1261 gatgaatgtg ccatggccaa tagcaatcct tgtgagcatg caggaaaatg tgtgaacacg
1321 gatggcgcct tccactgtga gtgtctgaag ggttatgcag gacctcgttg tgagatggac
1381 atcaatgagt gccattcaga cccctgccag aatgatgcta cctgtctgga taagattgga
1441 ggcttcacat gtctgtgcat gccaggtttc aaaggtgtgc attgtgaatt agaaataaat
1501 gaatgtcaga gcaacccttg tgtgaacaat gggcagtgtg tggataaagt caatcgtttc
1561 cagtgcctgt gtcctcctgg tttcactggg ccagtttgcc agattgatat tgatgactgt
1621 tccagtactc cgtgtctgaa tggggcaaag tgtatcgatc acccgaatgg ctatgaatgc
1681 cagtgtgcca caggtttcac tggtgtgttg tgtgaggaga acattgacaa ctgtgacccc
1741 gatccttgcc accatggtca gtgtcaggat ggtattgatt cctacacctg catctgcaat
1801 cccgggtaca tgggcgccat ctgcagtgac cagattgatg aatgttacag cagcccttgc
1861 ctgaacgatg gtcgctgcat tgacctggtc aatggctacc agtgcaactg ccagccaggc
1921 acgtcagggg ttaattgtga aattaatttt gatgactgtg caagtaaccc ttgtatccat
1981 ggaatctgta tggatggcat taatcgctac agttgtgtct gctcaccagg attcacaggg
2041 cagagatgta acattgacat tgatgagtgt gcctccaatc cctgtcgcaa gggtgcaaca
2101 tgtatcaacg gtgtgaatgg tttccgctgt atatgccccg agggacccca tcaccccagc
2161 tgctactcac aggtgaacga atgcctgagc aatccctgca tccatggaaa ctgtactgga
2221 ggtctcagtg gatataagtg tctctgtgat gcaggctggg ttggcatcaa ctgtgaagtg
2281 gacaaaaatg aatgcctttc gaatccatgc cagaatggag gaacttgtga caatctggtg
2341 aatggataca ggtgtacttg caagaagggc tttaaaggct ataactgcca ggtgaatatt
2401 gatgaatgtg cctcaaatcc atgcctgaac caaggaacct gctttgatga cataagtggc
2461 tacacttgcc actgtgtgct gccatacaca ggcaagaatt gtcagacagt attggctccc
2521 tgttccccaa acccttgtga gaatgctgct gtttgcaaag agtcaccaaa ttttgagagt
2581 tatacttgct tgtgtgctcc tggctggcaa ggtcagcggt gtaccattga cattgacgag
2641 tgtatctcca agccctgcat gaaccatggt ctctgccata acacccaggg cagctacatg
2701 tgtgaatgtc caccaggctt cagtggtatg gactgtgagg aggacattga tgactgcctt
2761 gccaatcctt gccagaatgg aggttcctgt atggatggag tgaatacttt ctcctgcctc
2821 tgccttccgg gtttcactgg ggataagtgc cagacagaca tgaatgagtg tctgagtgaa
2881 ccctgtaaga atggagggac ctgctctgac tacgtcaaca gttacacttg caagtgccag
2941 gcaggatttg atggagtcca ttgtgagaac aacatcaatg agtgcactga gagctcctgt
3001 ttcaatggtg gcacatgtgt tgatgggatt aactccttct cttgcttgtg ccctgtgggt
3061 ttcactggat ccttctgcct ccatgagatc aatgaatgca gctctcatcc atgcctgaat
3121 gagggaacgt gtgttgatgg cctgggtacc taccgctgca gctgccccct gggctacact
3181 gggaaaaact gtcagaccct ggtgaatctc tgcagtcggt ctccatgtaa aaacaaaggt
3241 acttgtgttc agaaaaaagc agagtcccag tgcctatgtc catctggatg ggctggtgcc
```

Figure 19B

```
3301 tattgtgacg tgcccaatgt ctcttgtgac atagcagcct ccaggagagg tgtgcttgtt
3361 gaacacttgt gccagcactc aggtgtctgc atcaatgctg gcaacacgca ttactgtcag
3421 tgcccccctgg gctatactgg gagctactgt gaggagcaac tcgatgagtg tgcgtccaac
3481 ccctgccagc acggggcaac atgcagtgac ttcattggtg gatacagatg cgagtgtgtc
3541 ccaggctatc agggtgtcaa ctgtgagtat gaagtggatg agtgccagaa tcagccctgc
3601 cagaatggag gcacctgtat tgaccttgtg aaccatttca agtgctcttg cccaccaggc
3661 actcggggcc tactctgtga agagaacatt gatgactgtg cccggggtcc ccattgcctt
3721 aatggtggtc agtgcatgga taggattgga ggctacagtt gtcgctgctt gcctggcttt
3781 gctggggagc gttgtgaggg agacatcaac gagtgcctct ccaacccctg cagctctgag
3841 ggcagcctgg actgtataca gctcaccaat gactacctgt gtgtttgccg tagtgccttt
3901 actggccggc actgtgaaac cttcgtcgat gtgtgtcccc agatgccctg cctgaatgga
3961 gggacttgtg ctgtggccag taacatgcct gatggtttca tttgccgttg tcccccggga
4021 ttttccgggg caaggtgcca gagcagctgt ggacaagtga aatgtaggaa gggggagcag
4081 tgtgtgcaca ccgcctctgg accccgctgc ttctgcccca gtccccggga ctgcgagtca
4141 ggctgtgcca gtagcccctg ccagcacggg ggcagctgcc accctcagcg ccagcctcct
4201 tattactcct gcc 4213
```

Figure 20A

```
  77                       atgg ggccgggggc ccgtggccgc cgccgccgcc gtcgccccgat
 121 gtcgccgcca ccgccaccgc cacccgtgcg ggcgctgccc ctgctgctgc tgctagcggg
 181 gccgggggct gcagcccccc cttgcctgga cggaagcccg tgtgcaaatg gaggtcgttg
 241 cacccagctg ccctcccggg aggctgcctg cctgtgcccg cctggctggg tgggtgagcg
 301 gtgtcagctg gaggacccct gtcactcagg cccctgtgct ggccgtggtg tctgccagag
 361 ttcagtggtg gctggcaccg cccgattctc atgccggtgc ccccgtggct tccgaggccc
 421 tgactgctcc ctgccagatc cctgcctcag cagcccttgt gcccacggtg cccgctgctc
 481 agtgggggccc gatggacgct tcctctgctc ctgcccacct ggctaccagg gccgcagctg
 541 ccgaagcgac gtggatgagt gccgggtggg tgagccctgc cgccatggtg gcacctgcct
 601 caacacacct ggctccttcc gctgccagtg tccagctggc tacacagggc cactatgtga
 661 gaaccccgcg gtgccctgtg caccctcacc atgccgtaac gggggcacct gcaggcagag
 721 tggcgacctc acttacgact gtgcctgtct tcctgggttt gagggtcaga attgtgaagt
 781 gaacgtggac gactgtccag gacaccgatg tctcaatggg gggacatgcg tggatggcgt
 841 caacacctat aactgccagt gccctcctga gtggacaggc cagttctgca cggaggacgt
 901 ggatgagtgt cagctgcagc ccaacgcctg ccacaatggg ggtacctgct tcaacacgct
 961 gggtggccac agctgcgtgt gtgtcaatgg ctggacaggc gagagctgca gtcagaatat
1021 cgatgactgt gccacagccg tgtgcttcca tggggccacc tgccatgacc gcgtggcttc
1081 tttctactgt gcctgcccca tgggcaagac tggcctcctg tgtcacctgg atgacgcctg
1141 tgtcagcaac ccctgccacg aggatgctat ctgtgacaca aatccggtga acggccgggc
1201 catttgcacc tgtcctcccg gcttcacggg tggggcatgt gaccaggatg tggacgagtg
1261 ctctatcggc gccaacccct gcgagcactt gggcaggtgc gtgaacacgc agggctcctt
1321 cctgtgccag tgcggtcgtg gctacactgg acctcgctgt gagaccgatg tcaacgagtg
1381 tctgtcgggg ccctgccgaa accaggccac gtgcctcgac cgcataggcc agttcacctg
1441 tatctgtatg gcaggcttca caggaaccta ttgcgaggtg gacattgacg agtgtcagag
1501 tagcccctgt gtcaacggtg ggtctgcaa ggaccgagtc aatggcttca gctgcacctg
1561 cccctcgggc ttcagcggct ccacgtgtca gctggacgtg gacgaatgcg ccagcacgcc
1621 ctgcaggaat ggcgccaaat gcgtggacca gcccgatggc tacgagtgcc gctgtgccga
1681 gggctttgag ggcacgctgt gtgatcgcaa cgtggacgac tgctcccctg acccatgcca
1741 ccatggtcgc tgcgtggatg gcatcgccag cttctcatgt gcctgtgctc ctggctacac
1801 gggcacacgc tgcgagagcc aggtggacga atgccgcagc cagccctgcc gccatggcgg
1861 caaatgccta gacctggtgg acaagtacct ctgccgctgc ccttctggga ccacaggtgt
1921 gaactgcgaa gtgaacattg acgactgtgc cagcaacccc tgcacctttg gagtctgccg
1981 tgatggcatc aaccgctacg actgtgtctg ccaacctggc ttcacagggc cccttttgtaa
2041 cgtggagatc aatgagtgtg cttccagccc atgcggcgag ggaggttcct gtgtggatgg
2101 ggaaaatggc ttccgctgcc tctgcccgcc tggctccttg cccccactct gcctcccccc
2161 gagccatccc tgtgcccatg agccctgcag tcacggcatc tgctatgatg cacctggcgg
2221 gttccgctgt gtgtgtgagc ctggctggag tggcccccgc tgcagccaga gcctggcccg
2281 agacgcctgt gagtcccagc cgtgcagggc cggtgggaca tgcagcagcg atggaatggg
2341 tttccactgc acctgcccgc ctggtgtcca gggacgtcag tgtgaactcc tctccccctg
2401 caccccgaac ccctgtgagc atgggggccg ctgcgagtct gcccctggcc agctgcctgt
2461 ctgctcctgc ccccagggct ggcaaggccc acgatgccag caggatgtgg acgagtgtgc
2521 tggcccccgca ccctgtggcc ctcatggtat ctgcaccaac ctggcaggga gtttcagctg
2581 cacctgccat ggagggtaca ctggcccttc ctgcgatcag gacatcaatg actgtgaccc
2641 caacccatgc ctgaacggtg gctcgtgcca agacggcgtg ggctcctttt cctgctcctg
2701 cctccctggt ttcgccggcc cacgatgcgc ccgcgatgtg gatgagtgcc tgagcaaccc
2761 ctgcggcccg ggcacctgta ccgaccacgt ggcctccttc acctgcacct gcccgccagg
2821 ctacggaggc ttccactgcg aacaggacct gcccgactgc agccccagct cctgcttcaa
2881 tggcgggacc tgtgtggacg gcgtgaactc gttcagctgc ctgtgccgtc ccggctacac
2941 aggagcccac tgccaacatg aggcagaccc ctgcctctcg cggccctgcc tacacggggg
3001 cgtctgcagc gccgcccacc ctggcttccg ctgcacctgc ctcgagagct tcacgggccc
3061 gcagtgccag acgctggtgg attggtgcag ccgccagcct tgtcaaaacg gggtcgctg
3121 cgtccagact ggggcctatt gcctttgtcc ccctggatgg agcggacgcc tctgtgacat
3181 ccgaagcttg ccctgcaggg aggccgcagc ccagatcggg gtgcggctgg agcagctgtg
3241 tcaggcgggt gggcagtgtg tggatgaaga cagctcccac tactgcgtgt gcccagaggg
3301 ccgtactggt agccactgtg agcaggaggt ggacccctgc ttggcccagc cctgccagca
```

Figure 20B

```
3361 tgggggacc tgccgtggct atatgggggg ctacatgtgt gagtgtcttc ctggctacaa
3421 tggtgataac tgtgaggacg acgtggacga gtgtgcctcc cagccctgcc agcacggggg
3481 ttcatgcatt gacctcgtgg cccgctatct ctgctcctgt cccccaggaa cgctgggggt
3541 gctctgcgag attaatgagg atgactgcgg cccaggccca ccgctggact cagggccccg
3601 gtgcctacac aatggcacct gcgtggacct ggtgggtggt ttccgctgca cctgtccccc
3661 aggatacact ggtttgcgct gcgaggcaga catcaatgag tgtcgctcag gtgcctgcca
3721 cgcggcacac acccgggact gcctgcagga cccaggcgga ggtttccgtt gcctttgtca
3781 tgctggcttc tcaggtcctc gctgtcagac tgtcctgtct ccctgcgagt cccagccatg
3841 ccagcatgga ggccagtgcc gtcctagccc gggtcctggg ggtgggctga ccttcacctg
3901 tcactgtgcc cagccgttct ggggtccgcg ttgcgagcgg gtggcgcgct cctgccggga
3961 gctgcagtgc ccggtgggcg tcccatgcca gcagacgccc cgcgggccgc gctgcgcctg
4021 ccccccaggg ttgtcgggac cctcctgccg 4050
```

Figure 21A

```
  91                                            atgcagcccc cttcactgct gctgctgctg
 121 ctgctgctgc tgctgctatg tgtctcagtg gtcagaccca gagggctgct gtgtgggagt
 181 ttcccagaac cctgtgccaa tggaggcacc tgcctgagcc tgtctctggg acaagggacc
 241 tgccagtgtg cccctggctt cctgggtgag acgtgccagt ttcctgaccc ctgccagaac
 301 gcccagctct gccaaaatgg aggcagctgc caagccctgc ttcccgctcc cctagggctc
 361 cccagctctc cctctccatt gacacccagc ttcttgtgca cttgcctccc tggcttcact
 421 ggtgagagat gccaggccaa gcttgaagac ccttgtcctc cctccttctg ttccaaaagg
 481 ggccgctgcc acatccaggc ctcgggccgc ccacagtgct cctgcatgcc tggatggaca
 541 ggtgagcagt gccagcttcg ggacttctgt tcagccaacc catgtgttaa tggaggggtg
 601 tgtctggcca catacccccca gatccagtgc cactgcccac cgggcttcga gggccatgcc
 661 tgtgaacgtg atgtcaacga gtgcttccag gacccaggac cctgccccaa aggcacctcc
 721 tgccataaca ccctgggctc cttccagtgc ctctgccctg tggggcagga gggtccacgt
 781 tgtgagctgc gggcaggacc ctgccctcct aggggctgtt cgaatggggg cacctgccag
 841 ctgatgccag agaaagactc cacctttcac ctctgcctct gtcccccagg tttcataggc
 901 ccagactgtg aggtgaatcc agacaactgt gtcagccacc agtgtcagaa tgggggcact
 961 tgccaggatg ggctggacac ctacacctgc ctctgcccag aaacctggac aggctgggac
1021 tgctccgaag atgtggatga gtgtgagacc cagggtcccc ctcactgcag aaacgggggc
1081 acctgccaga actctgctgg tagctttcac tgcgtgtgtg tgagtggctg gggcggcaca
1141 agctgtgagg agaacctgga tgactgtatt gctgccacct gtgccccggg atccacctgc
1201 attgaccggg tgggctcttt ctcctgcctc tgcccacctg gacgcacagg actcctgtgc
1261 cacttggaag acatgtgtct gagccagccg tgccatgggg atgcccaatg cagcaccaac
1321 cccctcacag gctccacact ctgcctgtgt cagcctggct attcggggcc cacctgccac
1381 caggacctgg acgagtgtct gatggcccag caaggcccaa gtccctgtga acatggcggt
1441 tcctgcctca acactcctgg ctccttcaac tgcctctgtc cacctggcta cacaggctcc
1501 cgttgtgagg ctgatcacaa tgagtgcctc tcccagccct gccacccagg aagcacctgt
1561 ctggacctac ttgccacctt ccactgcctc tgcccgccag gcttagaagg gcagctctgt
1621 gaggtggaga ccaacgagtg tgcctcagct ccctgcctga accacgcgga ttgccatgac
1681 ctgctcaacg gcttccagtg catctgcctg cctggattct ccggcacccg atgtgaggag
1741 gatatcgatg agtgcagaag ctctccctgt gccaatggtg ggcagtgcca ggaccagcct
1801 ggagccttcc actgcaagtg tctcccaggc tttgaagggc cacgctgtca aacagaggtg
1861 gatgagtgcc tgagtgaccc atgtcccgtt ggagccagct gccttgatct tccaggagcc
1921 ttcttttgcc tctgcccctc tggtttcaca ggccagctct gtgaggttcc cctgtgtgct
1981 cccaacctgt gccagcccaa gcagatatgt aaggaccaga aagacaaggc caactgcctc
2041 tgtcctgatg gaagccctgg ctgtgcccca cctgaggaca actgcacctg ccaccacggg
2101 cactgccaga gatcctcatg tgtgtgtgac gtgggttgga cggggccaga gtgtgaggca
2161 gagctagggg gctgcatctc tgcaccctgt gcccatgggg ggacctgcta cccccagccc
2221 tctggctaca actgcacctg ccctacaggc tacacaggac ccacctgtag tgaggagatg
2281 acagcttgtc actcagggcc atgtctcaat ggcggctcct gcaaccctag ccctggaggc
2341 tactactgca cctgccctcc aagccacaca gggccccagt gccaaaccag cactgactac
2401 tgtgtgtctg ccccgtgctt caatgggggt acctgtgtga acaggcctgg caccttctcc
2461 tgcctctgtg ccatgggctt ccagggcccg cgctgtgagg gaaagctccg ccccagctgt
2521 gcagacagcc cctgtaggaa tagggcaacc tgccaggaca gccctcaggg tccccgctgc
2581 ctctgcccca ctggctacac cggaggcagc tgccagactc tgatggactt atgtgcccag
2641 aagccctgcc cacgcaattc ccactgcctc cagactgggc cctccttcca ctgcttgtgc
2701 ctccagggat ggaccgggcc tctctgcaac cttccactgt cctcctgcca gaaggctgca
2761 ctgagccaag gcatagacgt ctcttccctt tgccacaatg gaggcctctg tgtcgacagc
2821 ggcccctcct atttctgcca ctgccccccct ggattccaag gcagcctgtg ccaggatcac
2881 gtgaacccat gtgagtccag gccttgccag aacggggcca cctgcatggc ccagcccagt
2941 gggtatctct gccagtgtgc cccaggctac gatggacaga actgctcaaa ggaactcgat
3001 gcttgtcagt cccaaccctg tcacaaccat ggaacctgta ctcccaaacc tggaggattc
3061 cactgtgcct gccctccagg ctttgtgggg ctacgctgtg agggagacgt ggacgagtgt
3121 ctggaccagc cctgccaccc cacaggcact gcagcctgcc actctctggc caatgccttc
3181 tactgccagt gtctgcctgg acacacaggc cagtggtgtg aggtggagat agacccctgc
3241 cacagccaac cctgctttca tggagggacc tgtgaggcca cagcaggatc acccctgggt
3301 ttcatctgcc actgccccaa gggttttgaa ggccccacct gcagccacag ggccccttcc
```

Figure 21B

```
3361 tgcggcttcc atcactgcca ccacggaggc ctgtgtctgc cctcccctaa gccaggcttc
3421 ccaccacgct gtgcctgcct cagtggctat gggggtcctg actgcctgac cccaccagct
3481 cctaaaggct gtggccctcc ctccccatgc ctatacaatg gcagctgctc agagaccacg
3541 ggcttggggg gcccaggctt tcgatgctcc tgccctcaca gctctccagg gccccggtgt
3601 cagaaacccg ga
```

Figure 32A

```
   1 atggggccgg gggcccgtgg ccgccgccgc cgccgtcgcc cgatgtcgcc gccaccgcca
  61 ccgccacccg tgcgggcgct gcccctgctg ctgctgctag cggggccggg ggctgcagcc
 121 cccccttgcc tggacggaag cccgtgtgca aatggaggtc gttgcaccca gctgccctcc
 181 cgggaggctg cctgcctgtg cccgcctggc tgggtgggtg agcggtgtca gctggaggac
 241 ccctgtcact caggcccctg tgctggccgt ggtgtctgcc agagttcagt ggtggctggc
 301 accgcccgat tctcatgccg gtgcccccgt ggcttccgag gccctgactg ctccctgcca
 361 gatccctgcc tcagcagccc ttgtgcccac ggtgcccgct gctcagtggg gcccgatgga
 421 cgcttcctct gctcctgccc acctggctac cagggccgca gctgccgaag cgacgtggat
 481 gagtgccggg tgggtgagcc ctgccgccat ggtggcacct gcctcaacac acctggctcc
 541 ttccgctgcc agtgtccagc tggctacaca gggccactat gtgagaaccc cgcggtgccc
 601 tgtgcgccct caccatgccg taacgggggc acctgcaggc agagtggcga cctcacttac
 661 gactgtgcct gtcttcctgg gtttgagggt cagaattgtg aagtgaacgt ggacgactgt
 721 ccaggacacc gatgtctcaa tgggggacca tgcgtggatg gcgtcaacac ctataactgc
 781 cagtgccctc ctgagtggac aggccagttc tgcacggagg acgtggatga gtgtcagctg
 841 cagcccaacg cctgccacaa tgggggtacc tgcttcaaca cgctgggtgg ccacagctgc
 901 gtgtgtgtca atggctggac aggcgagagc tgcagtcaga atatcgatga ctgtgccaca
 961 gccgtgtgct tccatggggc cacctgccat gaccgcgtgg cttctttcta ctgtgcctgc
1021 cccatgggca agactggcct cctgtgtcac ctggatgacg cctgtgtcag caacccctgc
1081 cacgaggatg ctatctgtga cacaaatccg gtgaacggcc gggccatttg cacctgtcct
1141 cccggcttca cgggtggggc atgtgaccag gatgtggacg agtgctctat cggcgccaac
1201 ccctgcgagc acttgggcag gtgcgtgaac acgcagggct ccttcctgtg ccagtgcggt
1261 cgtggctaca ctggacctcg ctgtgagacc gatgtcaacg agtgtctgtc ggggccctgc
1321 cgaaaccagg ccacgtgcct cgaccgcata ggccagttca cctgtatctg tatggcaggc
1381 ttcacaggaa cctattgcga ggtggacatt gacgagtgtc agagtagccc ctgtgtcaac
1441 ggtggggtct gcaaggaccg agtcaatggc ttcagctgca cctgcccctc gggcttcagc
1501 ggctccacgt gtcagctgga cgtggacgaa tgcgccagca cgccctgcag gaatggcgcc
1561 aaatgcgtgg accagcccga tggctacgag tgccgctgtg ccgagggctt tgagggcacg
1621 ctgtgtgatc gcaacgtgga cgactgctcc cctgacccat gccaccatgg tcgctgcgtg
1681 gatggcatcg ccagcttctc atgtgcctgt gctcctggct acacgggcac acgctgcgag
1741 agccaggtgg acgaatgccg cagccagccc tgccgccatg gcggcaaatg cctagacctg
1801 gtggacaagt acctctgccg ctgcccttct gggaccacag gtgtgaactg cgaagtgaac
1861 attgacgact gtgccagcaa cccctgcacc tttggagtct gccgtgatgg catcaaccgc
1921 tacgactgtg tctgccaacc tggcttcaca gggccccttt gtaacgtgga gatcaatgag
1981 tgtgcttcca gcccatgcgg cgagggaggt tcctgtgtgg atggggaaaa tggcttccgc
2041 tgcctctgcc cgcctggctc cttgccccca ctctgcctcc ccccgagcca tccctgtgcc
2101 catgagccct gcagtcacgg catctgctat gatgcacctg gcgggttccg ctgtgtgtgt
2161 gagcctggct ggagtggccc ccgctgcagc cagagcctgg cccgagacgc ctgtgagtcc
2221 cagccgtgca gggccggtgg gacatgcagc agcgatggaa tgggtttcca ctgcacctgc
2281 ccgcctggtg tccagggacg tcagtgtgaa ctcctctccc cctgcacccc gaacccctgt
2341 gagcatgggg gccgctgcga gtctgcccct ggccagctgc ctgtctgctc ctgcccccag
2401 ggctggcaag gcccacgatg ccagcaggat gtggacgagt gtgctggccc cgcaccctgt
2461 ggccctcatg gtatctgcac caacctggca gggagtttca gctgcacctg ccatggaggg
2521 tacactggcc cttcctgtga tcaggacatc aatgactgtg accccaaccc atgcctgaac
2581 ggtggctcgt gccaagacgg cgtgggctcc ttttcctgct cctgcctccc tggtttcgcc
2641 ggcccacgat gcgcccgcga tgtggatgag tgcctgagca acccctgcgg cccgggcacc
```

Figure 32B

```
2701 tgtaccgacc acgtggcctc cttcacctgc acctgcccgc caggctacgg aggcttccac
2761 tgcgaacagg acctgcccga ctgcagcccc agctcctgct tcaatggcgg gacctgtgtg
2821 gacggcgtga actcgttcag ctgcctgtgc cgtcccggct acacaggagc ccactgccaa
2881 catgaggcag acccctgcct ctcgcggccc tgcctacacg gggcgtctg cagcgccgcc
2941 caccctggct tccgctgcac ctgcctcgag agcttcacgg gcccgcagtg ccagacgctg
3001 gtggattggt gcagccgcca gccttgtcaa aacggggtc gctgcgtcca gactggggcc
3061 tattgccttt gtccccctgg atggagcgga cgcctctgtg acatccgaag cttgccctgc
3121 agggaggccg cagcccagat cggggtgcgg ctggagcagc tgtgtcaggc gggtgggcag
3181 tgtgtggatg aagacagctc ccactactgc gtgtgcccag agggccgtac tggtagccac
3241 tgtgagcagg aggtggaccc ctgcttggcc cagccctgcc agcatggggg gacctgccgt
3301 ggctatatgg ggggctacat gtgtgagtgt cttcctggct acaatggtga taactgtgag
3361 gacgacgtgg acgagtgtgc ctcccagccc tgccagcacg gggttcatg cattgacctc
3421 gtggcccgct atctctgctc ctgtccccca ggaacgctgg gggtgctctg cgagattaat
3481 gaggatgact gcggcccagg cccaccgctg gactcagggc cccggtgcct acacaatggc
3541 acctgcgtgg acctggtggg tggtttccgc tgcacctgtc cccaggata cactggtttg
3601 cgctgcgagg cagacatcaa tgagtgtcgc tcaggtgcct gccacgcggc acacacccgg
3661 gactgcctgc aggacccagg cggaggtttc cgttgccttt gtcatgctgg cttctcaggt
3721 cctcgctgtc agactgtcct gtctccctgc gagtcccagc catgccagca tggaggccag
3781 tgccgtccta gcccgggtcc tgggggtggg ctgaccttca cctgtcactg tgcccagccg
3841 ttctggggtc cgcgttgcga gcgggtggcg cgctcctgcc gggagctgca gtgcccggtg
3901 ggcgtcccat gccagcagac gccccgcggg ccgcgctgcg cctgccccc agggttgtcg
3961 ggaccctcct gccgcagctt cccggggtcg ccgccggggg ccagcaacgc cagctgcgcg
4021 gccgccccct gtctccacgg gggctcctgc cgccccgcgc cgctcgcgcc cttcttccgc
4081 tgcgcttgcg cgcagggctg gaccgggccg cgctgcgagg cgcccgccgc ggcacccgag
4141 gtctcggagg agccgcggtg cccgcgcgcc gcctgccagg ccaagcgcgg ggaccagcgc
4201 tgcgaccgcg agtgcaacag cccaggctgc ggctgggacg gcggcgactg ctcgctgagc
4261 gtgggcgacc cctggcggca atgcgaggcg ctgcagtgct ggcgcctctt caacaacagc
4321 cgctgcgacc ccgcctgcag ctcgcccgcc tgcctctacg acaacttcga ctgccacgcc
4381 ggtggccgcg agcgcacttg caacccggtg tacgagaagt actgcgccga ccactttgcc
4441 gacggccgct gcgaccaggg ctgcaacacg gaggagtgcg gctgggatgg gctggattgt
4501 gccagcgagg tgccggccct gctggcccgc ggcgtgctgg tgctcacagt gctgctgccg
4561 ccagaggagc tactgcgttc cagcgccgac tttctgcagc ggctcagcgc catcctgcgc
4621 acctcgctgc gcttccgcct ggacgcgcac ggccaggcca tggtcttccc ttaccaccgg
4681 cctagtcctg gctccgaacc ccgggcccgt cgggagctgg cccccgaggt gatcggctcg
4741 gtagtaatgc tggagattga caaccggctc tgcctgcagt cgcctgagaa tgatcactgc
4801 ttccccgatg cccagagcgc cgctgactac ctgggagcgt tgtcagcggt ggagcgcctg
4861 gacttcccgt acccactgcg ggacgtgcgg ggggagccgc tggagcctcc agaacccagc
4921 gtcccgctgc tgccactgct agtggcgggc gctgtcttgc tgctggtcat tctcgtcctg
4981 ggtgtcatgg tggcccggcg caagcgcgag cacagcaccc tctggttccc tgagggcttc
5041 tcactgcaca aggacgtggc ctctggtcac aagggccggc gggaacccgt gggccaggac
5101 gcgctgggca tgaagaacat ggccaagggt gagagcctga tgggggaggt ggccacagac
5161 tggatggaca cagagtgccc agaggccaag cggctaaagg tagaggagcc aggcatgggg
5221 gctgaggagg ctgtggattg ccgtcagtgg actcaacacc atctggttgc tgctgacatc
5281 cgcgtggcac cagccatggc actgacacca ccacagggcg acgcagatgc tgatggcatg
5341 gatgtcaatg tgcgtggccc agatggcttc accccgctaa tgctggcttc cttctgtggg
5401 ggggctctgg agccaatgcc aactgaagag gatgaggcag atgacacatc agctagcatc
5461 atctccgacc tgatctgcca gggggctcag cttggggcac ggactgaccg tactggcgag
5521 actgctttgc acctggctgc ccgttatgcc cgtgctgatg cagccaagcg gctgctggat
```

Figure 32C

```
5581 gctggggcag acaccaatgc ccaggaccac tcaggccgca ctcccctgca cacagctgtc
5641 acagccgatg cccagggtgt cttccagatt ctcatccgaa accgctctac agacttggat
5701 gcccgcatgg cagatggctc aacggcactg atcctggcgg cccgcctggc agtagagggc
5761 atggtggaag agctcatcgc cagccatgct gatgtcaatg ctgtggatga gcttgggaaa
5821 tcagccttac actgggctgc ggctgtgaac aacgtggaag ccactttggc cctgctcaaa
5881 aatggagcca ataaggacat gcaggatagc aaggaggaga cccccctatt cctggccgcc
5941 cgcgagggca gctatgaggc tgccaagctg ctgttggacc actttgccaa ccgtgagatc
6001 accgaccacc tggacaggct gccgcgggac gtagcccagg agagactgca ccaggacatc
6061 gtgcgcttgc tggatcaacc cagtgggccc cgcagccccc ccggtcccca cggcctgggg
6121 cctctgctct gtcctccagg ggccttcctc cctggcctca aagcggcaca gtcggggtcc
6181 aagaagagca ggaggccccc cgggaaggcg gggctggggc cgcaggggcc ccgggggcgg
6241 ggcaagaagc tgacgctggc ctgcccgggc cccctggctg acagctcggt cacgctgtcg
6301 cccgtggact cgctggactc cccgcggcct ttcggtgggc cccctgcttc ccctggtggc
6361 ttcccccttg aggggcccta tgcagctgcc actgccactg cagtgtctct ggcacagctt
6421 ggtggcccag gccgggcggg tctagggcgc cagcccccctg gaggatgtgt actcagcctg
6481 ggcctgctga accctgtggc tgtgcccctc gattgggccc ggctgccccc acctgcccct
6541 ccaggcccct cgttcctgct gccactggcg ccgggacccc agctgctcaa cccagggacc
6601 cccgtctccc cgcaggagcg gcccccgcct tacctggcag tcccaggaca tggcgaggag
6661 tacccggcgg ctggggcaca cagcagcccc ccaaaggccc gcttcctgcg ggttcccagt
6721 gagcaccctt acctgacccc atcccccgaa tcccctgagc actgggccag cccctcacct
6781 ccctccctct cagactggtc cgaatccacg cctagcccag ccactgccac tggggccatg
6841 gccaccacca ctggggcact gcctgcccag ccacttccct tgtctgttcc cagctccctt
6901 gctcaggccc agacccagct ggggccccag ccggaagttac ccccaagag gcaagtgttg
6961 gcc[redacted]
```

Figure 33

MGPGARGRRRRRRPMSPPPPPPPVRALPLLLLLAGPGAAAPPCLDGSPCANGGRCTQLPSREAACLCPPGWVGE
RCQLEDPCHSGPCAGRGVCQSSVVAGTARFSCRCPRGFRGPDCSLPDPCLSSPCAHGARCSVGPDGRFLCSCPP
GYQGRSCRSDVDECRVGEPCRHGGTCLNTPGSFRCQCPAGYTGPLCENPAVPCAPSPCRNGGTCRQSGDLTYDC
ACLPGFEGQNCEVNVDDCPGHRCLNGGTCVDGVNTYNCQCPPEWTGQFCTEDVDECQLQPNACHNGGTCFNTLG
GHSCVCVNGWTGESCSQNIDDCATAVCFHGATCHDRVASFYCACPMGKTGLLCHLDDACVSNPCHEDAICDTNP
VNGRAICTCPPGFTGGACDQDVDECSIGANPCEHLGRCVNTQGSFLCQCGRGYTGPRCETDVNECLSGPCRNQA
TCLDRIGQFTCICMAGFTGTYCEVDIDECQSSPCVNGGVCKDRVNGFSCTCPSGFSGSTCQLDVDECASTPCRN
GAKCVDQPDGYECRCAEGFEGTLCDRNVDDCSPDPCHHGRCVDGIASFSCACAPGYTGTRCESQVDECRSQPCR
HGGKCLDLVDKYLCRCPSGTTGVNCEVNIDDCASNPCTFGVCRDGINRYDCVCQPGFTGPLCNVEINECASSPC
GEGGSCVDGENGFRCLCPPGSLPPLCLPPSHPCAHEPCSHGICYDAPGGFRCVCEPGWSGPRCSQSLARDACES
QPCRAGGTCSSDGMGFHCTCPPGVQGRQCELLSPCTPNPCEHGGRCESAPGQLPVCSCPQGWQGPRCQQDVDEC
AGPAPCGPHGICTNLAGSFSCTCHGGYTGPSCDQDINDCDPNPCLNGGSCQDGVGSFSCSCLPGFAGPRCARDV
DECLSNPCGPGTCTDHVASFTCTCPPGYGGFHCEQDLPDCSPSSCFNGGTCVDGVNSFSCLCRPGYTGAHCQHE
ADPCLSRPCLHGGVCSAAHPGFRCTCLESFTGPQCQTLVDWCSRQPCQNGGRCVQTGAYCLCPPGWSGRLCDIR
SLPCREAAAQIGVRLEQLCQAGGQCVDEDSSHYCVCPEGRTGSHCEQEVDPCLAQPCQHGGTCRGYMGGYMCEC
LPGYNGDNCEDDVDECASQPCQHGGSCIDLVARYLCSCPPGTLGVLCEINEDDCGPGPPLDSGPRCLHNGTCVD
LVGGFRCTCPPGYTGLRCEADINECRSGACHAAHTRDCLQDPGGGFRCLCHAGFSGPRCQTVLSPCESQPCQHG
GQCRPSPGPGGGLTFTCHCAQPFWGPRCERVARSCRELQCPVGVPCQQTPRGPRCACPPGLSGPSCRSFPGSPP
GASNASCAAAPCLHGGSCRPAPLAPFFRCACAQGWTGPRCEAPAAAPEVSEEPRCPRAACQAKRGDQRCDRECN
SPGCGWDGGDCSLSVGDPWRQCEALQCWRLFNNSRCDPACSSPACLYDNFDCHAGGRERTCNPVYEKYCADHFA
DGRCDQGCNTEECGWDGLDCASEVPALLARGVLVLTVLLPPEELLRSSADFLQRLSAILRTSLRFRLDAHGQAM
VFPYHRPSPGSEPRARRELAPEVIGSVVMLEIDNRLCLQSPENDHCFPDAQSAADYLGALSAVERLDFPYPLRD
VRGEPLEPPEPSVPLLPLLVAGAVLLLVILVLGVMVARRKREHSTLWFPEGFSLHKDVASGHKGRREPVGQDAL
GMKNMAKGESLMGEVATDWMDTECPEAKRLKVEEPGMGAEEAVDCRQWTQHHLVAADIRVAPAMALTPPQGDAD
ADGMDVNVRGPDGFTPLMLASFCGGALEPMPTEEDEADDTSASIISDLICQGAQLGARTDRTGETALHLAARYA
RADAAKRLLDAGADTNAQDHSGRTPLHTAVTADAQGVFQILIRNRSTDLDARMADGSTALILAARLAVEGMVEE
LIASHADVNAVDELGKSALHWAAAVNNVEATLALLKNGANKDMQDSKEETPLFLAAREGSYEAAKLLLDHFANR
EITDHLDRLPRDVAQERLHQDIVRLLDQPSGPRSPPGPHGLGPLLCPPGAFLPGLKAAQSGSKKSRRPPGKAGL
GPQGPRGRGKKLTLACPGPLADSSVTLSPVDSLDSPRPFGGPPASPGGFPLEGPYAAATATAVSLAQLGGPGRA
GLGRQPPGGCVLSLGLLNPVAVPLDWARLPPPAPPGPSFLLPLAPGPQLLNPGTPVSPQERPPPYLAVPGHGEE
YPAAGAHSSPPKARFLRVPSEHPYLTPSPESPEHWASPSPPSLSDWSESTPSPATATGAMATTTGALPAQPLPL
SVPSSLAQAQTQLGPQPEVTPKRQVLA

Figure 34
Human Notch3 Decoys
h-Notch3$^{(1-34)}$ decoy
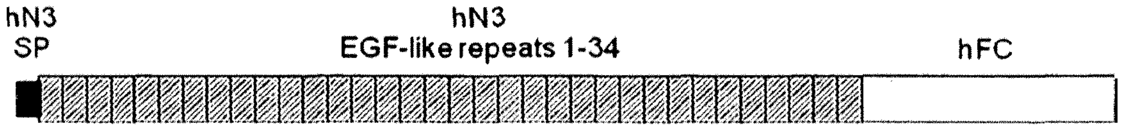
h-sp$^{HC}$Notch3$^{(1-34)}$ decoy
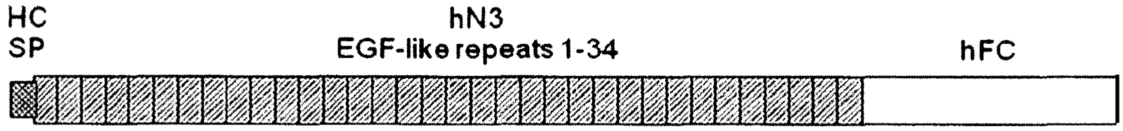

Figure 35

```
                                                             gatct gggcccgggc
 781 gagcccaaat cttgtgacaa aactcacaca tgcccaccgt gcccagcacc tgaactcctg
 841 gggggaccgt cagtcttcct cttcccccca aaacccaagg acaccctcat gatctcccgg
 901 acccctgagg tcacatgcgt ggtggtggac gtgagccacg aagaccctga ggtcaagttc
 961 aactggtacg tggacggcgt ggaggtgcat aatgccaaga caaagccgcg ggaggagcag
1021 tacaacagca cgtaccgtgt ggtcagcgtc ctcaccgtcc tgcaccagga ctggctgaat
1081 ggcaaggagt acaagtgcaa ggtctccaac aaagccctcc cagcccccat cgagaaaacc
1141 atctccaaag ccaaagggca gccccgagaa ccacaggtgt acaccctgcc cccatcccgg
1201 gatgagctga ccaagaacca ggtcagcctg acctgcctgg tcaaaggctt ctatcccagc
1261 gacatcgccg tggagtggga gagcaatggg cagccggaga acaactacaa gaccacgcct
1321 cccgtgctgg actccgacgg ctccttcttc ctctacagca agctcaccgt ggacaagagc
1381 aggtggcagc aggggaacgt cttctcatgc tccgtgatgc atgaggctct gcacaaccac
1441 tacacgcaga agagcctctc cctgtctccg ggtaaatga
```

Figure 36

DLGPGEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK

Figure 37

Human Notch3 decoy (EGF-LR 1-34)

Human N3

```
gag gag ccg cgg (SEQ ID NO:19)
ctc ctc ggc gcc (SEQ ID NO:20)
 E   E   P   R  (SEQ ID NO:21)
```

Add BglII site switch last nucleotide

```
gag gag ccg cga GAT CT  (SEQ ID NO:22)
ctc ctc ggc gct CTA GA  (SEQ ID NO:23)
 E   E   P   R (SEQ ID NO:21)
```

N3/FC fusion

```
gag gag ccg cga GAT CTG GGC CCG (SEQ ID NO:24)
ctc ctc ggc gct CTA GAC CCG GGC (SEQ ID NO:25)
 E   E   P   R   D   L   G   P  (SEQ ID NO:26)
```

Figure 38
Human Notch3 Signal Peptide
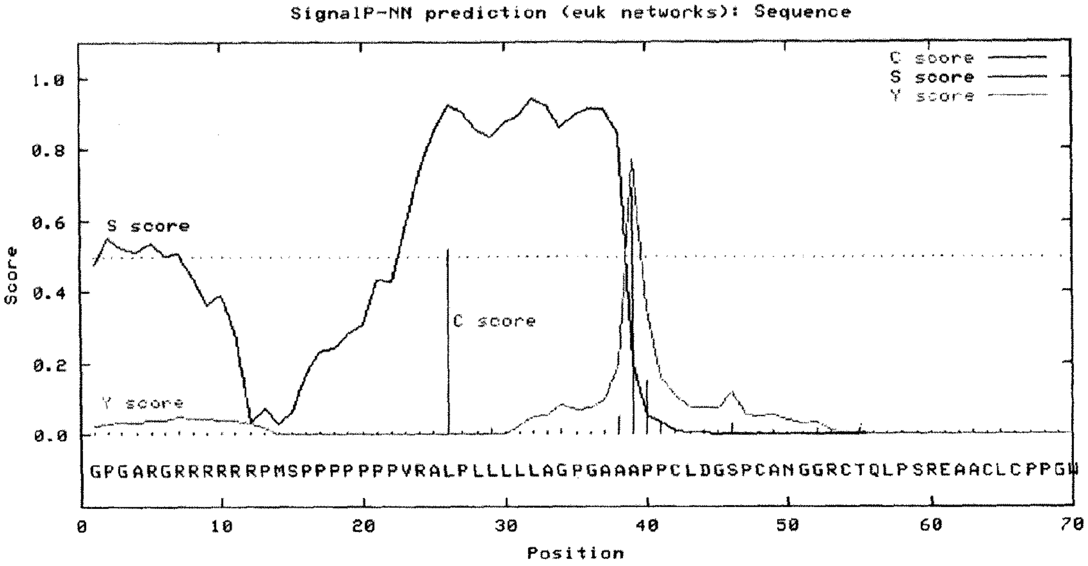
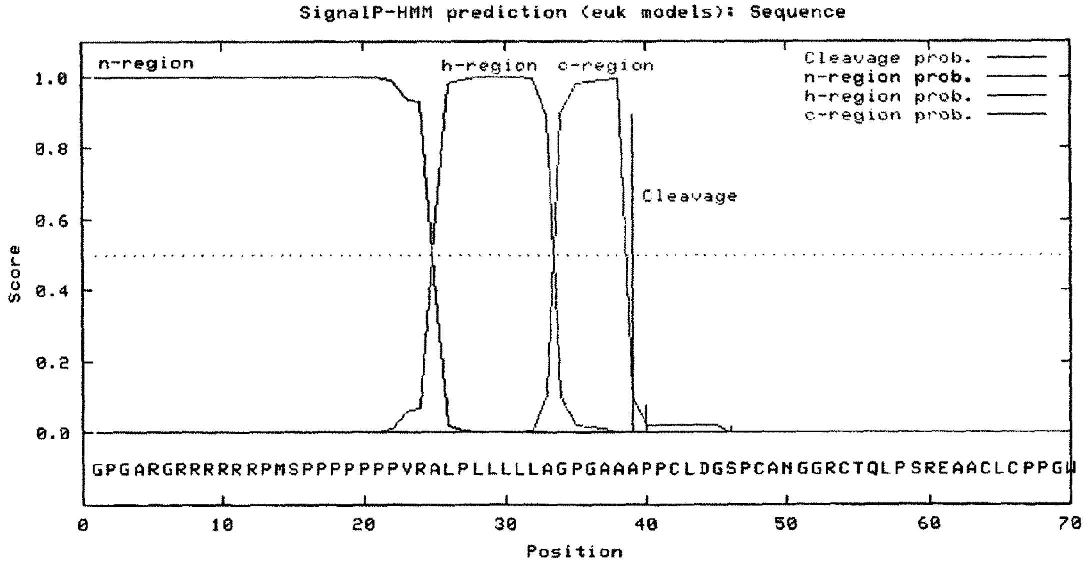
MGPGARGRRRRRRPMSPPPPPPPVRALPLLLLLAGPGAA/A (SEQ ID NO
1 atggggccgg gggcccgtgg ccgccgccgc cgccgtcgcc cgatgtcgcc gccaccgcca ccgccacccg tgcgggcgct gcccctgctg ctgctgctag cggggccggg ggctgca/gcc 120 (SEQ ID NO:28)

Figure 39
Human HC Signal Peptide
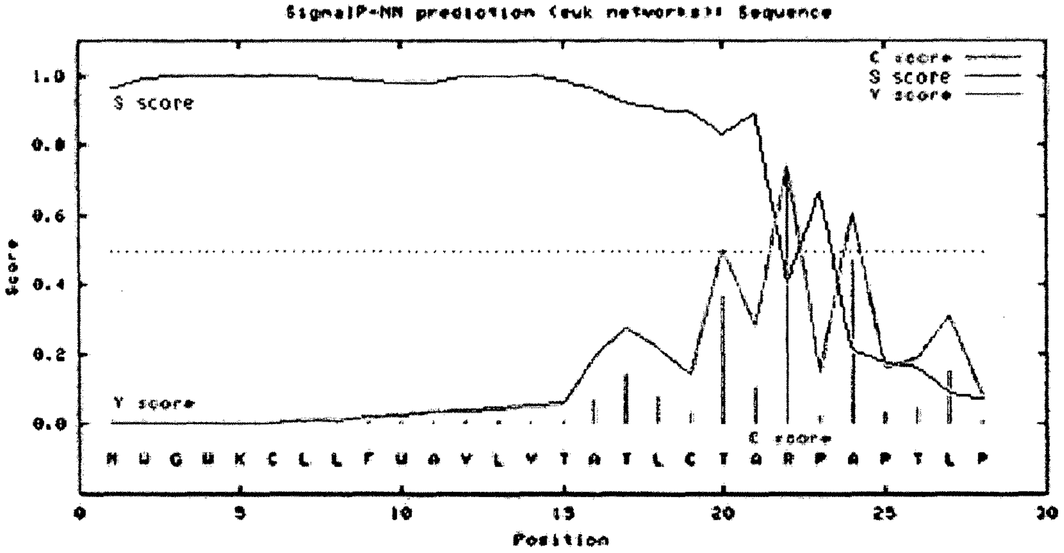
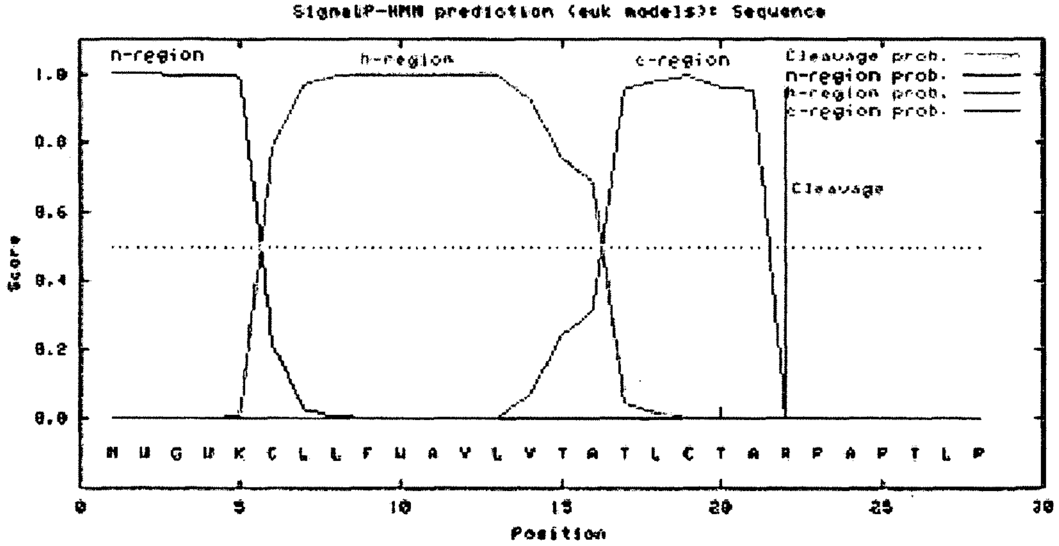
MWGWKCLLFWAVLVTATLCTA/R (SEQ ID NO:29)
1 atgtggggct ggaagtgcct cctcttctgg gctgtgctgg tcacagccac tctctgcact gccagg 66

Figure 40A

```
   1 atggggccgg gggcccgtgg ccgccgccgc cgccgtcgcc cgatgtcgcc gccaccgcca
  61 ccgccacccg tgcgggcgct gcccctgctg ctgctgctag cggggccggg ggctgcagcc
 121 ccccccttgcc tggacggaag cccgtgtgca aatggaggtc gttgcaccca gctgccctcc
 181 cgggaggctg cctgcctgtg cccgcctggc tgggtgggtg agcggtgtca gctggaggac
 241 ccctgtcact caggcccctg tgctggccgt ggtgtctgcc agagttcagt ggtggctggc
 301 accgcccgat tctcatgccg gtgccccgt ggcttccgag gccctgactg ctccctgcca
 361 gatccctgcc tcagcagccc ttgtgcccac ggtgcccgct gctcagtggg gcccgatgga
 421 cgcttcctct gctcctgccc acctggctac cagggccgca gctgccgaag cgacgtggat
 481 gagtgccggg tgggtgagcc ctgccgccat ggtggcacct gcctcaacac acctggctcc
 541 ttccgctgcc agtgtccagc tggctacaca gggccactat gtgagaaccc cgcggtgccc
 601 tgtgcgccct caccatgccg taacgggggc acctgcaggc agagtggcga cctcacttac
 661 gactgtgcct gtcttcctgg gtttgagggt cagaattgtg aagtgaacgt ggacgactgt
 721 ccaggacacc gatgtctcaa tgggggacga tgcgtggatg gcgtcaacac ctataactgc
 781 cagtgccctc ctgagtggac aggccagttc tgcacggagg acgtggatga gtgtcagctg
 841 cagcccaacg cctgccacaa tgggggtacc tgcttcaaca cgctgggtgg ccacagctgc
 901 gtgtgtgtca atggctggac aggcgagagc tgcagtcaga atatcgatga ctgtgccaca
 961 gccgtgtgct tccatggggc cacctgccat gaccgcgtgg cttctttcta ctgtgcctgc
1021 cccatgggca agactggcct cctgtgtcac ctggatgacg cctgtgtcag caacccctgc
1081 cacgaggatg ctatctgtga cacaaatccg gtgaacggcc gggccatttg cacctgtcct
1141 cccggcttca cgggtggggc atgtgaccag gatgtggacg agtgctctat cggcgccaac
1201 ccctgcgagc acttgggcag gtgcgtgaac acgcagggct ccttcctgtg ccagtgcggt
1261 cgtggctaca ctggacctcg ctgtgagacc gatgtcaacg agtgtctgtc ggggccctgc
1321 cgaaaccagg ccacgtgcct cgaccgcata ggccagttca cctgtatctg tatggcaggc
1381 ttcacaggaa cctattgcga ggtggacatt gacgagtgtc agagtagccc ctgtgtcaac
1441 ggtggggtct gcaaggaccg agtcaatggc ttcagctgca cctgcccctc gggcttcagc
1501 ggctccacgt gtcagctgga cgtggacgaa tgcgccagca cgccctgcag gaatggcgcc
1561 aaatgcgtgg accagcccga tggctacgag tgccgctgtg ccgagggctt tgagggcacg
1621 ctgtgtgatc gcaacgtgga cgactgctcc cctgacccat gccaccatgg tcgctgcgtg
1681 gatggcatcg ccagcttctc atgtgcctgt gctcctggct acacgggcac acgctgcgag
1741 agccaggtgg acgaatgccg cagccagccc tgccgccatg gcggcaaatg cctagacctg
1801 gtggacaagt acctctgccg ctgcccttct gggaccacag gtgtgaactg cgaagtgaac
1861 attgacgact gtgccagcaa cccctgcacc tttggagtct gccgtgatgg catcaaccgc
1921 tacgactgtg tctgccaacc tggcttcaca gggccccttt gtaacgtgga gatcaatgag
1981 tgtgcttcca gcccatgcgg cgagggaggt tcctgtgtgg atggggaaaa tggcttccgc
2041 tgcctctgcc cgcctggctc cttgcccccca ctctgcctcc ccccgagcca tccctgtgcc
2101 catgagccct gcagtcacgg catctgctat gatgcacctg gcgggttccg ctgtgtgtgt
2161 gagcctggct ggagtggccc ccgctgcagc cagagcctgg cccgagacgc ctgtgagtcc
2221 cagccgtgca gggccggtgg gacatgcagc agcgatggaa tgggtttcca ctgcacctgc
2281 ccgcctggtg tccagggacg tcagtgtgaa ctcctctccc cctgcacccc gaacccctgt
2341 gagcatgggg gccgctgcga gtctgcccct ggccagctgc ctgtctgctc ctgcccccag
2401 ggctggcaag gcccacgatg ccagcaggat gtggacgagt gtgctggccc cgcaccctgt
2461 ggccctcatg gtatctgcac caacctggca gggagtttca gctgcacctg ccatggaggg
2521 tacactggcc cttcctgtga tcaggacatc aatgactgtg accccaaccc atgcctgaac
2581 ggtggctcgt gccaagacgg cgtgggctcc ttttcctgct cctgcctccc tggtttcgcc
2641 ggcccacgat gcgcccgcga tgtggatgag tgcctgagca acccctgcgg cccgggcacc
2701 tgtaccgacc acgtggcctc cttcacctgc acctgcccgc caggctacgg aggcttccac
2761 tgcgaacagg acctgcccga ctgcagcccc agctcctgct tcaatggcgg gacctgtgtg
```

Figure 40B

2821 gacggcgtga actcgttcag ctgcctgtgc cgtcccggct acacaggagc ccactgccaa
2881 catgaggcag acccctgcct ctcgcggccc tgcctacacg ggggcgtctg cagcgccgcc
2941 caccctggct tccgctgcac ctgcctcgag agcttcacgg gcccgcagtg ccagacgctg
3001 gtggattggt gcagccgcca gccttgtcaa aacgggggtc gctgcgtcca gactggggcc
3061 tattgccttt gtccccctgg atggagcgga cgcctctgtg acatccgaag cttgccctgc
3121 agggaggccg cagcccagat cggggtgcgg ctggagcagc tgtgtcaggc gggtgggcag
3181 tgtgtggatg aagacagctc ccactactgc gtgtgcccag agggccgtac tggtagccac
3241 tgtgagcagg aggtggaccc ctgcttggcc cagccctgcc agcatggggg gacctgccgt
3301 ggctatatgg ggggctacat gtgtgagtgt cttcctggct acaatggtga taactgtgag
3361 gacgacgtgg acgagtgtgc ctcccagccc tgccagcacg gggttcatg cattgacctc
3421 gtggcccgct atctctgctc ctgtccccca ggaacgctgg gggtgctctg cgagattaat
3481 gaggatgact gcggcccagg cccaccgctg gactcagggc cccggtgcct acacaatggc
3541 acctgcgtgg acctggtggg tggtttccgc tgcacctgtc ccccaggata cactggtttg
3601 cgctgcgagg cagacatcaa tgagtgtcgc tcaggtgcct gccacgcggc acacaccgg
3661 gactgcctgc aggacccagg cggaggtttc cgttgccttt gtcatgctgg cttctcaggt
3721 cctcgctgtc agactgtcct gtctccctgc gagtcccagc catgccagca tggaggccag
3781 tgccgtccta gcccgggtcc tgggggtggg ctgaccttca cctgtcactg tgcccagccg
3841 ttctggggtc cgcgttgcga gcgggtggcg cgctcctgcc gggagctgca gtgcccggtg
3901 ggcgtcccat gccagcagac gccccgcggg ccgcgctgcg cctgcccccc agggttgtcg
3961 ggaccctcct gccgcagctt cccggggtcg ccgccggggg ccagcaacgc cagctgcgcg
4021 gccgccccct gtctccacgg gggctcctgc cgccccgcgc cgctcgcgcc cttcttccgc
4081 tgcgcttgcg cgcagggctg gaccgggccg cgctgcgagg cgcccgccgc ggcacccgag
4141 gtctcggagg agccgcga*ga tctgggcccg ggcgagccca aatcttgtga caaaactcac*
*4201 acatgcccac cgtgcccagc acctgaactc ctggggggac cgtcagtctt cctcttcccc*
*4261 ccaaaaccca aggacaccct catgatctcc cggacccctg aggtcacatg cgtggtggtg*
*4321 gacgtgagcc acgaagaccc tgaggtcaag ttcaactggt acgtggacgg cgtggaggtg*
*4381 cataatgcca agacaaagcc gcgggaggag cagtacaaca gcacgtaccg tgtggtcagc*
*4441 gtcctcaccg tcctgcacca ggactggctg aatggcaagg agtacaagtg caaggtctcc*
*4501 aacaaagccc tcccagcccc catcgagaaa accatctcca aagccaaagg gcagccccga*
*4561 gaaccacagg tgtacaccct gcccccatcc cgggatgagc tgaccaagaa ccaggtcagc*
*4621 ctgacctgcc tggtcaaagg cttctatccc agcgacatcg ccgtggagtg ggagagcaat*
*4681 gggcagccgg agaacaacta caagaccacg cctcccgtgc tggactccga cggctccttc*
*4741 ttcctctaca gcaagctcac cgtggacaag agcaggtggc agcaggggaa cgtcttctca*
*4801 tgctccgtga tgcatgaggc tctgcacaac cactacacgc agaagagcct ctccctgtct*
*4861 ccgggtaaat ga*

Figure 41

MGPGARGRRRRRRPMSPPPPPPPVRALPLLLLLAGPGAAAPPCLDGSPCANGGRCTQLPSREAACLCPPGWVGE
RCQLEDPCHSGPCAGRGVCQSSVVAGTARFSCRCPRGFRGPDCSLPDPCLSSPCAHGARCSVGPDGRFLCSCPP
GYQGRSCRSDVDECRVGEPCRHGGTCLNTPGSFRCQCPAGYTGPLCENPAVPCAPSPCRNGGTCRQSGDLTYDC
ACLPGFEGQNCEVNVDDCPGHRCLNGGTCVDGVNTYNCQCPPEWTGQFCTEDVDECQLQPNACHNGGTCFNTLG
GHSCVCVNGWTGESCSQNIDDCATAVCFHGATCHDRVASFYCACPMGKTGLLCHLDDACVSNPCHEDAICDTNP
VNGRAICTCPPGFTGGACDQDVDECSIGANPCEHLGRCVNTQGSFLCQCGRGYTGPRCETDVNECLSGPCRNQA
TCLDRIGQFTCICMAGFTGTYCEVDIDECQSSPCVNGGVCKDRVNGFSCTCPSGFSGSTCQLDVDECASTPCRN
GAKCVDQPDGYECRCAEGFEGTLCDRNVDDCSPDPCHHGRCVDGIASFSCACAPGYTGTRCESQVDECRSQPCR
HGGKCLDLVDKYLCRCPSGTTGVNCEVNIDDCASNPCTFGVCRDGINRYDCVCQPGFTGPLCNVEINECASSPC
GEGGSCVDGENGFRCLCPPGSLPPLCLPPSHPCAHEPCSHGICYDAPGGFRCVCEPGWSGPRCSQSLARDACES
QPCRAGGTCSSDGMGFHCTCPPGVQGRQCELLSPCTPNPCEHGGRCESAPGQLPVCSCPQGWQGPRCQQDVDEC
AGPAPCGPHGICTNLAGSFSCTCHGGYTGPSCDQDINDCDPNPCLNGGSCQDGVGSFSCSCLPGFAGPRCARDV
DECLSNPCGPGTCTDHVASFTCTCPPGYGGFHCEQDLPDCSPSSCFNGGTCVDGVNSFSCLCRPGYTGAHCQHE
ADPCLSRPCLHGGVCSAAHPGFRCTCLESFTGPQCQTLVDWCSRQPCQNGGRCVQTGAYCLCPPGWSGRLCDIR
SLPCREAAAQIGVRLEQLCQAGGQCVDEDSSHYCVCPEGRTGSHCEQEVDPCLAQPCQHGGTCRGYMGGYMCEC
LPGYNGDNCEDDVDECASQPCQHGGSCIDLVARYLCSCPPGTLGVLCEINEDDCGPGPPLDSGPRCLHNGTCVD
LVGGFRCTCPPGYTGLRCEADINECRSGACHAAHTRDCLQDPGGGFRCLCHAGFSGPRCQTVLSPCESQPCQHG
GQCRPSPGPGGGLTFTCHCAQPFWGPRCERVARSCRELQCPVGVPCQQTPRGPRCACPPGLSGPSCRSFPGSPP
GASNASCAAAPCLHGGSCRPAPLAPFFRCACAQGWTGPRCEAPAAAPEVSEEPR*DLGPGEPKSCDKTHTCPPCP*
*APELLGGPSVFLFPPKPKDTLMISRTPEVTCVVVDVSHEDPEVKFNWYVDGVEVHNAKTKPREEQYNSTYRVVS*
*VLTVLHQDWLNGKEYKCKVSNKALPAPIEKTISKAKGQPREPQVYTLPPSRDELTKNQVSLTCLVKGFYPSDIA*
*VEWESNGQPENNYKTTPPVLDSDGSFFLYSKLTVDKSRWQQGNVFSCSVMHEALHNHYTQKSLSLSPGK*

Figure 42

MWGWKCLLFWAVLVTATLCTARPPCLDGSPCANGGRCTQLPSREAACLCPPGWVGERCQL
EDPCHSGPCAGRGVCQSSVVAGTARFSCRCPRGFRGPDCSLPDPCLSSPCAHGARCSVGP
DGRFLCSCPPGYQGRSCRSDVDECRVGEPCRHGGTCLNTPGSFRCQCPAGYTGPLCENPA
VPCAPSPCRNGGTCRQSGDLTYDCACLPGFEGQNCEVNVDDCPGHRCLNGGTCVDGVNTY
NCQCPPEWTGQFCTEDVDECQLQPNACHNGGTCFNTLGGHSCVCVNGWTGESCSQNIDDC
ATAVCFHGATCHDRVASFYCACPMGKTGLLCHLDDACVSNPCHEDAICDTNPVNGRAICT
CPPGFTGGACDQDVDECSIGANPCEHLGRCVNTQGSFLCQCGRGYTGPRCETDVNECLSG
PCRNQATCLDRIGQFTCICMAGFTGTYCEVDIDECQSSPCVNGGVCKDRVNGFSCTCPSG
FSGSTCQLDVDECASTPCRNGAKCVDQPDGYECRCAEGFEGTLCDRNVDDCSPDPCHHGR
CVDGIASFSCACAPGYTGTRCESQVDECRSQPCRHGGKCLDLVDKYLCRCPSGTTGVNCE
VNIDDCASNPCTFGVCRDGINRYDCVCQPGFTGPLCNVEINECASSPCGEGGSCVDGENG
FRCLCPPGSLPPLCLPPSHPCAHEPCSHGICYDAPGGFRCVCEPGWSGPRCSQSLARDAC
ESQPCRAGGTCSSDGMGFHCTCPPGVQGRQCELLSPCTPNPCEHGGRCESAPGQLPVCSC
PQGWQGPRCQQDVDECAGPAPCGPHGICTNLAGSFSCTCHGGYTGPSCDQDINDCDPNPC
LNGGSCQDGVGSFSCSCLPGFAGPRCARDVDECLSNPCGPGTCTDHVASFTCTCPPGYGG
FHCEQDLPDCSPSSCFNGGTCVDGVNSFSCLCRPGYTGAHCQHEADPCLSRPCLHGGVCS
AAHPGFRCTCLESFTGPQCQTLVDWCSRQPCQNGGRCVQTGAYCLCPPGWSGRLCDIRSL
PCREAAAQIGVRLEQLCQAGGQCVDEDSSHYCVCPEGRTGSHCEQEVDPCLAQPCQHGGT
CRGYMGGYMCECLPGYNGDNCEDDVDECASQPCQHGGSCIDLVARYLCSCPPGTLGVLCE
INEDDCGPGPPLDSGPRCLHNGTCVDLVGGFRCTCPPGYTGLRCEADINECRSGACHAAH
TRDCLQDPGGGFRCLCHAGFSGPRCQTVLSPCESQPCQHGGQCRPSPGPGGGLTFTCHCA
QPFWGPRCERVARSCRELQCPVGVPCQQTPRGPRCACPPGLSGPSCRSFPGSPPGASNAS
CAAAPCLHGGSCRPAPLAPFFRCACAQGWTGPRCEAPAAAPEVSEEPR*DLGPGEPKSCDK*
*THTCPPCPAPELLGGPSVFLFPPKPKDTLMISRTPEVTCVVVDVSHEDPEVKFNWYVDGV*
*EVHNAKTKPREEQYNSTYRVVSVLTVLHQDWLNGKEYKCKVSNKALPAPIEKTISKAKGQ*
*PREPQVYTLPPSRDELTKNQVSLTCLVKGFYPSDIAVEWESNGQPENNYKTTPPVLDSDG*
*SFFLYSKLTVDKSRWQQGNVFSCSVMHEALHNHYTQKSLSLSPGK-*

Figure 43A

```
   1 atgtggggct ggaagtgcct cctcttctgg gctgtgctgg tcacagccac tctctgcact
  61 gccaggccac cttgcctgga cggaagcccg tgtgcaaatg gaggtcgttg cacccagctg
 121 ccctcccggg aggctgcctg cctgtgcccg cctggctggg tgggtgagcg gtgtcagctg
 181 gaggacccct gtcactcagg cccctgtgct ggccgtggtg tctgccagag ttcagtggtg
 241 gctggcaccg cccgattctc atgccggtgc cccgtggct tccgaggccc tgactgctcc
 301 ctgccagatc cctgcctcag cagcccttgt gcccacggtg cccgctgctc agtggggccc
 361 gatggacgct tcctctgctc ctgcccacct ggctaccagg gccgcagctg ccgaagcgac
 421 gtggatgagt gccgggtggg tgagccctgc cgccatggtg gcacctgcct caacacacct
 481 ggctccttcc gctgccagtg tccagctggc tacacagggc cactatgtga gaaccccgcg
 541 gtgccctgtg cgccctcacc atgccgtaac gggggcacct gcaggcagag tggcgacctc
 601 acttacgact gtgcctgtct tcctgggttt gagggtcaga attgtgaagt gaacgtggac
 661 gactgtccag gacaccgatg tctcaatggg gggacatgcg tggatggcgt caacacctat
 721 aactgccagt gccctcctga gtggacaggc cagttctgca cggaggacgt ggatgagtgt
 781 cagctgcagc ccaacgcctg ccacaatggg ggtacctgct tcaacacgct gggtggccac
 841 agctgcgtgt gtgtcaatgg ctggacaggc gagagctgca gtcagaatat cgatgactgt
 901 gccacagccg tgtgcttcca tggggccacc tgccatgacc gcgtggcttc tttctactgt
 961 gcctgcccca tgggcaagac tggcctcctg tgtcacctgg atgacgcctg tgtcagcaac
1021 ccctgccacg aggatgctat ctgtgacaca aatccggtga acggccgggc catttgcacc
1081 tgtcctcccg gcttcacggg tggggcatgt gaccaggatg tggacgagtg ctctatcggc
1141 gccaacccct gcgagcactt gggcaggtgc gtgaacacgc agggctcctt cctgtgccag
1201 tgcggtcgtg gctacactgg acctcgctgt gagaccgatg tcaacgagtg tctgtcgggg
1261 ccctgccgaa accaggccac gtgcctcgac cgcataggcc agttcacctg tatctgtatg
1321 gcaggcttca caggaaccta ttgcgaggtg gacattgacg agtgtcagag tagcccctgt
1381 gtcaacggtg ggtctgcaa ggaccgagtc aatggcttca gctgcacctg cccctcgggc
1441 ttcagcggct ccacgtgtca gctggacgtg gacgaatgcg ccagcacgcc ctgcaggaat
1501 ggcgccaaat gcgtggacca gcccgatggc tacgagtgcc gctgtgccga gggctttgag
1561 ggcacgctgt gtgatcgcaa cgtggacgac tgctcccctg acccatgcca ccatggtcgc
1621 tgcgtggatg gcatcgccag cttctcatgt gcctgtgctc ctggctacac gggcacacgc
1681 tgcgagagcc aggtggacga atgccgcagc cagccctgcc gccatggcgg caaatgccta
1741 gacctggtgg acaagtacct ctgccgctgc ccttctggga ccacaggtgt gaactgcgaa
1801 gtgaacattg acgactgtgc cagcaacccc tgcacctttg gagtctgccg tgatggcatc
1861 aaccgctacg actgtgtctg ccaacctggc ttcacagggc ccctttgtaa cgtggagatc
1921 aatgagtgtg cttccagccc atgcggcgag ggaggttcct gtgtggatgg ggaaaatggc
1981 ttccgctgcc tctgcccgcc tggctccttg cccccactct gcctcccccc gagccatccc
2041 tgtgcccatg agccctgcag tcacggcatc tgctatgatg cacctggcgg gttccgctgt
2101 gtgtgtgagc ctggctggag tggcccccgc tgcagccaga gcctggcccg agacgcctgt
2161 gagtcccagc cgtgcagggc cggtgggaca tgcagcagcg atggaatggg tttccactgc
2221 acctgcccgc ctggtgtcca gggacgtcag tgtgaactcc tctcccctg caccccgaac
2281 ccctgtgagc atgggggccg ctgcgagtct gcccctggcc agctgcctgt ctgctcctgc
2341 ccccagggct ggcaaggccc acgatgccag caggatgtgg acgagtgtgc tggccccgca
2401 ccctgtggcc ctcatggtat ctgcaccaac ctggcaggga gtttcagctg cacctgccat
2461 ggagggtaca ctggcccttc ctgtgatcag gacatcaatg actgtgaccc caacccatgc
2521 ctgaacggtg gctcgtgcca agacggcgtg ggctcctttt cctgctcctg cctccctggt
2581 ttcgccggcc cacgatgcgc ccgcgatgtg gatgagtgcc tgagcaaccc ctgcggcccg
2641 ggcacctgta ccgaccacgt ggcctccttc acctgcacct gcccgccagg ctacggaggc
2701 ttccactgcg aacaggacct gcccgactgc agccccagct cctgcttcaa tggcgggacc
2761 tgtgtggacg gcgtgaactc gttcagctgc ctgtgccgtc ccggctacac aggagcccac
2821 tgccaacatg aggcagaccc ctgcctctcg cggccctgcc tacacggggg cgtctgcagc
```

Figure 43B

2881 gccgcccacc ctggcttccg ctgcacctgc ctcgagagct tcacgggccc gcagtgccag
2941 acgctggtgg attggtgcag ccgccagcct tgtcaaaacg ggggtcgctg cgtccagact
3001 ggggcctatt gcctttgtcc ccctggatgg agcggacgcc tctgtgacat ccgaagcttg
3061 ccctgcaggg aggccgcagc ccagatcggg gtgcggctgg agcagctgtg tcaggcgggt
3121 gggcagtgtg tggatgaaga cagctcccac tactgcgtgt gcccagaggg ccgtactggt
3181 agccactgtg agcaggaggt ggacccctgc ttggcccagc cctgccagca tgggggggacc
3241 tgccgtggct atatgggggg ctacatgtgt gagtgtcttc ctggctacaa tggtgataac
3301 tgtgaggacg acgtggacga gtgtgcctcc cagccctgcc agcacggggg ttcatgcatt
3361 gacctcgtgg cccgctatct ctgctcctgt cccccaggaa cgctgggggt gctctgcgag
3421 attaatgagg atgactgcgg cccaggccca ccgctggact cagggccccg gtgcctacac
3481 aatggcacct gcgtggacct ggtgggtggt ttccgctgca cctgtccccc aggatacact
3541 ggtttgcgct gcgaggcaga catcaatgag tgtcgctcag gtgcctgcca cgcggcacac
3601 acccgggact gcctgcagga cccaggcgga ggtttccgtt gcctttgtca tgctggcttc
3661 tcaggtcctc gctgtcagac tgtcctgtct ccctgcgagt cccagccatg ccagcatgga
3721 ggccagtgcc gtcctagccc gggtcctggg ggtgggctga ccttcacctg tcactgtgcc
3781 cagccgttct ggggtccgcg ttgcgagcgg gtggcgcgct cctgccggga gctgcagtgc
3841 ccggtgggcg tcccatgcca gcagacgccc cgcgggccgc gctgcgcctg cccccccaggg
3901 ttgtcgggac cctcctgccg cagcttcccg gggtcgccgc cgggggccag caacgccagc
3961 tgcgcggccg ccccctgtct ccacgggggc tcctgccgcc ccgcgccgct cgcgcccttc
4021 ttccgctgcg cttgcgcgca gggctggacc gggccgcgct gcgaggcgcc cgccgcggca
4081 cccgaggtct cggaggagcc gcgagatctg ggcccgggcg agcccaaatc ttgtgacaaa
4141 actcacacat gcccaccgtg cccagcacct gaactcctgg ggggaccgtc agtcttcctc
4201 ttccccccaa aacccaagga caccctcatg atctcccgga cccctgaggt cacatgcgtg
4261 gtggtggacg tgagccacga agaccctgag gtcaagttca actggtacgt ggacggcgtg
4321 gaggtgcata atgccaagac aaagccgcgg gaggagcagt acaacagcac gtaccgtgtg
4381 gtcagcgtcc tcaccgtcct gcaccaggac tggctgaatg gcaaggagta caagtgcaag
4441 gtctccaaca aagccctccc agcccccatc gagaaaacca tctccaaagc caaagggcag
4501 ccccgagaac cacaggtgta caccctgccc ccatcccggg atgagctgac caagaaccag
4561 gtcagcctga cctgcctggt caaaggcttc tatcccagcg acatcgccgt ggagtgggag
4621 agcaatgggc agccggagaa caactacaag accacgcctc ccgtgctgga ctccgacggc
4681 tccttcttcc tctacagcaa gctcaccgtg gacaagagca ggtggcagca ggggaacgtc
4741 ttctcatgct ccgtgatgca tgaggctctg cacaaccact acacgcagaa gagcctctcc
4801 ctgtctccgg gtaaatga

Figure 44

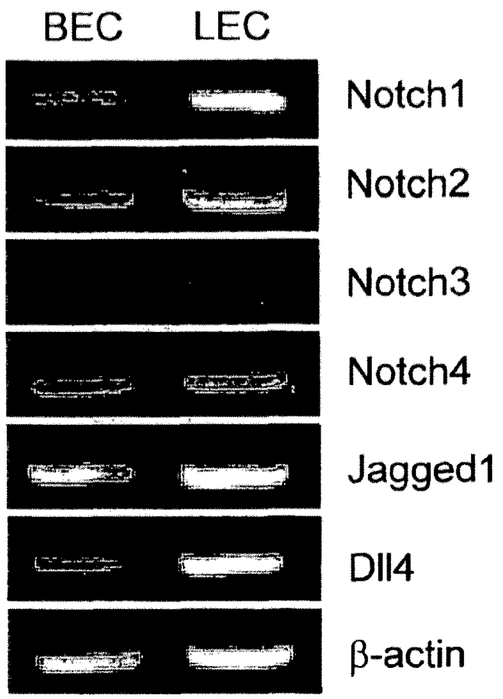

Expression of Notch proteins and ligands in blood and lymphatic endothelial cells. RT-PCR was performed for Notch1-4, Dll1, Dll4, and Jagged1 on RNA isolated from blood endothelial cells (BEC) and lymphatic endothelial cells (LEC) purified from HMVEC (Fig. 4A). Notch1, Notch2, Notch4, Dll4 and Jagged1 were expressed in both BEC and LEC at a similar level. Expression of Notch3 appears to be restricted to the LEC suggestive of Notch3 signaling functions in the lymphatic endothelium.

Notch3 is co-expressed with the lymphatic endothelial cell markers LYVE-1 and Prox1 in e13.5 embryos. 10 micron serial sections of embryonic day 13.5 mouse embryos were immunostained for either LYVE-1, Prox1 and Notch3. Notch3 was expressed in the cells that also expressed the lymphatic endothelial cell markers, LYVE-1 and Prox1.

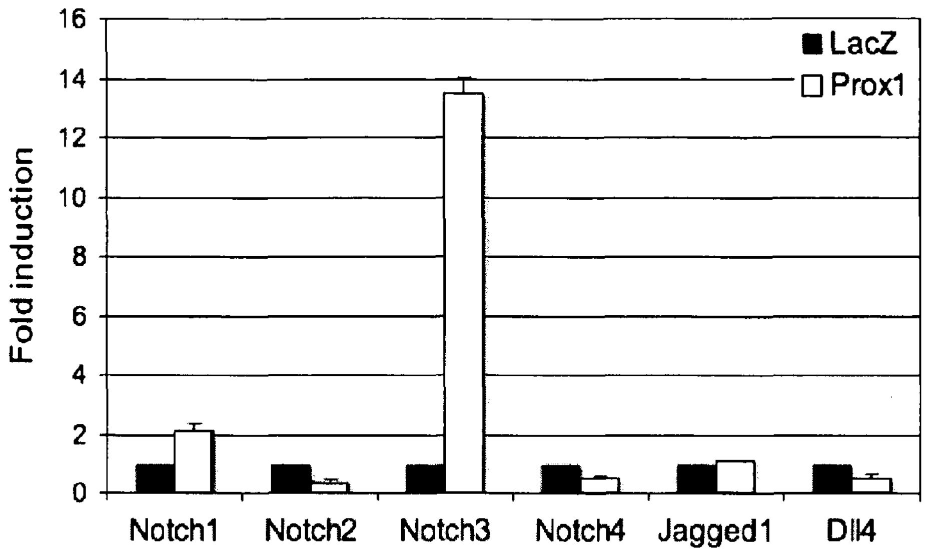

B

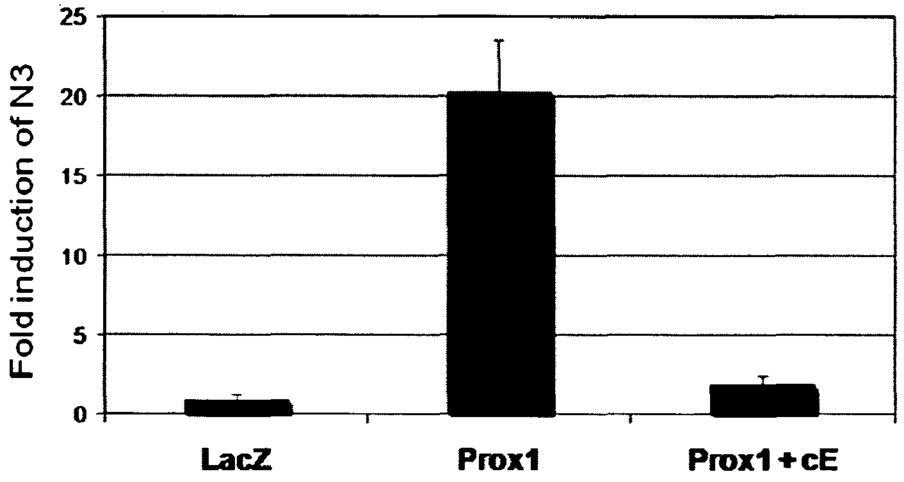

Prox1 induces Notch3 expression in blood endothelial cells. A. We examined if ectopic expression of Prox1 would alter the expression of Notch proteins or ligands. Twenty-four hours post adenoviral infection with either Ad-Prox1 or Ad-LacZ, HUVEC total RNA was isolated and quantitative RT-PCR for Notch1-4, Dll4, and Jagged1 performed. Prox-1 robustly upregulated the expression of Notch3. Notch1, Notch2, Notch4, Dll4, and Jagged1 expression was not significantly affected. B. Compound E (cE), Presenlin inhibitor that inhibits Notch signaling, was incubated for 24 hours on either Ad-LacZ or Ad-Prox1 infected HUVEC. Total RNA was isolated and quantitative RT-PCR performed to determine Notch3 expression. Prox1 induced Notch3 expression and this induction was inhibited by the addition of Compound E. This suggest that the Prox1 induction of Notch3 is dependent on Notch signal activation.

Figure 47

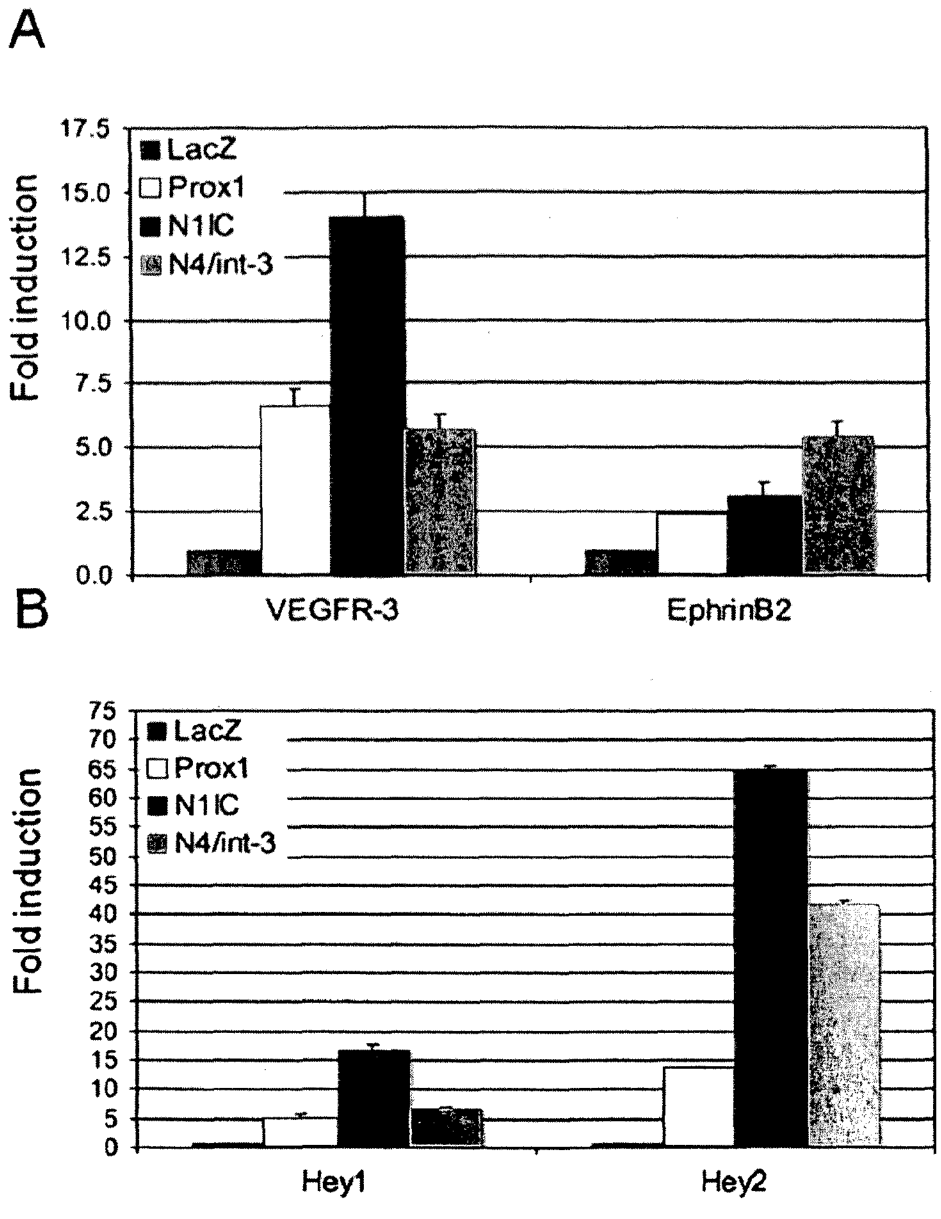

Prox1 induces Notch-target genes in blood endothelial cells. HUVEC were infected with adenoviruses encoding, LacZ, Prox1, N1IC or N4/int-3 and total RNA isolated 24 hours post-infection. Quantitative RT-PCR was performed for the endothelial Notch-target genes, VEGFR-3, EphrinB2, Hey1 and Hey2. Similar to Notch1 and Notch4 signal activation, Prox1 induced all four genes (A & B). Expression of Hey1 and Hey2 in the lymphatic endothelium is unknown.

Figure 48

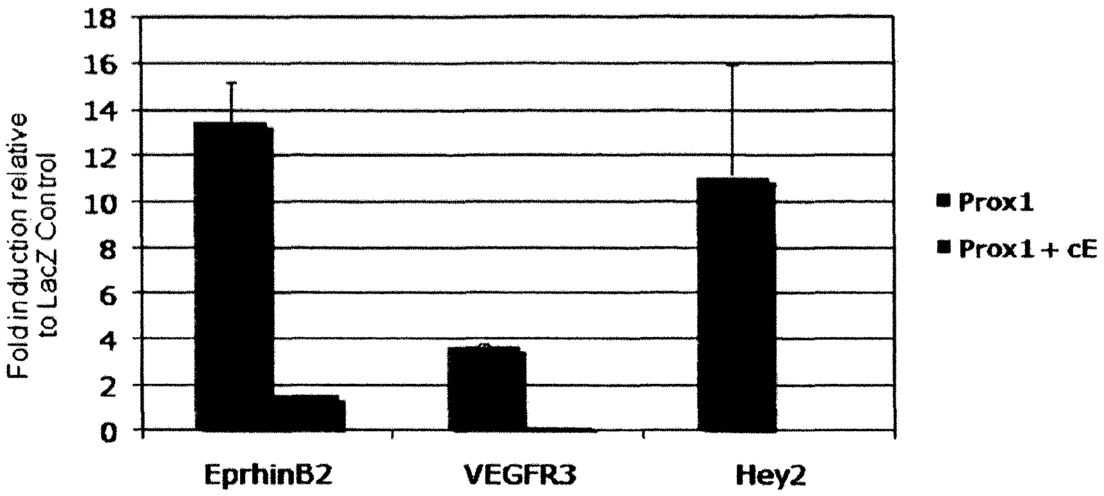

Prox1 induces Notch-target genes is dependent on Notch signaling in blood endothelial cells. HUVEC were infected with adenoviruses encoding, LacZ, Prox1, N1IC or N4/int-3. Compound E (cE), Presenlin inhibitor that inhibits Notch signaling, was incubated for 24 hours on either Ad-LacZ or Ad-Prox1 infected HUVEC and total RNA isolated. Quantitative RT-PCR was performed for the endothelial Notch-target genes, VEGFR-3, EphrinB2, and Hey2. The Prox1-mediated induction of the Notch target genes, ephrinB2, VEGFR-3 and Hey2 was inhibited by the addition of the Notch signaling inhibitor Compound E. Thus, Prox1 regulates the expression of ephrinB2, VEGFR-3 and Hey2 via Notch.

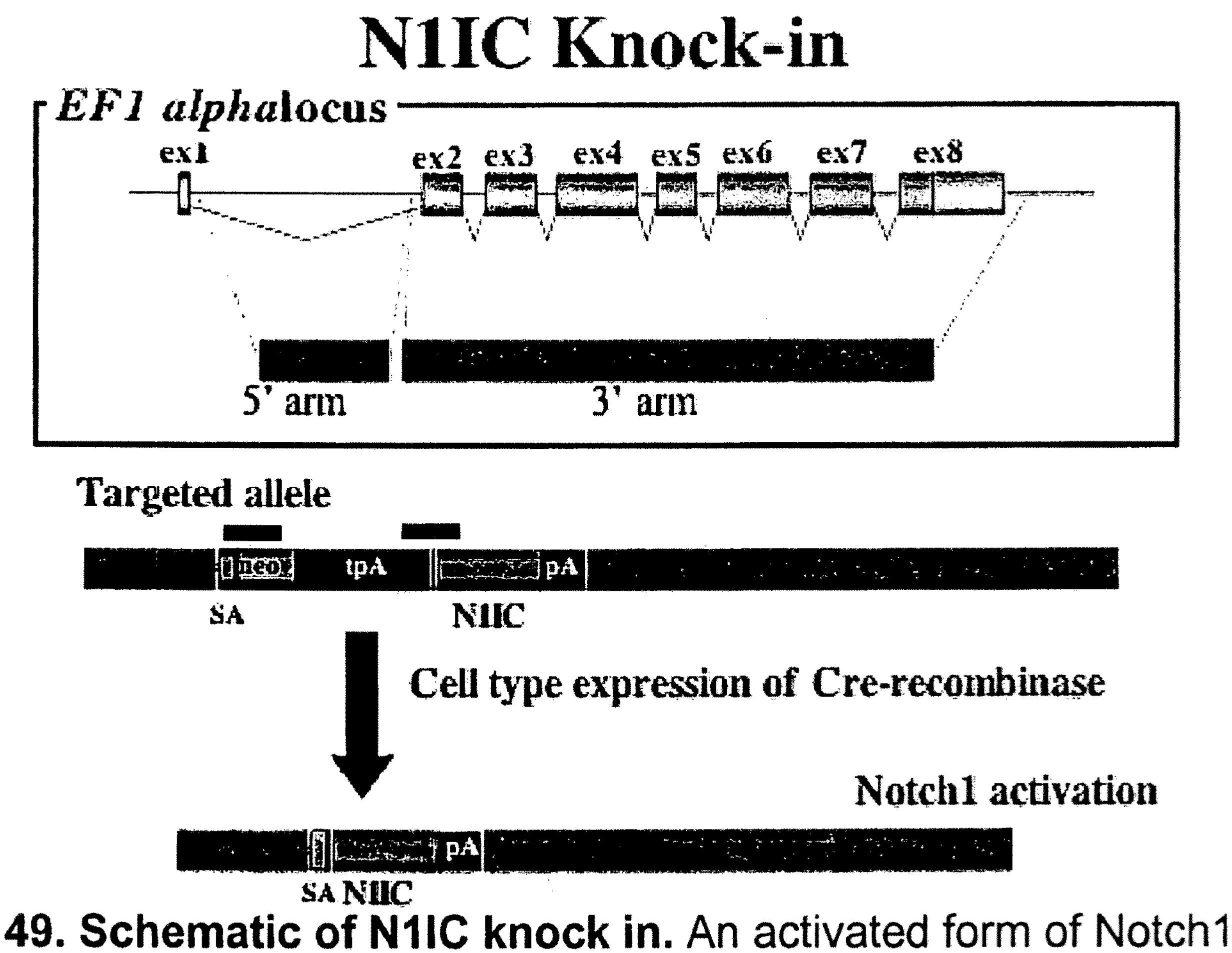
Figure 49. Schematic of N1IC knock in. An activated form of Notch1 was inserted into the EF1alpha locus flanked by two LoxP sites. Upon expression of Cre-recombinase, the neo/tpA cassette is lost and N1IC is expressed under the control of the ubiquitous EF1 alpha promoter.

| Genotype | Predicted | E9.5* | P21† |
| --- | --- | --- | --- |
| WT | 25% | 30.7% | 37.5% |
| $SM22^{Cre/+}$ | 25% | 22.7% | 30% |
| $EF1\alpha^{N1IC/+}$ | 25% | 22.7% | 37.5% |
| $SM22^{Cre/+}$; $EF1\alpha^{N1IC/+}$ | 25% | 21.3% | 0% |
| * n = 75, p > 0.2; † n = 80, p < 0.001 | | | |

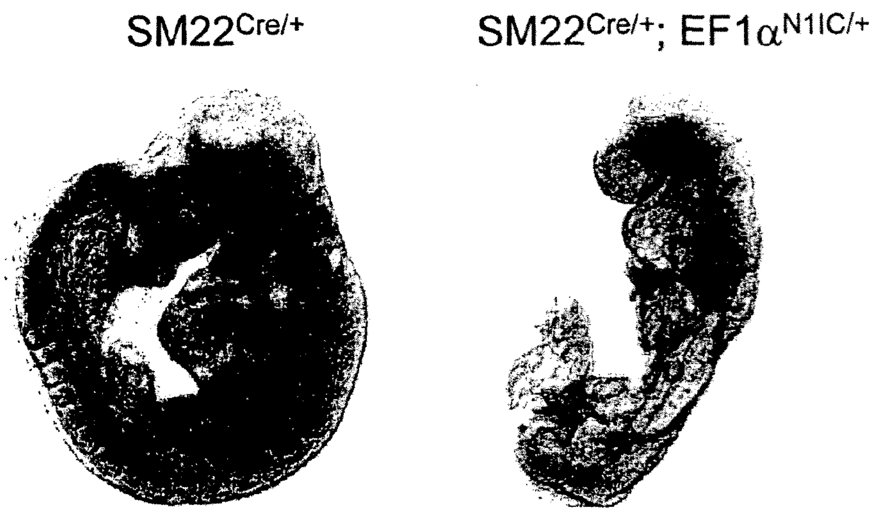

Figure 50. Notch activation in SM22 expressing vascular smooth muscle cells results in embryonic lethality before E10.5. No viable $SM22^{Cre/+}$; $EF1\alpha^{N1IC/}$ mice were observed at postnatal day 21 (P21) with a p value less than 0.001. At embryonic day E9.5, an predicted number of $SM22^{Cre/+}$; $EF1\alpha^{N1IC/+}$ embryos were observed, but they were severly growth retarded compared with their control litter mates (Lower panel).

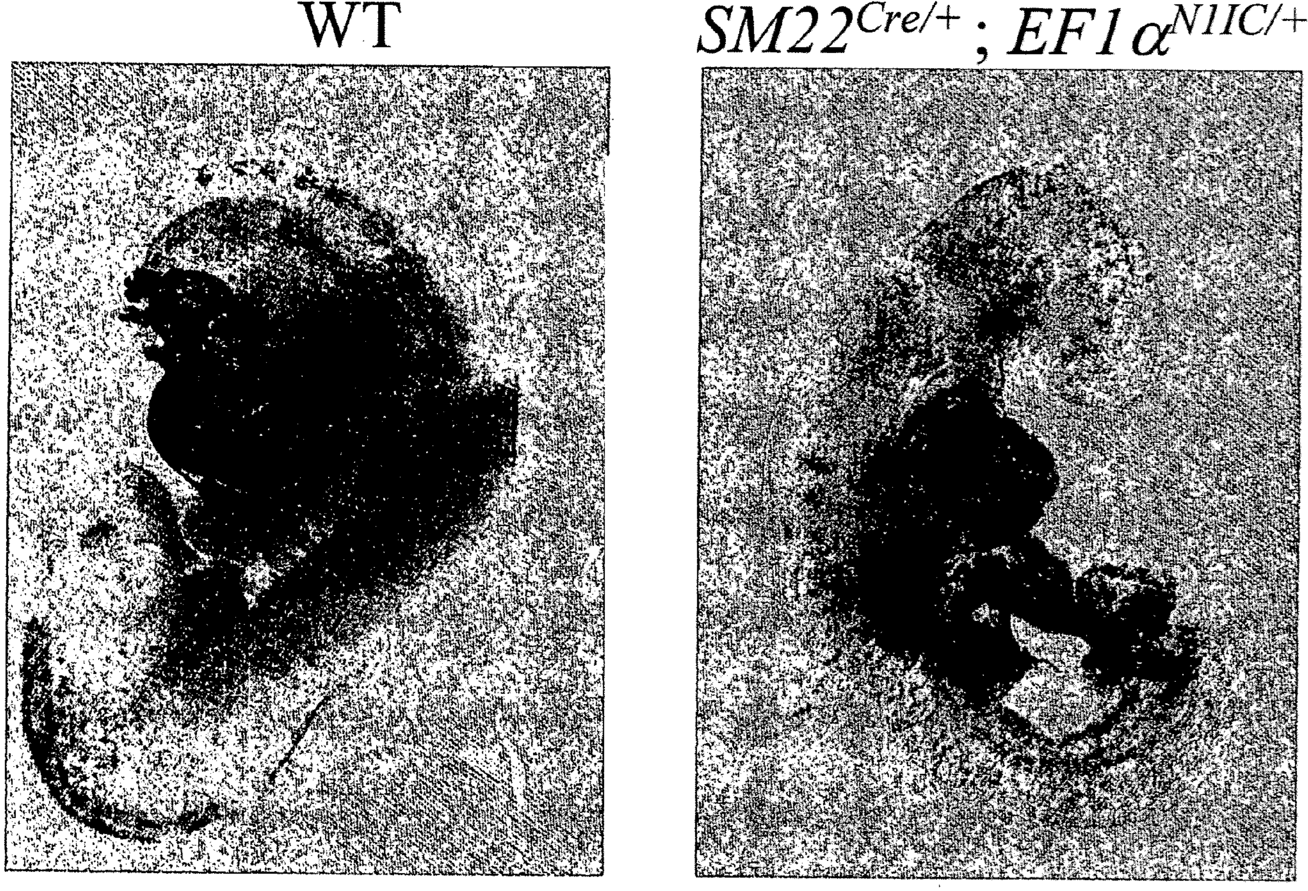

Figure 51. Notch activation in SM22 expressing vascular smooth muscle cells alters alpha smooth muscle cell actin expression. E9.5 embryos were wholemount immunostained for alpha smooth muscle cell actin. Expression of alpha smooth muscle cell actin was altered in the $SM22^{Cre/+}$; $EF1\alpha^{N1IC/+}$ embryos compared to the WT controls. Thus, Notch signal activation in vascular smooth muscle cells disrupts cardiovascular development.

HUMAN NOTCH3 BASED FUSION PROTEINS AS DECOY INHIBITORS OF NOTCH3 SIGNALING

This application is a §371 national stage of PCT International Application No. PCT/US2009/004765, filed Aug. 21, 2009, claiming the benefit of U.S. Provisional Application No. 61/189,930, filed Aug. 22, 2008, the contents of each of which are hereby incorporated by reference in their entirety.

This invention was made with government support under grant number HL62454 awarded by the National Institutes of Health and grant number DAMRDCW81XWH-04-1-054 awarded by the Department of Defense. The government has certain rights in the invention.

Throughout this application, various publications are referenced by arabic numbers within parentheses or by author and publication date within parentheses. Full citations for these publications may be found at the end of the specification. The disclosures of these publications are hereby incorporated by reference into this application to describe more fully the art to which this invention pertains.

BACKGROUND OF THE INVENTION

Vascular Development

During mammalian embryogenesis, formation of the vascular system is an early and essential process. In the embryo, vascular development initiates with the pluripotent hemangioblast derived from the paraxial and lateral plate mesoderm. The hemangioblast has the potential to differentiate into either a hematopoietic progenitor or an endothelial cell progenitor, known as the angioblast.

Vascular development begins with a process known as vasculogenesis whereby angioblasts differentiate into endothelial cells and migrate together to form the primitive vascular plexus. This initial vascular network consists of vessels that are homogenous in size and made up wholly of endothelial cells. The vascular plexus is then remodeled via angiogenesis.

Angiogenesis involves the sprouting of new vessels, the migration of these vessels into avascular regions, and the recruitment of accessory cells, pericytes and smooth muscle cells (Gale and Yancopoulos, 1999). The smooth muscle cells that differentiate and form the contractile vessel walls originate from multiple progenitors including neural crest cells, mesenchymal cells and even endothelial cells (Owens, 1995). In adults, angiogenesis is involved in follicular development, wound healing, and pathological processes such as tumor angiogenesis and heart disease.

The Notch Family and Notch Ligands

Studies of *Drosophila, C. Elegans*, zebrafish and mammals have demonstrated that the Notch pathway is an evolutionarily conserved signaling mechanism that functions to modulate numerous cell-fate decisions. Notch signaling is required for the proper patterning of cells originating from all three germ layers. Depending on the cellular context, Notch signaling may both inhibit and induce differentiation, induce proliferation, and promote cell survival (Artavanis-Tsakonas at al., 1995; Lewis, 1998; Weinmaster, 1997). In *Drosophila*, a single Notch protein is activated by two ligands, Serrate and Delta. In mammals these families have been expanded to four Notch genes (Notch1, Notch2, Notch3 and Notch4) and five ligands, 2 Serrate-like (Jagged1-2) and 3 Delta (Dl1, 3, 4) (Bettenhausen et al., 1995; Dunwoodie et al., 1997; Gallahan and Callahan, 1997; Lardelli et al., 1994; Lindsell et al., 1995; Shawber et al., 1996a; Shutter et al., 2000a; Uyttendaele et al., 1996; Weinmaster et al., 1992; Weinmaster et al., 1991). During embryogenesis, Notch receptors and ligands are expressed in dynamic spatial and temporal patterns. However, it is not known if all ligands activate all receptors.

Notch Signaling and Function

Notch signaling influences many different types of cell-fate decisions by providing inhibitory, inductive or proliferative signals depending on the environmental context (reviewed in Artavanis-Tsakonas et al., 1995; Greenwald, 1998; Robey, 1997; Vervoort et al., 1997). This pleiotropic function suggests that Notch modulates multiple signaling pathways in a spatio-temporal manner.

Consistent with Notch regulating cell-fate decisions, both the receptors and ligands are cell surface proteins with single transmembrane domains (FIG. 1). The regulatory extracellular domain of Notch proteins consists largely of tandemly arranged EGF-like repeats that are required for ligand binding (Artavanis-Tsakonas et al., 1995; Weinmaster, 1998). C-terminal to the EGF-like repeats are an additional three cysteine-rich repeats, designated the LIN12/Notch repeats (LNR) (Greenwald, 1994). Downstream of the LNR lies the proteolytic cleavage sequence (RXRR) that is recognized by a furin-like convertase. For Notch1, cleavage at this site yields a 180 kilodalton extracellular peptide and a 120 kilodalton intracellular peptide that are held together to generate a heterodimeric receptor at the cell surface (Blaumueller et al., 1997; Kopan et al., 1996; Logeat et al., 1998).

The intracellular domain of Notch (NotchICD, FIG. 1) rescues loss-of-function Notch phenotypes indicating that this form of Notch signals constitutively (Fortini and Artavanis-Tsakonas, 1993; Lyman and Young, 1993; Rebay et al., 1993; Struhl et al., 1993).

The cytoplasmic domain of Notch contains three identifiable domains: the RAM domain, the ankyrin repeat domain and the C-terminal PEST domain (FIG. 1). Upon ligand-activation Notch undergoes two additional proteolytic cleavages which results in the release of the cytoplasmic domain (Weinmaster, 1998). This Notch peptide translocates to the nucleus and interacts with transcriptional repressors known as CSL (CBF, Su (H), Lag-2) and converts it to transcriptional activator. The CSL/Notch interaction is dependent on the presence of the RAM domain of Notch; while, transcriptional activity also requires the presence of the ankyrin repeats (Hsieh et al., 1996; Hsieh at al., 1997; Roehl et al., 1996; Tamura et al., 1995; Wettstein et al., 1997). Both in vivo and in vitro studies indicate that the HES and Hey genes are the direct targets of Notch/CSL-dependent signaling (Bailey and Posakony, 1995; Eastman at al., 1997; Henderson et al., 2001; Jarriault et al., 1995; Nakagawa at al., 2000; Wettstein et al., 1997). The HES and Hey genes are bHLH transcriptional repressor that bind DNA at N-boxes (Nakagawa et al., 2000; Sasai et al., 1992; Tietze et al., 1992). Notch has also been proposed to signal by a CSL-independent pathway. In fact, expression of just the ankyrin repeat domain is necessary and sufficient for some forms of Notch signaling (Lieber et al., 1993; Matsuno et al., 1997; Shawber at al., 1996b).

Finally, the PEST domain has been implicated in protein turnover by a SEL-10/ubiquitin-dependent pathway (Greenwald, 1994; Oberg et al., 2001; Rogers et al., 1986; Wu et al., 1998; Wu et al., 2001). Similar to the receptors, the extracellular domain of the Notch ligands also consist mostly of tandemly arranged EGF-like repeats (FIG. 1). Upstream of these repeats is a divergent EGF-like repeat known as the DSL (Delta, Serrate, Lag-2) that is required for ligand binding and activation of the receptors (Artavanis-Tsakonas et al., 1995).

Notch Signaling and Vascular Development

Although many of the genes that function to induce vasculogenesis and angiogenesis have been identified, little is known about how cell-fate decisions are specified during vascular development. A number of observations suggest that the Notch signaling pathway may play a role in cell fate determination and patterning of the vascular system.

Notch1, Notch4, Jagged1 and Dll4 are all expressed in the developing vasculature, while Notch3 is expressed in the accessory smooth muscle cells (Krebs et al., 2000; Shutter et al., 2000b; Uyttendaele et al., 1996; Villa et al., 2001; Xue et al., 1999). Mice lacking Jagged1 are embryonic lethal and have severe vascular defects (Xue et al., 1999). Mice nullizygous for Notch1 are embryonic lethal and die of severe neuronal defects, but also have defects in angiogenesis (Krebs et al., 2000; Swiatek et al., 1994). Mice lacking Notch4 are born and appear to be normal, but embryos that have lost both Notch1 and Notch4 die at E9.5 of severe hemorrhaging and vascular patterning defects indicating Notch1 and Notch4 may be functionally redundant during vascular development (Krebs et al., 2000). Exogenous expression of an activated form of Notch4 in endothelium also resulted in vascular defects similar to those seen for the double Notch1/Notch4 nullizygous mice, suggesting that appropriate levels of Notch signaling is critical for proper development of the embryonic vasculature (Uyttendaele et al., 2001).

Taken together, the data from mice mutant for Notch/Notch signaling components uncover several processes dependent on Notch including vascular remodeling, arterial venous specification, vascular smooth muscle cell recruitment and heart/heart outflow vessel development.

Recent experiments have implicated Notch signaling in arterial/venous endothelial cell specification. In situ analysis of E13.5 embryos found that Notch1, Notch3, Notch4, Dl4, Jagged1 and Jagged2 expression was restricted to the arteries and absent in the veins (Villa et al., 2001). Consistent with expression data, disruption of Notch signaling in Zebrafish was associated with loss of the arterial marker ephrinB2; while, ectopic expression of an activated form of Notch lead to a loss in the venous cell marker EphB4 within the dorsal aorta (Lawson et al., 2001). These data suggest that Notch signaling may help to specify arterial and venous cell fates during angiogenesis.

Taken together, the data from mice mutant for Notch/Notch signaling components uncover several processes dependent on Notch including vascular remodeling, arterial venous specification, vascular smooth muscle cell recruitment and heart/heart outflow vessel development.

Notch signaling has also been suggested to function in the adult vascular system. In humans, missense mutations in the extracellular domain of Notch3 correlate with the development of the degenerative vascular disease, CADASIL (Caronti et al., 1998; Desmond et al., 1998; Joutel et al., 2000; Joutel et al., 1996). In a wound healing model, an increase in Jagged1 expression was observed at the regenerating endothelial wound edge, suggesting Notch signaling may function during processes of adult angiogenesis (Lindner et al., 2001). Taken together these data support Notch signaling functions at a number of critical steps during vascular development: vasculogenesis, vascular patterning/angiogenesis, and arterial/venous specification. However, the molecular mechanism(s) by which the Notch signaling pathways influence these different steps has yet to be elucidated.

Significance

Shimizu at al. (J. Biol. Chem. 274(46): 32961-32969 (1999)) describe the use of Notch1ECD/Fc, Notch2ECD/Fc and Notch3ECD/Fc in binding studies. However, Shimizu et al. do not mention the use of such proteins for inhibiting angiogenesis.

U.S. Pat. No. 6,379,925 issued Apr. 30, 2002 to Kitajewski et al. describes murine Notch4. However, it does not describe Notch-based fusion proteins as set forth in the subject application.

Notch proteins play key roles in developmental decisions involving the vasculature, the hematopoietic system, and the nervous system. As such, an understanding of their function is key to understanding how cell-fate decisions and commitment are controlled during development and in adult tissues. To date, several reports on Notch or Notch ligand gene disruptions have described vascular phenotypes providing emphasis that this pathway is a fundamental part of the machinery that guides vascular development. Aberrant Notch activity has been linked to human pathologies; including both cancer and vascular disorders (CADASIL). The analysis of Notch in tumor angiogenesis has only recently begun; however, our discovery of potential downstream targets of Notch suggests a role in pathological processes associated with angiogenesis. For instance, VEGFR-3 has been linked to both tumor angiogenesis and tumor lymphangiogenesis. The expression or function of several other potential Notch targets has also been linked to tumor angiogenesis; including ephrinB2, Id3, Angiopoietin 1, and PDGF-B. Insights on the role of these targets in Notch gene function will clearly facilitate future analysis of Notch in human pathologies.

SUMMARY OF THE INVENTION

This invention provides a fusion protein comprising a signal peptide, EGF repeats 1-x of the extracellular domain of human Notch3 receptor protein wherein X is any integer from 12 to 34, and an Fc portion of an antibody bound thereto.

This invention provides a fusion protein comprising a signal peptide, EGF repeats 1-X of the extracellular domain of human Notch3 receptor protein wherein X is any integer from 1 to 10, and an Fc portion of an antibody bound thereto.

This invention provides a fusion protein comprising a signal peptide, at least 12 EGF repeats of the extracellular domain of human Notch3 receptor, and an Fc portion of an antibody bound thereto.

This invention provides a fusion protein comprising a signal peptide, EGF repeats of the extracellular domain of human Notch3 receptor protein, wherein at least 12 EGF repeats are present, and an Fc portion of an antibody bound thereto.

This invention provides a method for treating a subject having a tumor comprising administering to the subject an amount of the above fusion protein effective to treat the subject, thereby treating the subject having a tumor.

This invention provides a method for inhibiting angiogenesis in a subject comprising administering to the subject an amount of the above fusion protein effective to inhibit angiogenesis in the subject, thereby inhibiting angiogenesis in the subject.

This invention provides a method for treating a subject having ovarian cancer comprising administering to the subject an amount of the above fusion protein effective to treat the subject, thereby treating the subject having ovarian cancer.

This invention provides use of the above fusion protein for the preparation of a pharmaceutical composition for the treatment of a subject having a tumor.

This invention provides use of the above fusion protein for the preparation of a pharmaceutical composition for inhibiting angiogenesis in a subject.

This invention provides use of the above fusion protein for the preparation of a pharmaceutical composition for treating a subject having ovarian cancer.

This invention provides use of the above fusion protein for the preparation of a pharmaceutical composition for for treating a subject having a metabolic disorder.

This invention provides a method for inhibiting physiological lymphangiogenesis or pathological lymphangiogenesis in a subject comprising administering to the subject an amount of the above fusion protein effective to inhibit physiological lymphangiogenesis or pathological lymphangiogenesis in the subject.

This invention provides a method of inhibiting tumor metastasis in a subject comprising administering to the subject an amount of the above fusion protein effective to inhibit tumor metastasis in the subject.

This invention provides a method of inhibiting growth of a secondary tumor in a subject comprising administering to the subject an amount of the above fusion protein of effective to inhibit growth of the secondary tumor in the subject.

This invention provides a method of inhibiting blood vessel cooption by a tumor in subject comprising administering to the subject an amount of the above fusion protein effective to inhibit blood vessel cooption by a tumor in the subject.

This invention provides a method of treating cancer in a subject comprising administering to the subject the above fusion protein and an inhibitor of Vascular Endothelial Growth Factor (VEGF), each in an amount effective to treat the cancer in the subject.

This invention provides a method of treating cancer in a subject comprising administering to the subject the above fusion protein and a VEGF receptor inhibitor, each in an amount effective to treat the cancer in the subject.

This invention provides a method of treating cancer in a subject comprising administering to the subject the above fusion protein and an inhibitor of Platelet Derived Growth Factor (PDGF), each in an amount effective to treat the cancer in the subject.

This invention provides a method of treating cancer in a subject comprising administering to the subject the above fusion protein and a PDGF receptor antagonist, each in an amount effective to treat the cancer in the subject.

This invention provides a method of treating cancer in a subject comprising administering to the subject the above fusion protein and an inhibitor of HER2/neu, each in an amount effective to treat the cancer in the subject.

This invention provides a method of treating breast cancer in a subject comprising administering to the subject an amount of the above fusion protein effective to treat the breast cancer in the subject.

This invention provides the use of the above fusion protein of for the preparation of a pharmaceutical composition for treating a subject having breast cancer.

Figure 1:
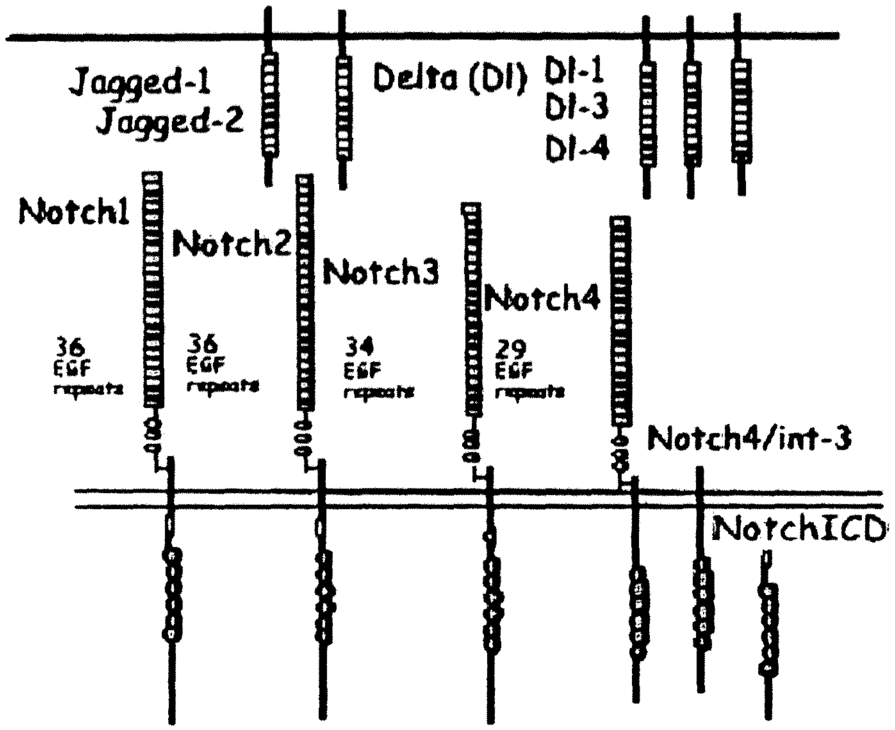
FIG. 1

This Figure shows the schematic structure of Notch and Notch ligands: Notch1, Notch2, Notch3, Notch4, Jagged-1, Jagged-2, Delta-like 1, Delta-like 3, Delta-like 4.

FIG. 2

This Figure shows the schematic design of Notch-based fusion proteins (NotchECD/Fc). The extracellular domain of Notch1, Notch2, Notch3, or Notch4 containing the EGF-repeats is fused to the Fc portion of an antibody.

FIG. 3

This Figure shows a co-culture assay for testing the activity of Notch-based fusion proteins. Notch and Notch responsive transcriptional reporters are expressed in a "Notch-responsive" cell, HeLa. Notch ligands, Jagged-1, Delta-like 1, or Delta-like 4 are expressed in a "ligand-presenting" cell, 293. Expression is mediated by transfection of individual cell populations, cells are co-cultured, and then assayed for Notch-dependent reporter activity.

FIG. 4

This Figure shows the inhibitory activity of Notch-based fusion protein against activation of Notch signaling by interaction between Notch and Notch ligand. Induction of Notch signaling was detected by co-cultivating both Notch1- and 3 types of Notch ligand-expressing cells and these inductions were inhibited by co-transfection of Notch-based fusion protein-expressing vector into Notch1-expressing cells. Therefore, Notch-based fusion proteins can be used as Notch inhibitor based on inhibition of interaction between Notch and Notch ligand.

FIG. 5

This Figure shows the expression of Notch1-based fusion protein (Notch1ECD/Fc) in 293. Panel A: expression in cell lystates (lys) or secreted into media (sup). Panel B: expression in 293 lysates of NECD/Fcs, as listed.

FIG. 6

This Figure shows activation of Notch signaling in HUVEC infected with adenoviral-encoding VEGF-165. Activation of Notch signaling can be detected by using CBF1 promoter activity. Transcriptional activity of CBF1 promoter is activated by binding of Notch-IC to CBF1. We measured CBF1 promoter activity in HUVEC which was infected with adenovirus-encoding VEGF-165 at different MOI. Induction of CBF1 promoter was clearly detected in Ad-VEGF-infected HUVEC, compared to Ad-LacZ-infected cells in the MOI dependent manner. This data showed overexpression of VEGF could activate Notch signaling in HUVEC.

FIG. 7

This Figure shows the effect of Notch-based fusion proteins on VEGF-induced activation of Notch signaling. Co-infection of Ad-Notch-based fusion protein with Ad-VEGF clearly reduced activation of CBF1 promoter activity induced by Ad-VEGF infection alone. In the case of infection at 40 MOI for each adenovirus in panel A, 60% inhibition at 24 hour and 90% inhibition at 48 hour after reporter gene transfection was detected. Panel B shows that this inhibitory activity of Notch trap was dependent on MOI of Ad-Notch-based fusion protein.

FIG. 8

This Figure shows an experiment in which we evaluated the effect of Notch-based fusion proteins on induction of budding by overexpressed VEGF-165 in HUVEC. When Ad-VEGF-infected HUVEC were cultured on type collagen gel for 8 days, budding was induced into collagen gel. This induction of budding by overexpressed VEGF was clearly inhibited by coinfection of adenoviral-encoding Notch-based fusion proteins. Ad-Notch-based fusion protein itself had less effect on morphology.

FIG. 9

This Figure shows the result of counting buds per field under microscope. Ad-VEGF-infection into HUVEC increased the number of buds depending on used MOI. Even though a half MOI of Notch-based fusion protein was used, compared to Ad-VEGF, Ad-VEGF-induced budding was clearly inhibited. These data suggested that VEGF induced budding of HUVEC through activation of Notch signaling and Notch-based fusion protein could inhibit VEGF-induced budding.

FIG. 10

This Figure shows the amino acid sequence of the extracellular domain of the rat Notch1 protein (SEQ ID NO:1) and a linker sequence (SEQ ID NO:2).

FIG. 11

This Figure shows the amino acid sequence of the extracellular domain of the rat Notch2 protein (SEQ ID NO:3) and a linker sequence (SEQ ID NO:2).

FIG. 12

This Figure shows the amino acid sequence of the extracellular domain of the mouse Notch3 protein (SEQ ID NO:4).

FIG. 13

This Figure shows the amino acid sequence of the extracellular domain of the mouse Notch4 protein (SEQ ID NO:5) and a linker sequence (SEQ ID NO:2).

FIGS. 14A and 14B

This Figure shows the nucleic acid sequence of the extracellular domain of the rat Notch1 gene (SEQ ID NO:6).

FIGS. 15A and 15B

This Figure shows the nucleic acid sequence of the extracellular domain of the rat Notch2 gene (SEQ ID NO:7).

FIGS. 16A and 16B

This Figure shows the nucleic acid sequence of the extracellular domain of the mouse Notch3 gene (SEQ ID NO:8).

FIGS. 17A and 17B

This Figure shows the nucleic acid sequence of the extracellular domain of the mouse Notch4 gene (SEQ ID NO:9) and the nucleic acid sequence (SEQ ID NO:10) and the amino acid sequence (SEQ ID NO:2) of a linker sequence.

FIGS. 18A and 18B

This Figure shows the nucleic acid sequence of the extracellular domain of the human Notch1 gene (SEQ ID NO:11).

FIGS. 19A and 19B

This Figure shows the nucleic acid sequence of the extracellular domain of the human Notch2 gene (SEQ ID NO:12).

FIGS. 20A and 20B

This Figure shows the nucleic acid sequence of the extracellular domain of the human Notch3 gene (SEQ ID NO:13).

FIGS. 21A and 21B

This Figure shows the nucleic acid sequence of the extracellular domain of the human Notch4 gene (SEQ ID NO:14).

FIGS. 22A-22I

Figure 22A:
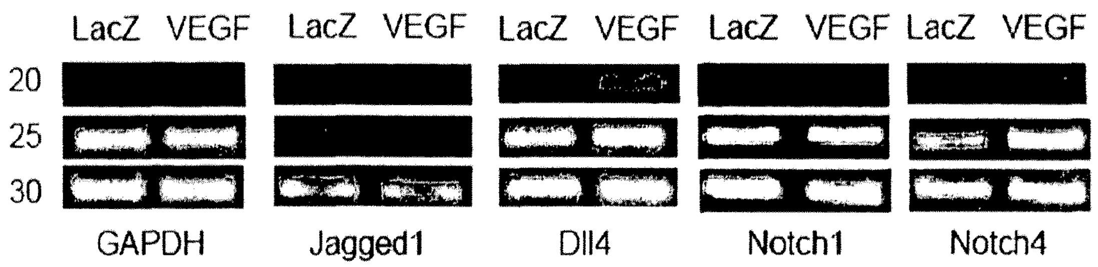
Figure 22B:
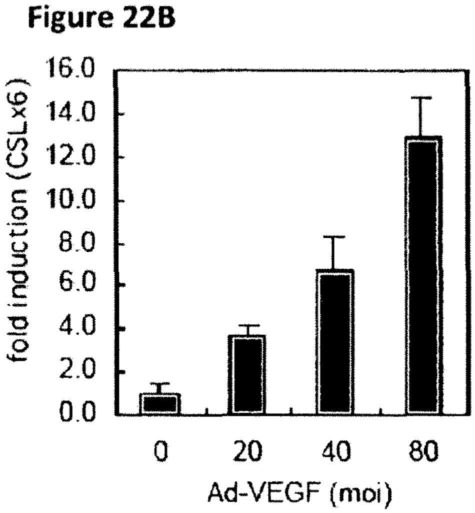
Figure 22C:
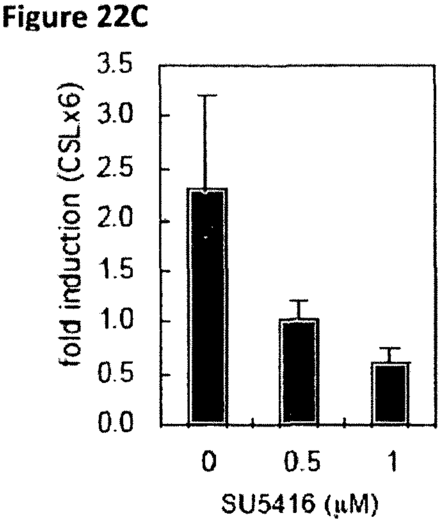
Figure 22D:
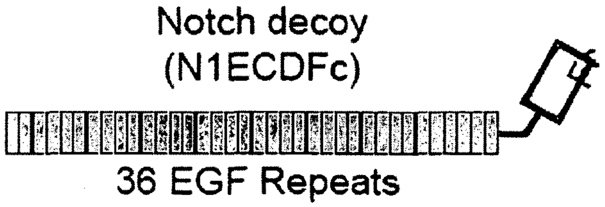
Figure 22E:
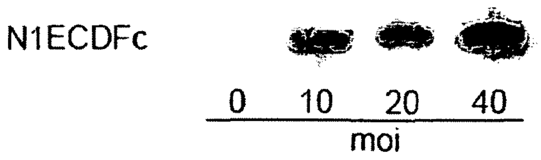
Figure 22F:
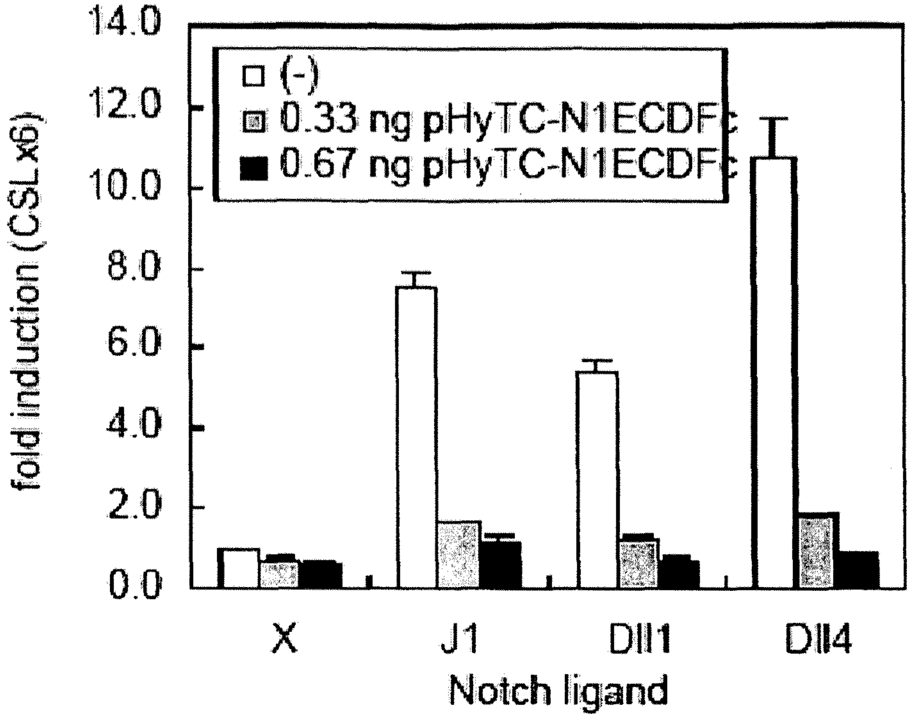
Figure 22G:
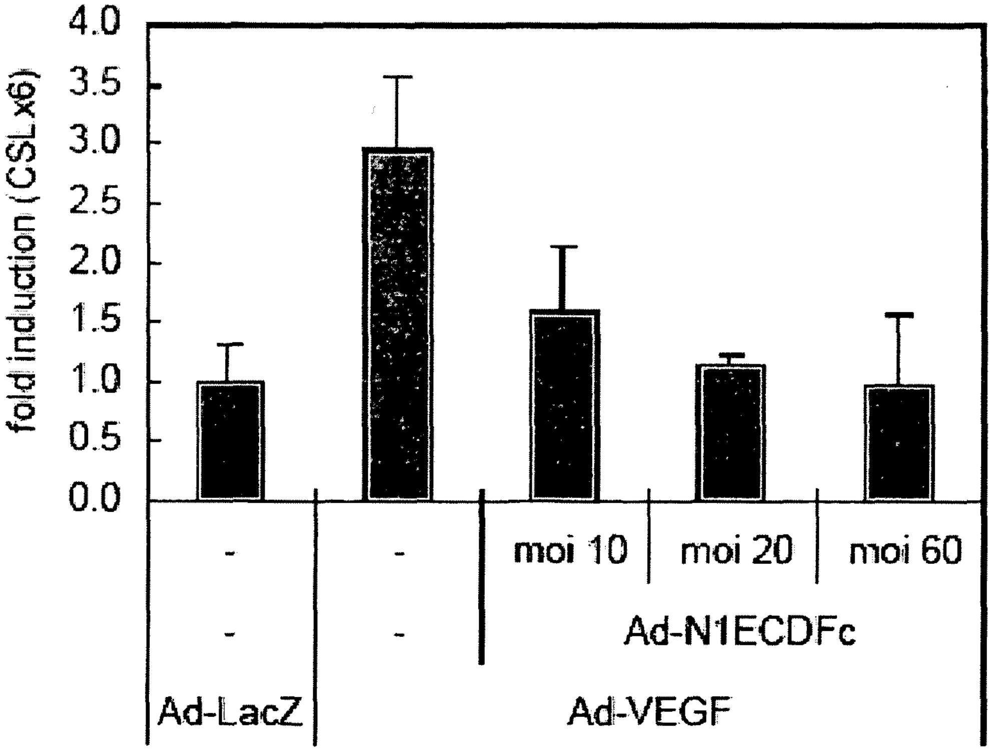
Figure 22H:
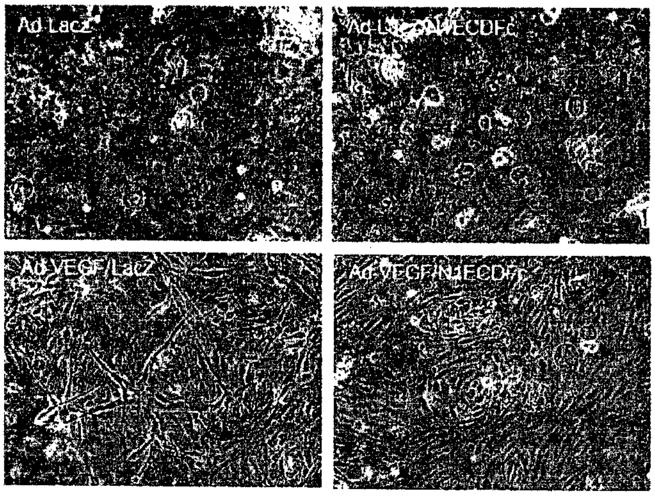
Figure 22I:
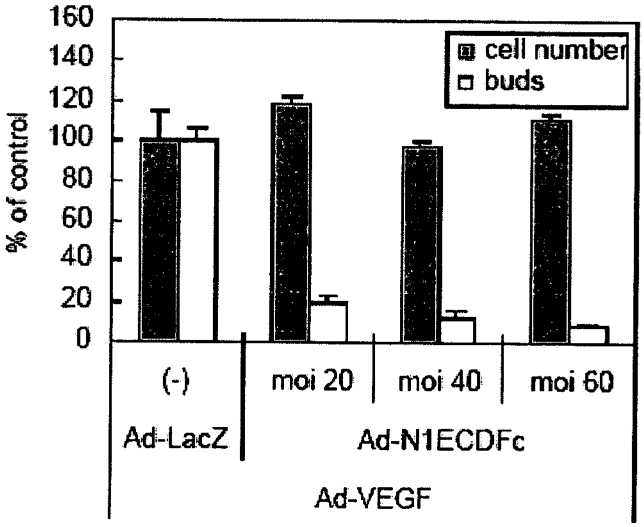

These Figures show that VEGF activates Notch signaling to induce HUVEC budding. HUVEC were transduced with Ad-VEGF at 40 MOI (FIGS. 22A, 22H, 22I) or 20 MOI (FIGS. 22C, 22G). Ad-LacZ was co-transduced to HUVEC to make the same total amount of adenovirus 60 MOI (FIG. 22G), 80 MOI (FIG. 22A) and 100 MOI (FIGS. 22H, 22I). FIG. 22A shows RT-PCR analysis of Notch and Notch ligand expression. Numbers show PCR cycles. FIG. 22B shows the effect of transduced VEGF on CSL reporter activity. FIG. 22C shows the effect of SU5416 on CSL reporter activity transactivated by Ad-VEGF. FIG. 22D shows the construct of Notch decoy (N1ECDFc). FIG. 22E shows secretion of N1ECDFc from HUVEC trasduced with Ad-N1ECDFc. FIG. 22F shows the effect of N1ECDFc against ligand-induced CSL reporter activity in a co-culture assay (□: (–); ■: 0.33 ng pHyTC-N1ECDFc; ■: 0.67 ng pHyTC-N1ECDFc). FIGS. 22G-I show the effect of N1ECDFc against Ad-VEGF-transduced HUVEC. Notch signaling was activated with transduction of Ad-VEGF in HUVEC in the absence or presence of co-transduction of Ad-N1ECDFc at indicated dosage. FIG. 22G shows the effect of N1ECDFc on CSL reporter activity transactivated by Ad-VEGF. FIG. 22H shows inhibition of budding of Ad-VEGF-transduced HUVEC with co-transduction of Ad-N1ECDFc at 40 MOI. FIG. 22I shows quantification of the effect of N1ECDFc on budding of Ad-VEGF-transduced HUVEC (□: bud; ■: cell number).

FIGS. 23A-23J

Figure 23A:
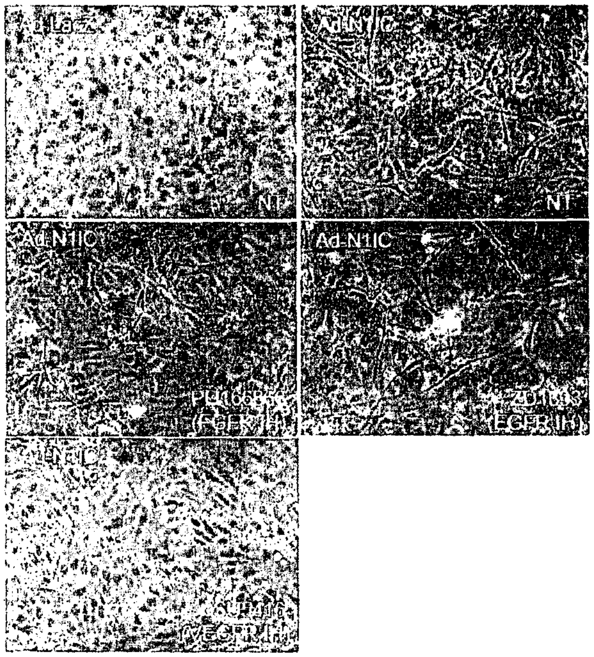
Figure 23B:
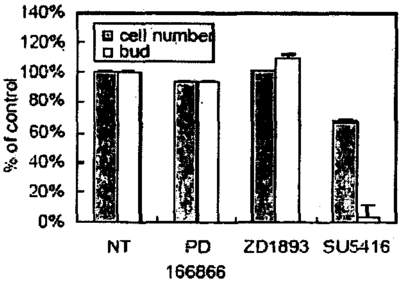
Figure 23C:
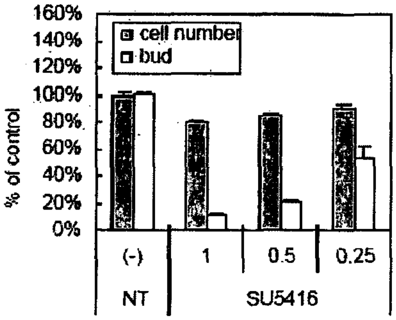
Figure 23D:
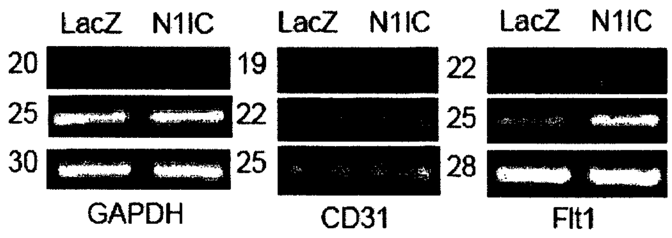
Figure 23E:
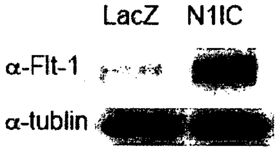
Figure 23F:
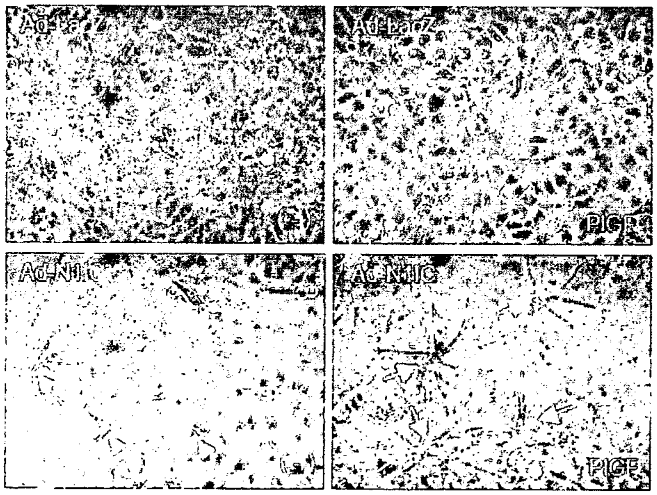
Figure 23G:
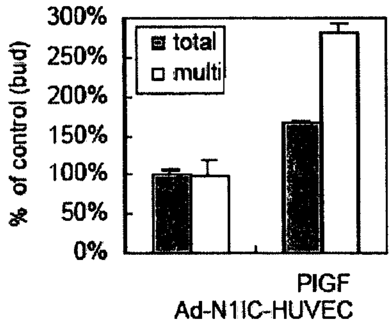
Figure 23H:
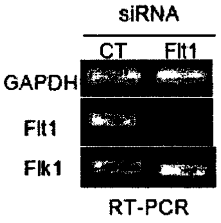
Figure 23I:
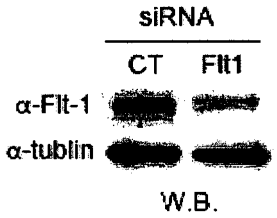
Figure 23J:
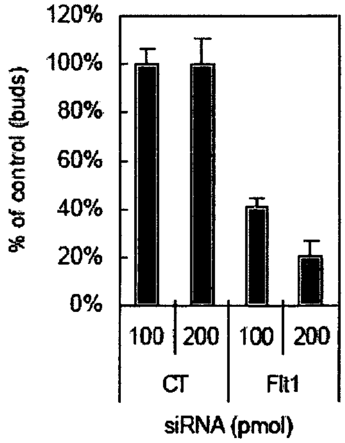

These Figures show that Notch signaling up-regulates Flt1 expression to induce HUVEC budding. HUVEC were transduced with either Ad-LacZ or Ad-N1IC at 40 MOI. FIGS. 23A-23C show the effect of inhibitors for receptor tyrosine kinases on Notch-induced HUVEC budding. FIG. 23A is a photograph of budding of Ad-N1IC-transduced HUVEC treated with PD166866, ZD1893 at 1 μm and SU5416 at 0.5 μm. FIG. 23B shows quantification of the effect of inhibitors at 1 μM (□: bud; ■: cell number). FIG. 23C shows dose-dependency of the effect of SU5416 (□: bud; ■: cell number). FIGS. 23D-E show induction of Flt-1 expression in Ad-N1IC-transduced HUVEC. FIG. 23D shows RT-PCR analysis of Flt-1 mRNA expression. FIG. 23E shows W. B. analysis of Flt-1 protein expression. FIGS. 23F-G show promotion of Notch-induced HUVEC budding with P1GF stimulation. Ad-N1IC-transduced HUVEC were cultured on collagen gel with SFM, instead of complete medium, in the absence or presence of 50 ng/ml P1GF. FIG. 23F shows P1GF-induced budding of Ad-N1IC-transduces HUVEC (arrow head: buds with single filopodia; arrow: buds with multiple filopodia). FIG. 23G shows the quantification of the effect of P1GF on budding of Ad-N1IC-transduced HUVEC (□: multi; ■: total). FIGS. 23H-I show the effect of Flt-1 siRNA transfection on Flt1 expression. Ad-N1IC-transduced HUVEC were transfected with 200 pmol of either control (CT) or Flt-1 siRNA. FIG. 23H shows the reduction of Flt-1 mRNA expression. FIG. 23I shows the reduction of Flt-1 protein expression. FIG. 23J shows the effect of Flt-1 siRNA transfection on Notch-induced HUVEC budding. Ad-N1IC-transduced HUVEC were transfected with either 100 or 200 pmol of siRNA and cultured on collagen gel for 2 days.

FIGS. 24A-24E

Figure 24A:
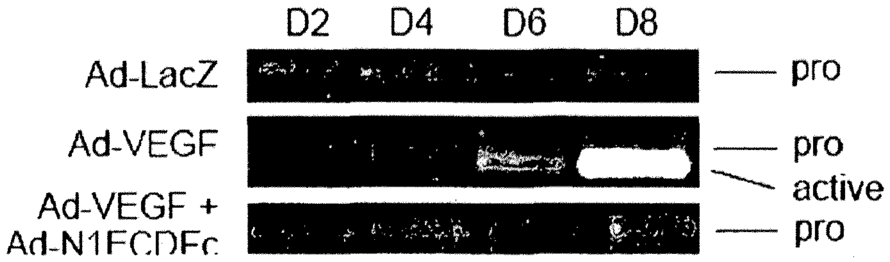
Figure 24B:
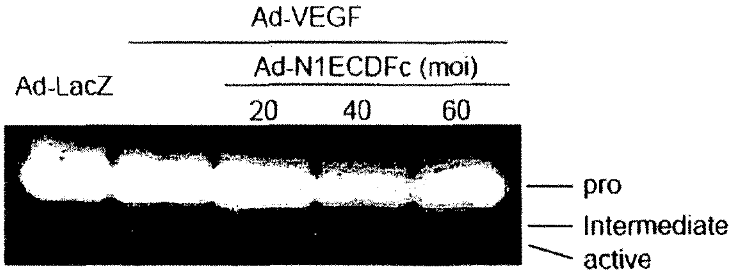
Figure 24C:
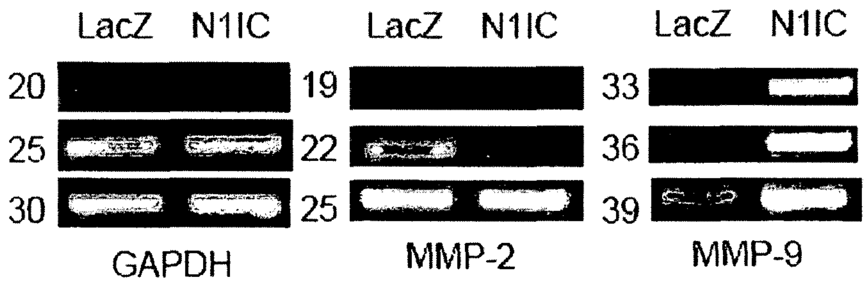
Figure 24D:
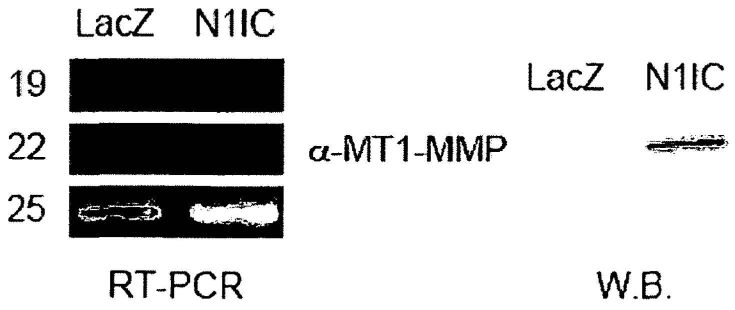
Figure 24E:
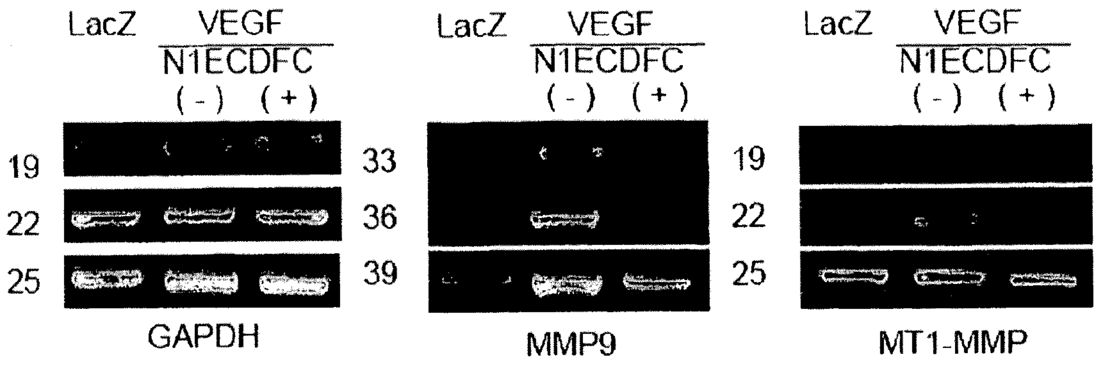

These Figures show that VEGF regulates gelatinase activity via Notch signaling by up-regulation of both MMP-9 and MT1-MMP. FIGS. 24A-B show gelatin zymography analysis of MMP-9 and MMP-2 activity stimulated by VEGF in HUVEC. FIG. 24A shows the effect of N1ECDFc on MMP-9 activity. Transduced HUVEC were cultured on fibrin gel on the indicated day (i.e. D2, D4, D6, D8). Similar results were also obtained by using collagen gel, although induction of MMP-9 was stronger on fibrin gel than collagen gel (data not shown). FIG. 24B shows the effect of N1ECDFc on MMP-2 activity. HUVEC were transduced with Ad-N1ECDFc at the indicated doses and condition medium was collected from HUVEC cultured on collagen gel at day 4. FIGS. 24C-D show up-regulation of MMP-9 and MT1-MMP with Notch signaling. HUVEC were transduced with either Ad-LacZ or Ad-N1IC at 40 MOI. Numbers show PCR cycles. FIG. 24C shows RT-PCR analysis of the effect of Notch signaling on expression of MMP-9 and MMP-2. FIG. 24D shows the induction of MT1-MMP expression of both transcript and protein with Notch signaling. FIG. 24E shows RT-PCR analysis of MMP-9 and MT1-MMP expression in Ad-VEGF-HUVEC with co-transduction of Ad-N1ECDFc. HUVEC were transduced with Ad-VEGF in the absence or presence of co-transduction of Ad-N1ECDFc at 40 MOI each. Ad-LacZ was co-transduced to make the same total amount of adenovirus at 80 MOI.

FIGS. 25A-25D

Figure 25A:
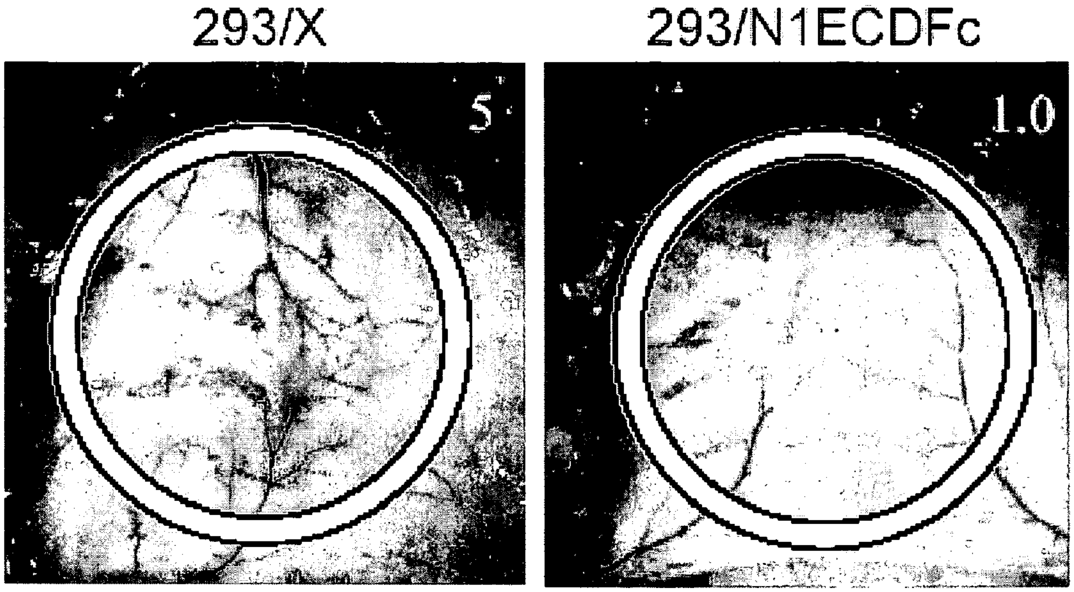
Figure 25:
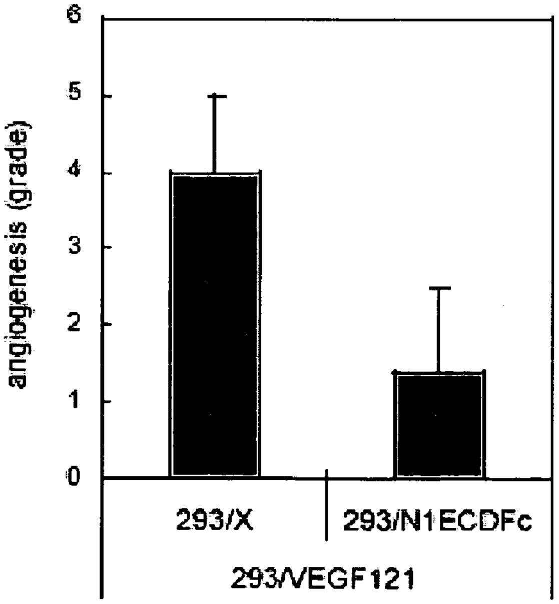
Figure 25C:
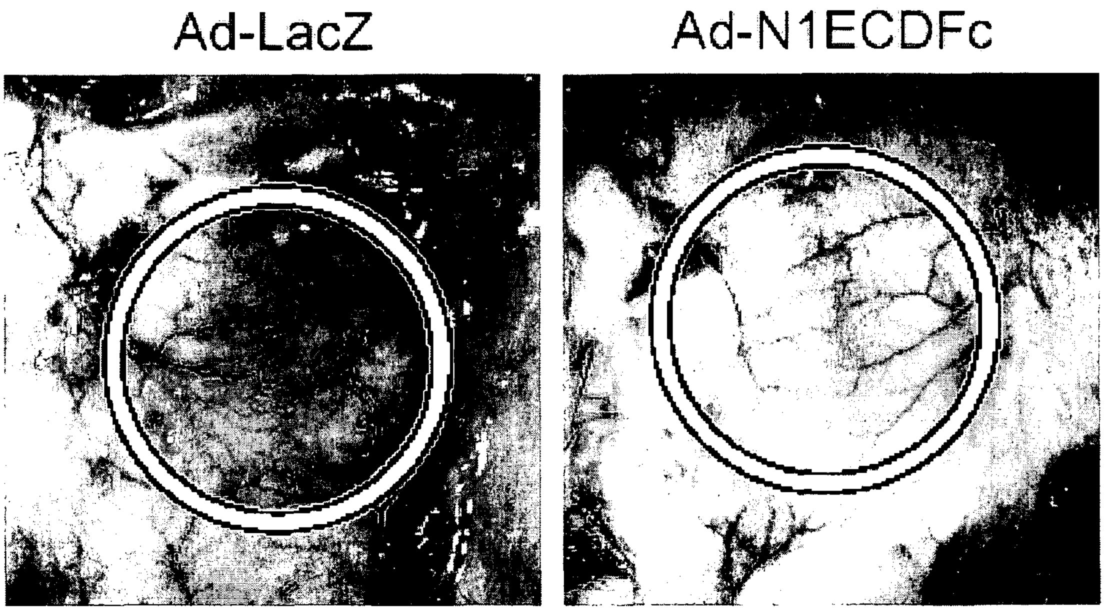
Figure 25D:
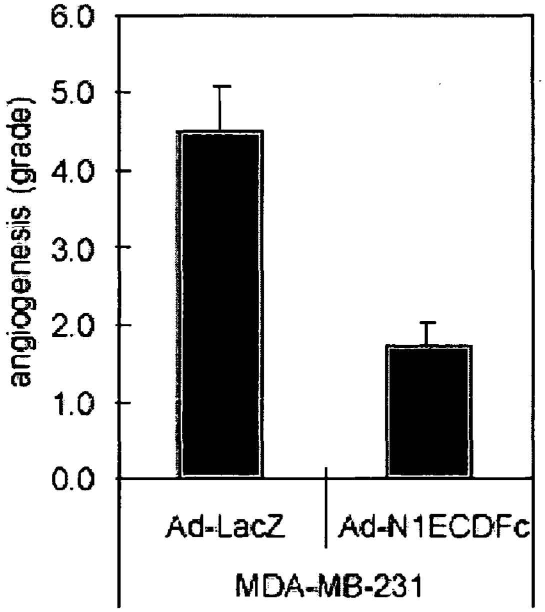

These Figures show the role of Notch signaling in VEGF-dependent in vivo angiogenesis. FIGS. 25A-25D show inhibition of VEGF-induced angiogenesis with N1ECDFc in mouse DAS assay. Representative photographs are shown. FIG. 25A show subcutaneous induced angiogenesis with 293/VEGF transfectant versus 293/VEGF also expressing Notch decoy (Notch-based fusion protein) N1ECDFc. FIG. 25B shows the quantitation of degree of vascularization induced by 293/VEGF in control versus 293 expressing Notch decoy (Notch-based fusion protein) N1ECDFc. FIG. 25C shows subcutaneous induced angiogenesis with Ad-LacZ infected MDA-MB-231 cells versus Ad-N1ECDFc (Notch-based fusion protein) infected MDA-MB-231 cells. MDA-MB-231 breast cancer cells produce VEGF (data not shown). FIG. 25D shows quantitation of degree of vascularization induced by Ad-LacZ infected MDA-MB-231 cells versus Ad-N1ECDFc (Notch-based fusion protein) infected MDA-MB-231 cells.

Figure 26A:
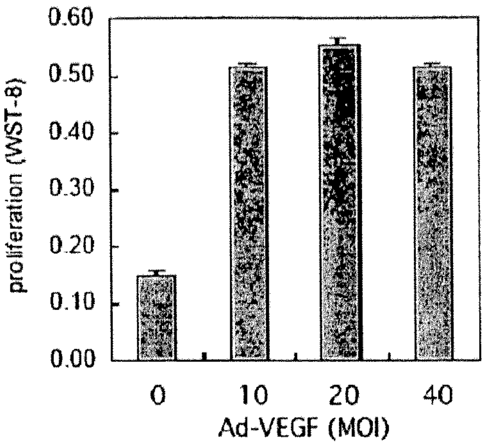
Figure 26B:
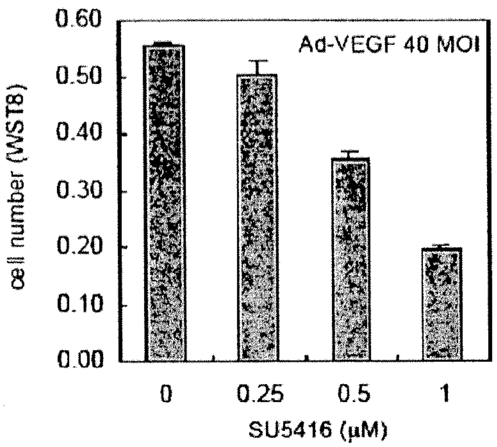

FIGS. 26A and 26B

These Figures show proliferation of Ad-VEGF165-transduced HUVEC. HUVEC were transduced with Ad-VEGF165 at the indicated dosages. Ad-LacZ was also co-infected to make the same total amount of adenovirus at a MOI of 40 pfu/cell. HUVEC were suspended in SFM supplemented with 1% FBS and then plated at $1\times10^4$ cells/well in 24-well multi-wll plates with 0.4 ml of medium. After 4 days, cell numbers were determined using the CCK-8 kit and the results are indicated as the ratio of cell numbers determined to the number of control cells, which were transduced with Ad-GFP at a MOI of 40 pfu/cell. FIG. 26A shows the effect of transduced VEGF on proliferation. FIG. 26B shows the inhibitory effect of SU5416. Ad-VEGF-transduced HUVEC were treated with SU5416 at the indicated dosages.

Figure 27A:
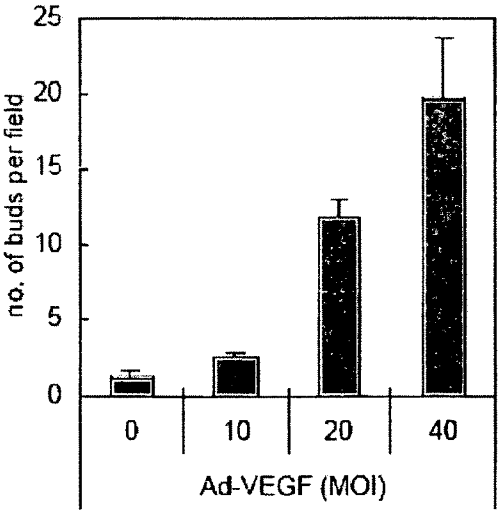
Figure 27B:
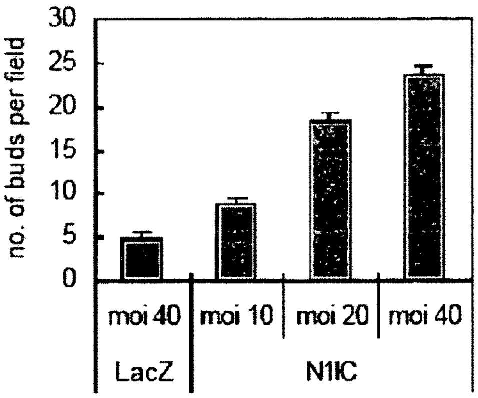

FIGS. 27A and 27B

These Figures show the induction of HUVEC buds on type I collagen gel. HUVEC were transduced with either Ad-VEGF165 or AD-N1IC at the indicated dosages. Ad-LacZ was also co-infected to make the same total amount of adenovirus at a MOI of 40 pfu/cell. Transduced HUVEC were cultured on collagen gel with complete medium. The amount of budding was evaluated under microscopy at day 7.

Figure 28A:
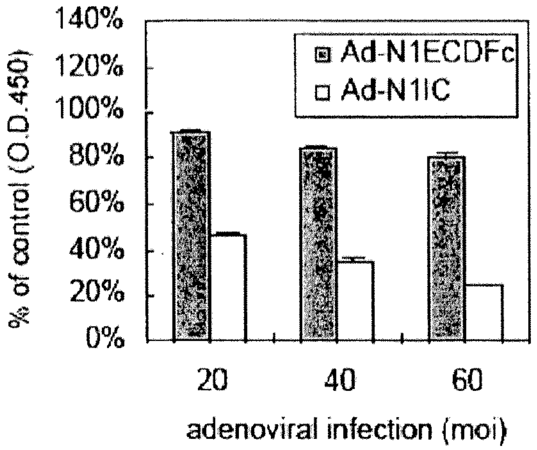
Figure 28B:
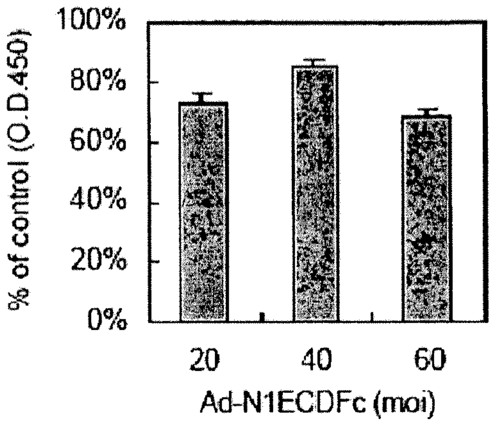

FIGS. 28A and 28B

These Figures show the effect of alteration of Notch signaling on cell proliferation. The cells were transduced with the indicated adenoviruses. Ad-GFP was also co-infected to make the same total amount of adenovirus at a MOI of 60 pfu/cell. After 4 days, cell numbers were determined using the CCK-8 kit and results are indicated as the ratio of cell numbers determined to the number of control cells, which were transduced with AD-GFP at MOI of 60 pfu/cell. FIG. 28A shows the effect of transduced N1IC and Notch fusion protein on the proliferation of HUVEC. Transduced HUVEC were suspended in complete medium and then plated at $1\times10^4$ cells/well in 24-well multiwell plates with 0.4 ml of indicated medium (□: Ad-N1IC; ■: Ad-N1ECDFc). FIG. 28B shows the effect of Notch fusion protein on proliferation of KP1/VEGF transfectants. Transduced KP1/VEGF transfectants were suspended in RPMI1640 medium and then plated at $2\times10^4$ cells/well in 24-well multiwell plates with 0.5 ml of medium.

FIG. 29

This Figure shows the RT-PCR analysis of induction of PIGF expression in Ad-N1IC-transduced HUVEC. HUVEC were infected with either Ad-LacZ or Ad-N1IC at a MOI of 40 pfu/cell. Total RNA was isolated from transduced HUVEC cultured on collagen gel for 5 days with complete medium.

FIGS. 30A-30C

Figure 30A:
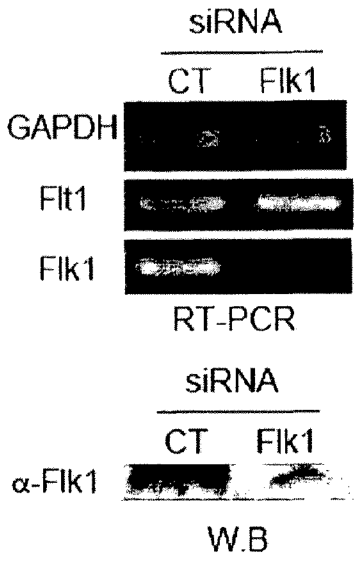
Figure 30B:
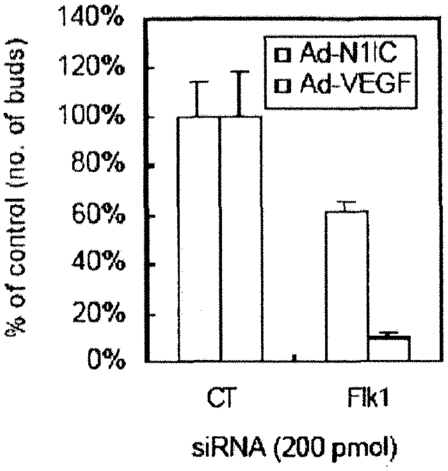
Figure 30C:
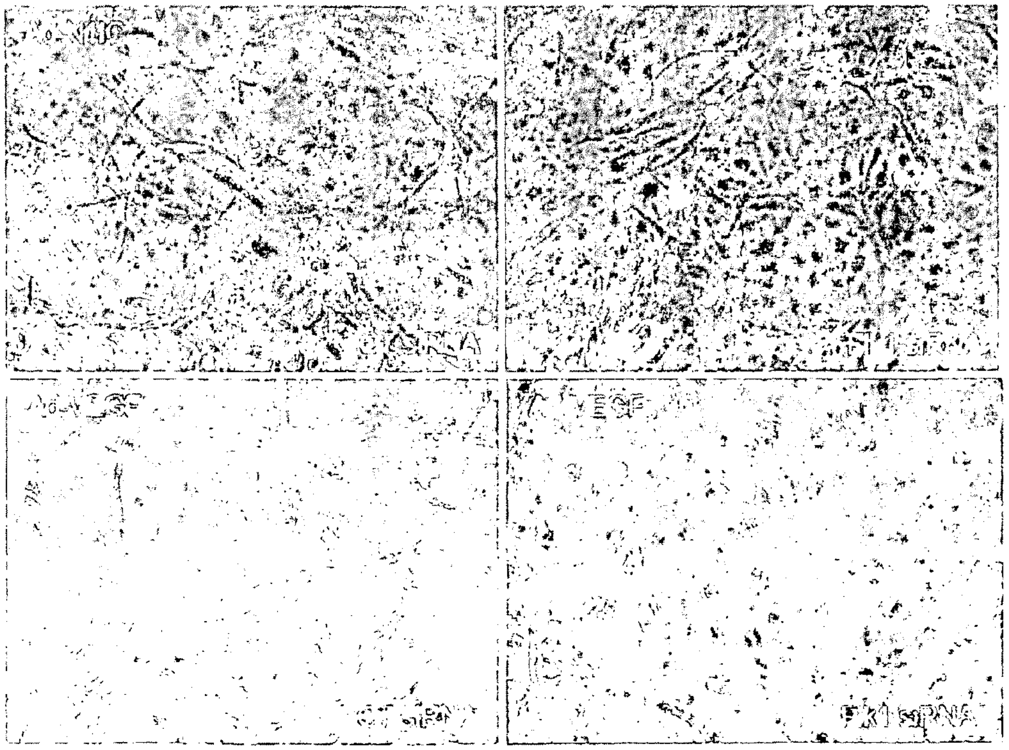

These Figures show inhibition of budding of either Ad-N1IC- or Ad-VEGF-transduced HUVEC with Flk-1 siRNA transfection. FIG. 30A shows reduction of Flk-1 mRNA and protein expression in Ad-VEGF-HUVEC with transfection of 200 pmol Flk-1 siRNA. Ad-VEGF-HUVEC at a MOI of 40 pfu/cell were transfected with 200 pmol of either control (CT) or Flk-1 siRNA. Total RNA was isolated 48 hours after transfection. Total cell lysate was collected from serum starved cells with SFM for 48 hours after transfection. FIGS. 30B and 30C show the inhibitory effect of Flk-1 siRNA transfection on either VEGF or Notch-induced HUVEC buds. Either Ad-N1IC- or Ad-VEGF-HUVEC at a MOI of 40 pfu/cell were transfected with 200 pmol of siRNA as indicated and cultured on collagen gel for 5 days. FIG. 30B shows the effect of Flk-1 siRNA transfection on HUVEC buds (□: Ad-VEGF; ■: Ad-N1IC). FIG. 30C shows quantification of the inhibitory effect of Flk-1 siRNA transfection.

Figure 31A:
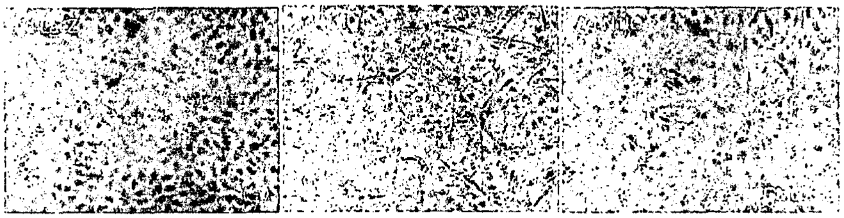
Figure 31B:
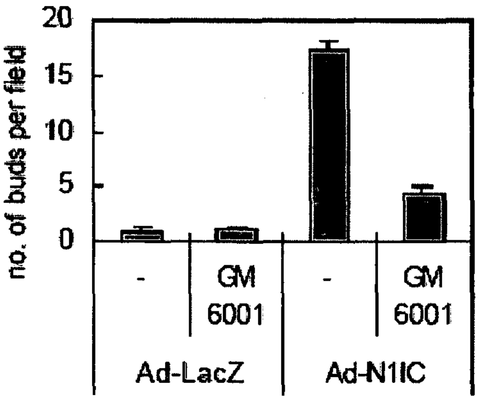

FIGS. 31A and 31B

These Figures show inhibition of budding of Ad-N1IC-transduced HUVEC with treatment of matrix metallo-proteinase inhibitor GM6001. Either Ad-LacZ or Ad-N1IC-HUVEC at a MOI of 40 pfu/cell were cultured on collagen gel for 5 days in the absence or presence of GM6001 at 50 μm. FIG. 31A shows the effect of GM6001 on Notch-induced HUVEC buds. FIG. 31B shows quantification of the inhibitory effect of GM6001.

FIGS. 32A, 32B and 32C:

This Figure shows the full-length nucleotide sequence of human Notch3 (SEQ ID NO:15), consisting of the initiating ATG (nt 1) to the stop (TGA; nt 6964). The signal peptide and first 34 EGF-like repeat domains are present in nt 1-4158 of this sequence. Nucleotides 1-4158 are utilized for the design of the human Notch3 decoy proteins, described herein. The nucleotides encompassing EGF-repeats 1-34 are underlined.

FIG. 33:

This Figure shows the full-length amino acid (aa) sequence of human Notch3 (SEQ ID NO:16), consisting of as 1(M=methionine) to as 2555 (K=lysine). The signal peptide and first 34 EGF-like repeat domains are present in as 1-1386 of this sequence. Amino acids 1-1386 are utilized for the design of the human Notch3 decoy proteins, described in the ensuing sections. The amino acids encompassing EGF-repeats 1-34 are underlined.

FIG. 34

This figure shows the schematization of two human Notch3 decoy proteins, h-Notch3$^{(1-34)}$decoy and h-sp$^{HC}$-Notch3$^{(1-34)}$ decoy.

FIG. 35

This figure shows the human Fc nucleotide sequence utilized to generate the Fc tag on Notch3 decoy proteins (SEQ ID NO:17). The 713 nucleotides of human Fc are fused at the 3'-end of the Notch3 decoy construct, just downstream of Notch3 EGF-like repeats. This region of human Fc allows for the detection and purification of the Notch decoys and serves to stabilize the secreted human Notch3-human Fc fusion proteins.

FIG. 36

This figure shows the human Fc amino acid sequence utilized to generate the Fc tage on Notch3 decoy proteins (SEQ ID NO:18). The 237 amino acids of human FC were fused at the C-terminus of all Notch3 decoy constructs, just downstream of the Notch3 EGF-like repeats. This region of human Fc allows for the detection and purification of the Notch decoys and serves to stabilize the secreted human Notch3-human Fc fusion proteins.

FIG. 37:

This figure shows the human Notch3/Fc fusion sequence for all constructs that end after EGF repeat 34 of human Notch 3.

FIG. 38

This Figure shows the signal sequence analysis of human Notch3 signal peptide that is predicted to encompass amino acids 1-40 of human Notch3. This determination was made using the signal IP 3.0 Server program provided by the Technical University of Denmark. These results predict a major site of cleavage located between alanine 39 (A39) and alanine 40 (A40). The cleavage site is indivated by the "/" in amino acid sequence 1-40 of human Notch3 as depicted in this figure.

FIG. 39:

This Figure shows the signal sequence analysis of human HC signal peptide that is predicted to encompass amino acids 1-22 of human HC. This determination was made using the signal IP 3.0 Server program provided by the Technical University of Denmark. These results predict a major site of cleavage located between alanine 21 (A21) and aringine 22 (A22). This cleavage site is indivated by the "/" in amino acid sequence 1-22 of human HC provided above.

FIGS. 40A and 40B:

This Figure shows the nucleotide sequence of h-Notch3$^{(1-34)}$ decoy protein (SEQ ID NO:31). The predicted human Notch3 signal peptide is underlined (nt 1-120). Notch3 EGF repeats 1-34 are encoded from nt 121-4158. The fusion junction, BglII site, is located at nt 4158-4163. The Fc tag sequence is underlined and italicized.

FIG. 41

This Figure shows the amino acid sequence of h-Notch3$^{(1-34)}$ decoy protein (SEQ ID NO:32). The predicted human Notch3 signal peptide is underlined (AA 1-40). Notch3 EGF repeats 1-34 are encoded from aa 41-1386. The FC tag sequence is underlined and italicized.

FIG. 42

This Figure shows the amino acid sequence of h-sp$^{HC}$-Notch3$^{(1-34)}$ decoy protein (SEQ ID NO:33). The predicted human Notch3 signal peptide is underlined (AA 1-22). Notch3 EGF repeats 1-34 are encoded from aa 22-1386. The FC tag sequence is underlined and italicized.

FIGS. 43A and 43B

This Figure shows the nucleotide sequence of h-sp$^{HC}$-Notch3$^{(1-34)}$ decoy protein (SEQ ID NO:34). The predicted human HC signal peptide is underlined (nt 1-66). Notch3 EGF-repeats are encoded from nt 67-4104. The fusion junction, BglII site, is from nt 4104 to 4109. The Fc tag sequence is underlined and italicized.

FIG. 44

This Figure shows expression of Notch proteins and ligands in blood and lymphatic endothelial cells. RT-PCT was performed for Notch1-4, Dll4, Dll4 and Jagged1 on RNA isolated from blood endothelial cells (BEC) and lymphatic endothelial cells (LEC) purified from HMVEC. Notch1, Notch1, Notch4, Dll4 and Jagged1 were expressed in both BEC and LEC at a similar level. Expression of Notch 3 appears to be restricted to the LEC suggestive of Notch3 signaling functions in the lymphatic endothelium.

FIG. 45

This Figure shows Notch3 is co-expressed with the lymphatic endothelial cell marker LYVE-1 and Prox1 in e13.5 embryos. 10 micron serial sections of embryonic day 13.5 mouse embryos were immunostained for either LYVE-1, Prox1 and Notch3. Notch3 was expressed in the cells that also expressed the lymphatic endothelial cell markers, LYVE-1 and Prox1.

FIG. 46

This Figure shows Prox1 induced Notch3 expression in blood endothelial cells. (A) It was examined if extopic expression of Prox1 would alter the expression of Notch proteins or ligands. Twenty-four hours post adenoviral infection with either Ad-Prox1 or Ad-LacZ, HUVEC total RNA was isolated and quantitative RT-PCR for Notch1-4, Dll4 and Jagged1 performed. Prox-1 robustly upregulated the expression of Notch3. Notch1, Notch2, Notch4, Dll4 and Jagged1 expression was not significantly affected. (B) Compound E (cE), Presenlin inhibitor that inhibits Notch signaling, was incubated for 24 hours on either Ad-LacZ or Ad-Prox1 infected HUVEC. Total RNA was isolated and quantitative PCR performed to determine Notch3 expression. Prox1 induced Notch3 expression and this induction was inhibited by the addition of compound E. This suggests that the Prox1 induction of Notch3 is dependent on Notch signal activation.

FIG. 47

This figure shows that Prox1 induces Notch-target genes in blood endothelial cells. HUVEC were infected with adenoviruses encoding, LacZ, Prox1, N1IC or N4/int-3 and total RNA isolated 24 hours post-infection. Quantitative RT-PCR was performed for the endothelial Notch-target genes, VEGFR-3, EphrinB2, Hey1 and Hey2. Similar to Notch1 and Notch4 signal activation, Prox1 induced all four genes (A and W. Expression of Hey1 and Hey2 in the lymphatic endothelium is unknown.

FIG. 48

This Figure shows that Prox1 induces Notch-target genes is dependent on Notch signaling in blood endothelial cells. HUVEC were infected with adenoviruses encoding LacZ, Prox1, N1Ic or N4/int-3. Compound E(cE), Presenlin inhibitor that inhibits Notch signaling, was incubated for 24 hours on either Ad-LacZ or Ad-Prox1 infected HUVEC and total RNA isolated. Quantitative RT-PCR was performed for the endothelial Notch-target genes, VEGFR-3, EphrinB2, and Hey2. The Prox-1 mediated induction of the Notch target genes, ephrinB2, VEGFR-3 and Hey2 was inhibited by the addition of the Notch signaling inhibitor Compound E. Thus, Prox1 regulates the expression of ephrinB2, VEGFR-3 and Hey2 via Notch.

FIG. 49

This figure shows a Schematic of N1IC knock in. An activated form of Notch1 was inserted into the EF1 alpha locus flanked by two LoxP sites. Upon expression of Cre-recombinase, the neo/tpA cassette is lost and N1IC is expressed under the control of the ubiquitous EF1 alpha promoter.

FIG. 50:

This Figure shows Notch activation in SM22 expressing vascular smooth muscle cells results in embryonic lethality before E10.5. No viable SM22Cre/+; EF1αN1IC/mice were observed at postnatal day 21 (P21) with a p value less than 0.001. At embryonic day E9.5, an predicted number of SM22Cre/+; EF1αN1IC/+ embryos were observed, but they were severely growth retarded compared with their control litter mates (Lower panel).

FIG. 51:

This Figure shows Notch activation in SM22 expressing vascular smooth muscle cells alters alpha smooth muscle cell actin expression. E9.5 embryos were wholemount immunostained for alpha smooth muscle cell actin. Expression of alpha smooth muscle cell actin was altered in the SM22Cre/+; EF1αN1IC/+ embryos compared to the WT controls. Thus, Notch signal activation in vascular smooth muscle cells disrupts cardiovascular development.

DETAILED DESCRIPTION OF THE INVENTION

Terms

As used in this application, except as otherwise expressly provided herein, each of the following terms shall have the meaning set forth below.

"Administering" may be effected or performed using any of the methods known to one skilled in the art. The methods comprise, for example, intralesional, intramuscular, subcutaneous, intravenous, intraperitoneal, liposome-mediated, transmucosal, intestinal, topical, nasal, oral, anal, ocular or otic means of delivery.

"Affixed" shall mean attached by any means. In one embodiment, affixed means attached by a covalent bond. In another embodiment, affixed means attached non-covalently.

"Amino acid," "amino acid residue" and "residue" are used interchangeably herein to refer to an amino acid that is incorporated into a protein, polypeptide or peptide. The amino acid can be, for example, a naturally occurring amino acid or an analog of a natural amino acid that can function in a manner similar to that of the naturally occurring amino acid.

"Antibody" shall include, without limitation, (a) an immunoglobulin molecule comprising two heavy chains and two light chains and which recognizes an antigen; (b) a polyclonal or monoclonal immunoglobulin molecule; and (c) a monovalent or divalent fragment thereof. Immunoglobulin molecules may derive from any of the commonly known classes, including but not limited to IgA, secretory IgA, IgG, IgE and IgM. IgG subclasses are well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Nonhuman antibodies may be humanized by recombinant methods to reduce their immunogenicity in humans. Antibody fragments include, without limitation, Fab and $F_c$ fragments. The "Fc portion of an antibody", in one embodiment, is a crystallizable fragment obtained by papain digestion of immunoglobulin that consists of the C-terminal half of two heavy chains linked by disulfide bonds and known as the "effector region" of the immunoglobulin. In another embodiment, "Fc portion of an antibody" means all, or substantially all, of one C-terminal half of a heavy chain.

"Humanized", with respect to an antibody, means an antibody wherein some, most or all of the amino acids outside the CDR region are replaced with corresponding amino acids derived from a human immunoglobulin molecule. Small additions, deletions, insertions, substitutions or modifications of amino acids are permissible as long as they do not abrogate the ability of the antibody to bind a given antigen. Suitable human immunoglobulin molecules include, without limitation, IgG1, IgG2, IgG3, IgG4, IgA and IgM molecules. Various publications describe how to make humanized antibodies, e.g., U.S. Pat. Nos. 4,816,567, 5,225,539, 5,585,089 and 5,693,761, and PCT International Publication No. WO 90/07861.

As used herein, the term "composition", as in pharmaceutical composition, is intended to encompass a product comprising the active ingredient(s) and the inert ingredient(s) that make up the carrier, as well as any product which results, directly or indirectly from combination, complexation, or aggregation of any two or more of the ingredients, or from dissociation of one or more of the ingredients, or from other types of reactions or interactions of one or more of the ingredients.

As used herein, "effective amount" refers to an amount which is capable of treating a subject having a tumor, a disease or a disorder. Accordingly, the effective amount will vary with the subject being treated, as well as the condition to be treated. A person of ordinary skill in the art can perform routine titration experiments to determine such sufficient amount. The effective amount of a compound will vary depending on the subject and upon the particular route of administration used. Based upon the compound, the amount can be delivered continuously, such as by continuous pump, or at periodic intervals (for example, on one or more separate occasions). Desired time intervals of multiple amounts of a particular compound can be determined without undue experimentation by one skilled in the art. In one embodiment, the effective amount is between about 1 μg/kg-10 mg/kg. In another embodiment, the effective amount is between about 10 μg/kg-1 mg/kg. In a further embodiment, the effective amount is 100 μg/kg.

"Extracellular domain" as used in connection with Notch receptor protein means all or a portion of Notch which (i) exists extracellularly (i.e. exists neither as a transmembrane portion or an intracellular portion) and (ii) binds to extracellular ligands to which intact Notch receptor protein binds. The extracellular domain of Notch may optionally include a signal peptide. "Extracellular domain", "ECD" and "Ectodomain" are synonymous.

"Half-life-increasing moiety" means a moiety which, when operably affixed to a second moiety, increases the in vivo half-life of the second moiety. Half-life-increasing moieties include, for example, Fc portions of antibodies, glycosylation tags (i.e. glycosylated polypeptides), polyethylene glycol (PEG), polypeptides having PEG affixed thereto, and lipid-modified polypeptides.

"Inhibiting" the onset of a disorder or undesirable biological process shall mean either lessening the likelihood of the disorder's or process' onset, or preventing the onset of the disorder or process entirely.

In the preferred embodiment, inhibiting the onset of a disorder or process means preventing its onset entirely.

"Notch", "Notch protein", and "Notch receptor protein" are synonymous. In addition, the terms "Notch-based fusion protein" and "Notch decoy" are synonymous. The following Notch amino acid sequences are known and hereby incorporated by reference: Notch1 (Genbank accession no. S18188 (rat)); Notch2 (Genbank accession no. NP_077334 (rat)); Notch3 (Genbank accession no. Q61982 (mouse)); and Notch4 (Genbank accession no. T09059 (mouse)). The following Notch nucleic acid sequences are known and hereby incorporated by reference: Notch1 (Genbank accession no. XM_342392 (rat) and NM_017617 (human));

Notch2 (Genbank accession no. NM_024358 (rat), M99437 (human and AF308601 (human)); Notch3 (Genbank accession no. NM_008716 (mouse) and XM_009303 (human)); and Notch4 (Genbank accession no. NM_010929 (mouse) and NM_004557 (human)).

The terms “nucleic acid”, “polynucleotide” and “nucleic acid sequence” are used interchangeably herein, and each refers to a polymer of deoxyribonucleotides and/or ribonucleotides. The deoxyribonucleotides and ribonucleotides can be naturally occurring or synthetic analogues thereof. “Nucleic acid” shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA). Nucleic acids include, without limitation, anti-sense molecules and catalytic nucleic acid molecules such as ribozymes and DNAzymes. Nucleic acids also include nucleic acids coding for peptide analogs, fragments or derivatives which differ from the naturally-occurring forms in terms of the identity of one or more amino acid residues (deletion analogs containing less than all of the specified residues; substitution analogs wherein one or more residues are replaced by one or more residues; and addition analogs, wherein one or more resides are added to a terminal or medial portion of the peptide) which share some or all of the properties of the naturally-occurring forms.

“Operably affixed” means, with respect to a first moiety affixed to a second moiety, affixed in a manner permitting the first moiety to function (e.g. binding properties) as it would were it not so affixed.

The terms “polypeptide,” “peptide” and “protein” are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, “pharmaceutically acceptable carrier” means that the carrier is compatible with the other ingredients of the formulation and is not deleterious to the recipient thereof, and encompasses any of the standard pharmaceutically accepted carriers. Such carriers include, for example, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer’s dextrose, dextrose and sodium chloride, lactated Ringer’s and fixed oils. Intravenous vehicles include fluid and nutrient replenishers, electrolyte replenishers such as those based on Ringer’s dextrose, and the like. Preservatives and other additives may also be present, such as, for example, antimicrobials, antioxidants, chelating agents, inert gases, and the like.

“Subject” shall mean any organism including, without limitation, a mammal such as a mouse, a rat, a dog, a guinea pig, a ferret, a rabbit and a primate. In the preferred embodiment, the subject is a human being.

“Treating” means either slowing, stopping or reversing the progression of a disease or disorder. As used herein, “treating” also means the amelioration of symptoms associated with the disease or disorder. Diseases include, but are not limited to, Tumor Angiogenesis, Atherosclerosis, Wound Healing, Macular degeneration, Retinopathy of Prematurity, Pre-eclampsia, Diabetic retinopathy, Ischemia, Stroke, Cardiovascular Disease, and Psoriasis.

Angiogenesis is encountered during wound healing processes, the female menstrual cycle and endometrial remodeling, as well as during embryonic development and organ growth. In the pathological setting, angiogenesis plays an important role in different diseases like rheumatoid arthritis, psoriasis, macular degeneration, diabetic retinopathy, and tumor growth.

There has been considerable evidence in vivo, including clinical observations, that abnormal angiogenesis is implicated in a number of disease conditions, which include rheumatoid arthritis, inflammation, cancer, psoriasis, degenerative eye conditions and others.

Units, prefixes and symbols may be denoted in their SI accepted form. Unless otherwise indicated, nucleic acid sequences are written left to right in 5' to 3' orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The following abbreviations are used herein: ECD: extracellular domain; IC: intracellular domain; NECD/Fc: Notch-based fusion protein; N1: Notch1; N2: Notch2; N3: Notch3; N4: Notch4; Dll: Delta-like; EC: endothelial cells; FGF: fibroblast growth factor; FGFR: fibroblast growth factor receptor; HUVEC: human umbilical vein endothelial cell; m.o.i.: multiplicity of infection; VMC: vascular mural cells; VEGF: vascular endothelial cell growth factor; VEGFR: vascular endothelial cell growth factor receptor; sp: signal peptide.; HC or Hc: Heavy Chain IgG; PDGF: Platelet derived growth factor; P1GF: placental growth factor;

EMBODIMENTS OF THE INVENTION

This invention provides a fusion protein comprising a signal peptide, EGF repeats 1-X of the extracellular domain of human Notch3 receptor protein wherein X is any integer from 12 to 34, and an Fc portion of an antibody bound thereto.

This invention provides a fusion protein comprising a signal peptide, EGF repeats 1-X of the extracellular domain of human Notch3 receptor protein wherein X is any integer from 1 to 10, and an Fc portion of an antibody bound thereto.

This invention provides a fusion protein comprising a signal peptide, at least 12 EGF repeats of the extracellular domain of human Notch3 receptor, and an Fc portion of an antibody bound thereto.

This invention provides a fusion protein comprising a signal peptide, EGF repeats of the extracellular domain of human Notch3 receptor protein, wherein at least 12 EGF repeats are present, and an Fc portion of an antibody bound thereto.

In one embodiment of the fusion protein, the extracellular domain of Notch3 receptor protein comprises EGF-like repeats 1-34.

In one embodiment of the dusion protein, the Fc portion of the antibody is the Fc portion of a human antibody.

In one embodiment of the fusion protein, the signal peptide is the signal peptide of Notch3 or the He (HC; Heavy Chain) portion of an antibody.

In one embodiment, the fusion protein comprises consecutive amino acids, the sequence of which is set forth in SEQ ID NO:32. In another embodiment, the fusion protein comprises consecutive amino acids, the sequence of which is set forth in SEQ ID NO:33.

In one embodiment, the fusion protein is encoded by consecutive nucleotide, the sequence of which is set forth in SEQ ID NO:31. In another embodiment, the fusion protein is encoded by consecutive nucleotide, the sequence of which is set forth in SEQ ID NO:34

This invention provides a method for treating a subject having a tumor comprising administering to the subject an amount of the above fusion protein effective to treat the subject, thereby treating the subject having a tumor.

This invention provides a method for inhibiting angiogenesis in a subject comprising administering to the subject an amount of the above fusion protein effective to inhibit angiogenesis in the subject, thereby inhibiting angiogenesis in the subject.

This invention provides a method for treating a subject having ovarian cancer comprising administering to the subject an amount of the above fusion protein effective to treat the subject, thereby treating the subject having ovarian cancer.

This invention provides use of the above fusion protein for the preparation of a pharmaceutical composition for treating a subject having cardiovascular disease. In one embodiment the cardiovascular disease is atherosclerosis, ischemia or stroke.

This invention provides use of the above fusion protein for the preparation of a pharmaceutical composition for the treatment of a subject having a tumor.

This invention provides use of the above fusion protein for the preparation of a pharmaceutical composition for inhibiting angiogenesis in a subject.

This invention provides use of the above fusion protein for the preparation of a pharmaceutical composition for treating a subject having ovarian cancer.

This invention provides a method for inhibiting physiological lymphangiogenesis or pathological lymphangiogenesis in a subject comprising administering to the subject an amount of the above fusion protein effective to inhibit physiological lymphangiogenesis or pathological lymphangiogenesis in the subject. In one embodiment the pathological lymphangiogenesis is tumor lymphangiogenesis or lymph node metastasis that may be dependent on tumor lymphangiogenesis.

This invention provides method of inhibiting tumor metastasis in a subject comprising administering to the subject an amount of the above fusion effective to inhibit tumor metastasis in the subject. In on embodiment, the metastasis occurs via a blood vessel, the lymphatic vasculature or a lymph node. Tumor metastasis is the spread of cancer from one organ to another non-adjacent organ.

This invention provides a method of inhibiting growth of a secondary tumor in a subject comprising administering to the subject an amount of the above fusion protein effective to inhibit growth of the secondary tumor in the subject. Inhibition may also be of the tumor angiogenesis associated with the secondary or metastatic tumor. In one embodiment the secondary tumor growth is inhibited by inhibition of angiogenesis associated with the secondary tumor.

This invention provides a method of inhibiting blood vessel cooption by a tumor in subject comprising administering to the subject an amount of the above fusion protein effective to inhibit blood vessel cooption by a tumor in the subject. The process of vessel cooption is a process whereby tumor cells associate with pre-existing vessels and growth with assistance of coopted vessels. This growth of tumors on coopted vessels may be in the absence of, precede, or be in conjunction with tumor angiogenesis.

This invention provides a method of treating cancer in a subject comprising administering to the subject the above fusion protein and an inhibitor of Vascular Endothelial Growth Factor (VEGF), each in an amount effective to treat the cancer in the subject. In one embodiment the inhibitor of VEGF is an inhibitor of VEGF-A, an inhibitor of PGIF, an inhibitor of VEGF-B, an inhibitor of VEGF-C, or an inhibitor of VEGF-D. Examples of VEGF-inhibitors include, but are not limited to, bevacizumab, PTK787, Bay43-9006, SU11248, AG013676, ZD6474, VEGF-trap and Anti-VEGFR2. Examples of such inhibitors are more fully described in Ferrara et al., (2004) *Nature Reviews Drug Discovery*, Vol. 3:391-400 and Ellis et al. (2008) *Nature Reviews Cancer* Vol 8:579-591, the contents of each of which are hereby incorporated by reference.

This invention provides a method of treating cancer in a subject comprising administering to the subject the above fusion protein and a VEGF receptor inhibitor, each in an amount effective to treat the cancer in the subject. In one embodiment, the VEGF receptor inhibitor is a VEGFR-1 inhibitor, a VEGFR-2 inhibitor, a VEGFR-3 inhibitor or a an inhibitor of any combination of VEGFRs.

This invention provides a method of treating cancer in a subject comprising administering to the subject the above fusion protein and an inhibitor of Platelet Derived Growth Factor (PDGF), each in an amount effective to treat the cancer in the subject. In on embodiment the inhibitor of Platelet Derived Growth Factors is an inhibitor of PDGF-A or an inhibitor of PDGF-B This invention provides a method of treating cancer in a subject comprising administering to the subject the above fusion protein and a PDGF receptor antagonist, each in an amount effective to treat the cancer in the subject. In one embodiment the PDGF receptor antagonist is a PDGF Receptor-B antagonist.

This invention provides a method of treating cancer in a subject comprising administering to the subject the above fusion protein and an inhibitor of HER2/neu, each in an amount effective to treat the cancer in the subject.

This invention provides a method of treating breast cancer in a subject comprising administering to the subject an amount of the above-fusion protein effective to treat the breast cancer in the subject.

This invention provides the use of the above fusion protein for the preparation of a pharmaceutical composition for treating a subject having breast cancer.

This invention also provides a first method for treating a subject having a tumor comprising administering to the subject an effective amount of a composition of matter comprising the extracellular domain of a Notch receptor protein operably affixed to a half-life-increasing moiety, so as to thereby treat the subject.

This invention also provides a second method for inhibiting angiogenesis in a subject comprising administering to the subject an effective amount of a composition of matter comprising the extracellular domain of a Notch receptor protein operably affixed to a half-life-increasing moiety, so as to thereby inhibit angiogenesis in the subject.

In a first embodiment of the above methods, the Notch receptor protein is Notch1 receptor protein. In one embodiment, the Notch1 receptor protein is human Notch1 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a second embodiment of the above methods, the Notch receptor protein is Notch2 receptor protein. In one embodiment, the Notch2 receptor protein is human Notch2 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a third embodiment of the above methods, the Notch receptor protein is Notch3 receptor protein. In one embodiment, the Notch3 receptor protein is human Notch3 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a fourth embodiment of the above methods, the Notch receptor protein is Notch4 receptor protein. In one embodiment, the Notch4 receptor protein is human Notch4 receptor protein. In another embodiment, the half-life-increasing moiety is an Fc portion of an antibody. In another embodiment, the Fc portion of the antibody is the Fc portion of a human antibody. In a further embodiment, the extracellular domain and the half-life-increasing moiety are within the same polypeptide chain.

In a fifth embodiment of the above methods, the subject is a mammal. In one embodiment, the mammal is a human.

In a sixth embodiment of the above methods, the angiogenesis is tumor angiogenesis.

In a further embodiment of the second method, the subject has a tumor. In another embodiment, the subject is afflicted with a pathologic vascular hyperplasia. In one embodiment, the pathologic vascular hyperplasia is a benign hemagioma. In a further embodiment, the subject is afflicted with a lymphatic vascular proliferative disease.

This invention provides a first composition of matter comprising the extracellular domain of Notch4 receptor protein operably affixed to a half-life-increasing moiety. In one embodiment, the extracellular domain is covalently bound to the half-life-increasing moiety. In another embodiment, the extracellular domain and the half-life-increasing moiety are within the same polypeptide chain.

This invention also provides a second composition of matter comprising the extracellular domain of Notch4 receptor protein operably affixed to a half-life-increasing moiety and a pharmaceutically acceptable carrier.

This invention further provides an article of manufacture comprising (i) a packaging material having therein a composition of matter comprising the extracellular domain of a Notch receptor protein operably affixed to a half-life-increasing moiety and (ii) a label indicating that the composition is intended for use in treating a subject having a tumor or other disorder treatable by inhibiting angiogenesis in the subject.

In a first embodiment of the above article, the Notch receptor protein is Notch1 receptor protein. In one embodiment, the Notch1 receptor protein is human Notch1 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a second embodiment of the above article, the Notch receptor protein is Notch2 receptor protein. In one embodiment, the Notch2 receptor protein is human Notch2 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a third embodiment of the above article, the Notch receptor protein is Notch3 receptor protein. In one embodiment, the Notch3 receptor protein is human Notch3 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In a fourth embodiment of the above article, the Notch receptor protein is Notch4 receptor protein. In one embodiment, the Notch4 receptor protein is human Notch4 receptor protein. In another embodiment, the half-life-increasing moiety is an Fc portion of an antibody. In another embodiment, the Fc portion of the antibody is the Fc portion of a human antibody. In a further embodiment, the extracellular domain and the Half-life-increasing moiety are within the same polypeptide chain.

In another embodiment of the above article, the composition is admixed with a pharmaceutical carrier. In a final embodiment, the subject is a human.

This invention provides a replicable vector which encodes a polypeptide comprising the extracellular domain of a Notch3 receptor protein operably affixed to a half-life-increasing moiety. In one embodiment, the half-life-increasing moiety is an Fc portion of an antibody. In another embodiment, the vector includes, without limitation, a plasmid, a cosmid, a retrovirus, an adenovirus, a lambda phage or a YAC.

This invention also provides a host vector system which comprises a replicable vector which encodes a polypeptide comprising the extracellular domain of a Notch receptor protein operably affixed to a half-life-increasing moiety and a suitable host cell. In one embodiment, the host cell is a eukaryotic cell. In another embodiment, the eukaryotic cell is a CHO cell. In a another embodiment, the eukaryotic cell is a HeLa cell. In a further embodiment, the host cell is a bacterial cell.

Finally, this invention provides a third method of producing a polypeptide which comprises growing a host vector system which comprises a replicable vector which encodes a polypeptide comprising the extracellular domain of a Notch receptor protein operably affixed to a half-life-increasing moiety and a suitable host cell under conditions permitting production of the polypeptide, and recovering the polypeptide so produced.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

First Series of Experiments

Human Notch3 Fusion Proteins (Notch Decoys)

The Notch3 decoys are assembled using sequences encoding a signal peptide, a portion of the Notch3 extracellular domain encompassing all the EGF-like repeat domains, and a portion of the human Fc protein (amino acids 1-237). The complete full-length nucleotide sequence of human Notch3 is provided in FIG. 32. The complete full length amino acid sequence of human Notch3 is provided in FIG. 33.

The signal peptides utilized are either the native Notch3 signal peptide or the human Hc signal peptide, each fused to a region of Notch3. The signal peptide allows for secretion of the Notch decoy proteins.

The Notch3 extracellular domains used are designed to bind to Notch ligands and consist of all or a subset of the 34 EGF-like repeat domains of the human Notch3 protein.

The Fc tag is fused to the C-terminus of a given EGF-like repeat of human Notch3 and serves to allow for purification, detection, and stabilization of the Notch3 decoy proteins.

The overall design of the human Notch3 decoys, two formulations, is to encode for; (1) a signal peptide to allow for secretion of Notch3 decoy proteins into the extracellular media of eukaryotic cells that are used to produce the proteins,(2) a portion of the extracellular domain of all the EGF-like repeats of human Notch3 to allow for association with Notch ligands, and (3) a portion of the human Fc protein to allow for detection.

The following two formulations of human Notch3 decoys will be described and are schematized in FIG. 34.

h-Notch3$^{(1-34)}$decoy 1)

h-sp$^{Hc}$Notch3$^{(1-34)}$decoy 4)

Human Notch3 Sequence

The full-length nucleotide (nt) sequence of human Notch3, consisting of the initiating ATG (nt 1) to the stop (TGA; nt 6964) is set forth in FIG. 32. The signal peptide and first 34 EGF-like repeat domains are present in nt 1-4158 of this sequence. Nucleotides 1-4158 are utilized for the design of the human Notch3 decoy proteins, described in the ensuing sections. The nucleotides encompassing EGF-repeats 1-34 are underlined.

The full-length amino acid (aa) sequence of human Notch3, consisting of as 1(M=methionine) to as 2555 (K=lysine) is set forth in FIG. 33. The signal peptide and first 34 EGF-like repeat domains are present in as 1-1386 of this sequence. Amino acids 1-1386 are utilized for the design of the human Notch3 decoy proteins, described in the ensuing sections. The amino acids encompassing EGF repeats 1-34 are underlined.

Human Fc Sequence Utilized to Generate the Fc Tag on Notch3 Decoy Proteins

The 713 nucleotides of human Fc, which are set forth in FIG. 35, are fused at the 3'-end of the Notch3 decoy construct, just downstream of Notch3 EGF-like repeats. This region of human fc allows for detection and purification of the Notch decoys and serves to stabilize the secreted human Notch3-human Fc fusion proteins.

The 237 amino acids of human Fc, shown in FIG. 36, were fused at the C-terminus of all Notch3 decoy constructs, just downstream of Notch3 EGF-like repeats. This region of human Fc allows for detection and purification of the Notch decoys and serves to stabilize the secreted human Notch3-human Fc fusion proteins.

Signal Peptides Utilized in Notch3 Decoy Proteins

Two distinct signal peptide sequences were incorporated into the design of the human Notch1 decoy proteins. The first is the human Notch3 signal peptide that is predicted to encompass amino acids 1-40 of human Notch3. This determination was made using the Signal IP 3.0 Server program provided by the Technical University of Denmark. The second is the human Hc signal peptide that is predicted to encompass amino acids 1-22 of human IgG heavy chain (HC) signal peptide.

1. Human Notch3 Signal Peptide (nt 1-20)

```
                                      (SEQ ID NO: 27)
MGPGARGRRRRRRPMSPPPPPPPVRALPLLLLLAGPGAA/A
```

Amino acid sequence of the predicted human Notch3 signal peptide is schematized in FIG. 37. The prediction results of analysis utilizing the SignalIP 3.0 Server provided online by the Technical University of Denmark are shown in FIG. 37. These results predict a major site of cleavage located between alanine 39 (A39) and alanine 40 (A40) These cleavage site is indicated by the "/" in amino acid sequence 1-40 of human Notch3, provided above.

2. Human HC Signal Peptide (aa 1-22)

The amino acid sequence of the predicted human Hc signal peptide is

```
MWGWECLLFWAVLVTATLCTA/R      (SEQ ID NO: 29)
```

The nucleotide sequence of the predicted human Hc signal peptide is:

The prediction results of analysis utilizing the SignalIP 3.0 Server provided online by the Technical University of Denmark are shown above. These results predict a major site of cleavage located between alanine 21 (A21) and arginine 22 (22). This cleavage site is indicated by the "/" in amino acid sequence 1-22 of human Hc provided above.

h-Notch3$^{(1-34)}$ Decoy h-Notch1$^{(1-34)}$ decoy denotes the human Notch3 decoy that encompass EGF-like repeats 1-34 of Notch3.

The amino acid sequence of h-Notch3$^{(1-34)}$ decoy protein which is set forth in FIG. 41. The predicted human Notch3 signal peptide is underlined (AA 1-40). Notch3 EGF-repeats 1-34 are encoded from as 41-1386. The Fc tage sequence is underlined and italicized.

The nucleotide sequence of h-Notch3$^{(1-34)}$ decoy protein which is set forth in FIG. 40. The predicted human Notch3 signal peptide is underlined (nt 1-120). Notch3 EGF repeats 1-34 are encoded from nt 121-4158. The fusion junction, BglII site is nt 4158 to 4163. The Fc tage sequence is underlined and italicized.

h-sp$^{Hc}$Notch1$^{(1-34)}$ Decoy h-sp$^{Hc}$Notch1$^{(1-34)}$ decoy denotes the human Notch3 decoy that encompass EGF-like repeats 1-34. The abbreviation sp$^{Hc}$ denotes that the human Hc signal peptide is used in this formulation.

The amino acid sequence of h-Notch3$^{(1-34)}$ decoy protein which is set forth in FIG. 42. The predicted human Hc signal peptide is underlined (AA 1-22). Notch3 EGF-repeats 1-34 are encoded from as 22-1386. The Fc tag sequence is underlined and italicized.

The nucleotide sequence of h-Notch3$^{(1-34)}$ decoy protein which is set forth in FIG. 43. The predicted human Hc signal peptide is underlined (nt 1-66). Notch3 EGF repeats 1-34 are encoded from nt 67-4104. The fusion junction, BglII site is nt 4104 to 4109. The Fc tag sequence is underlined and italicized.

Methods

Construction of Human Notch3 Decoys

Total RNA from either human aortic smooth muscle cells (AoSMC) or human umbilical venous endothelial cells (HUVEC) that overexpress Prox1 were used to generate human Notch3 decoy variants. Total RNA was reverse transcribed with M-MLV reverse transcriptase and either random hexamer primers or Notch3 decoy specific primers. The synthesized cDNA was then amplified with Notch3 decoy specific upstream (sense) and downstream (antisense) primers. The Notch3 decoy was constructed from 4 individual amplicons. The 3-prime amplicon was amplified with a downstream primer encoding a Bgl II restriction site at the 5-prime end for ligation into the BglII site in the Fc sequence to generate an in fram human Notch3/Fc chimera.

In the case of Notch3 decoys that generate the fusion after nucleotide sequence encoding EGF-like repeat 34, a BglIII site will be generated to create the fusion site and this fusion sequence is provided (Notch3, FIG. 37).

This applies to formulations h-Notch3(1-34)decoy and h-sp$^{HC}$Notch3 (1-34) decoy.

The amplified PCR products were subcloned into e pBluescript SK II Fc to generate the different human Notch3/Fc chimeras. The human Notch3/Fc decoy sequences are then shuttled into mammalian expression vectors (pAd-lox, pCCL or pcDNA3) for expression and purification of human Notch3 decoy proteins.

Second Series of Experiments

Materials & Methods

Plasmid Constructs

Adenovirus constructs encoding LacZ, full-length Notch4, or the activated form of Notch4/int3 have been previously described (Shawber et al., 2003). An activated form of Notch1 cDNA fused in frame with 6 myc tags (Kopan et al., 1994) was cloned into the adenovirus expression vector, pAd-lox. Both VEGF165 and N1ECDFc was also cloned into the pAd-lox. Adenoviral stocks were generated and titered as previously described (Hardy et al., 1997). The retroviral expression vector pHyTC encoding either LacZ, the activated form of Notch4/int3, J1, Dll1 and Dll4 have been previously described (Uyttendaele et al., 2000, Shawber et al., 2003, Das et al., 2004 in print). Plasmids encoding the intracellular domain of Notch1 (bp 5479-7833, Genbank accession# X57405) and the extracellular domain of Dll4 (bp 1-1545, Genbank accession# AF253468, provided by Chiron) fused in frame with a myc/His tag, were engineered into pHyTC.

Notch1ECD, Notch2ECD, Notch3ECD and Notch4ECD are engineered into the Fc containing plasmid pCMX-sFR1-IgG using the methods set forth in Clin. Exp. Immunol. (1992) 87(1):105-110 to create the Notch-based fusion proteins, i.e. Notch1ECD/Fc, Notch2ECD/Fc, Notch3ECD/Fc and Notch4ECD/Fc.

Adenoviral Gene Transfer $7.5\times10^5$ cells of HUVEC at passage 3 were seeded into type I collagen-coated 6 well plates on the day before adenoviral infection. Adenoviral infection with Ad-lacZ, Ad-VEGF165 or Ad-N1ECDFc was performed at indicated m.o.i., and incubated at 37° C. for 1 hr with occasional swirling of plates.

Luciferase Reporter Assays

To determine ligand-induced Notch signaling, co-culture assays were performed using HeLa and 293-derived Bosc cells. Transient transfections were performed by calcium phosphate precipitation. Hela cells plated 1-day prior in 10-cm plates at $1.5\times10^6$ were transfected with 333 ng of pBOS Notch1, 333 ng pGA981-6, and 83 ng pLNC lacZ with either 666 ng pCMV-Fc or pHyTC-N1ECDFc (333 ng for x1, 666 ng for x2). Bosc cells plated 1-day prior in 10-cm plates at $4\times10^6$ were transfected with either 680 ng pHyTc-Jagged1, pHyTc-Dll1, pHyTc-Dll4, or pHyTc-x (empty vector). One day after transfection, the cells were co-cultured in triplicate (HeLa:Bosc, 1:2) on 12-well plates for 24 hours. Cells were harvested and luciferase activity was determined 2-days post-transfection using the Enhanced Luciferase assay kit (BD PharMingen), and 3-galactosidase activity was determined using the Galacto-Light Plus kit (PE Biosystems). All assays were performed in a Berthold dual-injection luminometer.

To determine VEGF-induced Notch signaling, HUVEC which were infected with adenovirus were used. HUVEC plated 1-day prior in 6 well plates at $8.0\times10^5$ were infected with either Ad-LacZ as control or Ad-VEGF at indicated m.o.i. in the presence or absence of Ad-N1ECD/Fc. Two days after infection, infected HUVEC were re-seeded into 24-well plate at $1.5\times10^5$ cell in triplicate and cultured for 24 hours, and then transfected with 12.5 ng pRL-SV40 (Promega) and 137.5 ng pGA981-6 using Effectene transfection reagent (Qiagen). Cells were harvested either 1 or 2 days post-transfection and luciferase activity was determined by using the Dual-Luciferase® Reporter Assay System (Promega).

Sprouting Assay

For making collagen gels, an ice-cold solution of porcine type I collagen (Nitta gelatin, Tokyo, Japan) was mixed with 10xRPMI1640 medium and neutralization buffer at the ratio of 8:1:1. 400 μl aliquots of collagen gel were then added to 24-well plates and allowed to gel for at least 1 hour at 37° C. Following adenoviral infection (above), HUVEC was harvested and plated at $1.3\times10^5$ cells per well onto the top of the collagen gel in 24-well plates in 0.8 ml of EGM2 medium. HUVEC became nearly confluent 48 hours after plating. After seeding, medium was changed every 2 days for 1 week. Sprouting was observed and photographs taken after 8 days with an Olympus digital camera mounted to a microscope. For quantification of the number of sprouts, 5 fields per each well were randomly selected and sprouting was counted under microscopy in a blind manner by two investigators.

Results and Discussion

NOTCHECD/Fc Fusion Proteins

Function as Antagonists of Notch

Notch Antagonists-NotchECD/Fc Fusion Proteins

Figure 2:
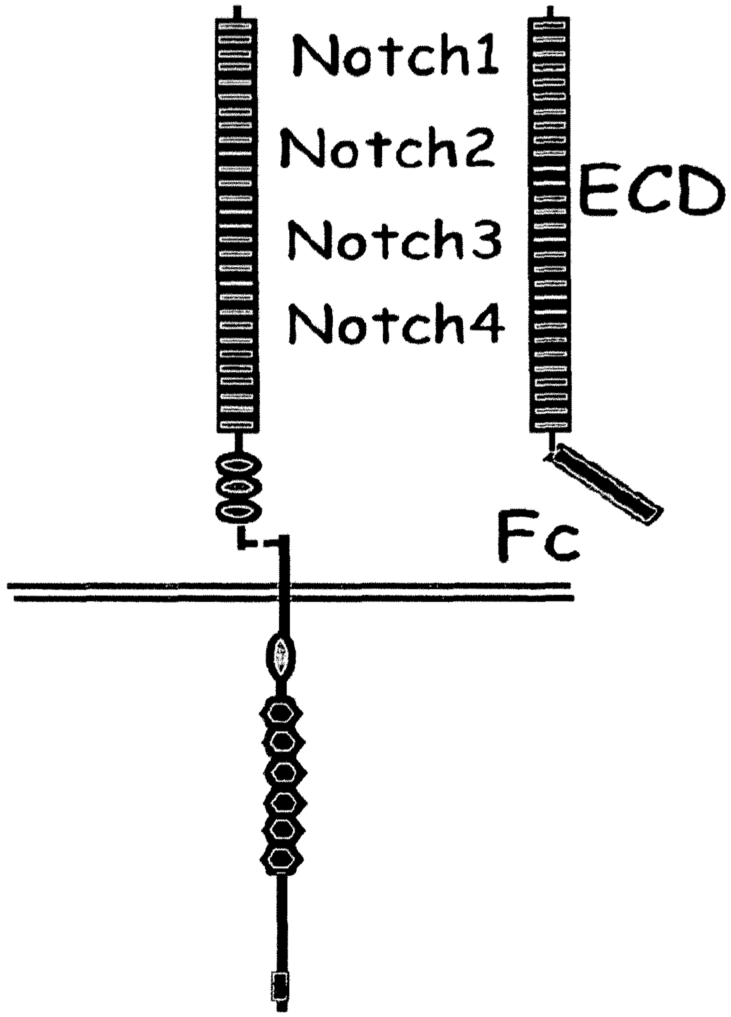

We have made several Notch antagonists (FIG. 2). Our strategy was to fuse the coding sequence of Notch EGF repeats in the Extracellular Domain (ECD) to the human or mouse Fc domain. This design makes a secreted protein without signaling function but which retains the ligand-binding domain and thus should bind to and inhibit ligand function. We refer to these proteins as "NotchECD/Fc" and all four Notch1-4ECD/Fcs have been made. The Fc domain facilitates affinity purification and protein detection by immunoblotting or immunohistochemistry.

Testing Notch Antagonists

Figure 3:
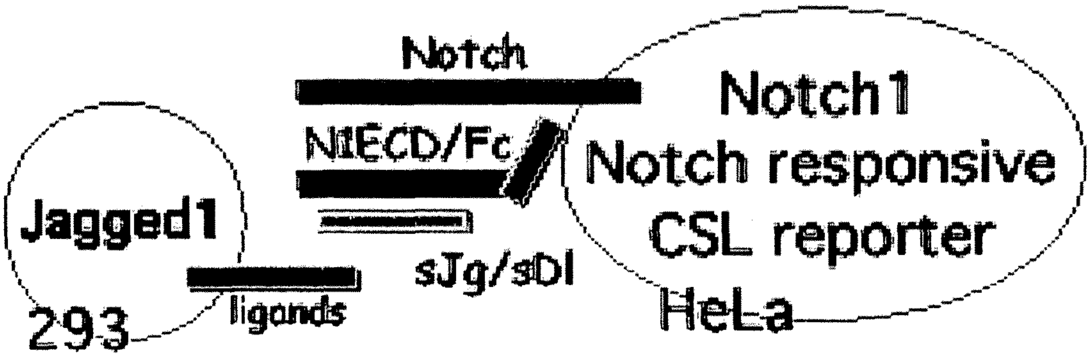
Figure 4:
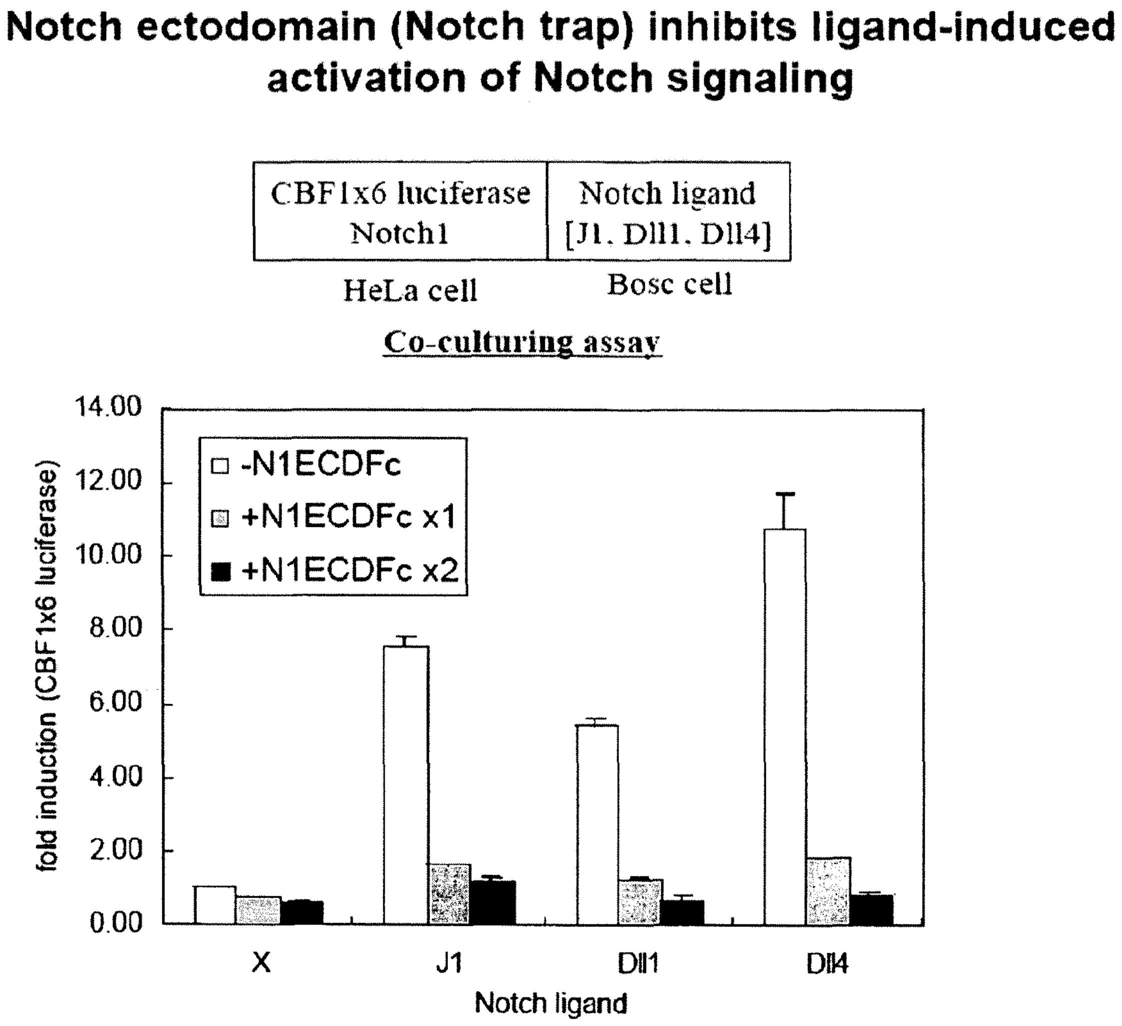

An in vitro co-culture system (FIG. 3) with ligands expressed on one cell and Notch receptor activation scored in another cell was used to measure transcriptional activation of the Notch pathway. We used this co-culture assay to show that Notch1ECD/Fc functions to block ligand-dependent Notch signaling (FIG. 4). The N1ECD/Fc expression vector was co-transfected at different ratios with full-length Notch1 and the CSL-luciferase reporter in HeLa cells, followed by co-culture with ligand expressing 293 cells. We observed that activation of Notch1 signaling by Notch ligands was reduced by N1ECD/Fc expression. This effect displayed concentration-dependency; a 2:1 ratio of N1ECD/Fc to Notch1 was more effective in inhibiting signaling than a 1:1 ratio. Notch1ECD/Fc could block signaling mediated by Jagged1, Delta-like 1 or Delta-like 4.

Expressing and Purifying Notch Antagonists

Figure 5:
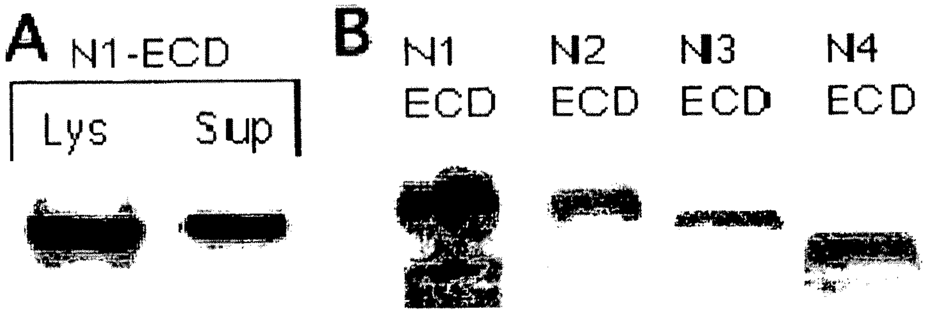

We have made CHO and HeLa cell lines expressing NotchECD/FCs using retroviral vectors for the purpose of protein purification. N1ECD/Fc proteins are secreted (FIG. 5); as shown in conditioned media collected from HeLa-NotchECD/Fc lines and purified with Protein-A(pA) agarose. The pA purified sample (Sup) and whole cell lysates (Lys) were immunoblotted with α-Fc antibody (FIG. 5, panel A) demonstrating that N1ECD/Fc is secreted into the media. Adenovirus vectors for NotchECD/Fc were used to infect HeLa cells and lysates from these cells were immunoblotted with α-Fc antibodies demonstrating that they express NotchECD/Fc(1, 2, 3, 4) proteins (FIG. 5, panel B). We are currently purifying N1ECD/Fc from CHO cell conditioned media using pA-affinity chromatography.

Defining Angiogenic Inhibition

Using Notch Fusion Proteins

Activation of Notch Signaling can be Detected by Using CBF1 Promoter Activity

Figure 6:
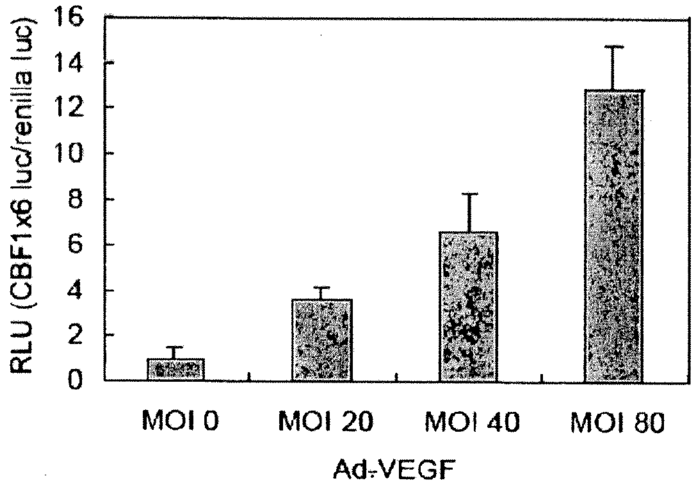

One can measure Notch signaling function by measuring transcriptional activity of CBF1 promoter, which is activated by binding of Notch-IC to CBF1. We measured CBF1 promoter activity in HUVEC which was infected with adenovirus encoding VEGF-165 at different MOI (FIG. 6). Induction of CBF1 promoter was clearly detected in Ad-VEGF-infected HUVEC, compared to Ad-LacZ-infected cells in the MOI dependent manner. This data showed over-expression of VEGF could activate Notch signaling in HUVEC. Thus VEGF induced Notch signaling activity.

We asked whether Notch fusion proteins could block VEGF-induced activation of Notch signaling. Co-infection of Ad-Notch fusion protein with Ad-VEGF clearly reduced activation of CBF1 promoter activity induced by Ad-VEGF infection alone (FIG. 7). In the case of infection at 40 MOI for each adenovirus in FIG. 7 (panel A), 60% inhibition at 24 hr and 90% inhibition at 48 hr after reporter gene transfection were detected also the inhibitory activity of Notch decoy was dependent on MOI of Ad-Notch fusion protein.

Notch Fusion Proteins Block Initiation of Angiogenic Sprouting Induced by VEGF

Figure 8:
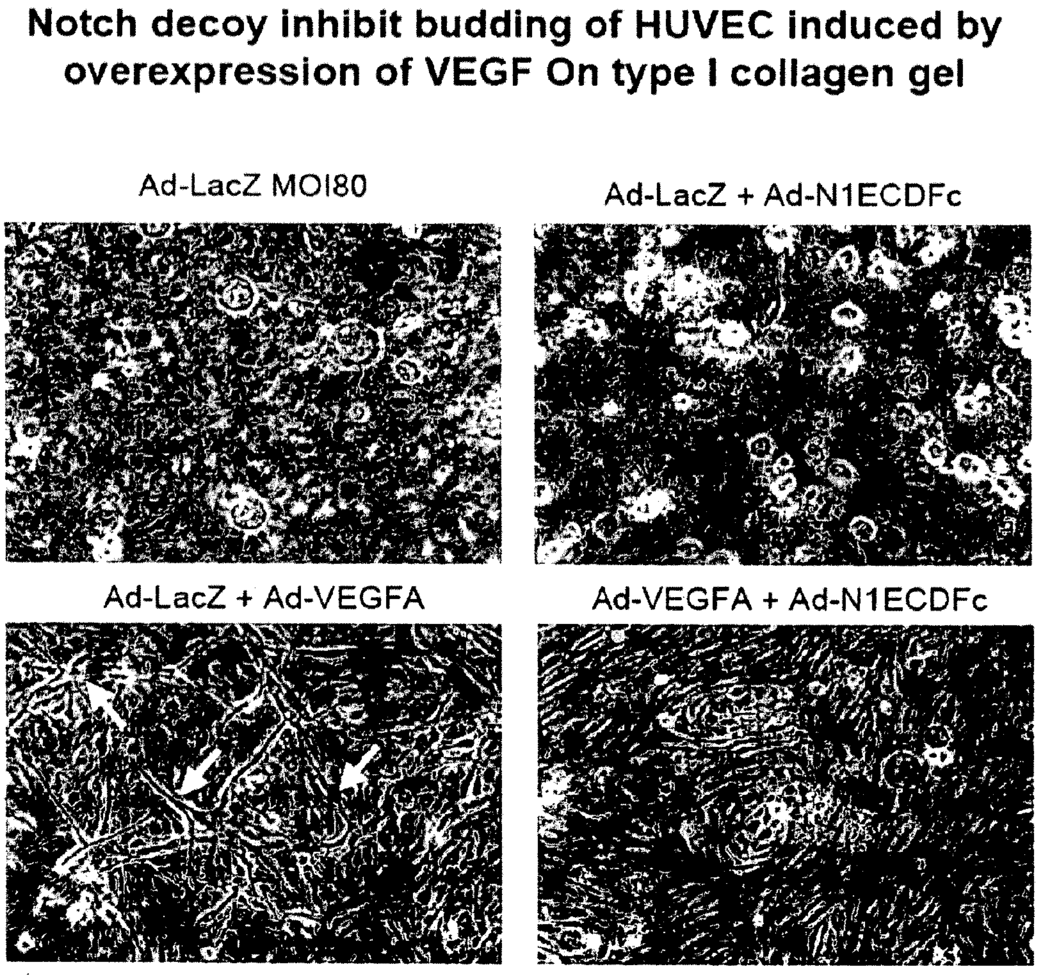

In this experiment, we evaluated the effect of Notch decoy on induction of budding (initiation of sprouting) by over-expressed VEGF-165 in HUVEC. When Ad-VEGF-infected HUVEC were cultured on type collagen gel for 8 days, budding was induced into collagen gel. This induction of budding by overexpressed VEGF was clearly inhibited by coinfection of adenoviral encoding Notch fusion protein (FIG. 8). Ad-Notch fusion protein itself had less effect on morphology.

Figure 9:
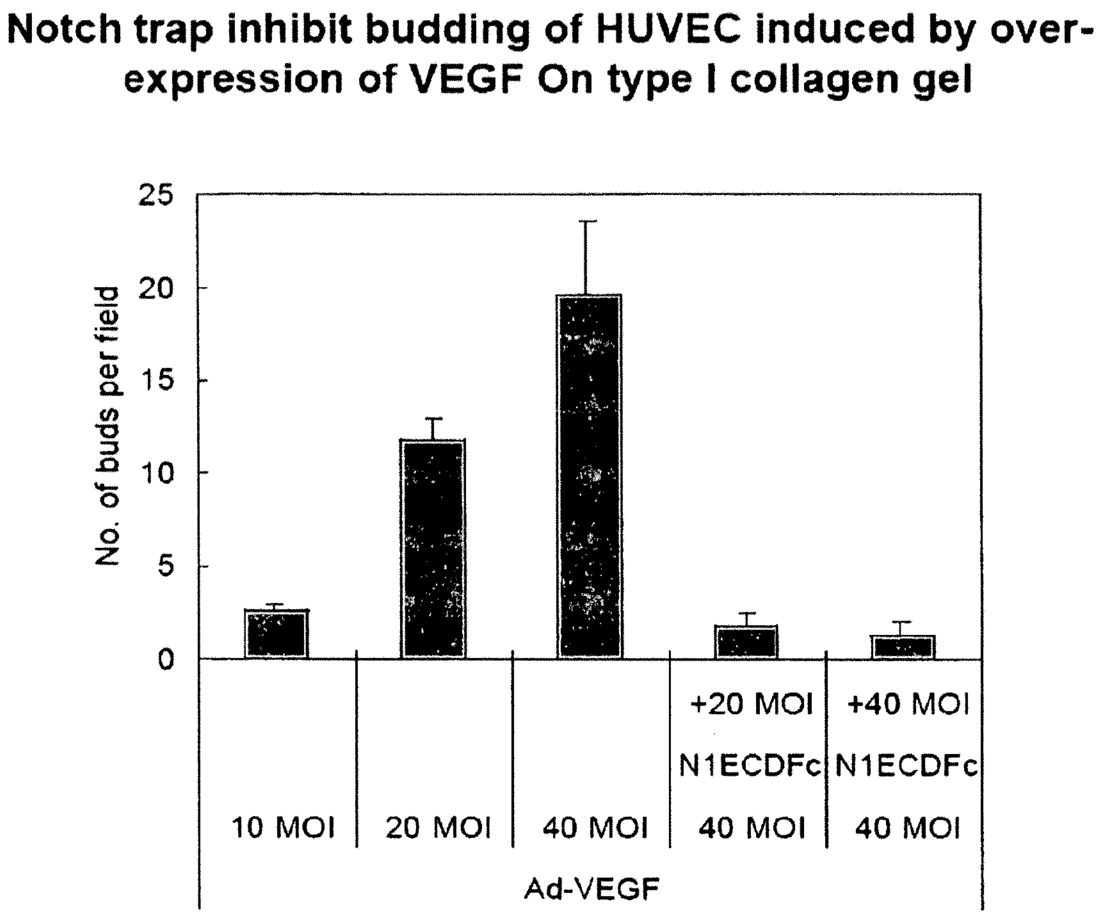

In FIG. 9 we counted buds per field using the microscope. Ad-VEGF-infection into HUVEC increased the number of buds depending on the MOI used. Ad-VEGF-induced budding was clearly inhibited. These data suggest that VEGF induced budding of HUVEC through activation of Notch signaling and that the Notch fusion protein could inhibit VEGF-induced budding.

REFERENCES CITED IN SECOND SERIES OF EXPERIMENTS

1. Artavanis-Tsakonas, S., K. Matsuno, and M. E. Fortini. 1995. Notch signaling. *Science* 268:225-232.
2. Bailey, A. M., and J. W. Posakony. 1995. Suppressor of hairless directly activates transcription of enhancer of split complex genes in response to Notch receptor activity. *Genes & Development* 9:2609-22.
3. Bettenhausen, B., M. Hrabe de Angelis, D. Simon, J. L. Guenet, and A. Gossler. 1995. Transient and restricted expression during mouse embryogenesis of Dll, a murine gene closely related to *Drosophila Delta. Development* 121:2407-18.
4. Blaumueller, C. M., H. Qi, P. Zagouras, and S. Artavanis-Tsakonas. 1997. Intracellular cleavage of Notch leads to a heterodimeric receptor on the plasma membrane. *Cell* 90:281-91.
5. Caronti, B., L. Calandriello, A. Francia, L. Scorretti, M. Manfredi, T. Sansolini, E. M. Pennisi, C. Calderaro, and G. Palladini. 1998. Cerebral autosomal dominant arteriopathy with subcortical infarcts and leucoencephalopathy (CADASIL). Neuropathological and in vitro studies of abnormal elastogenesis. *Acta Neurol Scand.* 98:259-67.
6. Desmond, D. W., J. T. Moroney, T. Lynch, S. Chan, S. S. Chin, D. C. Shungu, A. B. Naini, and J. P. Mohr. 1998. CADASIL in a North American family: clinical, pathologic, and radiologic findings [see comments]. *Neurology* 51:844-9.
7. Dunwoodie, S. L., D. Henrique, S. M. Harrison, and R. S. Beddington. 1997. Mouse D113: a novel divergent Delta gene which may complement the function of other Delta homologues during early pattern formation in the mouse embryo. *Development* 124:3065-76.
8. Eastman, D. S., R. Slee, E. Skoufos, L. Bangalore, S. Bray, and C. Delidakis. 1997. Synergy between suppressor of Hairless and Notch in regulation of Enhancer of split in gamma and m delta expression. *Mol Cell Biol.* 17:5620-5634.
9. Fortini, M. E., and S. Artavanis-Tsakonas. 1993. Notch: neurogenesis is only part of the picture. *Cell* 75:1245-7.
10. Gale, N. W., and G. D. Yancopoulos. 1999. Growth factors acting via endothelial cell-specific receptor tyrosine kinases: VEGFs, Angiopoietins, and ephrins in vascular development. *Genes and Development* 13:1055-1066.
11. Gallahan, D., and R. Callahan. 1997. The mouse mammary tumor associated gene INT3 is a unique member of the NOTCH gene family (NOTCH4). *Oncogene* 14:1883-90.
12. Greenwald, I. 1994. Structure/function studies of lin-12/Notch proteins. *Current Opinion in Genetics & Development* 4:556-62.
13. Greenwald, I. 1998. LIN-12/Notch signaling: lessons from worms and flies. *Genes Dev.* 12:1751-62.

14. Henderson, A. M., S. J. Wang, A. C. Taylor, M. Aitkenhead, and C. C. W. Hughes. 2001. The basic helix-loop-helix transcription factor HESR1 regulates endothelial cell tube formation. *J Biol Chem.* 276:6169-6176.
15. Hicks, C., S. H. Johnston, G. diSibio, A. Collazo, T. F. Vogt, and G. Weinmaster. 2000. Fringe differentially modulates Jagged1 and Delta1 signalling through Notch1 and Notch2. *Nature Cell Biology* 2:515-520.
16. Hsieh, J. J., T. Henkel, P. Salmon, E. Robey, M. G. Peterson, and S. D. Hayward. 1996. Truncated mammalian Notch1 activates CBF1/RBPJk-repressed genes by a mechanism resembling that of Epstein-Barr virus EBNA2. *Molecular & Cellular Biology* 16:952-9.
17. Hsieh, J. J., D. E. Nofziger, G. Weinmaster, and S. D. Hayward. 1997. Epstein-Barr virus immortalization: Notch2 interacts with CBF1 and blocks differentiation. *J. Virol.* 71:1938-45.
18. Jarriault, S., C. Brou, F. Logeat, E. H. Schroeter, R. Kopan, and A. Israel. 1995. Signaling downstream of activated mammalian Notch. *Nature* 377:355-358.
19. Joutel, A., F. Andreux, S. Gaulis, V. Domenga, M. Cecillon, N. Battail, N. Piga, F. Chapon, C. Godfrain, and E. Tournier-Lasserve. 2000. The ectodomain of the Notch3 receptor accumulates within the cerebrovasculature of CADASIL patients [see comments]. *J Clin Invest.* 105:597-605.
20. Joutel, A., C. Corpechot, A. Ducros, K. Vahedi, H. Chabriat, P. Mouton, S. Alamowitch, V. Domenga, M. Cecillion, E. Marechal, J. Maciazek, C. Vayssiere, C. Cruaud, E. A. Cabanis, M. M. Ruchoux, J. Weissenbach, J. F. Bach, M. G. Bousser, and E. Tournier-Lasserve. 1996. Notch3 mutations in CADASIL, a hereditary adult-onset condition causing stroke and dementia. *Nature* 383:707-10.
21. Kopan, R., E. H. Schroeter, H. Weintraub, and J. S. Nye. 1996. Signal transduction by activated mNotch: importance of proteolytic processing and its regulation by the extracellular domain. *Proc Natl Acad Sci USA* 93:1683-8.
22. Krebs, L. T., Y. Xue, C. R. Norton, J. R. Shutter, M. Maguire, J. P. Sundberg, D. Gallahan, V. Closson, J. Kitajewski, R. Callahan, G. H. Smith, K. L. Stark, and T. Gridley. 2000. Notch signaling is essential for vascular morphogenesis in mice. *Genes and Development* 14:1343-1352.
23. Lardelli, M., J. Dahlstrand, and U. Lendahl. 1994. The novel Notch homologue mouse Notch3 lacks specific epidermal growth factor-repeats and is expressed in proliferating neuroepithelium. *Mechanism of Development* 46:123-136.
24. Lawson, N. D., N. Scheer, V. N. Pham, C. Kim, A. B. Chitnis, J. A. Campos-Ortega, and B. M. Weinstein. 2001. Notch signaling is required for arterial-venous differentiation during embryonic vascular development. *Development* 128:3675-3683.
25. Lewis, J. 1998. Notch signaling and the control of cell fate choices in vertebrates. *Semin Cell Dev Biol.* 9:583-589.
26. Lieber, T., S. Kidd, E. Alcomo, V. Corbin, and M. W. Young. 1993. Antineurogenic phenotypes induced by truncated Notch proteins indicate a role in signal transduction and may point to a novel function for Notch in nuclei. *Genes Dev.* 7:1949-1965.
27. Lindner, V., C. Booth, I. Prudovsky, D. Small, T. Maciag, and L. Liaw. 2001. Members of the Jagged/Notch gene familites are expressed in injured arteries and regulate cell phenotype via alteration in cell matrix and cell-cell interations. *Pathology* 159:875-883.
28. Lindsell, C. E., C. J. Shawber, J. Boulter, and G. Weinmaster. 1995. Jagged: A mammalian ligand that activates Notch1. *Cell* 80:909-917.
29. Logeat, F., C. Bessia, C. Brou, O. LeBail, S. Jarriault, N. G. Seidah, and A. Israel. 1998. The Notch1 receptor is cleaved constitutively by a furin-like convertase. *Proc Natl Acad Sci USA* 95:8108-12.
30. Lyman, D., and M. W. Young. 1993. Further evidence for function of the *Drosophila* Notch protein as a transmembrane receptor. *Proc Natl Acad Sci USA* 90:10395-10399.
31. Matsuno, K., M. J. Go, X. Sun, D. S. Eastman, and S. Artavanis-Tsakonas. 1997. Suppressor of Hairless-independent events in Notch signaling imply novel pathway elements. *Development* 124:4265-4273.
32. Nakagawa, O., D. G. McFadden, M. Nakagawa, H. Yanagisawa, T. Hu, D. Srivastava, and E. N. Olson. 2000. Members of the HRT family of basic helix-loop-helix proteins act as transcriptional repressors downstream of Notch signaling. *Proc Natl Acad Sci USA* 97:13655-13660.
33. Oberg, C., J. Li, A. Pauley, E. Wolf, M. Gurney, and U. Lendahl. 2001. The Notch intracellular domain is ubiquitinated and negatively regulated by the mammalian Sel-10 homolog. *J Biol Chem.* 276:35847-35853.
34. Owens, G. K. 1995. Regulation of differentiation of vascular smooth muscle cells. *Physiol Rev.* 75:487-527.
35. Rebay, I., R. G. Fehon, and S. Artavanis-Tsakonas. 1993. Specific truncations of *Drosophila* Notch define dominant activated and dominant negative forms of the receptor. *Cell* 74:319-29.
36. Robey, E. 1997. Notch in vertebrates. *Curr Opin Genet Dev.* 7:551-7.
37. Roehl, H., M. Bosenberg, R. Blelloch, and J. Kimble. 1996. Roles of the RAM and ANK domains in signaling by the *C. elegans* GLP-1 receptor. *Embo J.* 15:7002-7012.
38. Rogers, S., R. Wells, and M. Rechsteiner. 1986. Amino acid sequences common to rapidly degrade proteins: The PEST hypothesis. *Science* 234:364-368.
39. Sasai, Y., R. Kageyama, Y. Tagawa, R. Shigemoto, and S. Nakanishi. 1992. Two mammalian helix-loop-helix factors structurally related to *Drosophila* hairy and Enhancer of split. *Genes & Dev.* 6:2620-2634.
40. Shawber, C., J. Boulter, C. E. Lindsell, and G. Weinmaster. 1996a. Jagged2: a serrate-like gene expressed during rat embryogenesis. *Dev Biol.* 180:370-6.
41. Shawber, C., D. Nofziger, J. J. Hsieh, C. Lindsell, O. Bogler, D. Hayward, and G. Weinmaster. 1996b. Notch signaling inhibits muscle cell differentiation through a CBF1-independent pathway. *Development* 122:3765-73.
42. Shimizu, K., S. Chiba, T. Saito, T. Takahashi, K. Kumano, H. Hamada, and H. Hirai. 2002. Integrity of intracellular domain of Notch ligand is indespensable for cleavage required for the release of the Notch2 intracellular domain. Embo J. 21:294-302.
43. Shutter, J. R., S. Scully, W. Fan, W. G. Richards, J. Kitajewski, G. A. Deblandre, C. R. Kintner, and K. L. Stark. 2000a. Dll4, a novel Notch ligand expressed in arterial endothelium. *Genes Dev.* 14:1313-1318.
44. Shutter, J. R., S. Scully, W. Fan, W. G. Richards, J. Kitajewski, G. A. Deblandre, C. R. Kitner, and K. L. Stark. 2000b. Dll4, a novel Notch ligand expressed in arterial endothelium. *Genes and Development* 14:1313-1318.
45. Struhi, G., K. Fitzgerald, and I. Greenwald. 1993. Intrinsic activity of the Lin-12 and Notch intracellular domains in vivo. *Cell* 74:331-45.

46. Swiatek, P. J., C. E. Lindsell, F. Franco del Amo, G. Weinmaster, and T. Gridley. 1994. Notch 1 is essential for postimplantation development in mice. *Genes & Development* 8:707-719.
47. Tamura, K., Y. Taniguchi, S. Minoguchi, T. Sakai, T. Tun, T. Furukawa, and T. Honjo. 1995. Physical interaction between a novel domain of the receptor Notch and the transcription factor RBP-J kappa/Su(H). *Curr Biol.* 5:1416-1423.
48. Tietze, K., N. Oellers, and E. Knust. 1992. Enhancer of splitD, a dominant mutation of *Drosophila*, and its use in the study of functional domains of a helix-loop-helix protein. *Proc Natl Acad Sci USA* 89:6152-6156.
49. Uyttendaele, H., J. Ho, J. Rossant, and J. Kitajewski. 2001. Vascular patterning defects associated with expression of activated Notch4 in embryonic endothelium. *PNAS.* 98:5643-5648.
50. Uyttendaele, H., G. Marazzi, G. Wu, Q. Yan, D. Sassoon, and J. Kitajewski. 1996. Notch4/int-3, a mammary proto-oncogene, is an endothelial cell-specific mammalian Notch gene. *Development* 122:2251-9.
51. Vervoort, M., C. Dambly-Chaudiere, and A. Ghysen. 1997. Cell fate determination in *Drosophila. Curr Opin Neurobiol.* 7:21-28.
52. Villa, N., L. Walker, C. E. Lindsell, J. Gasson, M. L. Iruela-Arispe, and G. Weinmaster. 2001. Vascular expression of Notch pathway receptors and ligands is restricted to arterial vessels. *Mechanisms of Development* 108:161-164.
53. Weinmaster, G. 1997. The Ins and Outs of Notch Signaling. *Mol Cel Neurosci.* 9:91-102.
54. Weinmaster, G. 1998. Notch signaling: direct or what? *Curr Opin Genet Dev.* 8:436-42.
55. Weinmaster, G., V. J. Roberts, and G. Lemke. 1992. Notch 2: a second mammalian Notch gene. *Development* 116:931-941.
56. Weinmaster, G., V. J. Roberts, and G. A. Lemke. 1991. A homolog of *Drosophila* Notch expressed during mammalian development. *Development* 113:199-205.
57. Wettstein, D. A., D. L. Turner, and C. Kintner. 1997. The Xenopus homolog of *Drosophila* Suppressor of Hairless mediates Notch signaling during primary neurogenesis. *Development* 124:693-702.
58. Wu, G., E. J. Hubbard, J. K. Kitajewski, and I. Greenwald. 1998. Evidence for functional and physical association between Caenorhabditis elegans SEL-10, a Cdc4p-related protein, and SEL-12 presenilin. *Proc Natl Aced Sci USA* 95:15787-91.
59. Wu, G., S. A. Lyapina, I. Das, J. Li, M. Gurney, A. Pauley, I. Chui, R. J. Deshaies, and J. Kitajewski. 2001. SEL-10 is an inhibitor of notch signaling that targets notch for ubiquitin-mediated protein degradation. *Mol Cell Biol.* 21:7403-7015.
60. Xue, Y., X. Gao, C. E. Lindsell, C. R. Norton, B. Chang, C. Hicks, M. Gendron-Maguire, E. B. Rand, G. Weinmaster, and T. Gridley. 1999. Embryonic lethality and vascular defects in mice lacking the Notch ligand Jagged1. *Hum Mol Genet.* 8:723-30.

Third Series of Experiments

VEGF Initiates Angiogenesis Via an Activation of Notch Signaling

Both the VEGF and Notch signaling pathways are critical for vascular development. Here we show that VEGF activates Notch signaling to initiate angiogenesis. VEGF increased the expression of Delta4 and Notch4 causing Notch signal activation and inducing filopodia in cultured primary endothelial cells. Studies using VEGF Receptor inhibitors show that Notch signal activation in turn enhances VEGF action by inducing VEGFR-1 (Flt-1) expression. Other elements of VEGF action, including the induction of MMP-9 and MT1-MMP, are mediated by Notch. Using in vivo assays to model VEGF-induced skin neovascularization, we found that a secreted Notch inhibitor (Notch-based fusion protein) blocks VEGF-induced neo-vascularization and induction of VEGFR-1 expression. Thus, Notch signaling is requisite for angiogenesis regulated by VEGF, likely at the level of initiation.

VEGF is a key regulator of angiogenesis progression consisting of multiple processes, such as degradation of ECM, budding (filopodia formation), proliferation, survival, and migration of endothelial cells. Although most of the steps might be co-operated with downstream molecules of VEGF signaling, it is not known how these steps are coordinately regulated to result in more complex morphogenetic events, such as angiogenic sprouting. Notch signaling is an evolutionarily conserved signaling mechanism that functions to regulate cell fate decisions (1). Upon binding by a ligand, such as Jagged and Delta-like, the cytoplasmic domain of Notch (NotchIC) is released by presenilin/γ-secretase, translocates to the nucleus, interacts with the transcriptional repressor CSL (CBF1/Su(H)/lag2), and converts it to a transcriptional activator (1). Roles of Notch signaling in vascular development were suggested by studies of mice with targeted mutation (2). Since Notch activation within the endothelium also disrupts vascular remodeling, proper Notch signaling is essential for vascular development (3). Although relevance of Notch to VEGF signaling is suggested (4-6), it is still unclear how Notch signaling has a role in VEGF-regulated angiogenesis and whether Notch signaling participates in physiological and pathological angiogenesis in the adult vasculature.

HUVEC (Human Umbilical Vein Endothelial cells) growth are dependent on VEGF (FIGS. 26A and 26B) and differentiation-related biological responses, such as sprouting, and can be evaluated at an early stage (7). At first, we examined whether adenovirally transduced VEGF induced both Notch and Notch ligand expression in HUVEC cultured with complete medium containing bFGF (FIG. 22A), as reported (5). RT-PCR analysis showed that both Dl4 and Notch4 mRNA was up-regulated in adenovirally-transduced VEGF HUVEC (Ad-VEGF-HUVEC), compared to adenovirally-transduced LacZ HUVEC (Ad-LacZ-HUVEC) (FIG. 22A). Transduced VEGF did not appear to induce Jagged1 and Notch1 expression. Transduced-VEGF also activated Notch signaling in a dose-dependent manner by measuring CSL-luciferase reporter activity (FIG. 22B), which was transactivated with Notch signaling (8). Notch signaling was activated at a higher dosage of Ad-VEGF, compared to proliferation (FIG. 26A). Since SU5416, which is an inhibitor of VEGFR kinases, decreased VEGF-induced CSL-luciferase reporter activity (FIG. 22C), VEGF induced Notch signaling through activation of receptor kinase. Since Notch mutants lacking both transmembrane and cytoplasmic domains functioned as dominant negative inhibitors against Notch signaling (9), we made a Notch-based fusion protein or decoy (N1ECDFc) to inhibit Notch signaling (FIG. 22D). Western blotting analysis of conditioned medium of Ad-N1ECDFc-transduced HUVEC (Ad-N1ECDFc-HUVEC) demonstrated that N1ECDFc was expressed and secreted well (FIG. 22E). By using a co-culture assay, in which Bosc cells expressing Notch ligands (either J1, Dll or Dl4) activated Notch signaling in HeLa cells expressing Notch1 compared to control Bosc cells, we determined inhibition of Notch signaling with transfection of a N1ECDFc-expression plasmid (FIG. 22F). Then, we examined whether N1ECDFc inhibited activation of Notch signaling by transduced VEGF in HUVEC (FIG. 22G). Co-transduction of Ad-N1ECDFc with Ad-VEGF into HUVEC clearly decreased CSL luciferase activity induced by VEGF. Gerhardt et al. reported that VEGF controlled angiogenesis in the early postnatal retina by guiding filopodia extension at the tips of the vascular sprouts (10). During angiogenic sprouting, the formation of a specialized endothelial cell making filopodia projections among quiescent endothelial cells, might be one of the early events. Here we mean formation of a single endothelial cell making filopodia protrusions as budding. Budding of the primary endothelial cells is induced by cultivating them 3-dimensionally on either fibrin or collagen gel (11). In the case where Ad-VEGF-HUVEC were cultured on collagen gel with complete medium, transduced-HUVEC made filopodia extensions into the collagen gel for 5 days (FIG. 22H) and the number of buds was increased in a dose-dependent manner (FIG. 27A). Activation of Notch signaling by adenovirus encoding the activated form of Notch4 (Ad-Notch4/int3) induced HUVEC budding (12) and that of Notch1 (Ad-N1IC) also induced HUVEC budding (FIGS. 23A & 27B). Since both VEGF and Notch signaling induce HUVEC budding, we examined whether N1ECDFc inhibited VEGF-induced HUVEC budding (FIG. 22H-I). Budding of Ad-VEGF-HUVEC was clearly inhibited by co-transduction of Ad-N1ECDFc. Neither Ad-LacZ or Ad-N1ECDFc-transduced HUVEC formed buds (FIG. 22H). N1ECDFc inhibited VEGF-induced HUVEC budding without affecting cell number (FIG. 22I). Transduced-N1ECDFc did not clearly alter proliferation of HUVEC, while that of Ad-N1IC-transduced HUVEC was inhibited in a dose-dependent manner (FIG. 28A), consistent with the inhibitory efficacy of Notch signaling against endothelial proliferation (13).

To test whether Notch signaling is down-stream of VEGF, we evaluated three distinct inhibitors for receptor tyrosine kinases, including VEGFR on N1IC-induced HUVEC budding, because three growth factors existed in complete medium (FIG. 23A-C). At a concentration of 1 μM, each compound showed selective inhibition against each kinase (data not shown). Neither P13166866 or ZD1893 affected budding of Ad-N1IC-HUVEC, while SU5416 clearly inhibited it (FIG. 23A-B). SU5416 selectively inhibited budding of Ad-N1IC-HUVEC with less reduction of viability at lower concentrations (FIG. 23C). Since Taylor et al. reported that Notch down-regulated Flk1/KDR/VEGFR2 expression (14), it was unlikely that Notch co-operated with Flk1 to promote budding. Thus, we examined whether activation of Notch signaling affected Flt1/VEGFR1 expression in HUVEC, because SU5416 inhibits both Flt1 and Flk1 kinase activity (15). RT-PCR analysis demonstrated that expression of Flt1 mRNA was up-regulated in Ad-N1IC-HUVEC, while expression of endothelial cell maker, CD31 mRNA, was not compared to that in Ad-LacZ-HUVEC (FIG. 23D). Western blotting analysis also showed that expression of Flt1 protein was up-regulated in Ad-N1IC-HUVEC (FIG. 23E). Thus, we examined whether P1GF, which is a selective ligand for Flt1, promoted budding of HUVEC in which Flt1 was up-regulated via activation of Notch signaling (FIG. 23F-G). P1GF increased the number of Ad-N1IC-HUVEC buds by 150%, compared to the absence of P1GF (FIG. 23F). Moreover, P1GF increased HUVEC buds containing multiple filopodia by 250% (FIG. 23G). While reduction of Flt1 expression using small interfering RNA (siRNA) for Flt1 inhibited budding of Ad-N1IC-HUVEC (FIG. 23J), transfection of which selectively decreased expression of Flt1 mRNA (FIG. 23H) and that of Flt1 protein (FIG. 23I). Although reduction of Flk1 expression with Flk1 siRNA also inhibited budding of Ad-N1IC-HUVEC (FIG. 30B), the inhibitory efficacy of Flk1 siRNA was less than that of Flt1 siRNA (FIG. 23J). Effects of Flk1 siRNA were more effective on budding of Ad-VEGF-HUVEC than that of Ad-N1IC-HUVEC (FIG. 30B-C). Transfection with Flt1 siRNA inhibited budding of both Ad-N1IC- and Ad-VEGF-HUVEC to a similar extent (data not shown).

Several studies demonstrated that VEGF regulated gelatinase activities in endothelial cells and the significance of gelatinase activity like MMP-2 and MMP-9 has been firmly established to induce angiogenic sprouting (16). We examined whether VEGF regulated gelatinase activity via Notch signaling in HUVEC.

In Gelatin zymography, conditioned medium of Ad-VEGF-HUVEC showed both induction and activation of MMP9, which started to be detected at day 6 (FIG. 24A) and activation of MMP2, which was detected at day 4 (FIG. 24B), compared to those of Ad-LacZ-HUVEC. Co-transduction of Ad-N1ECDFc with Ad-VEGF showed inhibition of both induction and activation of MMP9 (FIG. 24A) and an activation of MMP2 (FIG. 24B). RT-PCR analysis demonstrated that expression of MMP9 mRNA was up-regulated in Ad-N1IC-HUVEC, but expression of MMP2 mRNA was decreased in Ad-N1IC-HUVEC (FIG. 24C). Since induction of MMP2 activity was not detected in gelatin zymography (FIG. 24B), this result was a likely consequence. While expression of MT1-MMP, which is able to activate MMP2 at the cell surface (17), was up-regulated at both the transcript and protein levels in Ad-N1IC-HUVEC (FIG. 24D). As VEGF can regulate both gelatinase and MT1-MMP expression (16), RT-PCR analysis demonstrated that both MMP9 and MT1-MMP were up-regulated in Ad-VEGF-HUVEC, compared to Ad-LacZ-HUVEC and this induction was inhibited with co-transduction of Ad-N1ECDFc (FIG. 24E). Ad-N1ECDFc infection alone did not affect expression of either MMP9 or MT1-MMP in Ad-LacZ infected HUVEC (data not shown). Requisition of MMPs for angiogenic sprouting has been established by synthetic MMP inhibitors (16). GM6001 is one broad inhibitor against MMPs including MMP2, MMP9 and MT1-MMP (18). GM6001 clearly decreased budding of Ad-N1IC-HUVEC on both collagen (FIG. 31A-B) and fibrin gel (data not shown).

In the mouse Dorsa Air Sac (DAS) assay (19), stable transfectant of 293 cells over-expressing VEGF121 (293/VEGF) significantly induced in vivo angiogenesis (FIG. 25A, left panel). This VEGF-induced angiogenesis was clearly inhibited by coexpression of N1ECDFc, compared to 293/VEGF alone (FIG. 25A). Vessel density was measured and an index of angiogenesis given in FIG. 25B, demonstrating the 293/VEGF induced angiogenesis is inhibited by co-expression of 293/N1ECDFc (FIG. 25B).

Also, in the mouse Dorsa Air Sac (DAS) assay (19), the human breast cancer cell line, MDA-MB-231 significantly induced in vivo angiogenesis, presumably via the secretion of VEGF (FIG. 25C, left panel). This VEGF-induced angiogenesis was clearly inhibited by adenovirus mediated expression of N1ECDFc, compared to adenovirus expressing LacZ. (FIG. 25C). Vessel density was measured and an index of angiogenesis given in FIG. 25D, demonstrating the MDA-MB-231 induced angiogenesis is inhibited by expression of N1ECDFc.

Figure 29:
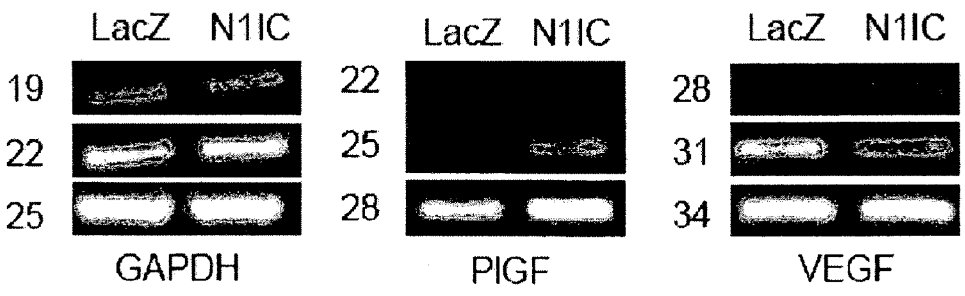

Flk1 is a major positive signal transducer for angiogenesis through its strong tyrosine kinase activity in the embryo, while Flt1 is thought to be a negative signal transducer for angiogenesis. However, a positive role for Flt-1 was demonstrated in adult mice, as in vivo growth of LLC overexpressing P1GF2 was severely compromised in mice lacking the cytoplasmic Flt-1 kinase domain (20). Notch might function to alter VEGF signaling by inducing Flt-1 signaling and moderate Flk-1 signaling either to induce filopodia extension or potentiate angiogenic sprouting, since P1GF/Flt-1 signaling altered the phospholyration site of Flk-1 and potentiated ischemic myocardial angiogenesis (21). Interestingly, Notch signaling also up-regulated P1GF expression (FIG. 29). However, continuous activation of Notch signaling inhibits formation of multi-cellular lumen-containing angiogenic sprouts, as previously reported (22). Notch signaling should be turned off after budding/filopodia formation and transient activation of the Notch pathway might be required. In a transgenic mouse model of pancreatic beta-cell carcinogenesis (Rip1Tag2 mice) in which tumor angiogenesis is VEGF dependent, the level of VEGF expression is not increased, but mobilization of extracellular VEGF stored in the matrix to VEGF receptors occurs. MMP-9 is responsible for this mobilization and tumor progression was inhibited in Rip1Tag23MMP-9-null double-transgenic mice (23). Notch up-regulated MMP-9 expression and might increase local VEGF level at the site for angiogenic sprouting. While Notch also up-regulates MT1-MMP expression, extracellular MMP-2 might be targeted to the cell membrane of Notch-activated endothelial cells. Notch might determine the site for angiogenic sprouting by regulating gelatinase activity and VEGF concentration. Since endothelial MMP-9 was regulated by Flt-1 in lung specific metastasis (20), Flt-1 might participate in induction of MMP-9 indirectly.

REFERENCES CITED IN THIRD SERIES OF EXPERIMENTS

1. Artavanis-Tsakonas 5, Rand M D, Lake R J. Notch Signaling: Cell Fate Control and Signal Integration in Development. Science 1999; 284(5415):770-776.
2. Shawber C J, J. K. Notch function in the vasculature: insights from zebrafish, mouse and man. Bioessays. 2004; 26(3):225-34.
3. Uyttendaele H, Ho J, Rossant J, J. K. Vascular patterning defects associated with expression of activated Notch4 in embryonic endothelium. Proc Natl Acad Sci USA. 2001; 98(10):5643-8.
4. Lawson N D, Vogel A M, BM. W. sonic hedgehog and vascular endothelial growth factor act upstream of the Notch pathway during arterial endothelial differentiation. Dev Cell 2002; 3(1):127-36.
5. Liu Z J, Shirakawa T, Li Y, Soma A, Oka M, Dotto G P, et al. Regulation of Notch1 and Dll4 by vascular endothelial growth factor in arterial endothelial cells: implications for modulating arteriogenesis and angiogenesis. Mol Cell Biol. 2003; 23(1):14-25.
6. Gale N W, Dominguez M G, Noguera I, Pan L, Hughes V, Valenzuela D M, et al. Haploinsufficiency of delta-like 4 ligand results in embryonic lethality due to major defects in arterial and vascular development. Proc Natl Acad Sci USA. 2004; 101(45):5949-54.
7. Montesano R, L. O. Phorbol esters induce angiogenesis in vitro from large-vessel endothelial cells. J Cell Physiol. 1987; 130(2):284-91.
8. Jarriault S. Brou C, Logeat F, Schroeter E H, Kopan R, A. I. Signalling downstream of activated mammalian Notch. Nature. 1995; 377(6547):355-8.
9. Small D, Kovalenko D, Kacer D, Liaw L, Landriscina M, Di Serio C, et al. Soluble Jagged 1 represses the function of its transmembrane form to induce the formation of the Src-dependent chord-like phenotype. J Biol Chem 2001; 276(34):32022-30.
10. Gerhardt H, Golding M, Fruttiger M, Ruhrberg C, Lundkvist A, Abramsson A, et al. VEGF guides angiogenic sprouting utilizing endothelial tip cell filopodia. J Cell Biol 2003; 161(6):1163-77.
11. Koolwijk P, van Erck M G, de Vree W J, Vermeer M A, Weich H A, Hanemaaijer R, et al. Cooperative effect of TNFalpha, bFGF, and VEGF on the formation of tubular structures of human microvascular endothelial cells in a fibrin matrix. Role of urokinase activity. J Cell Biol 1996; 132(6):1177-88.
12. Das I, Craig C, Funahashi Y, Jung K M, Kim T W, Byers R, et al. Notch oncoproteins depend on gamma-secretase/presenilin activity for processing and function. J Biol Chem 2004; 279(29):30771-80.
13. Noseda M, Chang L, McLean G, Grim J E, Clurman B E, Smith L L, et al. Notch activation induces endothelial cell cycle arrest and participates in contact inhibition: role of p21Cip1 repression. Mol Cell Biol 200424(20):8813-22.
14. Taylor K L, Henderson A M, CC. H. Notch activation during endothelial cell network formation in vitro targets the basic HLH transcription factor HESR-1 and down-regulates VEGFR-2/KDR expression. Microvasc Res 2002; 64(3):372-83.
15. Itokawa T, Nokihara H, Nishioka Y, Sone S. Iwamoto Y, Yamada Y, et al. Antiangiogenic effect by SU5416 is partly attributable to inhibition of Flt-1 receptor signaling. Mol Cancer Ther 2002; 1(5):295-302.
16. Pepper M S. Role of the matrix metalloproteinase and plasminogen activator-plasmin systems in angiogenesis. Arterioscler Thromb Vasc Biol 2001; 21(7):1104-17.
17. Seiki M, Koshikawa N, I. Y. Role of pericellular proteolysis by membrane-type 1 matrix metalloproteinase in cancer invasion and angiogenesis. Cancer Metastasis Rev 2003; 22(2-3):129-43.
18. Yamamoto M, Tsujishita H, Hori N, Ohishi Y, Inoue S, Ikeda S, et al. Inhibition of membrane-type 1 matrix metalloproteinase by hydroxamate inhibitors: an examination of the subsite pocket. J Med Chem 1998; 41(8): 1209-17.
19. Funahashi Y, Wakabayashi T, Samba T, Sonoda J, Kitoh K, K. Y. Establishment of a quantitative mouse dorsal air sac model and its application to evaluate a new angiogenesis inhibitor. Oncol Res. 1999; 11(7):319-29.
20. Hiratsuka S, Nakamura K, Iwai S, Murakami M, Itoh T, Kijima H, et al. MMP9 induction by vascular endothelial growth factor receptor-1 is involved in lung-specific metastasis. Cancer Cell 2002; 2(4):289-300.
21. Autiero M, Waltenberger J, Communi D, Kranz A, Moons L, Lambrechts D, et al. Role of P1GF in the intra- and intermolecular cross talk between the VEGF receptors Flt1 and Flk1. Nat Med 2003; 9(7):936-43.
22. Leong K G, Hu X L L, Noseda M, Larrivee B, Hull C, Hood L, et al. Activated Notch4 inhibits angiogenesis: role of beta 1-integrin activation. Mol Cell Biol 2002; 22(8):2830-41.

23. Bergers G, Brekken R, McMahon G, Vu T H, Itoh T, Tamaki K, et al. Matrix metalloproteinase-9 triggers the angiogenic switch during carcinogenesis. Nat Cell Biol 2000; 2(10):737-44.

Fourth Series of Experiments

Expression of Notch Proteins and Ligands in Blood and Lymphatic Endothelial Cells RT-PCR was performed for Notch1-4, Dll1, Dll4 and Jagged1 on RNA isolated from blood endothelial cells (BEC) and lymphatic endothelial cells (LEC) purified from HMVEC. As shown in in FIG. 44, Notch1, Notch2, Notch4, Dll4 and Jagged1 were expressed in both BEC and LEC at a similar level. Expression of Notch 3 appears to be restricted to the LEC suggestive of Notch3 signaling functions in the lymphatic endothelium.

Notch3 is Co-Expressed with the Lymphatic Endothelial Cell Marker LYVE-1 and Prox1 in e13.5 Embryos.

Figure 45:
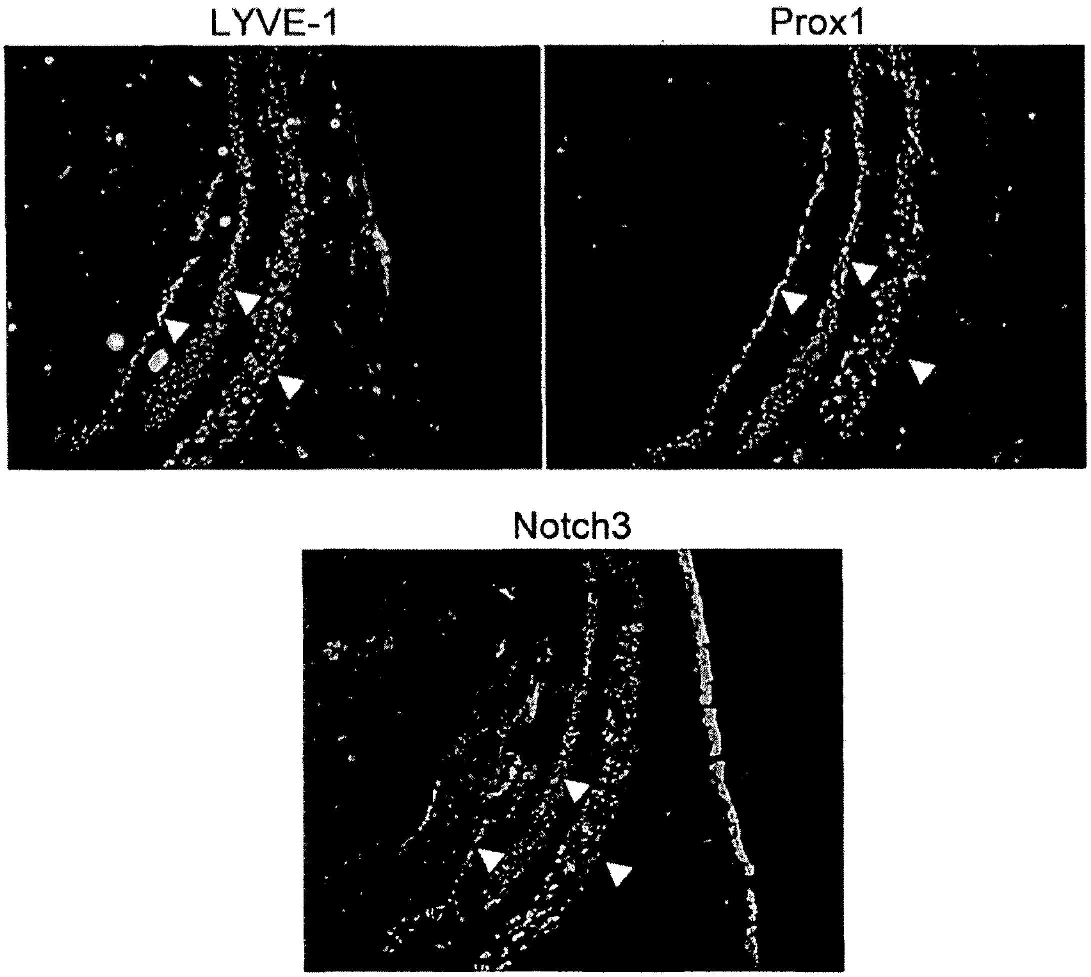

10 micron serial sections of embryonic day 13.5 mouse embryos were immunostained for either LYVE-1, Prox1 and Notch3. As shown in FIG. 45, Notch3 was expressed in the cells that also expressed the lymphatic endothelial cell markers, LYVE-1 and Prox1.

Prox1 Induced Notch3 Expression in Blood Endothelial Cells.

It was examined if ectopic expression of Prox1 would alter the expression of Notch proteins or ligands. As shown in FIG. 46, section A, twenty-four hours post adenoviral infection with either Ad-Prox1 or Ad-LacZ, HUVEC total RNA was isolated and quantitative RT-PCR for Notch1-4, Dll4 and Jagged1 performed. Prox-1 robustly upregulated the expression of Notch3. Notch1, Notch2, Notch4, Dll4 and Jagged1 expression was not significantly affected. As shown in FIG. 46, section B, Compound E (cE), Presenlin inhibitor that inhibits Notch signaling, was incubated for 24 hours on either Ad-LacZ or Ad-Prox1 infected HUVEC. Total RNA was isolated and quantitative RT-PCR performed to determine Notch3 expression. Prox1 induced Notch3 expression and this induction was inhibited by the addition of compound E.

This suggests that the Prox1 induction of Notch3 is dependent on Notch signal activation.

Prox1 Induces Notch-Target Genes in Blood Endothelial Cells.

HUVEC were infected with adenoviruses encoding, LacZ, Prox1, N1IC or N4/int-3 and total RNA isolated 24 hours post-infection. Quantitative RT-PCR was performed for the endothelial Notch-target genes, VEGFR-3, EphrinB2, Hey1 and Hey2. Similar to Notch1 and Notch4 signal activation, Prox1 induced all four genes (FIG. 47, sections A and B). Expression of Hey1 and Hey2 in the lymphatic endothelium is unknown.

Prox1 Induces Notch-Target Genes is Dependent on Notch Signaling in Blood Endothelial Cells.

HUVEC were infected with adenoviruses encoding LacZ, Prox1, N1Ic or N4/int-3. Compound E(cE), Presenlin inhibitor that inhibits Notch signaling, was incubated for 24 hours on either Ad-LacZ or Ad-Prox1 infected HUVEC and total RNA isolated. Quantitative RT-PCR was performed for the endothelial Notch-target genes, VEGFR-3, EphrinB2, and Hey2. The Prox-1 mediated induction of the Notch target genes, ephrinB2, VEGFR-3 and Hey2 was inhibited by the addition of the Notch signaling inhibitor Compound E, as shown in FIG. 48. Thus, Prox1 regulates the expression of ephrinB2, VEGFR-3 and Hey2 via Notch.

Fifth Series of Experiments

Background

Insights into a function for Notch in vascular homeostasis can be drawn from the human neurovascular disorder, Cerebral Autosomal Dominant Arteriopathy with Subcortical Infarcts and Leukoencephalopathy (CADASIL). In a majority of patients, CADASIL has been found to correlate with missense mutation in Notch3. CADASIL is a late-onset (average age of 45) autosomal dominant disorder characterized by migraines with aura and recurrent strokes that lead to psychiatric symptoms, progressive cognitive decline, dementia, and death[(81)]. These neuropathological symptoms arise secondary to a slow developing arteriopathy, associated with the disorganization and destruction of the vascular smooth muscle cells surrounding the cerebral arteries and arterioles. Regression of vascular smooth muscle cells is associated with a decrease in vessel wall thickness, a loss of extracellular matrix, and vessel wall weakness[(82)]. Within the vascular smooth muscle cells, there is an accumulation of the extracellular domain of Notch3 and in the extracellular matrix, an abnormal deposition of particles referred to as granular osmophilic materials (GOM)[(83)]. In this disorder, arterial lesions are not restricted to the brain and are found in arteries of the skin and retina[(83-85)].

The CADASIL phenotype correlates with the expression of Notch3 in vascular smooth muscle cells[(70,81)]. The hypothesis being that Notch3 functions to maintain cell-cell interactions or communication between vascular smooth muscle cells and arterial endothelial cells. A recent study has recreated the CADASIL vessel pathology in transgenic mice that express a Notch3 transgene encoding the CADASIL R90C mutation specifically in vascular smooth muscle cells [(86)]. The vasculature of these mice showed classic CADASIL arteriopathy, including GOM deposits and Notch3 accumulation. However, these hallmarks were preceded by the disruption of anchorage and adhesion of vascular smooth muscle cells to neighboring cells followed by degeneration of the vascular smooth muscle cells. Thus, CADASIL, results from reduced vascular smooth muscle cell contact and viability and the GOM deposition and accumulation of the extracellular domain of Notch3 are secondary consequences of this cellular deterioration. Consistent with a role for Notch3 in cell survival, expression of a constitutively active form of Notch3 in rat aortic smooth muscle cells resulted in the induction of cFlip, an antagonist of Fas-dependent apoptosis[(87)]. In addition, ectopic expression of Hey1 in cultured vascular smooth muscle cells promoted cell survival via Akt and thus inhibited apoptosis in response to serum starvation and Fas ligand[(88)]. Taken together, this data indicate that Notch3 maintains arterial vessel homeostasis by promoting vascular smooth muscle cell survival. The resulting arterial vessel wall leakiness could arise from vascular smooth muscle cell death or a failure of vascular smooth muscle cells to communicate to their neighboring endothelial cells. Disruption of Notch3 activity in mice may help define the nature of this defect.

The specific activity of CADASIL mutant Notch3 proteins is still poorly understood. One complication in interpreting mutant Notch3 function arises from conflicting in vitro studies that have shown that truncated cytoplasmic Notch3 can either inhibit or activate the CSL transcription factor[(89,90)].

Activation of Notch Signaling in Vascular Smooth Muscle Cells Results in Embryonic Lethality.

Notch3 is expressed and active in cells that surround blood vessels, the smooth muscle cells and pericytes. Smooth muscles cells are important for cardiovascular function and they must be healthy to prevent stroke. Pericytes can contribute to tumor vessel growth. Notch1 and Notch4 are not though to function in these cells types.

Therefore the Notch3 fusion proteins described herein may be useful to prevent stroke by preventing abnormal Notch3 activity. In addition, the Notch3 fusion proteins may be useful to maintain vascular smooth muscle cells, to restrain tumor pericyte growth or function, or to affect retinal angigogenesis by modulating pericyte function.

We have constructed a transgenic mouse that expresses an activated form of Notch1 (N1IC) under the control of the elongation factor 1-alpha promoter (EF1α) in tissues that express Cre-recombinase, referred to as EF1 $\alpha^{N1IC/+}$ (FIG. 49). EF1 $\alpha^{N1IC/+}$ is viable and fertile (FIG. 50). We have expressed N1IC in vascular smooth muscle cells by crossing EF1 $\alpha^{N1IC/+}$ with an SM22-Cre mouse line ($SM22^{cre/+}$).

The resulting $SM22^{Cre/+}$; EF1 $\alpha^{N1IC/+}$ double transgenic the at E9.5 (FIG. 50). $SM22^{cre/+}$; EF1 $\alpha^{N1IC/+}$ embryos display myocardial defects that we believe are responsible for embryonic lethality. Consistent with these myocardial smooth muscle cells defects, we observed an alteration in the expression of the vascular smooth muscle cell marker, alpha smooth muscle cell actin in E9.5 $SM22^{Cre/+}$; EF1 $\alpha^{N1IC/+}$ transgenic animals (FIG. 51). These results demonstrating that increased Notch signaling in vascular smooth muscle cells disrupts embryonic cardiovascular development.

REFERENCES CITED IN FIFTH SERIES OF EXPERIMENTS

81. Viitanen M, Kalimo H. CADASIL: Hereditary arteriopathy leading to multiple brain infarcts and dementia. Ann. N.Y. Acad. Sci. 2000; 903:273-84.

82. Brulin P. Godfraind C, Leteurtre E, Ruchoux M M. Morphometric analysis of ultrastructural vascular changes in CADASIL: analysis of 50 skin biopsy specimens and pathogenic implications. Acta. Neuropathol. 2002; 104: 241-8.

83. Uyama E, Tokunaga M, Suenaga A, Kotorii S, Kamimura K, Takahashi K, Tabira T, Uchino M. Arg133Cys mutation of Notch3 in two unrelated Japanese families with CADASIL. Intern. Med. 2000; 39(9):732-7.

84, Joutel A, Favrole P. Labauge P, Chabriat H, Lescoat C, Andreux F, Domenga V. Cecillon M, Vahedi K, Ducros A and others. Skin biospy immunostaining with a Notch3 monoclonal antibody for CADASIL diagnosis. Lancet 2001; 358:2049-51.

85. Smith B W, Henneberry J, Connolly T. Skin biopsy findings in CADASIL. Neurology 2002; 59(6):961.

86. Ruchoux M M, Domenga V, Brulin P, Maciazek J, Limol S. Tournier-Lasserve E, Joutel A. Transgenic mice expressing mutant Notch3 develop vascular alterations characteristic of cerebral autosomal dominant arteriopathy with subcortical infarcts and leuckoencephalopathy. Am. J. Path. 2003; 162(1):329-42.

87. Wang W, Prince C Z, Mou Y, Pollman M J. Notch3 signaling in vascular smooth muscle cells induces c-FLIP expression via ERK/MAPK activation. J Biol Chem 2002; 277(24):21723-9.

88. Wang W, Prince C Z, Hu X, Pollman M J. HRT1 modulates vascular smooth muscle cell proliferation and apoptosis. Biochem Biophys Res Commun 2003; 308(3): 596-601.

89. Beatus P. Lundkvist J, Oberg C, Lendahl U. The Notch3 intracellular domain represses Notch1-mediated activation through Hairy/Enhancer of split (HES) promoters. Development 1999; 126(17):3925-35.

90. Saxena M T, Schroeter E H, Mumm J S, Kopan R. Murine notch homologs (N1-4) undergo presenilin-dependent proteolysis. J. Biol. Chem. 2001; 276(43):40268-73.

What is claimed is:

1. A fusion protein the sequence of which (a) is identical to a sequence consisting of EGF repeats 1-X of the extracellular domain of human Notch3 receptor protein, wherein X is any integer from 12 to 33, followed by (b) a sequence identical to the sequence of an Fc portion of an antibody, wherein (b) is located to the carboxy terminal side of (a) and wherein (b) is attached to (a) either directly or by means of a linker sequence wherein the fusion protein has Notch3 ligand binding activity.

2. The fusion protein of claim 1, wherein the Fc portion of the antibody is the Fc portion of a human antibody.

3. The fusion protein of claim 1, wherein (b) is attached directly to (a).

4. The fusion protein of claim 1, wherein (b) is attached to (a) by means of a linker sequence.

* * * * *

UNITED STATES PATENT AND TRADEMARK OFFICE

CERTIFICATE OF CORRECTION

PATENT NO. : 9,475,855 B2

APPLICATION NO. : 13/060254

DATED : October 25, 2016

INVENTOR(S) : Jan Kitajewski and Carrie Shawber

It is certified that error appears in the above-identified patent and that said Letters Patent is hereby corrected as shown below:

In Column 1, the Federal sponsorship statement of the second paragraph should be revised to read:

This invention was made with government support under grants HL062454 and DK074629 awarded by the National Institutes of Health, and W81XWH-04-1-0540 awarded by the Army Medical and Materiel Command. The Government has certain rights in this invention.

Signed and Sealed this
Fourteenth Day of November, 2017

Joseph Matal

*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 34

<210> SEQ ID NO 1
<211> LENGTH: 1433
<212> TYPE: PRT
<213> ORGANISM: Rattus norvegicus

<400> SEQUENCE: 1

Met Pro Arg Leu Leu Ala Pro Leu Leu Cys Leu Thr Leu Leu Pro Ala
1               5                   10                  15

Leu Ala Ala Arg Gly Leu Arg Cys Ser Gln Pro Ser Gly Thr Cys Leu
            20                  25                  30

Asn Gly Gly Arg Cys Glu Val Ala Asn Gly Thr Glu Ala Cys Val Cys
        35                  40                  45

Ser Gly Ala Phe Val Gly Gln Arg Cys Gln Asp Pro Ser Pro Cys Leu
    50                  55                  60

Ser Thr Pro Cys Lys Asn Ala Gly Thr Cys Tyr Val Val Asp His Gly
65                  70                  75                  80

Gly Ile Val Asp Tyr Ala Cys Ser Cys Pro Leu Gly Phe Ser Gly Pro
                85                  90                  95

Leu Cys Leu Thr Pro Leu Ala Asn Ala Cys Leu Ala Asn Pro Cys Arg
            100                 105                 110
```

-continued

```
Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ser
145                 150                 155                 160

Ser Tyr Ile Cys Gly Cys Pro Pro Gly Phe His Gly Pro Thr Cys Arg
                165                 170                 175

Gln Asp Val Asn Glu Cys Ser Gln Asn Pro Gly Leu Cys Arg His Gly
            180                 185                 190

Gly Thr Cys His Asn Glu Ile Gly Ser Tyr Arg Cys Ala Cys Arg Ala
        195                 200                 205

Thr His Thr Gly Pro His Cys Glu Leu Pro Tyr Val Pro Cys Ser Pro
    210                 215                 220

Ser Pro Cys Gln Asn Gly Gly Thr Cys Arg Pro Thr Gly Asp Thr Thr
225                 230                 235                 240

His Glu Cys Ala Cys Leu Pro Gly Phe Ala Gly Gln Asn Cys Glu Glu
                245                 250                 255

Asn Val Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Ala Gly Thr Cys His Asn Ser His Gly Gly Tyr Asn
305                 310                 315                 320

Cys Val Cys Val Asn Gly Trp Thr Gly Glu Asp Cys Ser Asp Asn Ile
                325                 330                 335

Asp Asp Cys Ala Ser Ala Ala Cys Phe Gln Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Arg Gly Tyr Thr Gly Pro Ala Cys Ser Gln Asp Val Asp Glu Cys
                405                 410                 415

Ala Leu Gly Ala Asn Pro Cys Glu His Ala Gly Lys Cys Leu Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Ile Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val Tyr Cys Glu Ile Asn Thr Asp Glu Cys Ala Ser
                485                 490                 495

Ser Pro Cys Leu His Asn Gly Arg Cys Val Asp Lys Ile Asn Glu Phe
            500                 505                 510

Leu Cys Gln Cys Pro Lys Gly Phe Ser Gly His Leu Cys Gln Tyr Asp
        515                 520                 525

Val Asp Glu Cys Ala Ser Thr Pro Cys Lys Asn Gly Ala Lys Cys Leu
```

-continued

```
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Ile Gly Leu Cys Lys Asp Gly Val Ala Thr Phe Thr Cys Leu Cys Gln
            580                 585                 590

Pro Gly Tyr Thr Gly His His Cys Glu Thr Asn Ile Asn Glu Cys His
        595                 600                 605

Ser Gln Pro Cys Arg His Gly Gly Thr Cys Gln Asp Arg Asp Asn Tyr
    610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Val Asn Ile Asp Glu Cys Ala Gly Ser Pro Cys His
        675                 680                 685

Asn Gly Gly Thr Cys Glu Asp Gly Ile Ala Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Ile His Gly Ala Cys Arg Asp Gly Leu Asn Gly
                725                 730                 735

Tyr Lys Cys Asp Cys Ala Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Pro Leu Pro Tyr Thr Gly Ala Thr Cys Glu Val Val Leu Ala Pro
            820                 825                 830

Cys Ala Thr Ser Pro Cys Lys Asn Ser Gly Val Cys Lys Glu Ser Glu
        835                 840                 845

Asp Tyr Glu Ser Phe Ser Cys Val Cys Pro Thr Gly Trp Gln Gly Gln
    850                 855                 860

Thr Cys Glu Ile Asp Ile Asn Glu Cys Val Lys Ser Pro Cys Arg His
865                 870                 875                 880

Gly Ala Ser Cys Gln Asn Thr Asn Gly Ser Tyr Arg Cys Leu Cys Gln
                885                 890                 895

Ala Gly Tyr Thr Gly Arg Asn Cys Glu Ser Asp Ile Asp Asp Cys Arg
            900                 905                 910

Pro Asn Pro Cys His Asn Gly Gly Ser Cys Thr Asp Gly Val Asn Ala
        915                 920                 925

Ala Phe Cys Asp Cys Leu Pro Gly Phe Gln Gly Ala Phe Cys Glu Glu
    930                 935                 940

Asp Ile Asn Glu Cys Ala Thr Asn Pro Cys Gln Asn Gly Ala Asn Cys
945                 950                 955                 960
```

-continued

```
Thr Asp Cys Val Asp Ser Tyr Thr Cys Thr Cys Pro Thr Gly Phe Asn
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                1005

Cys Pro  Pro Gly Phe Thr Gly  Ser Tyr Cys Gln Tyr  Asp Val Asn
    1010                 1015                 1020

Glu Cys  Asp Ser Arg Pro Cys  Leu His Gly Gly Thr  Cys Gln Asp
    1025                 1030                 1035

Ser Tyr  Gly Thr Tyr Lys Cys  Thr Cys Pro Gln Gly  Tyr Thr Gly
    1040                 1045                 1050

Leu Asn  Cys Gln Asn Leu Val  Arg Trp Cys Asp Ser  Ala Pro Cys
    1055                 1060                 1065

Lys Asn  Gly Gly Lys Cys Trp  Gln Thr Asn Thr Gln  Tyr His Cys
    1070                 1075                 1080

Glu Cys  Arg Ser Gly Trp Thr  Gly Phe Asn Cys Asp  Val Leu Ser
    1085                 1090                 1095

Val Ser  Cys Glu Val Ala Ala  Gln Lys Arg Gly Ile  Asp Val Thr
    1100                 1105                 1110

Leu Leu  Cys Gln His Gly Gly  Leu Cys Val Asp Glu  Glu Asp Lys
    1115                 1120                 1125

His Tyr  Cys His Cys Gln Ala  Gly Tyr Thr Gly Ser  Tyr Cys Glu
    1130                 1135                 1140

Asp Glu  Val Asp Glu Cys Ser  Pro Asn Pro Cys Gln  Asn Gly Ala
    1145                 1150                 1155

Thr Cys  Thr Asp Tyr Leu Gly  Gly Phe Ser Cys Lys  Cys Val Ala
    1160                 1165                 1170

Gly Tyr  His Gly Ser Asn Cys  Ser Glu Glu Ile Asn  Glu Cys Leu
    1175                 1180                 1185

Ser Gln  Pro Cys Gln Asn Gly  Gly Thr Cys Ile Asp  Leu Thr Asn
    1190                 1195                 1200

Thr Tyr  Lys Cys Ser Cys Pro  Arg Gly Thr Gln Gly  Val His Cys
    1205                 1210                 1215

Glu Ile  Asn Val Asp Asp Cys  His Pro Pro Leu Asp  Pro Ala Ser
    1220                 1225                 1230

Arg Ser  Pro Lys Cys Phe Asn  Asn Gly Thr Cys Val  Asp Gln Val
    1235                 1240                 1245

Gly Gly  Tyr Thr Cys Thr Cys  Pro Pro Gly Phe Val  Gly Glu Arg
    1250                 1255                 1260

Cys Glu  Gly Asp Val Asn Glu  Cys Leu Ser Asn Pro  Cys Asp Pro
    1265                 1270                 1275

Arg Gly  Thr Gln Asn Cys Val  Gln Arg Val Asn Asp  Phe His Cys
    1280                 1285                 1290

Glu Cys  Arg Ala Gly His Thr  Gly Arg Arg Cys Glu  Ser Val Ile
    1295                 1300                 1305

Asn Gly  Cys Arg Gly Lys Pro  Cys Arg Asn Gly Gly  Val Cys Ala
    1310                 1315                 1320

Val Ala  Ser Asn Thr Ala Arg  Gly Phe Ile Cys Arg  Cys Pro Ala
    1325                 1330                 1335

Arg Phe  Glu Gly Ala Thr Cys  Glu Asn Asp Ala Arg  Thr Cys Gly
    1340                 1345                 1350
```

```
Ser Leu  Arg Cys Leu Asn Gly  Gly Thr Cys Ile Ser  Gly Pro Arg
    1355                1360                1365

Ser Pro  Thr Cys Leu Cys Leu  Gly Ser Phe Thr Gly  Pro Glu Cys
    1370                1375                1380

Gln Phe  Pro Ala Ser Ser Pro  Cys Val Gly Ser Asn  Pro Cys Tyr
    1385                1390                1395

Asn Gln  Gly Thr Cys Glu Pro  Thr Ser Glu Ser Pro  Phe Tyr Arg
    1400                1405                1410

Cys Leu  Cys Pro Ala Lys Phe  Asn Gly Leu Leu Cys  His Ile Leu
    1415                1420                1425

Asp Tyr  Ser Phe Thr
    1430


<210> SEQ ID NO 2
<211> LENGTH: 5
<212> TYPE: PRT
<213> ORGANISM: Rattus norvegius

<400> SEQUENCE: 2

Asp Leu Gly Pro Gly
1               5


<210> SEQ ID NO 3
<211> LENGTH: 1419
<212> TYPE: PRT
<213> ORGANISM: Rattus norvegicus

<400> SEQUENCE: 3

Met Pro Ala Leu Arg Pro Ala Ala Leu Arg Ala Leu Leu Trp Leu Trp
1               5                   10                  15

Leu Cys Gly Ala Gly Pro Ala His Ala Leu Gln Cys Arg Gly Gly Gln
            20                  25                  30

Glu Pro Cys Val Asn Glu Gly Thr Cys Val Thr Tyr His Asn Gly Thr
        35                  40                  45

Gly Tyr Cys Arg Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Thr Gln Ala Met Leu Gly Lys Ala Thr Cys Arg Cys Ala Pro Gly Phe
                85                  90                  95

Thr Gly Glu Asp Cys Gln Tyr Ser Thr Ser His Pro Cys Phe Val Ser
            100                 105                 110

Arg Pro Cys Gln Asn Gly Gly Thr Cys His Met Leu Ser Trp Asp Thr
        115                 120                 125

Tyr Glu Cys Thr Cys Gln Val Gly Phe Thr Gly Lys Gln Cys Gln Trp
    130                 135                 140

Thr Asp Val Cys Leu Ser His Pro Cys Glu Asn Gly Ser Thr Cys Ser
145                 150                 155                 160

Ser Val Ala Asn Gln Phe Ser Cys Arg Cys Pro Ala Gly Ile Thr Gly
                165                 170                 175

Gln Lys Cys Asp Ala Asp Ile Asn Glu Cys Asp Ile Pro Gly Arg Cys
            180                 185                 190

Gln His Gly Gly Thr Cys Leu Asn Leu Pro Gly Ser Tyr Arg Cys Gln
        195                 200                 205

Cys Pro Gln Arg Phe Thr Gly Gln His Cys Asp Ser Pro Tyr Val Pro
    210                 215                 220
```

-continued

```
Cys Ala Pro Ser Pro Cys Val Asn Gly Gly Thr Cys Arg Gln Thr Gly
225                 230                 235                 240

Asp Phe Thr Ser Glu Cys His Cys Leu Pro Gly Phe Glu Gly Ser Asn
                245                 250                 255

Cys Glu Arg Asn Ile Asp Asp Cys Pro Asn His Lys Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Thr Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Leu Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Ala Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Val Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Thr Leu Cys Asp Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Leu
625                 630                 635                 640

Asn Cys Glu Ile Asn Phe Asp Asp Cys Ala Ser Asn Pro Cys Leu His
```

-continued

```
                645                 650                 655

Gly Ala Cys Val Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Asp Ala Thr Cys Ile Asn Asp Val Asn Gly Phe
    690                 695                 700

Arg Cys Met Cys Pro Glu Gly Pro His His Pro Ser Cys Tyr Ser Gln
705                 710                 715                 720

Val Asn Glu Cys Leu Ser Ser Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asn Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Leu Asp Asp Val Ser Gly
                805                 810                 815

Tyr Thr Cys His Cys Met Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845

Lys Glu Ala Pro Asn Phe Glu Ser Phe Thr Cys Leu Cys Ala Pro Gly
    850                 855                 860

Trp Gln Gly Gln Arg Cys Thr Val Asp Val Asp Glu Cys Val Ser Lys
865                 870                 875                 880

Pro Cys Met Asn Asn Gly Ile Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asn Asp Cys Leu Ala Asn Pro Cys Gln Asn Gly Gly Ser Cys Val Asp
        915                 920                 925

Lys Val Asn Thr Phe Ser Cys Leu Cys Leu Pro Gly Phe Val Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Thr Cys Pro
                965                 970                 975

Ala Gly Phe His Gly Val His Cys Glu Asn Asn Ile Asp Glu Cys Thr
            980                 985                 990

Glu Ser Ser Cys Phe Asn Gly Gly  Thr Cys Val Asp Gly  Ile Asn Ser
        995                 1000                1005

Phe Ser  Cys Leu Cys Pro Val  Gly Phe Thr Gly Pro  Phe Cys Leu
    1010                1015                1020

His Asp  Ile Asn Glu Cys Ser  Ser Asn Pro Cys Leu  Asn Ser Gly
    1025                1030                1035

Thr Cys  Val Asp Gly Leu Gly  Thr Tyr Arg Cys Thr  Cys Pro Leu
    1040                1045                1050

Gly Tyr  Thr Gly Lys Asn Cys  Gln Thr Leu Val Asn  Leu Cys Ser
    1055                1060                1065
```

```
Pro Ser  Pro Cys Lys Asn Lys  Gly Thr Cys Ala Gln  Glu Lys Ala
    1070                 1075                 1080

Arg Pro  Arg Cys Leu Cys Pro  Pro Gly Trp Asp Gly  Ala Tyr Cys
    1085                 1090                 1095

Asp Val  Leu Asn Val Ser Cys  Lys Ala Ala Ala Leu  Gln Lys Gly
    1100                 1105                 1110

Val Pro  Val Glu His Leu Cys  Gln His Ser Gly Ile  Cys Ile Asn
    1115                 1120                 1125

Ala Gly  Asn Thr His His Cys  Gln Cys Pro Leu Gly  Tyr Thr Gly
    1130                 1135                 1140

Ser Tyr  Cys Glu Glu Gln Leu  Asp Glu Cys Ala Ser  Asn Pro Cys
    1145                 1150                 1155

Gln His  Gly Ala Thr Cys Ser  Asp Phe Ile Gly Gly  Tyr Arg Cys
    1160                 1165                 1170

Glu Cys  Val Pro Gly Tyr Gln  Gly Val Asn Cys Glu  Tyr Glu Val
    1175                 1180                 1185

Asp Glu  Cys Gln Asn Gln Pro  Cys Gln Asn Gly Gly  Thr Cys Ile
    1190                 1195                 1200

Asp Leu  Val Asn His Phe Lys  Cys Ser Cys Pro Pro  Gly Thr Arg
    1205                 1210                 1215

Gly Leu  Leu Cys Glu Glu Asn  Ile Asp Asp Cys Ala  Gly Ala Pro
    1220                 1225                 1230

His Cys  Leu Asn Gly Gly Gln  Cys Val Asp Arg Ile  Gly Gly Tyr
    1235                 1240                 1245

Ser Cys  Arg Cys Leu Pro Gly  Phe Ala Gly Glu Arg  Cys Glu Gly
    1250                 1255                 1260

Asp Ile  Asn Glu Cys Leu Ser  Asn Pro Cys Ser Ser  Glu Gly Ser
    1265                 1270                 1275

Leu Asp  Cys Ile Gln Leu Lys  Asn Asn Tyr Gln Cys  Val Cys Arg
    1280                 1285                 1290

Ser Ala  Phe Thr Gly Arg His  Cys Glu Thr Phe Leu  Asp Val Cys
    1295                 1300                 1305

Pro Gln  Lys Pro Cys Leu Asn  Gly Gly Thr Cys Ala  Val Ala Ser
    1310                 1315                 1320

Asn Val  Pro Asp Gly Phe Ile  Cys Arg Cys Pro Pro  Gly Phe Ser
    1325                 1330                 1335

Gly Ala  Arg Cys Gln Ser Ser  Cys Gly Gln Val Lys  Cys Arg Arg
    1340                 1345                 1350

Gly Glu  Gln Cys Val His Thr  Ala Ser Gly Pro His  Cys Phe Cys
    1355                 1360                 1365

Pro Asn  His Lys Asp Cys Glu  Ser Gly Cys Ala Ser  Asn Pro Cys
    1370                 1375                 1380

Gln His  Gly Gly Thr Cys Tyr  Pro Gln Arg Gln Pro  Pro Tyr Tyr
    1385                 1390                 1395

Ser Cys  Arg Cys Ser Pro Pro  Phe Trp Gly Ser His  Cys Glu Ser
    1400                 1405                 1410

Tyr Thr  Ala Pro Thr Ser
    1415
```

<210> SEQ ID NO 4
<211> LENGTH: 1379
<212> TYPE: PRT
<213> ORGANISM: Mus musculus

<400> SEQUENCE: 4

```
Met Gly Leu Gly Ala Arg Gly Arg Arg Arg Arg Arg Arg Leu Met Ala
1               5                   10                  15

Leu Pro Pro Pro Pro Pro Pro Met Arg Ala Leu Pro Leu Leu Leu Leu
            20                  25                  30

Leu Ala Gly Leu Gly Ala Ala Ala Pro Pro Cys Leu Asp Gly Ser Pro
        35                  40                  45

Cys Ala Asn Gly Gly Arg Cys Thr His Gln Gln Pro Ser Leu Glu Ala
    50                  55                  60

Ala Cys Leu Cys Leu Pro Gly Trp Val Gly Glu Arg Cys Gln Leu Glu
65                  70                  75                  80

Asp Pro Cys His Ser Gly Pro Cys Ala Gly Arg Gly Val Cys Gln Ser
                85                  90                  95

Ser Val Val Ala Gly Thr Ala Arg Phe Ser Cys Arg Cys Leu Arg Gly
            100                 105                 110

Phe Gln Gly Pro Asp Cys Ser Gln Pro Asp Pro Cys Val Ser Arg Pro
        115                 120                 125

Cys Val His Gly Ala Pro Cys Ser Val Gly Pro Asp Gly Arg Phe Ala
    130                 135                 140

Cys Ala Cys Pro Pro Gly Tyr Gln Gly Gln Ser Cys Gln Ser Asp Ile
145                 150                 155                 160

Asp Glu Cys Arg Ser Gly Thr Thr Cys Arg His Gly Gly Thr Cys Leu
                165                 170                 175

Asn Thr Pro Gly Ser Phe Arg Cys Gln Cys Pro Leu Gly Tyr Thr Gly
            180                 185                 190

Leu Leu Cys Glu Asn Pro Val Val Pro Cys Ala Pro Ser Pro Cys Arg
        195                 200                 205

Asn Gly Gly Thr Cys Arg Gln Ser Ser Asp Val Thr Tyr Asp Cys Ala
    210                 215                 220

Cys Leu Pro Gly Phe Glu Gly Gln Asn Cys Glu Val Asn Val Asp Asp
225                 230                 235                 240

Cys Pro Gly His Arg Cys Leu Asn Gly Gly Thr Cys Val Asp Gly Val
                245                 250                 255

Asn Thr Tyr Asn Cys Gln Cys Pro Pro Glu Trp Thr Gly Gln Phe Cys
            260                 265                 270

Thr Glu Asp Val Asp Glu Cys Gln Leu Gln Pro Asn Ala Cys His Asn
        275                 280                 285

Gly Gly Thr Cys Phe Asn Leu Leu Gly Gly His Ser Cys Val Cys Val
    290                 295                 300

Asn Gly Trp Thr Gly Glu Ser Cys Ser Gln Asn Ile Asp Asp Cys Ala
305                 310                 315                 320

Thr Ala Val Cys Phe His Gly Ala Thr Cys His Asp Arg Val Ala Ser
                325                 330                 335

Phe Tyr Cys Ala Cys Pro Met Gly Lys Thr Gly Leu Leu Cys His Leu
            340                 345                 350

Asp Asp Ala Cys Val Ser Asn Pro Cys His Glu Asp Ala Ile Cys Asp
        355                 360                 365

Thr Asn Pro Val Ser Gly Arg Ala Ile Cys Thr Cys Pro Pro Gly Phe
    370                 375                 380

Thr Gly Gly Ala Cys Asp Gln Asp Val Asp Glu Cys Ser Ile Gly Ala
385                 390                 395                 400

Asn Pro Cys Glu His Leu Gly Arg Cys Val Asn Thr Gln Gly Ser Phe
                405                 410                 415
```

-continued

```
Leu Cys Gln Cys Gly Arg Gly Tyr Thr Gly Pro Arg Cys Glu Thr Asp
            420                 425                 430

Val Asn Glu Cys Leu Ser Gly Pro Cys Arg Asn Gln Ala Thr Cys Leu
        435                 440                 445

Asp Arg Ile Gly Gln Phe Thr Cys Ile Cys Met Ala Gly Phe Thr Gly
    450                 455                 460

Thr Tyr Cys Glu Val Asp Ile Asp Glu Cys Gln Ser Ser Pro Cys Val
465                 470                 475                 480

Asn Gly Gly Val Cys Lys Asp Arg Val Asn Gly Phe Ser Cys Thr Cys
                485                 490                 495

Pro Ser Gly Phe Ser Gly Ser Met Cys Gln Leu Asp Val Asp Glu Cys
            500                 505                 510

Ala Ser Thr Pro Cys Arg Asn Gly Ala Lys Cys Val Asp Gln Pro Asp
        515                 520                 525

Gly Tyr Glu Cys Arg Cys Ala Glu Gly Phe Glu Gly Thr Leu Cys Glu
    530                 535                 540

Arg Asn Val Asp Asp Cys Ser Pro Asp Pro Cys His His Gly Arg Cys
545                 550                 555                 560

Val Asp Gly Ile Ala Ser Phe Ser Cys Ala Cys Ala Pro Gly Tyr Thr
                565                 570                 575

Gly Ile Arg Cys Glu Ser Gln Val Asp Glu Cys Arg Ser Gln Pro Cys
            580                 585                 590

Arg Tyr Gly Gly Lys Cys Leu Asp Leu Val Asp Lys Tyr Leu Cys Arg
        595                 600                 605

Cys Pro Pro Gly Thr Thr Gly Val Asn Cys Glu Val Asn Ile Asp Asp
    610                 615                 620

Cys Ala Ser Asn Pro Cys Thr Phe Gly Val Cys Arg Asp Gly Ile Asn
625                 630                 635                 640

Arg Tyr Asp Cys Val Cys Gln Pro Gly Phe Thr Gly Pro Leu Cys Asn
                645                 650                 655

Val Glu Ile Asn Glu Cys Ala Ser Ser Pro Cys Gly Glu Gly Gly Ser
            660                 665                 670

Cys Val Asp Gly Glu Asn Gly Phe His Cys Leu Cys Pro Pro Gly Ser
        675                 680                 685

Leu Pro Pro Leu Cys Leu Pro Ala Asn His Pro Cys Ala His Lys Pro
    690                 695                 700

Cys Ser His Gly Val Cys His Asp Ala Pro Gly Gly Phe Arg Cys Val
705                 710                 715                 720

Cys Glu Pro Gly Trp Ser Gly Pro Arg Cys Ser Gln Ser Leu Ala Pro
                725                 730                 735

Asp Ala Cys Glu Ser Gln Pro Cys Gln Ala Gly Gly Thr Cys Thr Ser
            740                 745                 750

Asp Gly Ile Gly Phe Arg Cys Thr Cys Ala Pro Gly Phe Gln Gly His
        755                 760                 765

Gln Cys Glu Val Leu Ser Pro Cys Thr Pro Ser Leu Cys Glu His Gly
    770                 775                 780

Gly His Cys Glu Ser Asp Pro Asp Arg Leu Thr Val Cys Ser Cys Pro
785                 790                 795                 800

Pro Gly Trp Gln Gly Pro Arg Cys Gln Gln Asp Val Asp Glu Cys Ala
                805                 810                 815

Gly Ala Ser Pro Cys Gly Pro His Gly Thr Cys Thr Asn Leu Pro Gly
            820                 825                 830
```

```
Asn Phe Arg Cys Ile Cys His Arg Gly Tyr Thr Gly Pro Phe Cys Asp
        835                 840                 845

Gln Asp Ile Asp Asp Cys Asp Pro Asn Pro Cys Leu His Gly Gly Ser
    850                 855                 860

Cys Gln Asp Gly Val Gly Ser Phe Ser Cys Ser Cys Leu Asp Gly Phe
865                 870                 875                 880

Ala Gly Pro Arg Cys Ala Arg Asp Val Asp Glu Cys Leu Ser Ser Pro
                885                 890                 895

Cys Gly Pro Gly Thr Cys Thr Asp His Val Ala Ser Phe Thr Cys Ala
            900                 905                 910

Cys Pro Pro Gly Tyr Gly Gly Phe His Cys Glu Ile Asp Leu Pro Asp
        915                 920                 925

Cys Ser Pro Ser Ser Cys Phe Asn Gly Gly Thr Cys Val Asp Gly Val
    930                 935                 940

Ser Ser Phe Ser Cys Leu Cys Arg Pro Gly Tyr Thr Gly Thr His Cys
945                 950                 955                 960

Gln Tyr Glu Ala Asp Pro Cys Phe Ser Arg Pro Cys Leu His Gly Gly
                965                 970                 975

Ile Cys Asn Pro Thr His Pro Gly Phe Glu Cys Thr Cys Arg Glu Gly
            980                 985                 990

Phe Thr Gly Ser Gln Cys Gln Asn  Pro Val Asp Trp Cys  Ser Gln Ala
        995                 1000                1005

Pro Cys  Gln Asn Gly Gly Arg  Cys Val Gln Thr Gly  Ala Tyr Cys
    1010                 1015                1020

Ile Cys  Pro Pro Gly Trp Ser  Gly Arg Leu Cys Asp  Ile Gln Ser
    1025                 1030                1035

Leu Pro  Cys Thr Glu Ala Ala  Ala Gln Met Gly Val  Arg Leu Glu
    1040                 1045                1050

Gln Leu  Cys Gln Glu Gly Gly  Lys Cys Ile Asp Lys  Gly Arg Ser
    1055                 1060                1065

His Tyr  Cys Val Cys Pro Glu  Gly Arg Thr Gly Ser  His Cys Glu
    1070                 1075                1080

His Glu  Val Asp Pro Cys Thr  Ala Gln Pro Cys Gln  His Gly Gly
    1085                 1090                1095

Thr Cys  Arg Gly Tyr Met Gly  Gly Tyr Val Cys Glu  Cys Pro Ala
    1100                 1105                1110

Gly Tyr  Ala Gly Asp Ser Cys  Glu Asp Asn Ile Asp  Glu Cys Ala
    1115                 1120                1125

Ser Gln  Pro Cys Gln Asn Gly  Gly Ser Cys Ile Asp  Leu Val Ala
    1130                 1135                1140

Arg Tyr  Leu Cys Ser Cys Pro  Pro Gly Thr Leu Gly  Val Leu Cys
    1145                 1150                1155

Glu Ile  Asn Glu Asp Asp Cys  Asp Leu Gly Pro Ser  Leu Asp Ser
    1160                 1165                1170

Gly Val  Gln Cys Leu His Asn  Gly Thr Cys Val Asp  Leu Val Gly
    1175                 1180                1185

Gly Phe  Arg Cys Asn Cys Pro  Pro Gly Tyr Thr Gly  Leu His Cys
    1190                 1195                1200

Glu Ala  Asp Ile Asn Glu Cys  Arg Pro Gly Ala Cys  His Ala Ala
    1205                 1210                1215

His Thr  Arg Asp Cys Leu Gln  Asp Pro Gly Gly His  Phe Arg Cys
    1220                 1225                1230

Val Cys  His Pro Gly Phe Thr  Gly Pro Arg Cys Gln  Ile Ala Leu
```

```
    1235                1240                1245

Ser Pro  Cys Glu Ser Gln Pro  Cys Gln His Gly Gly  Gln Cys Arg
    1250                1255                1260

His Ser  Leu Gly Arg Gly Gly  Gly Leu Thr Phe Thr  Cys His Cys
    1265                1270                1275

Val Pro  Pro Phe Trp Gly Leu  Arg Cys Glu Arg Val  Ala Arg Ser
    1280                1285                1290

Cys Arg  Glu Leu Gln Cys Pro  Val Gly Ile Pro Cys  Gln Gln Thr
    1295                1300                1305

Ala Arg  Gly Pro Arg Cys Ala  Cys Pro Pro Gly Leu  Ser Gly Pro
    1310                1315                1320

Ser Cys  Arg Val Ser Arg Ala  Ser Pro Ser Gly Ala  Thr Asn Ala
    1325                1330                1335

Ser Cys  Ala Ser Ala Pro Cys  Leu His Gly Gly Ser  Cys Leu Pro
    1340                1345                1350

Val Gln  Ser Val Pro Phe Phe  Arg Cys Val Cys Ala  Pro Gly Trp
    1355                1360                1365

Gly Gly  Pro Arg Cys Glu Thr  Pro Ser Ala Ala
    1370                1375


<210> SEQ ID NO 5
<211> LENGTH: 1170
<212> TYPE: PRT
<213> ORGANISM: Mus musculus

<400> SEQUENCE: 5

Met Gln Pro Gln Leu Leu Leu Leu Leu Leu Leu Pro Leu Asn Phe Pro
1               5                   10                  15

Val Ile Leu Thr Arg Glu Leu Leu Cys Gly Gly Ser Pro Glu Pro Cys
            20                  25                  30

Ala Asn Gly Gly Thr Cys Leu Arg Leu Ser Arg Gly Gln Gly Ile Cys
        35                  40                  45

Gln Cys Ala Pro Gly Phe Leu Gly Glu Thr Cys Gln Phe Pro Asp Pro
    50                  55                  60

Cys Arg Asp Thr Gln Leu Cys Lys Asn Gly Gly Ser Cys Gln Ala Leu
65                  70                  75                  80

Leu Pro Thr Pro Pro Ser Ser Arg Ser Pro Thr Ser Pro Leu Thr Pro
                85                  90                  95

His Phe Ser Cys Thr Cys Pro Ser Gly Phe Thr Gly Asp Arg Cys Gln
            100                 105                 110

Thr His Leu Glu Glu Leu Cys Pro Pro Ser Phe Cys Ser Asn Gly Gly
        115                 120                 125

His Cys Tyr Val Gln Ala Ser Gly Arg Pro Gln Cys Ser Cys Glu Pro
    130                 135                 140

Gly Trp Thr Gly Glu Gln Cys Gln Leu Arg Asp Phe Cys Ser Ala Asn
145                 150                 155                 160

Pro Cys Ala Asn Gly Gly Val Cys Leu Ala Thr Tyr Pro Gln Ile Gln
                165                 170                 175

Cys Arg Cys Pro Pro Gly Phe Glu Gly His Thr Cys Glu Arg Asp Ile
            180                 185                 190

Asn Glu Cys Phe Leu Glu Pro Gly Pro Cys Pro Gln Gly Thr Ser Cys
        195                 200                 205

His Asn Thr Leu Gly Ser Tyr Gln Cys Leu Cys Pro Val Gly Gln Glu
    210                 215                 220
```

-continued

```
Gly Pro Gln Cys Lys Leu Arg Lys Gly Ala Cys Pro Pro Gly Ser Cys
225                 230                 235                 240

Leu Asn Gly Gly Thr Cys Gln Leu Val Pro Glu Gly His Ser Thr Phe
                245                 250                 255

His Leu Cys Leu Cys Pro Pro Gly Phe Thr Gly Leu Asp Cys Glu Met
            260                 265                 270

Asn Pro Asp Asp Cys Val Arg His Gln Cys Gln Asn Gly Ala Thr Cys
        275                 280                 285

Leu Asp Gly Leu Asp Thr Tyr Thr Cys Leu Cys Pro Lys Thr Trp Lys
    290                 295                 300

Gly Trp Asp Cys Ser Glu Asp Ile Asp Glu Cys Glu Ala Arg Gly Pro
305                 310                 315                 320

Pro Arg Cys Arg Asn Gly Gly Thr Cys Gln Asn Thr Ala Gly Ser Phe
                325                 330                 335

His Cys Val Cys Val Ser Gly Trp Gly Gly Ala Gly Cys Glu Glu Asn
            340                 345                 350

Leu Asp Asp Cys Ala Ala Ala Thr Cys Ala Pro Gly Ser Thr Cys Ile
        355                 360                 365

Asp Arg Val Gly Ser Phe Ser Cys Leu Cys Pro Pro Gly Arg Thr Gly
    370                 375                 380

Leu Leu Cys His Leu Glu Asp Met Cys Leu Ser Gln Pro Cys His Val
385                 390                 395                 400

Asn Ala Gln Cys Ser Thr Asn Pro Leu Thr Gly Ser Thr Leu Cys Ile
                405                 410                 415

Cys Gln Pro Gly Tyr Ser Gly Ser Thr Cys His Gln Asp Leu Asp Glu
            420                 425                 430

Cys Gln Met Ala Gln Gln Gly Pro Ser Pro Cys Glu His Gly Gly Ser
        435                 440                 445

Cys Ile Asn Thr Pro Gly Ser Phe Asn Cys Leu Cys Leu Pro Gly Tyr
    450                 455                 460

Thr Gly Ser Arg Cys Glu Ala Asp His Asn Glu Cys Leu Ser Gln Pro
465                 470                 475                 480

Cys His Pro Gly Ser Thr Cys Leu Asp Leu Leu Ala Thr Phe His Cys
                485                 490                 495

Leu Cys Pro Pro Gly Leu Glu Gly Arg Leu Cys Glu Val Glu Val Asn
            500                 505                 510

Glu Cys Thr Ser Asn Pro Cys Leu Asn Gln Ala Ala Cys His Asp Leu
        515                 520                 525

Leu Asn Gly Phe Gln Cys Leu Cys Leu Pro Gly Phe Thr Gly Ala Arg
    530                 535                 540

Cys Glu Lys Asp Met Asp Glu Cys Ser Ser Thr Pro Cys Ala Asn Gly
545                 550                 555                 560

Gly Arg Cys Arg Asp Gln Pro Gly Ala Phe Tyr Cys Glu Cys Leu Pro
                565                 570                 575

Gly Phe Glu Gly Pro His Cys Glu Lys Glu Val Asp Glu Cys Leu Ser
            580                 585                 590

Asp Pro Cys Pro Val Gly Ala Ser Cys Leu Asp Leu Pro Gly Ala Phe
        595                 600                 605

Phe Cys Leu Cys Arg Pro Gly Phe Thr Gly Gln Leu Cys Glu Val Pro
    610                 615                 620

Leu Cys Thr Pro Asn Met Cys Gln Pro Gly Gln Gln Cys Gln Gly Gln
625                 630                 635                 640

Glu His Arg Ala Pro Cys Leu Cys Pro Asp Gly Ser Pro Gly Cys Val
```

-continued

```
                645                 650                 655

Pro Ala Glu Asp Asn Cys Pro Cys His His Gly His Cys Gln Arg Ser
            660                 665                 670

Leu Cys Val Cys Asp Glu Gly Trp Thr Gly Pro Glu Cys Glu Thr Glu
        675                 680                 685

Leu Gly Gly Cys Ile Ser Thr Pro Cys Ala His Gly Gly Thr Cys His
    690                 695                 700

Pro Gln Pro Ser Gly Tyr Asn Cys Thr Cys Pro Ala Gly Tyr Met Gly
705                 710                 715                 720

Leu Thr Cys Ser Glu Glu Val Thr Ala Cys His Ser Gly Pro Cys Leu
                725                 730                 735

Asn Gly Gly Ser Cys Ser Ile Arg Pro Glu Gly Tyr Ser Cys Thr Cys
            740                 745                 750

Leu Pro Ser His Thr Gly Arg His Cys Gln Thr Ala Val Asp His Cys
        755                 760                 765

Val Ser Ala Ser Cys Leu Asn Gly Gly Thr Cys Val Asn Lys Pro Gly
    770                 775                 780

Thr Phe Phe Cys Leu Cys Ala Thr Gly Phe Gln Gly Leu His Cys Glu
785                 790                 795                 800

Glu Lys Thr Asn Pro Ser Cys Ala Asp Ser Pro Cys Arg Asn Lys Ala
                805                 810                 815

Thr Cys Gln Asp Thr Pro Arg Gly Ala Arg Cys Leu Cys Ser Pro Gly
            820                 825                 830

Tyr Thr Gly Ser Ser Cys Gln Thr Leu Ile Asp Leu Cys Ala Arg Lys
        835                 840                 845

Pro Cys Pro His Thr Ala Arg Cys Leu Gln Ser Gly Pro Ser Phe Gln
    850                 855                 860

Cys Leu Cys Leu Gln Gly Trp Thr Gly Ala Leu Cys Asp Phe Pro Leu
865                 870                 875                 880

Ser Cys Gln Lys Ala Ala Met Ser Gln Gly Ile Glu Ile Ser Gly Leu
                885                 890                 895

Cys Gln Asn Gly Gly Leu Cys Ile Asp Thr Gly Ser Ser Tyr Phe Cys
            900                 905                 910

Arg Cys Pro Pro Gly Phe Gln Gly Lys Leu Cys Gln Asp Asn Val Asn
        915                 920                 925

Pro Cys Glu Pro Asn Pro Cys His His Gly Ser Thr Cys Val Pro Gln
    930                 935                 940

Pro Ser Gly Tyr Val Cys Gln Cys Ala Pro Gly Tyr Glu Gly Gln Asn
945                 950                 955                 960

Cys Ser Lys Val Leu Asp Ala Cys Gln Ser Gln Pro Cys His Asn His
                965                 970                 975

Gly Thr Cys Thr Ser Arg Pro Gly Gly Phe His Cys Ala Cys Pro Pro
            980                 985                 990

Gly Phe Val Gly Leu Arg Cys Glu  Gly Asp Val Asp Glu  Cys Leu Asp
        995                 1000                1005

Arg Pro  Cys His Pro Ser Gly  Thr Ala Ala Cys His  Ser Leu Ala
    1010                1015                1020

Asn Ala  Phe Tyr Cys Gln Cys  Leu Pro Gly His Thr  Gly Gln Arg
    1025                1030                1035

Cys Glu  Val Glu Met Asp Leu  Cys Gln Ser Gln Pro  Cys Ser Asn
    1040                1045                1050

Gly Gly  Ser Cys Glu Ile Thr  Thr Gly Pro Pro Pro  Gly Phe Thr
    1055                1060                1065
```

```
Cys His Cys Pro Lys Gly Phe Glu Gly Pro Thr Cys Ser His Lys
    1070                1075                1080

Ala Leu Ser Cys Gly Ile His His Cys His Asn Gly Gly Leu Cys
    1085                1090                1095

Leu Pro Ser Pro Lys Pro Gly Ser Pro Pro Leu Cys Ala Cys Leu
    1100                1105                1110

Ser Gly Phe Gly Gly Pro Asp Cys Leu Thr Pro Pro Ala Pro Pro
    1115                1120                1125

Gly Cys Gly Pro Pro Ser Pro Cys Leu His Asn Gly Thr Cys Thr
    1130                1135                1140

Glu Thr Pro Gly Leu Gly Asn Pro Gly Phe Gln Cys Thr Cys Pro
    1145                1150                1155

Pro Asp Ser Pro Gly Pro Arg Cys Gln Arg Pro Gly
    1160                1165                1170


<210> SEQ ID NO 6
<211> LENGTH: 4293
<212> TYPE: DNA
<213> ORGANISM: Rattus norvegicus

<400> SEQUENCE: 6

atgacaggct tccagggctg ccaggccctg ctgcatctgg ccaaggccgt ggttcgcttg     60

agatgctccc agccaagtgg gacctgcctg aatggaggga ggtgcgaagt ggccaacggc    120

actgaagcct gtgtctgcag cggagcgttc gtgggccagc gatgccagga ccccagccct    180

tgcctcagca caccatgtaa gaatgctgga acgtgctatg ttgtggacca tggcggcatc    240

gtggactatg cctgcagttg cccccctgggt ttctctgggc ccctctgcct gacacctctg    300

gccaatgcct gcctggccaa cccctgccgc aacgggggga cctgtgacct gctcactctc    360

acagaataca agtgccggtg cccgccaggg tggtcaggaa agtcatgtca gcaagccgac    420

ccctgtgcct ccaacccctg tgccaatggt ggccagtgcc tgccctttga gtcttcatac    480

atctgtggct gcccgcccgg cttccatggc cccacctgca gacaagatgt taacgagtgc    540

agccagaacc ctgggttgtg ccgtcatggc ggcacgtgcc acaatgagat tggctcctat    600

cgctgtgcct gccgtgccac ccacactggt ccccactgcg agctgcccta cgtgccctgc    660

agcccctcac cctgccagaa cggaggcacc tgccgcccta cgggggacac cacccacgag    720

tgtgcctgcc tgccaggctt tgctggacag aactgtgaag aaaatgtgga tgactgccca    780

ggaaacaact gcaagaacgg gggtgcctgt gtggacggtg tgaataccta caattgccgc    840

tgcccaccgg agtggacagg tcagtactgc acagaggatg tggacgagtg tcagctcatg    900

cccaacgcct gccagaatgg cggaacctgc cacaactccc acggtggcta caactgcgtg    960

tgtgtcaatg gctggactgg tgaggactgc agtgagaaca ttgatgactg tgccagtgcc   1020

gcctgttttc agggtgccac ctgccatgac cgtgtggctt ccttctactg cgagtgtcca   1080

catgggcgca caggcctgct gtgccacctg aacgatgcgt gtatcagcaa cccctgcaac   1140

gagggctcca actgcgacac caaccctgtc aacggcaagg ccatctgcac ttgcccctcg   1200

gggtacacgg ggccagcctg cagccaggac gtggatgagt gcgctctagg tgccaacccg   1260

tgtgagcacg cgggcaagtg cctcaacaca ctgggctctt tcgagtgtca gtgtctacag   1320

ggctacactg ggccccgctg tgagattgat gtcaacgagt gcatctccaa cccatgtcag   1380

aatgatgcca cgtgcctgga ccagattggg gagtttcagt gtatatgtat gccaggttat   1440

gagggtgtat actgtgagat caacacggac gagtgtgcca gcagcccctg tctacacaat   1500
```

-continued

```
ggccgctgcg tggacaagat caacgagttc ctgtgtcagt gtcccaaagg cttcagcggg   1560
cacctgtgcc agtatgacgt ggatgagtgc gccagcacac catgcaagaa cggcgccaag   1620
tgcctggatg ggcccaacac ctacacctgc gtgtgcacag aaggttacac ggggacccac   1680
tgcgaggtgg acattgacga gtgtgaccct gacccctgtc actatggttt gtgcaaggat   1740
ggtgtggcca cctttacctg cctctgccag ccaggctaca caggccatca ctgtgagacc   1800
aacattaatg agtgtcacag ccagccgtgc cgccatggcg gcacctgcca ggaccgtgac   1860
aactactacc tctgcttatg cctcaagggg accacaggac ccaactgtga gatcaatctg   1920
gatgactgtg cgagcaaccc ctgtgactct ggcacgtgtc tggacaagat cgatggctac   1980
gagtgtgcgt gcgagccagg ctacacaggg agcatgtgta atgtcaacat tgacgaatgt   2040
gcgggcagcc cctgccacaa cgggggcacc tgtgaggatg gcatcgccgg cttcacttgc   2100
cgctgccccg agggctacca cgaccctacg tgcctgtctg aggtcaacga gtgcaacagt   2160
aacccctgca tccatggagc ttgccgggat ggcctcaatg gatacaaatg tgactgtgcc   2220
cctgggtgga gtgggacaaa ctgtgacatc aacaacaatg agtgtgagtc caacccttgt   2280
gtcaacggtg gcacctgcaa agacatgacc agtggctacg tatgcacctg ccgagaaggc   2340
ttcagtggcc ctaactgcca gaccaacatt aacgaatgtg cttccaaccc ctgcctgaac   2400
cagggcacct gcattgatga tgtcgctggg tacaaatgca actgccctct gccctataca   2460
ggagccacat gtgaggtggt gttggcccca tgtgccacca gcccctgcaa aaacagtggg   2520
gtatgcaagg agtctgagga ctatgagagc ttttcctgtg tctgtcccac aggctggcaa   2580
ggtcaaacct gcgagatcga catcaatgag tgtgtgaaaa gcccgtgtcg ccatggtgcc   2640
tcttgccaga acaccaatgg cagctaccgc tgcctctgcc aggctggcta cacgggtcgc   2700
aactgcgaga gtgacatcga tgactgccga cccaacccat gtcacaacgg gggttcctgc   2760
actgacgggg tcaacgcggc cttctgcgac tgcctgcccg gcttccaggg tgccttctgt   2820
gaggaggaca tcaacgaatg cgccagcaat ccatgccaaa atggcgccaa ctgcactgac   2880
tgcgtggaca gctacacgtg cacctgcccc acgggcttca atggcatcca ttgcgagaac   2940
aacacacctg actgtaccga gagctcctgt ttcaatggtg gcacctgtgt ggatggtatc   3000
aactccttca cctgtctgtg cccacctggc ttcacgggca gctactgcca gtatgacgtc   3060
aatgagtgtg actcacggcc ctgtctgcat ggtggcacct gccaagacag ctatggtacc   3120
tataagtgta cctgcccaca gggctacact ggtctcaact gccagaacct tgtgcgctgg   3180
tgtgactcag ctccctgcaa gaatggcggc aagtgctggc agaccaacac acagtaccac   3240
tgcgagtgcc gcagcggctg gactggcttc aactgcgacg tgctcagtgt gtcctgcgag   3300
gtggctgcac agaagcgagg catcgatgtc actctcctat gccagcacgg agggctctgt   3360
gtggatgagg aagacaagca ttactgccac tgccaggcag gatacacggg cagctactgt   3420
gaggacgagg tggacgagtg ctcacctaat ccctgccaga acggagccac ctgcactgac   3480
tatctcggtg gcttttcctg caagtgtgtg gctgggtacc atggctctaa ctgctctgag   3540
gagatcaacg agtgcctatc ccaaccctgc cagaatgggg gtacctgcat tgatctgacc   3600
aacacctaca agtgctcctg ccccaggggc acacagggtg tacactgtga gatcaacgtc   3660
gatgactgcc atcctcccct agaccctgct tcccgaagcc ccaaatgctt caataatggc   3720
acctgcgtgg accaggtggg tggctatacc tgcacctgcc cgccaggctt cgtcggggag   3780
cggtgcgagg gcgatgtcaa tgagtgtctc tccaacccct gtgacccacg tggcacccag   3840
```

-continued

```
aactgcgtgc agcgtgttaa tgacttccac tgcgagtgcc gggctggcca cactggacgc   3900

cgctgtgagt cggtcattaa tggctgcagg ggcaaaccat gcaggaatgg aggtgtctgt   3960

gctgtggcct ccaacaccgc ccgtggattc atctgtaggt gccctgcggg cttcgagggt   4020

gccacttgtg aaaatgacgc ccgcacttgt ggcagtttgc gctgcctcaa cggtggtacg   4080

tgcatctcag gcccacgcag tcccacctgc ctatgcctgg gctccttcac tggccctgaa   4140

tgccagttcc cagccagcag cccctgtgtg ggtagcaacc cctgctacaa tcagggcacc   4200

tgtgagccca catccgagag ccctttctac cgctgtctat gccctgccaa attcaacggg   4260

ctgctgtgcc acatcctgga ctacagcttc aca                                4293


<210> SEQ ID NO 7
<211> LENGTH: 4257
<212> TYPE: DNA
<213> ORGANISM: Rattus norvegicus

<400> SEQUENCE: 7

atgcccgctc tgcgtcccgc cgcgctgcgg gcgctgctgt ggctctggct gtgcggcgcg     60

ggccccgcgc acgctttgca gtgtcgaggt ggtcaagagc cctgtgtaaa tgaggggacc    120

tgtgttacct accacaacgg cacaggctac tgccgatgtc cagagggctt cttgggagaa    180

tattgtcaac atcgagaccc ttgtgagaag aaccgctgtc agaatggtgg tacttgtgtg    240

acgcaggcca tgttgggaaa agccacctgt cgatgtgctc cagggttcac aggggaggac    300

tgccaatact cgacctctca cccctgtttt gtttcccgcc cctgtcagaa tggaggtacc    360

tgccacatgc tcagctggga cacctatgag tgcacctgtc aagttggctt cacaggaaag    420

cagtgtcagt ggacagatgt ctgtctgtct catccctgtg aaaatggaag cacctgtagc    480

tctgtggcca accagttctc ctgcagatgt cctgcaggca tcacaggcca gaagtgtgac    540

gccgacatca atgaatgtga cattccagga cgctgccaac atggtggcac ctgcctcaac    600

cttcctgggt cctaccgatg ccaatgccct cagcggttca caggccagca ctgtgacagc    660

ccttacgtgc cctgtgcacc ctcaccctgc gtcaatggag gcacctgccg tcagactgga    720

gacttcactt ctgaatgcca ttgcctgcca ggctttgaag ggagcaactg cgagcggaat    780

atcgacgact gccctaacca caagtgtcag aatggagggg tgtgtgtgga tggcgtcaat    840

acttacaact gccgctgccc ccctcagtgg actgggcagt tctgcacaga agacgtggat    900

gagtgtctgc tgcagcccaa tgcttgtcag aatggaggca cttgcaccaa ccgcaacgga    960

ggctacggct gcgtgtgcgt gaacggctgg agtggggatg actgcagcga gaacatcgat   1020

gactgtgcct tcgcttcctg cacgccaggc tccacctgta ttgaccgtgt ggcctccttc   1080

tcctgccttt gtccagaggg aaaggcaggg ctcctgtgtc atctggatga tgcctgtatc   1140

agcaaccctt gtcacaaggg ggcgctgtgt gataccaacc ccctgaatgg gcagtacatt   1200

tgcacctgcc cacaggcgta caagggcgct gactgcacag aagacgtgga tgagtgtgct   1260

atggccaaca gtaacccttg tgagcatgca ggaaagtgtg tgaatacaga tggcgccttc   1320

cactgcgagt gtctgaaggg ctacgcaggg cctcgctgtg agatggacat caacgagtgt   1380

cactcagacc cctgtcagaa cgacgccacc tgcctggata agattggagg cttcacctgt   1440

ctctgcatgc cgggtttcaa aggtgtgcat tgtgaactgg aggtgaatga atgccagagc   1500

aacccgtgtg taaacaatgg gcagtgtgtg gacaaagtca atcgcttcca gtgtctgtgt   1560

ccccctggtt tcacaggacc agtgtgccag atcgacattg acgactgctc cagtactccc   1620

tgcctgaatg gggccaagtg catcgatcac ccgaatggct atgaatgcca gtgtgccaca   1680
```

-continued ggattcactg gcacactgtg tgatgagaac atcgacaact gtgacccgga tccttgccac 1740
catggccagt gccaggatgg gattgactcc tacacctgca tctgcaaccc cgggtacatg 1800
ggagccatct gtagtgacca gattgatgaa tgctacagca gcccctgcct gaatgatgga 1860
cgctgcatcg acctggtgaa cggctaccag tgcaactgcc aaccgggtac ctcaggcctt 1920
aattgtgaaa ttaattttga tgactgtgcc agcaaccctt gtctgcacgg agcctgtgtg 1980
gacggcatca accgttacag ttgtgtgtgc tctccgggat tcacagggca gaggtgcaac 2040
atagacattg atgagtgtgc ctccaacccc tgtcgcaagg atgcgacgtg catcaatgac 2100
gtgaatggtt tccggtgtat gtgccctgag ggaccacacc atcccagctg ctactcacag 2160
gtgaacgagt gtttgagcag tccctgcatc catggaaact gtactggagg tctcagtggc 2220
tataagtgcc tctgcgatgc aggctgggtt ggtatcaact gcgaagtgga caaaaatgag 2280
tgtctttcta acccgtgcca gaatggaggg acatgtaata acctggtgaa tggctacagg 2340
tgtacatgca agaaggggtt caaaggctat aactgccagg tgaacataga tgagtgtgcc 2400
tcgaacccgt gtctgaacca agggacctgc ctcgatgacg tcagtggcta cacctgccac 2460
tgcatgctgc cttacacagg caagaattgt caaacggtgt tggcgccctg ctcccctaac 2520
ccgtgtgaga acgctgcagt ttgtaaagag gcacccaact ttgagagctt cacctgcctg 2580
tgtgcccctg gctggcaagg tcagcgctgt acagttgacg ttgatgagtg tgtctccaag 2640
ccgtgtatga acaatggcat ctgccataat actcagggca gctacatgtg cgagtgccct 2700
cccggcttca gtggtatgga ctgtgaggag gacatcaatg actgccttgc caacccctgc 2760
cagaacggag gctcctgtgt ggacaaagtg aacaccttct cctgcctgtg ccttcctggc 2820
ttcgtagggg acaagtgcca aacagacatg aatgaatgtc tgagcgagcc ctgtaagaat 2880
ggggggacct gctctgacta cgtcaacagc tacacctgca cgtgccctgc gggcttccat 2940
ggagtccact gtgaaaacaa catcgatgag tgcactgaga gctcctgttt caatggcggc 3000
acgtgtgttg atgggatcaa ctctttctct tgcttatgcc ctgtgggttt cactggtccc 3060
ttctgcctcc atgatatcaa tgagtgcagc tctaacccgt gcctgaattc gggaacgtgt 3120
gttgatggcc tgggtaccta ccgatgcacc tgtcccttgg gctacactgg gaaaaactgt 3180
cagaccctgg tgaacctctg cagcccctct ccatgtaaaa acaaaggaac ttgtgctcag 3240
gaaaaggcaa ggccacgctg cctgtgtccg cctggatggg atggcgcata ctgtgatgtg 3300
ctcaatgtgt cctgtaaggc ggcagccttg cagaaaggag tacctgttga acacttgtgc 3360
cagcactcgg gtatctgtat caatgctggc aacacgcatc actgccagtg cccccctgggc 3420
tacacgggga gctactgcga ggaacagctt gacgagtgtg cgtccaatcc atgccagcat 3480
ggtgccacct gcagtgactt catcggagga tacagatgtg agtgtgttcc agggtatcag 3540
ggtgtcaact gtgagtatga agtggacgag tgccagaacc agccctgtca gaacggaggc 3600
acctgcatcg acctcgtgaa ccatttcaag tgctcgtgcc caccaggcac ccggggcctg 3660
ctttgtgaag agaacattga tgactgtgct ggggcccccc actgccttaa tggtggccag 3720
tgtgtggacc ggattggagg ctacagttgt cgctgtttgc ctggctttgc tggggagcgg 3780
tgtgaggggg acatcaatga atgcctgtcc aatccttgca gctcagaggg cagcctggac 3840
tgcattcagc tcaaaaataa ctaccagtgt gtctgccgca gcgccttcac aggccgacac 3900
tgcgaaacct tcctagatgt gtgtccccag aagccttgcc tgaatggagg gacttgtgct 3960
gtggctagca acgtgcctga tggcttcatt tgtcgttgtc ccccagggtt ctccggggca 4020

```
agatgccaga gcagctgtgg acaagtgaag tgcagaagag gggagcagtg tgtgcacacc   4080

gcctcgggac cccactgctt ctgcccgaac cacaaggact gcgagtcagg ttgcgctagt   4140

aacccctgcc agcacggagg cacctgctac cctcagcgcc agcctcctta ctactcttgc   4200

cgctgctccc caccgttctg ggcagccac tgcgagagct acacagcccc caccagc       4257
```

<210> SEQ ID NO 8
<211> LENGTH: 4137
<212> TYPE: DNA
<213> ORGANISM: Mus musculus

<400> SEQUENCE: 8

```
atggggctgg gggcccgggg ccgccgccgc cgtcgtcgcc tgatggcctt gccaccgcca     60

ccaccgccca tgcgggcgct gcccctgctg ctgctgctag cggggctggg ggctgcagca    120

ccccccttgtc tggatggaag cccatgtgca aatggaggtc ggtgcaccca ccagcagccc    180

tccctggagg ctgcttgcct gtgcctgcca ggctgggtgg gtgagcggtg ccagctggaa    240

gacccttgcc actcaggccc ttgtgctggc cgaggcgttt gccagagttc agtggtggcg    300

ggcaccgccc gattctcctg tcgttgtctc cgtggcttcc aaggcccaga ctgctcccag    360

ccagacccct gcgtcagcag gccctgtgtt catggtgccc cctgctcagt ggggccggat    420

ggccgatttg cctgtgcctg cccacctggc taccagggtc aaagctgcca aagtgacata    480

gatgagtgcc gatctggtac aacttgccgt catggtggta cctgtctcaa tacacctgga    540

tccttccgct gccagtgtcc tcttggttat acagggctgc tgtgtgagaa ccccgtagtg    600

ccctgtgccc cttccccgtg tcgtaatggt ggcacctgta ggcagagcag tgatgtcaca    660

tatgactgtg cttgccttcc tggcttcgag ggccagaact gtgaagtcaa cgtggatgac    720

tgtcctggac atcggtgtct caatgggggga acgtgtgtag acggtgtcaa tacttacaac    780

tgccagtgcc ctccggagtg gacaggccag ttctgtacag aagatgtgga tgagtgtcag    840

ctgcagccca atgcctgcca caatgggggt acctgcttca acctactggg tggccacagc    900

tgtgtatgtg tcaatggctg gacgggtgag agctgcagtc agaatatcga tgactgtgct    960

acagccgtgt gtttccatgg ggccacctgc catgaccgtg tggcctcttt ctactgtgcc   1020

tgccctatgg ggaagacagg cctcttgtgt catctggatg atgcatgtgt cagcaacccc   1080

tgccatgagg atgctatctg tgacacaaac cctgtgagtg gccgggccat ctgcacctgc   1140

ccacctggct tcactggagg ggcatgtgac caggatgtgg atgagtgctc gattggtgcc   1200

aacccctgtg aacatttggg tcggtgtgtg aatacacagg gctcattctt gtgccaatgt   1260

ggccgtggct atactggacc tcgctgtgag actgatgtca atgagtgtct ctccgggccc   1320

tgccgcaacc aggccacgtg tcttgaccga attggccagt ttacttgcat ctgcatggca   1380

ggcttcacag ggacctactg tgaggtggac atcgacgaat gtcagagcag cccatgtgtc   1440

aatggtggtg tctgcaagga cagagtcaat ggcttcagct gcacctgccc atcaggattc   1500

agtgggtcca tgtgtcagct ggatgtggat gagtgtgcaa gcactccctg ccggaatggt   1560

gccaagtgtg tggaccagcc tgacggctat gagtgtcgct gtgcagaggg ctttgagggc   1620

actttgtgtg agcgaaacgt ggatgactgc tctccggatc cctgccacca cgggcgctgt   1680

gtcgatggca ttgctagctt ctcgtgtgct tgtgccccag gctatacggg catacgctgt   1740

gagagccagg tggatgagtg ccgcagccag ccctgtcgat atgggggcaa atgtctagac   1800

ttggtggaca agtacctctg ccgttgtcct cccggaacca caggtgtgaa ctgtgaagtc   1860

aacattgatg actgtgccag taacccctgt acctttggag tttgccgtga tggcatcaac   1920
```

-continued

```
cgttatgact gtgtctgtca gcctggattc acagggcccc tctgcaacgt ggagatcaat   1980

gagtgtgcat ccagcccatg tggagagggt ggctcctgtg tggatgggga aaatggcttc   2040

cactgcctct gtccacctgg ctccctgcct ccactttgcc tacctgcgaa ccatccctgt   2100

gcccacaagc cctgtagtca tggagtctgc catgatgcac caggcgggtt ccgctgtgtt   2160

tgtgagcccg ggtggagtgg ccctcgctgt agccagagcc tggctccaga tgcctgtgag   2220

tcccagccct gccaggctgg tggcacctgc accagtgatg gaataggctt tcgctgcacc   2280

tgtgcccctg gattccaggg ccatcagtgt gaggtgctgt ccccctgtac tccaagcctc   2340

tgtgagcacg gaggccactg tgagtctgac cctgaccggc tgactgtctg ttcctgtccc   2400

ccaggctggc aaggcccacg atgccagcag gatgtggatg aatgtgccgg tgcctcaccc   2460

tgcggccccc atggtacctg caccaacctg ccagggaatt tcaggtgcat ctgccacagg   2520

ggatacactg gccccttctg tgatcaagac attgacgact gtgaccccaa cccgtgcctc   2580

catggtggct cctgccagga tggcgtgggc tccttttcct gttcttgcct cgacggcttt   2640

gctggtcctc gctgtgcccg agatgtggac gaatgtctga gcagcccctg tggccctggc   2700

acctgtactg atcacgtggc ctccttcacc tgtgcctgtc cacctggtta tggaggcttc   2760

cactgtgaga ttgacttgcc ggactgcagc cccagttcct gcttcaatgg agggacctgt   2820

gtggatggcg tgagctcctt cagctgtctg tgtcgccccg gctacacagg cacacactgc   2880

caatacgagg ctgacccctg cttttcccgg ccctgtctgc acgggggcat ctgcaacccc   2940

acccacccag gatttgaatg cacctgccgg gagggcttca ctgggagtca gtgtcagaac   3000

ccagtggact ggtgcagcca ggcaccctgt cagaatgggg gtcgctgtgt ccagactggg   3060

gcttactgca tttgtccacc tggatggagt ggccgcctgt gcgacataca aagcctgccc   3120

tgcacggagg ccgcagccca gatgggggtg aggttggagc agctgtgtca ggaaggtgga   3180

aagtgcatag acaagggccg ctcccactac tgtgtgtgtc cagagggccg tacgggtagt   3240

cactgtgaac acgaggtgga tccctgcacg gcccagcctt gccagcacgg gggcacttgc   3300

cgtggttaca tggggggcta tgtgtgtgag tgtccagctg gctatgctgg tgacagttgt   3360

gaggataata tagatgagtg tgcttcccag ccctgccaga acggaggctc ctgtatcgat   3420

cttgtggccc gctatctctg ttcctgtccc cctggcacac tgggagttct ctgtgagatc   3480

aatgaggacg actgtgacct aggcccatcc ttggactcag gcgttcagtg cctacacaat   3540

ggcacctgtg tggacctggt gggtggcttc cgctgtaact gtcccccagg atacacaggt   3600

ctgcactgtg aggcagacat caatgagtgt cgcccgggtg cctgccatgc agcgcatact   3660

cgggactgcc tacaagatcc aggtgggcat ttccgctgcg tctgccatcc tggcttcaca   3720

gggcctcgct gtcagattgc tctgtccccc tgtgagtccc agccatgtca gcatggaggc   3780

cagtgccgtc acagcctagg ccgtggaggt gggctgacct tcacctgtca ctgtgtcccg   3840

ccattctggg gtctgcgttg tgagcgggtg gcacgctctt gccgagagct gcagtgccca   3900

gtgggtatcc catgccagca gacagcccgt ggaccacgct gcgcttgtcc tccggggctg   3960

tccgggccct cctgccgggt ttctagggcg tcaccctcag gagctactaa cgccagctgc   4020

gcctctgccc cttgtctgca tggggggctca tgcctacctg tacagagtgt ccctttcttc   4080

cgctgtgtgt gcgctccggg ctggggcggc ccgcgttgtg agaccccttc cgcagcc      4137
```

<210> SEQ ID NO 9
<211> LENGTH: 3510
<212> TYPE: DNA

<213> ORGANISM: Mus musculus

<400> SEQUENCE: 9

```
atgcagcccc agttgctgct gctgctgctc ttgccactca atttccctgt catcctgacc     60
agagagcttc tgtgtggagg atccccagag ccctgtgcca acggaggcac ctgcctgagg    120
ctatctcagg gacaagggat ctgccagtgt gcccctggat ttctgggtga gacttgccag    180
tttcctgacc cctgcaggga tacccaactc tgcaagaatg gtggcagctg ccaagccctg    240
ctccccacac ccccaagctc ccgtagtcct acttctccac tgacccctca cttctcctgc    300
acctgcccct ctggcttcac cggtgatcga tgccaaaccc atctggaaga gctctgtcca    360
ccttctttct gttccaacgg gggtcactgc tatgttcagg cctcaggccg cccacagtgc    420
tcctgcgagc ctgggtggac aggtgagcaa tgccagctcc gagacttctg ctcagccaac    480
ccctgtgcca acggaggcgt gtgcctggcc acatacccc  agatccagtg ccgctgtcca    540
cctgggttcg agggtcacac ctgtgaacgc gacatcaacg agtgcttcct ggagccggga    600
ccctgccctc agggcacctc ctgccataac accttgggtt cctaccagtg tctctgccct    660
gtggggcagg aaggtcccca gtgcaagctc aggaagggag cctgccctcc tggaagctgt    720
ctcaatgggg gcacctgcca gctggtccca gagggacact ccacctttca tctctgcctc    780
tgtcccccag gtttcacggg gctggactgt gagatgaacc cagatgactg tgtcaggcac    840
cagtgtcaga acggggccac ctgtctggat gggctggata cctacacctg cctctgcccc    900
aagacatgga agggctggga ctgctctgaa gatatagatg aatgtgaagc ccggggtccc    960
cctcgctgca ggaacggtgg cacctgccag aacacagctg gcagctttca ctgtgtgtgc   1020
gtgagtggct ggggcggtgc aggttgtgag gagaacctgg atgactgtgc agctgccacc   1080
tgtgccccgg gatccacctg catcgaccgt gtgggctctt tctcctgcct ctgcccacct   1140
ggacgcacag gcctcctgtg ccacctggaa gacatgtgtt tgagtcagcc gtgccacgtg   1200
aatgcccagt gcagcaccaa ccctctgaca ggctccaccc tctgcatatg ccagcctggc   1260
tactcaggat ccacctgtca ccaagatctg gatgagtgcc aaatggccca gcaaggaccc   1320
agtccctgcg aacatggcgg ctcctgcatc aacacccctg gctccttcaa ctgcctctgc   1380
ctgcctggtt acacgggctc ccgctgtgaa gctgaccaca atgagtgcct gtcacagccc   1440
tgccacccag gcagcacctg cctggacctg cttgcaacct tccactgcct ctgcccacca   1500
ggcttggaag ggaggctctg tgaggtggag gtcaatgagt gcacctctaa tccctgcctg   1560
aaccaagctg cctgccatga cctgctcaac ggcttccagt gcctctgcct tcctggattc   1620
accggcgccc gatgtgagaa agacatggac gagtgtagca gcacccccctg tgccaatggg  1680
gggcgctgcc gagaccagcc tggagccttc tactgcgagt gtctcccagg ctttgaaggg   1740
ccacactgtg agaaagaagt ggacgaatgt ctgagtgacc cctgccccgt gggagccagc   1800
tgccttgatc tccccggagc attcttctgc ctctgccgtc ctggtttcac aggtcaactt   1860
tgtgaggttc ccttgtgcac ccccaacatg tgccaacctg gacagcaatg ccaaggtcag   1920
gaacacagag ccccctgcct ctgccctgac ggaagtcctg gctgtgttcc tgccgaggac   1980
aactgcccct gtcaccatgg ccattgccag agatccttgt gtgtgtgtga tgagggctgg   2040
actggaccag aatgcgagac agaactgggt ggctgcatct ccacaccctg tgcccatggg   2100
gggacctgcc acccacagcc gtctggctac aactgtacct gccctgcagg ctacatgggg   2160
ttgacctgta gtgaggaggt gacagcttgt cactcagggc cctgtctcaa tggtggctct   2220
tgcagcatcc gtcctgaggg ctattcctgc acctgccttc caagtcacac aggtcgccac   2280
```

-continued tgccagactg ccgtggacca ctgtgtgtct gcctcgtgcc tcaatggggg tacctgtgtg 2340
aacaagcctg gcactttctt ctgcctctgt gccactggct tccaggggct gcactgtgag 2400
gagaagacta accccagctg tgcagacagc ccctgcagga acaaggcaac ctgccaagac 2460
acacctcgag ggcccgctg cctctgcagc cctggctata caggaagcag ctgccagact 2520
ctgatagact tgtgtgcccg gaagccctgt ccacacactg ctcgatgcct ccagagtggg 2580
ccctcgttcc agtgcctgtg cctccaggga tggacagggg ctctctgtga cttcccactg 2640
tcctgccaga tggccgcaat gagccaaggc atagagatct ctggcctgtg ccagaatgga 2700
ggcctctgta ttgacacggg ctcctcctat ttctgccgct gccctcctgg attccaaggc 2760
aagttatgcc aggataatat gaacccctgc gagcccaatc cctgccatca cgggtctacc 2820
tgtgtgcctc agcccagtgg ctatgtctgc cagtgtgccc caggctatga gggacagaac 2880
tgctcaaaag tacttgaagc ttgtcagtcc cagccctgcc acaaccacgg aacctgtacc 2940
tccaggcctg gaggcttcca ctgtgcctgc cctccaggct tcgtgggact gcgctgtgag 3000
ggagatgtgg atgagtgtct ggaccggccc tgtcacccct cgggcactgc agcttgccac 3060
tctttagcca acgccttcta ctgccagtgt ctgcctgggc acacaggcca gcggtgtgag 3120
gtggagatgg acctctgtca gagccaaccc tgctccaatg gaggatcctg tgagatcaca 3180
acagggccac cccctggctt cacctgtcac tgccccaagg gttttgaagg ccccacctgc 3240
agccacaaag ccctttcctg cggcatccat cactgccaca atggaggcct atgtctgccc 3300
tcccctaagc cagggtcacc accactctgt gcctgcctca gtggttttgg gggccctgac 3360
tgtctgacac ctccagctcc accgggctgc ggtcccccct caccctgcct gcacaatggt 3420
acctgcactg agacccctgg gttgggcaac ccgggctttc aatgcacctg ccctcctgac 3480
tctccagggc cccggtgtca aaggccaggg 3510

<210> SEQ ID NO 10
<211> LENGTH: 15
<212> TYPE: DNA
<213> ORGANISM: Mus musculus

<400> SEQUENCE: 10
gatctgggcc cgggc 15

<210> SEQ ID NO 11
<211> LENGTH: 4299
<212> TYPE: DNA
<213> ORGANISM: Homo sapiens

<400> SEQUENCE: 11
atgccgccgc tcctggcgcc cctgctctgc ctggcgctgc tgcccgcgct cgccgcacga 60
ggcccgcgat gctcccagcc cggtgagacc tgcctgaatg gcgggaagtg tgaagcggcc 120
aatggcacgg aggcctgcgt ctgtggcggg gccttcgtgg gcccgcgatg ccaggacccc 180
aacccgtgcc tcagcacccc ctgcaagaac gccgggacat gccacgtggt ggaccgcaga 240
ggcgtggcag actatgcctg cagctgtgcc ctgggcttct ctgggcccct ctgcctgaca 300
cccctggaca atgcctgcct caccaacccc tgccgcaacg gggcacctg cgacctgctc 360 acgctgacgg agtacaagtg ccgctgcccg cccggctggt cagggaaatc gtgccagcag 420
gctgacccgt gcgcctccaa cccctgcgcc aacggtggcc agtgcctgcc cttcgaggcc 480
tcctacatct gccactgccc acccagcttc catggcccca cctgccggca ggatgtcaac 540

-continued

```
gagtgtggcc agaagcccgg gctttgccgc cacggaggca cctgccacaa cgaggtcggc    600
tcctaccgct gcgtctgccg cgccacccac actggcccca actgcgagcg gccctacgtg    660
ccctgcagcc cctcgccctg ccagaacggg ggcacctgcc gccccacggg cgacgtcacc    720
cacgagtgtg cctgcctgcc aggcttcacc ggccagaact gtgaggaaaa tatcgacgat    780
tgtccaggaa acaactgcaa gaacgggggt gcctgtgtgg acggcgtgaa cacctacaac    840
tgccgctgcc cgccagagtg gacaggtcag tactgtaccg aggatgtgga cgagtgccag    900
ctgatgccaa atgcctgcca gaacggcggg acctgccaca acacccacgg tggctacaac    960
tgcgtgtgtg tcaacggctg gactggtgag gactgcagcg agaacattga tgactgtgcc   1020
agcgccgcct gcttccacgg cgccacctgc catgaccgtg tggcctcctt ctactgcgag   1080
tgtccccatg gccgcacagg tctgctgtgc cacctcaacg acgcatgcat cagcaacccc   1140
tgtaacgagg gctccaactg cgacaccaac cctgtcaatg gcaaggccat ctgcacctgc   1200
ccctcggggt acacgggccc ggcctgcagc caggacgtgg atgagtgctc gctgggtgcc   1260
aacccctgcg agcatgcggg caagtgcatc aacacgctgg gctccttcga gtgccagtgt   1320
ctgcagggct acacgggccc ccgatgcgag atcgacgtca acgagtgcgt ctcgaacccg   1380
tgccagaacg acgccacctg cctggaccag attggggagt tccagtgcat ctgcatgccc   1440
ggctacgagg gtgtgcactg cgaggtcaac acagacgagt gtgccagcag cccctgcctg   1500
cacaatggcc gctgcctgga caagatcaat gagttccagt gcgagtgccc cacgggcttc   1560
actgggcatc tgtgccagta cgatgtggac gagtgtgcca gcacccccctg caagaatggt  1620
gccaagtgcc tggacggacc caacacttac acctgtgtgt gcacggaagg gtacacgggg   1680
acgcactgcg aggtggacat cgatgagtgc gaccccgacc cctgccacta cggctcctgc   1740
aaggacggcg tcgccacctt cacctgcctc tgccgcccag gctacacggg ccaccactgc   1800
gagaccaaca tcaacgagtg ctccagccag ccctgccgcc acgggggcac ctgccaggac   1860
cgcgacaacg cctacctctg cttctgcctg aaggggacca caggacccaa ctgcgagatc   1920
aacctggatg actgtgccag cagcccctgc gactcgggca cctgtctgga caagatcgat   1980
ggctacgagt gtgcctgtga gccgggctac acagggagca tgtgtaacat caacatcgat   2040
gagtgtgcgg gcaacccctg ccacaacggg ggcacctgcg aggacggcat caatggcttc   2100
acctgccgct gccccgaggg ctaccacgac cccacctgcc tgtctgaggt caatgagtgc   2160
aacagcaacc cctgcgtcca cggggcctgc cgggacagcc tcaacgggta caagtgcgac   2220
tgtgaccctg ggtggagtgg gaccaactgt gacatcaaca acaatgagtg tgaatccaac   2280
ccttgtgtca acggcggcac ctgcaaagac atgaccagtg gctacgtgtg cacctgccgg   2340
gagggcttca gcggtcccaa ctgccagacc aacatcaacg agtgtgcgtc caacccatgt   2400
ctgaaccagg gcacgtgtat tgacgacgtt gccgggtaca agtgcaactg cctgctgccc   2460
tacacaggtg ccacgtgtga ggtggtgctg gccccgtgtg cccccagccc ctgcagaaac   2520
ggcggggagt gcaggcaatc cgaggactat gagagcttct cctgtgtctg ccccacgggc   2580
tggcaagcag ggcagacctg tgaggtcgac atcaacgagt gcgttctgag cccgtgccgg   2640
cacggcgcat cctgccagaa cacccacggc ggctaccgct gccactgcca ggccggctac   2700
agtgggcgca actgcgagac cgacatcgac gactgccggc ccaacccgtg tcacaacggg   2760
ggctcctgca cagacggcat caacacggcc ttctgcgact gcctgcccgg cttccggggc   2820
actttctgtg aggaggacat caacgagtgt gccagtgacc cctgccgcaa cggggccaac   2880
tgcacggact gcgtggacag ctacacgtgc acctgccccg caggcttcag cgggatccac   2940
```

tgtgagaaca acacgcctga ctgcacagag agctcctgct tcaacggtgg cacctgcgtg 3000
gacggcatca actcgttcac ctgcctgtgt ccacccggct tcacgggcag ctactgccag 3060
cacgatgtca atgagtgcga ctcacagccc tgcctgcatg gcggcacctg tcaggacggc 3120
tgcggctcct acaggtgcac ctgcccccag ggctacactg gccccaactg ccagaacctt 3180
gtgcactggt gtgactcctc gccctgcaag aacggcggca aatgctggca gacccacacc 3240
cagtaccgct gcgagtgccc cagcggctgg accggccttt actgcgacgt gcccagcgtg 3300
tcctgtgagg tggctgcgca gcgacaaggt gttgacgttg cccgcctgtg ccagcatgga 3360
gggctctgtg tggacgcggg caacacgcac cactgccgct gccaggcggg ctacacaggc 3420
agctactgtg aggacctggt ggacgagtgc tcacccagcc cctgccagaa cggggccacc 3480
tgcacggact acctgggcgg ctactcctgc aagtgcgtgg ccggctacca cggggtgaac 3540
tgctctgagg agatcgacga gtgcctctcc cacccctgcc agaacggggg cacctgcctc 3600
gacctcccca acacctacaa gtgctcctgc ccacggggca ctcagggtgt gcactgtgag 3660
atcaacgtgg acgactgcaa tcccccgtt gaccccgtgt cccggagccc caagtgcttt 3720
aacaacggca cctgcgtgga ccaggtgggc ggctacagct gcacctgccc gccgggcttc 3780
gtgggtgagc gctgtgaggg ggatgtcaac gagtgcctgt ccaatccctg cgacgcccgt 3840
ggcacccaga actgcgtgca gcgcgtcaat gacttccact gcgagtgccg tgctggtcac 3900
accgggcgcc gctgcgagtc cgtcatcaat ggctgcaaag gcaagccctg caagaatggg 3960
ggcacctgcg ccgtggcctc caacaccgcc cgcgggttca tctgcaagtg ccctgcgggc 4020
ttcgagggcg ccacgtgtga gaatgacgct cgtacctgcg gcagcctgcg ctgcctcaac 4080
ggcggcacat gcatctccgg cccgcgcagc cccacctgcc tgtgcctggg ccccttcacg 4140
ggccccgaat gccagttccc ggccagcagc ccctgcctgg gcggcaaccc ctgctacaac 4200
caggggacct gtgagcccac atccgagagc cccttctacc gttgcctgtg ccccgccaaa 4260
ttcaacgggc tcttgtgcca catcctggac tacagcttc 4299

<210> SEQ ID NO 12
<211> LENGTH: 4213
<212> TYPE: DNA
<213> ORGANISM: Homo sapiens

<400> SEQUENCE: 12
tcatctggaa ttatgcccgc cctgcgcccc gctctgctgt gggcgctgct ggcgctctgg 60
ctgtgctgcg cggcccccgc gcatgcattg cagtgtcgag atggctatga accctgtgta 120
aatgaaggaa tgtgtgttac ctaccacaat ggcacaggat actgcaaatg tccagaaggc 180
ttcttggggg aatattgtca acatcgagac ccctgtgaga agaaccgctg ccagaatggt 240
gggacttgtg tggcccaggc catgctgggg aaagccacgt gccgatgtgc ctcagggttt 300
acaggagagg actgccagta ctcaacatct catccatgct ttgtgtctcg accctgcctg 360
aatggcggca catgccatat gctcagccgg gatacctatg agtgcacctg tcaagtcggg 420
tttacaggta aggagtgcca atggacggat gcctgcctgt ctcatccctg tgcaaatgga 480
agtacctgta ccactgtggc caaccagttc tcctgcaaat gcctcacagg cttcacaggg 540
cagaaatgtg agactgatgt caatgagtgt gacattccag gacactgcca gcatggtggc 600
acctgcctca acctgcctgg ttcctaccag tgccagtgcc ctcagggctt cacaggccag 660
tactgtgaca gcctgtatgt gccctgtgca ccctcacctt gtgtcaatgg aggcacctgt 720

-continued

```
cggcagactg gtgacttcac ttttgagtgc aactgccttc caggttttga agggagcacc    780
tgtgagagga atattgatga ctgccctaac cacaggtgtc agaatggagg ggtttgtgtg    840
gatggggtca acacttacaa ctgccgctgt cccccacaat ggacaggaca gttctgcaca    900
gaggatgtgg atgaatgcct gctgcagccc aatgcctgtc aaaatggggg cacctgtgcc    960
aaccgcaatg gaggctatgg ctgtgtatgt gtcaacggct ggagtggaga tgactgcagt   1020
gagaacattg atgattgtgc cttcgcctcc tgtactccag gctccacctg catcgaccgt   1080
gtggcctcct tctcttgcat gtgcccagag gggaaggcag gtctcctgtg tcatctggat   1140
gatgcatgca tcagcaatcc ttgccacaag ggggcactgt gtgacaccaa ccccctaaat   1200
gggcaatata tttgcacctg cccacaaggc tacaaagggg ctgactgcac agaagatgtg   1260
gatgaatgtg ccatggccaa tagcaatcct tgtgagcatg caggaaaatg tgtgaacacg   1320
gatggcgcct tccactgtga gtgtctgaag ggttatgcag gacctcgttg tgagatggac   1380
atcaatgagt gccattcaga cccctgccag aatgatgcta cctgtctgga taagattgga   1440
ggcttcacat gtctgtgcat gccaggtttc aaaggtgtgc attgtgaatt agaaataaat   1500
gaatgtcaga gcaacccttg tgtgaacaat gggcagtgtg tggataaagt caatcgtttc   1560
cagtgcctgt gtcctcctgg tttcactggg ccagtttgcc agattgatat tgatgactgt   1620
tccagtactc cgtgtctgaa tggggcaaag tgtatcgatc acccgaatgg ctatgaatgc   1680
cagtgtgcca caggtttcac tggtgtgttg tgtgaggaga acattgacaa ctgtgacccc   1740
gatccttgcc accatggtca gtgtcaggat ggtattgatt cctacacctg catctgcaat   1800
cccgggtaca tgggcgccat ctgcagtgac cagattgatg aatgttacag cagcccttgc   1860
ctgaacgatg gtcgctgcat tgacctggtc aatggctacc agtgcaactg ccagccaggc   1920
acgtcagggg ttaattgtga aattaatttt gatgactgtg caagtaaccc ttgtatccat   1980
ggaatctgta tggatggcat taatcgctac agttgtgtct gctcaccagg attcacaggg   2040
cagagatgta acattgacat tgatgagtgt gcctccaatc cctgtcgcaa gggtgcaaca   2100
tgtatcaacg gtgtgaatgg tttccgctgt atatgccccg agggacccca tcaccccagc   2160
tgctactcac aggtgaacga atgcctgagc aatccctgca tccatggaaa ctgtactgga   2220
ggtctcagtg gatataagtg tctctgtgat gcaggctggg ttggcatcaa ctgtgaagtg   2280
gacaaaaatg aatgcctttc gaatccatgc cagaatggag gaacttgtga caatctggtg   2340
aatggataca ggtgtacttg caagaagggc tttaaaggct ataactgcca ggtgaatatt   2400
gatgaatgtg cctcaaatcc atgcctgaac caaggaacct gctttgatga cataagtggc   2460
tacacttgcc actgtgtgct gccatacaca ggcaagaatt gtcagacagt attggctccc   2520
tgttccccaa acccttgtga gaatgctgct gtttgcaaag agtcaccaaa ttttgagagt   2580
tatacttgct tgtgtgctcc tggctggcaa ggtcagcggt gtaccattga cattgacgag   2640
tgtatctcca agccctgcat gaaccatggt ctctgccata acacccaggg cagctacatg   2700
tgtgaatgtc caccaggctt cagtggtatg gactgtgagg aggacattga tgactgcctt   2760
gccaatcctt gccagaatgg aggttcctgt atggatggag tgaatacttt ctcctgcctc   2820
tgccttccgg gtttcactgg ggataagtgc cagacagaca tgaatgagtg tctgagtgaa   2880
ccctgtaaga atggagggac ctgctctgac tacgtcaaca gttacacttg caagtgccag   2940
gcaggatttg atggagtcca ttgtgagaac aacatcaatg agtgcactga gagctcctgt   3000
ttcaatggtg gcacatgtgt tgatgggatt aactccttct cttgcttgtg ccctgtgggt   3060
ttcactggat ccttctgcct ccatgagatc aatgaatgca gctctcatcc atgcctgaat   3120
```

-continued gagggaacgt gtgttgatgg cctgggtacc taccgctgca gctgccccct gggctacact 3180
gggaaaaact gtcagaccct ggtgaatctc tgcagtcggt ctccatgtaa aaacaaaggt 3240
acttgtgttc agaaaaaagc agagtcccag tgcctatgtc catctggatg ggctggtgcc 3300
tattgtgacg tgcccaatgt ctcttgtgac atagcagcct ccaggagagg tgtgcttgtt 3360
gaacacttgt gccagcactc aggtgtctgc atcaatgctg gcaacacgca ttactgtcag 3420
tgccccctgg gctatactgg gagctactgt gaggagcaac tcgatgagtg tgcgtccaac 3480
ccctgccagc acggggcaac atgcagtgac ttcattggtg gatacagatg cgagtgtgtc 3540
ccaggctatc agggtgtcaa ctgtgagtat gaagtggatg agtgccagaa tcagccctgc 3600
cagaatggag gcacctgtat tgaccttgtg aaccatttca agtgctcttg cccaccaggc 3660
actcggggcc tactctgtga agagaacatt gatgactgtg cccggggtcc ccattgcctt 3720
aatggtggtc agtgcatgga taggattgga ggctacagtt gtcgctgctt gcctggcttt 3780
gctggggagc gttgtgaggg agacatcaac gagtgcctct ccaacccctg cagctctgag 3840
ggcagcctgg actgtataca gctcaccaat gactacctgt gtgtttgccg tagtgccttt 3900
actggccggc actgtgaaac cttcgtcgat gtgtgtcccc agatgccctg cctgaatgga 3960
gggacttgtg ctgtggccag taacatgcct gatggtttca tttgccgttg tcccccggga 4020
ttttccgggg caaggtgcca gagcagctgt ggacaagtga aatgtaggaa gggggagcag 4080
tgtgtgcaca ccgcctctgg accccgctgc ttctgcccca gtccccggga ctgcgagtca 4140
ggctgtgcca gtagcccctg ccagcacggg ggcagctgcc accctcagcg ccagcctcct 4200
tattactcct gcc 4213

<210> SEQ ID NO 13
<211> LENGTH: 3974
<212> TYPE: DNA
<213> ORGANISM: Homo sapiens

<400> SEQUENCE: 13
atggggccgg gggcccgtgg ccgccgccgc cgccgtcgcc cgatgtcgcc gccaccgcca 60
ccgccacccg tgcgggcgct gcccctgctg ctgctgctag cggggccggg ggctgcagcc 120 ccccccttgcc tggacggaag cccgtgtgca aatggaggtc gttgcaccca gctgccctcc 180
cgggaggctg cctgcctgtg cccgcctggc tgggtgggtg agcggtgtca gctggaggac 240
ccctgtcact caggcccctg tgctggccgt ggtgtctgcc agagttcagt ggtggctggc 300
accgcccgat tctcatgccg gtgcccccgt ggcttccgag gccctgactg ctccctgcca 360
gatccctgcc tcagcagccc ttgtgcccac ggtgcccgct gctcagtggg gcccgatgga 420
cgcttcctct gctcctgccc acctggctac cagggccgca gctgccgaag cgacgtggat 480
gagtgccggg tgggtgagcc ctgccgccat ggtggcacct gcctcaacac acctggctcc 540
ttccgctgcc agtgtccagc tggctacaca gggccactat gtgagaaccc cgcggtgccc 600
tgtgcaccct caccatgccg taacgggggc acctgcaggc agagtggcga cctcacttac 660
gactgtgcct gtcttcctgg gtttgagggt cagaattgtg aagtgaacgt ggacgactgt 720
ccaggacacc gatgtctcaa tgggggggaca tgcgtggatg gcgtcaacac ctataactgc 780
cagtgccctc ctgagtggac aggccagttc tgcacggagg acgtggatga gtgtcagctg 840
cagcccaacg cctgccacaa tgggggtacc tgcttcaaca cgctgggtgg ccacagctgc 900
gtgtgtgtca atggctggac aggcgagagc tgcagtcaga atatcgatga ctgtgccaca 960
gccgtgtgct tccatggggc cacctgccat gaccgcgtgg cttctttcta ctgtgcctgc 1020
cccatgggca agactggcct cctgtgtcac ctggatgacg cctgtgtcag caacccctgc 1080
cacgaggatg ctatctgtga cacaaatccg gtgaacggcc gggccatttg cacctgtcct 1140
cccggcttca cgggtggggc atgtgaccag gatgtggacg agtgctctat cggcgccaac 1200
ccctgcgagc acttgggcag gtgcgtgaac acgcagggct ccttcctgtg ccagtgcggt 1260
cgtggctaca ctggacctcg ctgtgagacc gatgtcaacg agtgtctgtc ggggccctgc 1320
cgaaaccagg ccacgtgcct cgaccgcata ggccagttca cctgtatctg tatggcaggc 1380
ttcacaggaa cctattgcga ggtggacatt gacgagtgtc agagtagccc ctgtgtcaac 1440
ggtggggtct gcaaggaccg agtcaatggc ttcagctgca cctgcccctc gggcttcagc 1500
ggctccacgt gtcagctgga cgtggacgaa tgcgccagca cgccctgcag gaatggcgcc 1560
aaatgcgtgg accagcccga tggctacgag tgccgctgtg ccgagggctt tgagggcacg 1620
ctgtgtgatc gcaacgtgga cgactgctcc cctgacccat gccaccatgg tcgctgcgtg 1680
gatggcatcg ccagcttctc atgtgcctgt gctcctggct acacgggcac acgctgcgag 1740
agccaggtgg acgaatgccg cagccagccc tgccgccatg gcggcaaatg cctagacctg 1800
gtggacaagt acctctgccg ctgcccttct gggaccacag gtgtgaactg cgaagtgaac 1860
attgacgact gtgccagcaa cccctgcacc tttggagtct gccgtgatgg catcaaccgc 1920
tacgactgtg tctgccaacc tggcttcaca gggcccettt gtaacgtgga gatcaatgag 1980
tgtgcttcca gcccatgcgg cgagggaggt tcctgtgtgg atggggaaaa tggcttccgc 2040
tgcctctgcc cgcctggctc cttgcccccca ctctgcctcc ccccgagcca tccctgtgcc 2100
catgagccct gcagtcacgg catctgctat gatgcacctg gcgggttccg ctgtgtgtgt 2160
gagcctggct ggagtggccc ccgctgcagc cagagcctgg cccgagacgc ctgtgagtcc 2220
cagccgtgca gggccggtgg gacatgcagc agcgatggaa tgggtttcca ctgcacctgc 2280
ccgcctggtg tccagggacg tcagtgtgaa ctcctctccc cctgcacccc gaacccctgt 2340
gagcatgggg gccgctgcga gtctgcccct ggccagctgc ctgtctgctc ctgcccccag 2400
ggctggcaag gcccacgatg ccagcaggat gtggacgagt gtgctggccc cgcaccctgt 2460
ggccctcatg gtatctgcac caacctggca gggagtttca gctgcacctg ccatggaggg 2520
tacactggcc cttcctgcga tcaggacatc aatgactgtg accccaaccc atgcctgaac 2580
ggtggctcgt gccaagacgg cgtgggctcc ttttcctgct cctgcctccc tggtttcgcc 2640
ggcccacgat gcgcccgcga tgtggatgag tgcctgagca acccctgcgg cccgggcacc 2700
tgtaccgacc acgtggcctc cttcacctgc acctgcccgc caggctacgg aggcttccac 2760
tgcgaacagg acctgcccga ctgcagcccc agctcctgct tcaatggcgg gacctgtgtg 2820
gacggcgtga actcgttcag ctgcctgtgc cgtcccggct acacaggagc ccactgccaa 2880
catgaggcag acccctgcct ctcgcggccc tgcctacacg ggggcgtctg cagcgccgcc 2940
caccctggct tccgctgcac ctgcctcgag agcttcacgg gcccgcagtg ccagacgctg 3000
gtggattggt gcagccgcca gccttgtcaa aacgggggtc gctgcgtcca gactggggcc 3060
tattgccttt gtccccctgg atggagcgga cgcctctgtg acatccgaag cttgccctgc 3120
agggaggccg cagcccagat cggggtgcgg ctggagcagc tgtgtcaggc gggtgggcag 3180
tgtgtggatg aagacagctc ccactactgc gtgtgcccag agggccgtac tggtagccac 3240
tgtgagcagg aggtggaccc ctgcttggcc cagccctgcc agcatggggg gacctgccgt 3300
ggctatatgg ggggctacat gtgtgagtgt cttcctggct acaatggtga taactgtgag 3360
gacgacgtgg acgagtgtgc ctcccagccc tgccagcacg ggggttcatg cattgacctc 3420
gtggcccgct atctctgctc ctgtccccca ggaacgctgg gggtgctctg cgagattaat 3480
gaggatgact gcggcccagg cccaccgctg gactcagggc cccggtgcct acacaatggc 3540
acctgcgtgg acctggtggg tggtttccgc tgcacctgtc ccccaggata cactggtttg 3600
cgctgcgagg cagacatcaa tgagtgtcgc tcaggtgcct gccacgcggc acacacccgg 3660
gactgcctgc aggacccagg cggaggtttc cgttgccttt gtcatgctgg cttctcaggt 3720
cctcgctgtc agactgtcct gtctccctgc gagtcccagc catgccagca tggaggccag 3780
tgccgtccta gcccgggtcc tgggggtggg ctgaccttca cctgtcactg tgcccagccg 3840
ttctggggtc cgcgttgcga gcgggtggcg cgctcctgcc gggagctgca gtgcccggtg 3900
ggcgtcccat gccagcagac gccccgcggg ccgcgctgcg cctgcccccc agggttgtcg 3960
ggaccctcct gccg 3974

<210> SEQ ID NO 14
<211> LENGTH: 3522
<212> TYPE: DNA
<213> ORGANISM: Homo sapiens

<400> SEQUENCE: 14
atgcagcccc cttcactgct gctgctgctg ctgctgctgc tgctgctatg tgtctcagtg 60
gtcagaccca gagggctgct gtgtgggagt ttcccagaac cctgtgccaa tggaggcacc 120
tgcctgagcc tgtctctggg acaagggacc tgccagtgtg cccctggctt cctgggtgag 180
acgtgccagt ttcctgaccc ctgccagaac gcccagctct gccaaaatgg aggcagctgc 240
caagccctgc ttcccgctcc cctagggctc cccagctctc cctctccatt gacacccagc 300
ttcttgtgca cttgcctccc tggcttcact ggtgagagat gccaggccaa gcttgaagac 360
ccttgtcctc cctccttctg ttccaaaagg ggccgctgcc acatccaggc ctcgggccgc 420
ccacagtgct cctgcatgcc tggatggaca ggtgagcagt gccagcttcg ggacttctgt 480
tcagccaacc catgtgttaa tggaggggtg tgtctggcca cataccccca gatccagtgc 540
cactgcccac cgggcttcga gggccatgcc tgtgaacgtg atgtcaacga gtgcttccag 600
gacccaggac cctgccccaa aggcacctcc tgccataaca ccctgggctc cttccagtgc 660
ctctgccctg tggggcagga gggtccacgt tgtgagctgc gggcaggacc ctgccctcct 720
aggggctgtt cgaatggggg cacctgccag ctgatgccag agaaagactc cacctttcac 780
ctctgcctct gtcccccagg tttcataggc ccagactgtg aggtgaatcc agacaactgt 840
gtcagccacc agtgtcagaa tgggggcact tgccaggatg ggctggacac ctacacctgc 900
ctctgcccag aaacctggac aggctgggac tgctccgaag atgtggatga gtgtgagacc 960
cagggtcccc ctcactgcag aaacgggggc acctgccaga actctgctgg tagctttcac 1020
tgcgtgtgtg tgagtggctg gggcggcaca agctgtgagg agaacctgga tgactgtatt 1080
gctgccacct gtgccccggg atccacctgc attgaccggg tgggctcttt ctcctgcctc 1140
tgcccacctg gacgcacagg actcctgtgc cacttggaag acatgtgtct gagccagccg 1200
tgccatgggg atgcccaatg cagcaccaac cccctcacag gctccacact ctgcctgtgt 1260
cagcctggct attcggggcc cacctgccac caggacctgg acgagtgtct gatggcccag 1320
caaggcccaa gtccctgtga acatggcggt tcctgcctca acactcctgg ctccttcaac 1380
tgcctctgtc cacctggcta cacaggctcc cgttgtgagg ctgatcacaa tgagtgcctc 1440

-continued

```
tcccagccct gccacccagg aagcacctgt ctggacctac ttgccacctt ccactgcctc   1500
tgcccgccag gcttagaagg gcagctctgt gaggtggaga ccaacgagtg tgcctcagct   1560
ccctgcctga accacgcgga ttgccatgac ctgctcaacg gcttccagtg catctgcctg   1620
cctggattct ccggcacccg atgtgaggag gatatcgatg agtgcagaag ctctccctgt   1680
gccaatggtg ggcagtgcca ggaccagcct ggagccttcc actgcaagtg tctcccaggc   1740
tttgaagggc cacgctgtca aacagaggtg gatgagtgcc tgagtgaccc atgtcccgtt   1800
ggagccagct gccttgatct tccaggagcc ttcttttgcc tctgcccctc tggtttcaca   1860
ggccagctct gtgaggttcc cctgtgtgct cccaacctgt gccagcccaa gcagatatgt   1920
aaggaccaga aagacaaggc caactgcctc tgtcctgatg gaagccctgg ctgtgcccca   1980
cctgaggaca actgcacctg ccaccacggg cactgccaga gatcctcatg tgtgtgtgac   2040
gtgggttgga cggggccaga gtgtgaggca gagctagggg gctgcatctc tgcaccctgt   2100
gcccatgggg ggacctgcta cccccagccc tctggctaca actgcacctg ccctacaggc   2160
tacacaggac ccacctgtag tgaggagatg acagcttgtc actcagggcc atgtctcaat   2220
ggcggctcct gcaaccctag ccctggaggc tactactgca cctgccctcc aagccacaca   2280
gggccccagt gccaaaccag cactgactac tgtgtgtctg ccccgtgctt caatgggggt   2340
acctgtgtga acaggcctgg caccttctcc tgcctctgtg ccatgggctt ccagggcccg   2400
cgctgtgagg gaaagctccg ccccagctgt gcagacagcc cctgtaggaa tagggcaacc   2460
tgccaggaca gccctcaggg tccccgctgc ctctgcccca ctggctacac cggaggcagc   2520
tgccagactc tgatggactt atgtgcccag aagccctgcc cacgcaattc ccactgcctc   2580
cagactgggc cctccttcca ctgcttgtgc ctccagggat ggaccgggcc tctctgcaac   2640
cttccactgt cctcctgcca gaaggctgca ctgagccaag gcatagacgt ctcttccctt   2700
tgccacaatg gaggcctctg tgtcgacagc ggcccctcct atttctgcca ctgcccccct   2760
ggattccaag gcagcctgtg ccaggatcac gtgaacccat gtgagtccag gccttgccag   2820
aacggggcca cctgcatggc ccagcccagt gggtatctct gccagtgtgc cccaggctac   2880
gatggacaga actgctcaaa ggaactcgat gcttgtcagt cccaaccctg tcacaaccat   2940
ggaacctgta ctcccaaacc tggaggattc cactgtgcct gccctccagg ctttgtgggg   3000
ctacgctgtg agggagacgt ggacgagtgt ctggaccagc cctgccaccc cacaggcact   3060
gcagcctgcc actctctggc caatgccttc tactgccagt gtctgcctgg acacacaggc   3120
cagtggtgtg aggtggagat agacccctgc cacagccaac cctgctttca tggagggacc   3180
tgtgaggcca cagcaggatc acccctgggt ttcatctgcc actgccccaa gggttttgaa   3240
ggccccacct gcagccacag ggcccccttcc tgcggcttcc atcactgcca ccacggaggc  3300
ctgtgtctgc cctcccctaa gccaggcttc ccaccacgct gtgcctgcct cagtggctat   3360
gggggtcctg actgcctgac cccaccagct cctaaaggct gtggccctcc ctccccatgc   3420
ctatacaatg gcagctgctc agagaccacg ggcttggggg gcccaggctt tcgatgctcc   3480
tgccctcaca gctctccagg gccccggtgt cagaaacccg ga                      3522
```

<210> SEQ ID NO 15
<211> LENGTH: 6966
<212> TYPE: DNA
<213> ORGANISM: Homo sapiens

<400> SEQUENCE: 15

```
atggggccgg gggcccgtgg ccgccgccgc cgccgtcgcc cgatgtcgcc gccaccgcca     60
```

-continued

```
ccgccacccg tgcgggcgct gcccctgctg ctgctgctag cggggccggg ggctgcagcc    120
ccccccttgcc tggacggaag cccgtgtgca aatggaggtc gttgcaccca gctgccctcc    180
cgggaggctg cctgcctgtg cccgcctggc tgggtgggtg agcggtgtca gctggaggac    240
ccctgtcact caggcccctg tgctggccgt ggtgtctgcc agagttcagt ggtggctggc    300
accgccccgat tctcatgccg gtgccccccgt ggcttccgag gccctgactg ctccctgcca    360
gatccctgcc tcagcagccc ttgtgcccac ggtgcccgct gctcagtggg gcccgatgga    420
cgcttcctct gctcctgccc acctggctac cagggccgca gctgccgaag cgacgtggat    480
gagtgccggg tgggtgagcc ctgccgccat ggtggcacct gcctcaacac acctggctcc    540
ttccgctgcc agtgtccagc tggctacaca gggccactat gtgagaaccc cgcggtgccc    600
tgtgcgccct caccatgccg taacgggggc acctgcaggc agagtggcga cctcacttac    660
gactgtgcct gtcttcctgg gtttgagggt cagaattgtg aagtgaacgt ggacgactgt    720
ccaggacacc gatgtctcaa tgggggggaca tgcgtggatg gcgtcaacac ctataactgc    780
cagtgccctc ctgagtggac aggccagttc tgcacggagg acgtggatga gtgtcagctg    840
cagcccaacg cctgccacaa tgggggtacc tgcttcaaca cgctgggtgg ccacagctgc    900
gtgtgtgtca atggctggac aggcgagagc tgcagtcaga atatcgatga ctgtgccaca    960
gccgtgtgct tccatggggc cacctgccat gaccgcgtgg cttctttcta ctgtgcctgc   1020
cccatgggca agactggcct cctgtgtcac ctggatgacg cctgtgtcag caacccctgc   1080
cacgaggatg ctatctgtga cacaaatccg gtgaacggcc gggccatttg cacctgtcct   1140
cccggcttca cgggtggggc atgtgaccag gatgtggacg agtgctctat cggcgccaac   1200
ccctgcgagc acttgggcag gtgcgtgaac acgcagggct ccttcctgtg ccagtgcggt   1260
cgtggctaca ctggacctcg ctgtgagacc gatgtcaacg agtgtctgtc ggggccctgc   1320
cgaaaccagg ccacgtgcct cgaccgcata ggccagttca cctgtatctg tatggcaggc   1380
ttcacaggaa cctattgcga ggtggacatt gacgagtgtc agagtagccc ctgtgtcaac   1440
ggtggggtct gcaaggaccg agtcaatggc ttcagctgca cctgcccctc gggcttcagc   1500
ggctccacgt gtcagctgga cgtggacgaa tgcgccagca cgccctgcag gaatggcgcc   1560
aaatgcgtgg accagcccga tggctacgag tgccgctgtg ccgagggctt tgagggcacg   1620
ctgtgtgatc gcaacgtgga cgactgctcc cctgacccat gccaccatgg tcgctgcgtg   1680
gatggcatcg ccagcttctc atgtgcctgt gctcctggct acacgggcac acgctgcgag   1740
agccaggtgg acgaatgccg cagccagccc tgccgccatg gcggcaaatg cctagacctg   1800
gtggacaagt acctctgccg ctgcccttct gggaccacag gtgtgaactg cgaagtgaac   1860
attgacgact gtgccagcaa cccctgcacc tttggagtct gccgtgatgg catcaaccgc   1920
tacgactgtg tctgccaacc tggcttcaca gggccccttt gtaacgtgga gatcaatgag   1980
tgtgcttcca gcccatgcgg cgagggaggt tcctgtgtgg atggggaaaa tggcttccgc   2040
tgcctctgcc cgcctggctc cttgccccca ctctgcctcc ccccgagcca tccctgtgcc   2100
catgagccct gcagtcacgg catctgctat gatgcacctg gcgggttccg ctgtgtgtgt   2160
gagcctggct ggagtggccc ccgctgcagc cagagcctgg cccgagacgc ctgtgagtcc   2220
cagccgtgca gggccggtgg gacatgcagc agcgatggaa tgggtttcca ctgcacctgc   2280
ccgcctggtg tccagggacg tcagtgtgaa ctcctctccc cctgcacccc gaacccctgt   2340
gagcatgggg gccgctgcga gtctgcccct ggccagctgc ctgtctgctc ctgcccccag   2400
```

-continued

```
ggctggcaag gcccacgatg ccagcaggat gtggacgagt gtgctggccc cgcaccctgt   2460
ggccctcatg gtatctgcac caacctggca gggagtttca gctgcacctg ccatggaggg   2520
tacactggcc cttcctgtga tcaggacatc aatgactgtg accccaaccc atgcctgaac   2580
ggtggctcgt gccaagacgg cgtgggctcc ttttcctgct cctgcctccc tggtttcgcc   2640
ggcccacgat gcgcccgcga tgtggatgag tgcctgagca acccctgcgg cccgggcacc   2700
tgtaccgacc acgtggcctc cttcacctgc acctgcccgc caggctacgg aggcttccac   2760
tgcgaacagg acctgcccga ctgcagcccc agctcctgct tcaatggcgg gacctgtgtg   2820
gacggcgtga actcgttcag ctgcctgtgc cgtcccggct acacaggagc ccactgccaa   2880
catgaggcag acccctgcct ctcgcggccc tgcctacacg gggggcgtctg cagcgccgcc   2940
caccctggct tccgctgcac ctgcctcgag agcttcacgg gcccgcagtg ccagacgctg   3000
gtggattggt gcagccgcca gccttgtcaa aacgggggtc gctgcgtcca gactggggcc   3060
tattgccttt gtccccctgg atggagcgga cgcctctgtg acatccgaag cttgccctgc   3120
agggaggccg cagcccagat cggggtgcgg ctggagcagc tgtgtcaggc gggtgggcag   3180
tgtgtggatg aagacagctc ccactactgc gtgtgcccag agggccgtac tggtagccac   3240
tgtgagcagg aggtggaccc ctgcttggcc cagccctgcc agcatggggg gacctgccgt   3300
ggctatatgg ggggctacat gtgtgagtgt cttcctggct acaatggtga taactgtgag   3360
gacgacgtgg acgagtgtgc ctcccagccc tgccagcacg gggttcatg cattgacctc   3420
gtggcccgct atctctgctc ctgtccccca ggaacgctgg gggtgctctg cgagattaat   3480
gaggatgact gcggcccagg cccaccgctg gactcagggc cccggtgcct acacaatggc   3540
acctgcgtgg acctggtggg tggtttccgc tgcacctgtc ccccaggata cactggtttg   3600
cgctgcgagg cagacatcaa tgagtgtcgc tcaggtgcct gccacgcggc acacacccgg   3660
gactgcctgc aggacccagg cggaggtttc cgttgccttt gtcatgctgg cttctcaggt   3720
cctcgctgtc agactgtcct gtctccctgc gagtcccagc catgccagca tggaggccag   3780
tgccgtccta gcccgggtcc tgggggtggg ctgaccttca cctgtcactg tgcccagccg   3840
ttctggggtc cgcgttgcga gcgggtggcg cgctcctgcc gggagctgca gtgcccggtg   3900
ggcgtcccat gccagcagac gccccgcggg ccgcgctgcg cctgcccccc agggttgtcg   3960
ggaccctcct gccgcagctt cccggggtcg ccgccggggg ccagcaacgc cagctgcgcg   4020
gccgcccccct gtctccacgg gggctcctgc cgccccgcgc cgctcgcgcc cttcttccgc   4080
tgcgcttgcg cgcagggctg gaccgggccg cgctgcgagg cgcccgccgc ggcacccgag   4140
gtctcggagg agccgcggtg cccgcgcgcc gcctgccagg ccaagcgcgg ggaccagcgc   4200
tgcgaccgcg agtgcaacag cccaggctgc ggctgggacg gcggcgactg ctcgctgagc   4260
gtgggcgacc cctggcggca atgcgaggcg ctgcagtgct ggcgcctctt caacaacagc   4320
cgctgcgacc ccgcctgcag ctcgcccgcc tgcctctacg acaacttcga ctgccacgcc   4380
ggtggccgcg agcgcacttg caacccggtg tacgagaagt actgcgccga ccactttgcc   4440
gacggccgct gcgaccaggg ctgcaacacg gaggagtgcg gctgggatgg gctggattgt   4500
gccagcgagg tgccggccct gctggcccgc ggcgtgctgg tgctcacagt gctgctgccg   4560
ccagaggagc tactgcgttc cagcgccgac tttctgcagc ggctcagcgc catcctgcgc   4620
acctcgctgc gcttccgcct ggacgcgcac ggccaggcca tggtcttccc ttaccaccgg   4680
cctagtcctg gctccgaacc ccgggcccgt cgggagctgg cccccgaggt gatcggctcg   4740
gtagtaatgc tggagattga caaccggctc tgcctgcagt cgcctgagaa tgatcactgc   4800
```

ttccccgatg cccagagcgc cgctgactac ctgggagcgt tgtcagcggt ggagcgcctg 4860
gacttcccgt acccactgcg ggacgtgcgg ggggagccgc tggagcctcc agaacccagc 4920
gtcccgctgc tgccactgct agtggcgggc gctgtcttgc tgctggtcat tctcgtcctg 4980
ggtgtcatgg tggcccggcg caagcgcgag cacagcaccc tctggttccc tgagggcttc 5040
tcactgcaca aggacgtggc ctctggtcac aagggccggc gggaacccgt gggccaggac 5100
gcgctgggca tgaagaacat ggccaagggt gagagcctga tgggggaggt ggccacagac 5160
tggatggaca cagagtgccc agaggccaag cggctaaagg tagaggagcc aggcatgggg 5220
gctgaggagg ctgtggattg ccgtcagtgg actcaacacc atctggttgc tgctgacatc 5280
cgcgtggcac cagccatggc actgacacca ccacagggcg acgcagatgc tgatggcatg 5340
gatgtcaatg tgcgtggccc agatggcttc accccgctaa tgctggcttc cttctgtggg 5400
ggggctctgg agccaatgcc aactgaagag gatgaggcag atgacacatc agctagcatc 5460
atctccgacc tgatctgcca gggggctcag cttggggcac ggactgaccg tactggcgag 5520
actgctttgc acctggctgc ccgttatgcc cgtgctgatg cagccaagcg gctgctggat 5580
gctggggcag acaccaatgc ccaggaccac tcaggccgca ctcccctgca cacagctgtc 5640
acagccgatg cccagggtgt cttccagatt ctcatccgaa accgctctac agacttggat 5700
gcccgcatgg cagatggctc aacggcactg atcctggcgg cccgcctggc agtagagggc 5760
atggtggaag agctcatcgc cagccatgct gatgtcaatg ctgtggatga gcttgggaaa 5820
tcagccttac actgggctgc ggctgtgaac aacgtggaag ccactttggc cctgctcaaa 5880
aatggagcca ataaggacat gcaggatagc aaggaggaga ccccccctatt cctggccgcc 5940 cgcgagggca gctatgaggc tgccaagctg ctgttggacc actttgccaa ccgtgagatc 6000
accgaccacc tggacaggct gccgcgggac gtagcccagg agagactgca ccaggacatc 6060
gtgcgcttgc tggatcaacc cagtgggccc cgcagccccc ccggtcccca cggcctgggg 6120
cctctgctct gtcctccagg ggccttcctc cctggcctca aagcggcaca gtcggggtcc 6180
aagaagagca ggaggccccc cgggaaggcg gggctggggc cgcaggggcc ccgggggcgg 6240
ggcaagaagc tgacgctggc ctgcccgggc cccctggctg acagctcggt cacgctgtcg 6300
cccgtggact cgctggactc cccgcggcct ttcggtgggc cccctgcttc ccctggtggc 6360 ttccccccttg aggggcccta tgcagctgcc actgccactg cagtgtctct ggcacagctt 6420
ggtggcccag gccgggcggg tctagggcgc cagcccccctg gaggatgtgt actcagcctg 6480
ggcctgctga accctgtggc tgtgcccctc gattgggccc ggctgccccc acctgcccct 6540
ccaggcccct cgttcctgct gccactggcg ccgggacccc agctgctcaa cccagggacc 6600
cccgtctccc cgcaggagcg gcccccgcct tacctggcag tcccaggaca tggcgaggag 6660
tacccggcgg ctggggcaca cagcagcccc ccaaaggccc gcttcctgcg ggttcccagt 6720
gagcaccctt acctgacccc atcccccgaa tcccctgagc actgggccag cccctcacct 6780
ccctccctct cagactggtc cgaatccacg cctagcccag ccactgccac tggggccatg 6840
gccaccacca ctggggcact gcctgcccag ccacttccct tgtctgttcc cagctccctt 6900
gctcaggccc agacccagct ggggccccag ccggaagtta cccccaagag gcaagtgttg 6960
gcctga 6966

<210> SEQ ID NO 16
<211> LENGTH: 2321
<212> TYPE: PRT

<213> ORGANISM: Homo sapiens

<400> SEQUENCE: 16

Met Gly Pro Gly Ala Arg Gly Arg Arg Arg Arg Arg Arg Pro Met Ser
1 5 10 15

Pro Pro Pro Pro Pro Pro Pro Val Arg Ala Leu Pro Leu Leu Leu Leu
20 25 30

Leu Ala Gly Pro Gly Ala Ala Ala Pro Pro Cys Leu Asp Gly Ser Pro
35 40 45

Cys Ala Asn Gly Gly Arg Cys Thr Gln Leu Pro Ser Arg Glu Ala Ala
50 55 60

Cys Leu Cys Pro Pro Gly Trp Val Gly Glu Arg Cys Gln Leu Glu Asp
65 70 75 80

Pro Cys His Ser Gly Pro Cys Ala Gly Arg Gly Val Cys Gln Ser Ser
85 90 95

Val Val Ala Gly Thr Ala Arg Phe Ser Cys Arg Cys Pro Arg Gly Phe
100 105 110

Arg Gly Pro Asp Cys Ser Leu Pro Asp Pro Cys Leu Ser Ser Pro Cys
115 120 125

Ala His Gly Ala Arg Cys Ser Val Gly Pro Asp Gly Arg Phe Leu Cys
130 135 140

Ser Cys Pro Pro Gly Tyr Gln Gly Arg Ser Cys Arg Ser Asp Val Asp
145 150 155 160

Glu Cys Arg Val Gly Glu Pro Cys Arg His Gly Gly Thr Cys Leu Asn
165 170 175

Thr Pro Gly Ser Phe Arg Cys Gln Cys Pro Ala Gly Tyr Thr Gly Pro
180 185 190

Leu Cys Glu Asn Pro Ala Val Pro Cys Ala Pro Ser Pro Cys Arg Asn
195 200 205

Gly Gly Thr Cys Arg Gln Ser Gly Asp Leu Thr Tyr Asp Cys Ala Cys
210 215 220

Leu Pro Gly Phe Glu Gly Gln Asn Cys Glu Val Asn Val Asp Asp Cys
225 230 235 240

Pro Gly His Arg Cys Leu Asn Gly Gly Thr Cys Val Asp Gly Val Asn
245 250 255

Thr Tyr Asn Cys Gln Cys Pro Pro Glu Trp Thr Gly Gln Phe Cys Thr
260 265 270

Glu Asp Val Asp Glu Cys Gln Leu Gln Pro Asn Ala Cys His Asn Gly
275 280 285

Gly Thr Cys Phe Asn Thr Leu Gly Gly His Ser Cys Val Cys Val Asn
290 295 300

Gly Trp Thr Gly Glu Ser Cys Ser Gln Asn Ile Asp Asp Cys Ala Thr
305 310 315 320

Ala Val Cys Phe His Gly Ala Thr Cys His Asp Arg Val Ala Ser Phe
325 330 335

Tyr Cys Ala Cys Pro Met Gly Lys Thr Gly Leu Leu Cys His Leu Asp
340 345 350

Asp Ala Cys Val Ser Asn Pro Cys His Glu Asp Ala Ile Cys Asp Thr
355 360 365

Asn Pro Val Asn Gly Arg Ala Ile Cys Thr Cys Pro Pro Gly Phe Thr
370 375 380

Gly Gly Ala Cys Asp Gln Asp Val Asp Glu Cys Ser Ile Gly Ala Asn
385 390 395 400

-continued

```
Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
    450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
    530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
    610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
```

```
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
        915                 920                 925

Ser Pro Ser Ser Cys Phe Asn Gly Gly Thr Cys Val Asp Gly Val Asn
    930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu  Val Asp Trp Cys Ser  Arg Gln Pro
        995                 1000                1005

Cys Gln  Asn Gly Gly Arg Cys  Val Gln Thr Gly Ala  Tyr Cys Leu
    1010                1015                1020

Cys Pro  Pro Gly Trp Ser Gly  Arg Leu Cys Asp Ile  Arg Ser Leu
    1025                1030                1035

Pro Cys  Arg Glu Ala Ala Ala  Gln Ile Gly Val Arg  Leu Glu Gln
    1040                1045                1050

Leu Cys  Gln Ala Gly Gly Gln  Cys Val Asp Glu Asp  Ser Ser His
    1055                1060                1065

Tyr Cys  Val Cys Pro Glu Gly  Arg Thr Gly Ser His  Cys Glu Gln
    1070                1075                1080

Glu Val  Asp Pro Cys Leu Ala  Gln Pro Cys Gln His  Gly Gly Thr
    1085                1090                1095

Cys Arg  Gly Tyr Met Gly Gly  Tyr Met Cys Glu Cys  Leu Pro Gly
    1100                1105                1110

Tyr Asn  Gly Asp Asn Cys Glu  Asp Asp Val Asp Glu  Cys Ala Ser
    1115                1120                1125

Gln Pro  Cys Gln His Gly Gly  Ser Cys Ile Asp Leu  Val Ala Arg
    1130                1135                1140

Tyr Leu  Cys Ser Cys Pro Pro  Gly Thr Leu Gly Val  Leu Cys Glu
    1145                1150                1155

Ile Asn  Glu Asp Asp Cys Gly  Pro Gly Pro Pro Leu  Asp Ser Gly
    1160                1165                1170

Pro Arg  Cys Leu His Asn Gly  Thr Cys Val Asp Leu  Val Gly Gly
    1175                1180                1185

Phe Arg  Cys Thr Cys Pro Pro  Gly Tyr Thr Gly Leu  Arg Cys Glu
    1190                1195                1200

Ala Asp  Ile Asn Glu Cys Arg  Ser Gly Ala Cys His  Ala Ala His
    1205                1210                1215

Thr Arg  Asp Cys Leu Gln Asp  Pro Gly Gly Gly Phe  Arg Cys Leu
    1220                1225                1230
```

```
Cys His  Ala Gly Phe Ser Gly  Pro Arg Cys Gln Thr  Val Leu Ser
    1235                 1240                 1245

Pro Cys  Glu Ser Gln Pro Cys  Gln His Gly Gly Gln  Cys Arg Pro
    1250                 1255                 1260

Ser Pro  Gly Pro Gly Gly Gly  Leu Thr Phe Thr Cys  His Cys Ala
    1265                 1270                 1275

Gln Pro  Phe Trp Gly Pro Arg  Cys Glu Arg Val Ala  Arg Ser Cys
    1280                 1285                 1290

Arg Glu  Leu Gln Cys Pro Val  Gly Val Pro Cys Gln  Gln Thr Pro
    1295                 1300                 1305

Arg Gly  Pro Arg Cys Ala Cys  Pro Pro Gly Leu Ser  Gly Pro Ser
    1310                 1315                 1320

Cys Arg  Ser Phe Pro Gly Ser  Pro Pro Gly Ala Ser  Asn Ala Ser
    1325                 1330                 1335

Cys Ala  Ala Ala Pro Cys Leu  His Gly Gly Ser Cys  Arg Pro Ala
    1340                 1345                 1350

Pro Leu  Ala Pro Phe Phe Arg  Cys Ala Cys Ala Gln  Gly Trp Thr
    1355                 1360                 1365

Gly Pro  Arg Cys Glu Ala Pro  Ala Ala Ala Pro Glu  Val Ser Glu
    1370                 1375                 1380

Glu Pro  Arg Cys Pro Arg Ala  Ala Cys Gln Ala Lys  Arg Gly Asp
    1385                 1390                 1395

Gln Arg  Cys Asp Arg Glu Cys  Asn Ser Pro Gly Cys  Gly Trp Asp
    1400                 1405                 1410

Gly Gly  Asp Cys Ser Leu Ser  Val Gly Asp Pro Trp  Arg Gln Cys
    1415                 1420                 1425

Glu Ala  Leu Gln Cys Trp Arg  Leu Phe Asn Asn Ser  Arg Cys Asp
    1430                 1435                 1440

Pro Ala  Cys Ser Ser Pro Ala  Cys Leu Tyr Asp Asn  Phe Asp Cys
    1445                 1450                 1455

His Ala  Gly Gly Arg Glu Arg  Thr Cys Asn Pro Val  Tyr Glu Lys
    1460                 1465                 1470

Tyr Cys  Ala Asp His Phe Ala  Asp Gly Arg Cys Asp  Gln Gly Cys
    1475                 1480                 1485

Asn Thr  Glu Glu Cys Gly Trp  Asp Gly Leu Asp Cys  Ala Ser Glu
    1490                 1495                 1500

Val Pro  Ala Leu Leu Ala Arg  Gly Val Leu Val Leu  Thr Val Leu
    1505                 1510                 1515

Leu Pro  Pro Glu Glu Leu Leu  Arg Ser Ser Ala Asp  Phe Leu Gln
    1520                 1525                 1530

Arg Leu  Ser Ala Ile Leu Arg  Thr Ser Leu Arg Phe  Arg Leu Asp
    1535                 1540                 1545

Ala His  Gly Gln Ala Met Val  Phe Pro Tyr His Arg  Pro Ser Pro
    1550                 1555                 1560

Gly Ser  Glu Pro Arg Ala Arg  Arg Glu Leu Ala Pro  Glu Val Ile
    1565                 1570                 1575

Gly Ser  Val Val Met Leu Glu  Ile Asp Asn Arg Leu  Cys Leu Gln
    1580                 1585                 1590

Ser Pro  Glu Asn Asp His Cys  Phe Pro Asp Ala Gln  Ser Ala Ala
    1595                 1600                 1605

Asp Tyr  Leu Gly Ala Leu Ser  Ala Val Glu Arg Leu  Asp Phe Pro
    1610                 1615                 1620
```

Tyr Pro Leu Arg Asp Val Arg Gly Glu Pro Leu Glu Pro Pro Glu
1625 1630 1635

Pro Ser Val Pro Leu Leu Pro Leu Leu Val Ala Gly Ala Val Leu
1640 1645 1650

Leu Leu Val Ile Leu Val Leu Gly Val Met Val Ala Arg Arg Lys
1655 1660 1665

Arg Glu His Ser Thr Leu Trp Phe Pro Glu Gly Phe Ser Leu His
1670 1675 1680

Lys Asp Val Ala Ser Gly His Lys Gly Arg Arg Glu Pro Val Gly
1685 1690 1695

Gln Asp Ala Leu Gly Met Lys Asn Met Ala Lys Gly Glu Ser Leu
1700 1705 1710

Met Gly Glu Val Ala Thr Asp Trp Met Asp Thr Glu Cys Pro Glu
1715 1720 1725

Ala Lys Arg Leu Lys Val Glu Glu Pro Gly Met Gly Ala Glu Glu
1730 1735 1740

Ala Val Asp Cys Arg Gln Trp Thr Gln His His Leu Val Ala Ala
1745 1750 1755

Asp Ile Arg Val Ala Pro Ala Met Ala Leu Thr Pro Pro Gln Gly
1760 1765 1770

Asp Ala Asp Ala Asp Gly Met Asp Val Asn Val Arg Gly Pro Asp
1775 1780 1785

Gly Phe Thr Pro Leu Met Leu Ala Ser Phe Cys Gly Gly Ala Leu
1790 1795 1800

Glu Pro Met Pro Thr Glu Glu Asp Glu Ala Asp Asp Thr Ser Ala
1805 1810 1815

Ser Ile Ile Ser Asp Leu Ile Cys Gln Gly Ala Gln Leu Gly Ala
1820 1825 1830

Arg Thr Asp Arg Thr Gly Glu Thr Ala Leu His Leu Ala Ala Arg
1835 1840 1845

Tyr Ala Arg Ala Asp Ala Ala Lys Arg Leu Leu Asp Ala Gly Ala
1850 1855 1860

Asp Thr Asn Ala Gln Asp His Ser Gly Arg Thr Pro Leu His Thr
1865 1870 1875

Ala Val Thr Ala Asp Ala Gln Gly Val Phe Gln Ile Leu Ile Arg
1880 1885 1890

Asn Arg Ser Thr Asp Leu Asp Ala Arg Met Ala Asp Gly Ser Thr
1895 1900 1905

Ala Leu Ile Leu Ala Ala Arg Leu Ala Val Glu Gly Met Val Glu
1910 1915 1920

Glu Leu Ile Ala Ser His Ala Asp Val Asn Ala Val Asp Glu Leu
1925 1930 1935

Gly Lys Ser Ala Leu His Trp Ala Ala Ala Val Asn Asn Val Glu
1940 1945 1950

Ala Thr Leu Ala Leu Leu Lys Asn Gly Ala Asn Lys Asp Met Gln
1955 1960 1965

Asp Ser Lys Glu Glu Thr Pro Leu Phe Leu Ala Ala Arg Glu Gly
1970 1975 1980

Ser Tyr Glu Ala Ala Lys Leu Leu Leu Asp His Phe Ala Asn Arg
1985 1990 1995

Glu Ile Thr Asp His Leu Asp Arg Leu Pro Arg Asp Val Ala Gln
2000 2005 2010

Glu Arg Leu His Gln Asp Ile Val Arg Leu Leu Asp Gln Pro Ser

```
    2015                2020                2025

Gly Pro  Arg Ser Pro Pro Gly  Pro His Gly Leu Gly  Pro Leu Leu
    2030                2035                2040

Cys Pro  Pro Gly Ala Phe Leu  Pro Gly Leu Lys Ala  Ala Gln Ser
    2045                2050                2055

Gly Ser  Lys Lys Ser Arg Arg  Pro Pro Gly Lys Ala  Gly Leu Gly
    2060                2065                2070

Pro Gln  Gly Pro Arg Gly Arg  Gly Lys Lys Leu Thr  Leu Ala Cys
    2075                2080                2085

Pro Gly  Pro Leu Ala Asp Ser  Ser Val Thr Leu Ser  Pro Val Asp
    2090                2095                2100

Ser Leu  Asp Ser Pro Arg Pro  Phe Gly Gly Pro Pro  Ala Ser Pro
    2105                2110                2115

Gly Gly  Phe Pro Leu Glu Gly  Pro Tyr Ala Ala Ala  Thr Ala Thr
    2120                2125                2130

Ala Val  Ser Leu Ala Gln Leu  Gly Gly Pro Gly Arg  Ala Gly Leu
    2135                2140                2145

Gly Arg  Gln Pro Pro Gly Gly  Cys Val Leu Ser Leu  Gly Leu Leu
    2150                2155                2160

Asn Pro  Val Ala Val Pro Leu  Asp Trp Ala Arg Leu  Pro Pro Pro
    2165                2170                2175

Ala Pro  Pro Gly Pro Ser Phe  Leu Leu Pro Leu Ala  Pro Gly Pro
    2180                2185                2190

Gln Leu  Leu Asn Pro Gly Thr  Pro Val Ser Pro Gln  Glu Arg Pro
    2195                2200                2205

Pro Pro  Tyr Leu Ala Val Pro  Gly His Gly Glu Glu  Tyr Pro Ala
    2210                2215                2220

Ala Gly  Ala His Ser Ser Pro  Pro Lys Ala Arg Phe  Leu Arg Val
    2225                2230                2235

Pro Ser  Glu His Pro Tyr Leu  Thr Pro Ser Pro Glu  Ser Pro Glu
    2240                2245                2250

His Trp  Ala Ser Pro Ser Pro  Pro Ser Leu Ser Asp  Trp Ser Glu
    2255                2260                2265

Ser Thr  Pro Ser Pro Ala Thr  Ala Thr Gly Ala Met  Ala Thr Thr
    2270                2275                2280

Thr Gly  Ala Leu Pro Ala Gln  Pro Leu Pro Leu Ser  Val Pro Ser
    2285                2290                2295

Ser Leu  Ala Gln Ala Gln Thr  Gln Leu Gly Pro Gln  Pro Glu Val
    2300                2305                2310

Thr Pro  Lys Arg Gln Val Leu  Ala
    2315                2320
```

<210> SEQ ID NO 17
<211> LENGTH: 714
<212> TYPE: DNA
<213> ORGANISM: Homo sapiens

<400> SEQUENCE: 17

```
gatctgggcc cgggcgagcc caaatcttgt gacaaaactc acacatgccc accgtgccca     60

gcacctgaac tcctgggggg accgtcagtc ttcctcttcc ccccaaaacc caaggacacc    120

ctcatgatct cccggacccc tgaggtcaca tgcgtggtgg tggacgtgag ccacgaagac    180

cctgaggtca agttcaactg gtacgtggac ggcgtggagg tgcataatgc caagacaaag    240

ccgcgggagg agcagtacaa cagcacgtac cgtgtggtca gcgtcctcac cgtcctgcac    300
```

-continued caggactggc tgaatggcaa ggagtacaag tgcaaggtct ccaacaaagc cctcccagcc 360
cccatcgaga aaaccatctc caaagccaaa gggcagcccc gagaaccaca ggtgtacacc 420
ctgcccccat cccgggatga gctgaccaag aaccaggtca gcctgacctg cctggtcaaa 480
ggcttctatc ccagcgacat cgccgtggag tgggagagca atgggcagcc ggagaacaac 540
tacaagacca cgcctcccgt gctggactcc gacggctcct tcttcctcta cagcaagctc 600
accgtggaca agagcaggtg gcagcagggg aacgtcttct catgctccgt gatgcatgag 660
gctctgcaca accactacac gcagaagagc ctctccctgt ctccgggtaa atga 714

<210> SEQ ID NO 18
<211> LENGTH: 237
<212> TYPE: PRT
<213> ORGANISM: Homo sapiens

<400> SEQUENCE: 18

Asp Leu Gly Pro Gly Glu Pro Lys Ser Cys Asp Lys Thr His Thr Cys
1 5 10 15

Pro Pro Cys Pro Ala Pro Glu Leu Leu Gly Gly Pro Ser Val Phe Leu
20 25 30

Phe Pro Pro Lys Pro Lys Asp Thr Leu Met Ile Ser Arg Thr Pro Glu
35 40 45

Val Thr Cys Val Val Val Asp Val Ser His Glu Asp Pro Glu Val Lys
50 55 60

Phe Asn Trp Tyr Val Asp Gly Val Glu Val His Asn Ala Lys Thr Lys
65 70 75 80

Pro Arg Glu Glu Gln Tyr Asn Ser Thr Tyr Arg Val Val Ser Val Leu
85 90 95

Thr Val Leu His Gln Asp Trp Leu Asn Gly Lys Glu Tyr Lys Cys Lys
100 105 110

Val Ser Asn Lys Ala Leu Pro Ala Pro Ile Glu Lys Thr Ile Ser Lys
115 120 125

Ala Lys Gly Gln Pro Arg Glu Pro Gln Val Tyr Thr Leu Pro Pro Ser
130 135 140

Arg Asp Glu Leu Thr Lys Asn Gln Val Ser Leu Thr Cys Leu Val Lys
145 150 155 160

Gly Phe Tyr Pro Ser Asp Ile Ala Val Glu Trp Glu Ser Asn Gly Gln
165 170 175

Pro Glu Asn Asn Tyr Lys Thr Thr Pro Pro Val Leu Asp Ser Asp Gly
180 185 190

Ser Phe Phe Leu Tyr Ser Lys Leu Thr Val Asp Lys Ser Arg Trp Gln
195 200 205

Gln Gly Asn Val Phe Ser Cys Ser Val Met His Glu Ala Leu His Asn
210 215 220

His Tyr Thr Gln Lys Ser Leu Ser Leu Ser Pro Gly Lys
225 230 235

<210> SEQ ID NO 19
<211> LENGTH: 12
<212> TYPE: DNA
<213> ORGANISM: Homo sapiens

<400> SEQUENCE: 19
gaggagccgc gg 12

<210> SEQ ID NO 20
<211> LENGTH: 12
<212> TYPE: DNA
<213> ORGANISM: Homo sapiens

<400> SEQUENCE: 20
ccgcggctcc tc 12

<210> SEQ ID NO 21
<211> LENGTH: 4
<212> TYPE: PRT
<213> ORGANISM: Homo sapiens

<400> SEQUENCE: 21

Glu Glu Pro Arg
1

<210> SEQ ID NO 22
<211> LENGTH: 17
<212> TYPE: DNA
<213> ORGANISM: Homo sapiens

<400> SEQUENCE: 22
gaggagccgc gagatct 17

<210> SEQ ID NO 23
<211> LENGTH: 17
<212> TYPE: DNA
<213> ORGANISM: Homo sapiens

<400> SEQUENCE: 23
agatctcgcg gctcctc 17

<210> SEQ ID NO 24
<211> LENGTH: 24
<212> TYPE: DNA
<213> ORGANISM: Homo sapiens

<400> SEQUENCE: 24
gaggagccgc gagatctggg cccg 24

<210> SEQ ID NO 25
<211> LENGTH: 24
<212> TYPE: DNA
<213> ORGANISM: Homo sapiens

<400> SEQUENCE: 25
cgggcccaga tctcgcggct cctc 24

<210> SEQ ID NO 26
<211> LENGTH: 8
<212> TYPE: PRT
<213> ORGANISM: Homo sapiens

<400> SEQUENCE: 26

Glu Glu Pro Arg Asp Leu Gly Pro
1 5

<210> SEQ ID NO 27
<211> LENGTH: 40
<212> TYPE: PRT
<213> ORGANISM: Homo sapiens

<400> SEQUENCE: 27

-continued

```
Met Gly Pro Gly Ala Arg Gly Arg Arg Arg Arg Arg Arg Pro Met Ser
1               5                   10                  15

Pro Pro Pro Pro Pro Pro Pro Val Arg Ala Leu Pro Leu Leu Leu Leu
            20                  25                  30

Leu Ala Gly Pro Gly Ala Ala Ala
        35                  40


<210> SEQ ID NO 28
<211> LENGTH: 120
<212> TYPE: DNA
<213> ORGANISM: Homo sapiens

<400> SEQUENCE: 28

atggggccgg gggcccgtgg ccgccgccgc cgccgtcgcc cgatgtcgcc gccaccgcca      60

ccgccacccg tgcgggcgct gcccctgctg ctgctgctag cggggccggg ggctgcagcc     120


<210> SEQ ID NO 29
<211> LENGTH: 22
<212> TYPE: PRT
<213> ORGANISM: Homo sapiens

<400> SEQUENCE: 29

Met Trp Gly Trp Lys Cys Leu Leu Phe Trp Ala Val Leu Val Thr Ala
1               5                   10                  15

Thr Leu Cys Thr Ala Arg
            20


<210> SEQ ID NO 30
<211> LENGTH: 66
<212> TYPE: DNA
<213> ORGANISM: Homo sapiens

<400> SEQUENCE: 30

atgtggggct ggaagtgcct cctcttctgg gctgtgctgg tcacagccac tctctgcact      60

gccagg                                                                 66


<210> SEQ ID NO 31
<211> LENGTH: 4872
<212> TYPE: DNA
<213> ORGANISM: Homo sapiens

<400> SEQUENCE: 31

atggggccgg gggcccgtgg ccgccgccgc cgccgtcgcc cgatgtcgcc gccaccgcca      60

ccgccacccg tgcgggcgct gcccctgctg ctgctgctag cggggccggg ggctgcagcc     120

ccccccttgcc tggacggaag cccgtgtgca aatggaggtc gttgcaccca gctgccctcc    180

cgggaggctg cctgcctgtg cccgcctggc tgggtgggtg agcggtgtca gctggaggac     240

ccctgtcact caggcccctg tgctggccgt ggtgtctgcc agagttcagt ggtggctggc     300

accgcccgat tctcatgccg gtgccccccgt ggcttccgag gccctgactg ctccctgcca    360

gatccctgcc tcagcagccc ttgtgcccac ggtgcccgct gctcagtggg gcccgatgga     420

cgcttcctct gctcctgccc acctggctac cagggccgca gctgccgaag cgacgtggat     480

gagtgccggg tgggtgagcc ctgccgccat ggtggcacct gcctcaacac acctggctcc     540

ttccgctgcc agtgtccagc tggctacaca gggccactat gtgagaaccc cgcggtgccc     600

tgtgcgccct caccatgccg taacgggggc acctgcaggc agagtggcga cctcacttac     660

gactgtgcct gtcttcctgg gtttgagggt cagaattgtg aagtgaacgt ggacgactgt     720
```

```
ccaggacacc gatgtctcaa tggggggaca tgcgtggatg gcgtcaacac ctataactgc    780
cagtgccctc ctgagtggac aggccagttc tgcacggagg acgtggatga gtgtcagctg    840
cagcccaacg cctgccacaa tgggggtacc tgcttcaaca cgctgggtgg ccacagctgc    900
gtgtgtgtca atggctggac aggcgagagc tgcagtcaga atatcgatga ctgtgccaca    960
gccgtgtgct tccatggggc cacctgccat gaccgcgtgg cttctttcta ctgtgcctgc   1020
cccatgggca agactggcct cctgtgtcac ctggatgacg cctgtgtcag caacccctgc   1080
cacgaggatg ctatctgtga cacaaatccg gtgaacggcc gggccatttg cacctgtcct   1140
cccggcttca cgggtggggc atgtgaccag gatgtggacg agtgctctat cggcgccaac   1200
ccctgcgagc acttgggcag gtgcgtgaac acgcagggct ccttcctgtg ccagtgcggt   1260
cgtggctaca ctggacctcg ctgtgagacc gatgtcaacg agtgtctgtc ggggccctgc   1320
cgaaaccagg ccacgtgcct cgaccgcata ggccagttca cctgtatctg tatggcaggc   1380
ttcacaggaa cctattgcga ggtggacatt gacgagtgtc agagtagccc ctgtgtcaac   1440
ggtggggtct gcaaggaccg agtcaatggc ttcagctgca cctgcccctc gggcttcagc   1500
ggctccacgt gtcagctgga cgtggacgaa tgcgccagca cgccctgcag gaatggcgcc   1560
aaatgcgtgg accagcccga tggctacgag tgccgctgtg ccgagggctt tgagggcacg   1620
ctgtgtgatc gcaacgtgga cgactgctcc cctgacccat gccaccatgg tcgctgcgtg   1680
gatggcatcg ccagcttctc atgtgcctgt gctcctggct acacgggcac acgctgcgag   1740
agccaggtgg acgaatgccg cagccagccc tgccgccatg gcggcaaatg cctagacctg   1800
gtggacaagt acctctgccg ctgcccttct gggaccacag gtgtgaactg cgaagtgaac   1860
attgacgact gtgccagcaa cccctgcacc tttggagtct gccgtgatgg catcaaccgc   1920
tacgactgtg tctgccaacc tggcttcaca gggccccttt gtaacgtgga gatcaatgag   1980
tgtgcttcca gcccatgcgg cgagggaggt tcctgtgtgg atggggaaaa tggcttccgc   2040
tgcctctgcc cgcctggctc cttgcccccca ctctgcctcc ccccgagcca tccctgtgcc   2100
catgagccct gcagtcacgg catctgctat gatgcacctg gcgggttccg ctgtgtgtgt   2160
gagcctggct ggagtggccc ccgctgcagc cagagcctgg cccgagacgc ctgtgagtcc   2220
cagccgtgca gggccggtgg gacatgcagc agcgatggaa tgggtttcca ctgcacctgc   2280
ccgcctggtg tccagggacg tcagtgtgaa ctcctctccc cctgcacccc gaacccctgt   2340
gagcatgggg gccgctgcga gtctgcccct ggccagctgc ctgtctgctc ctgcccccag   2400
ggctggcaag gcccacgatg ccagcaggat gtggacgagt gtgctggccc cgcaccctgt   2460
ggccctcatg gtatctgcac caacctggca gggagtttca gctgcacctg ccatggaggg   2520
tacactggcc cttcctgtga tcaggacatc aatgactgtg accccaaccc atgcctgaac   2580
ggtggctcgt gccaagacgg cgtgggctcc ttttcctgct cctgcctccc tggtttcgcc   2640
ggcccacgat gcgcccgcga tgtggatgag tgcctgagca acccctgcgg cccgggcacc   2700
tgtaccgacc acgtggcctc cttcacctgc acctgcccgc caggctacgg aggcttccac   2760
tgcgaacagg acctgcccga ctgcagcccc agctcctgct tcaatggcgg gacctgtgtg   2820
gacggcgtga actcgttcag ctgcctgtgc cgtcccggct acacaggagc ccactgccaa   2880
catgaggcag accccctgcct ctcgcggccc tgcctacacg gggggcgtctg cagcgccgcc   2940
caccctggct tccgctgcac ctgcctcgag agcttcacgg gcccgcagtg ccagacgctg   3000
gtggattggt gcagccgcca gccttgtcaa aacgggggtc gctgcgtcca gactggggcc   3060
tattgccttt gtccccctgg atggagcgga cgcctctgtg acatccgaag cttgccctgc   3120
```

-continued

```
agggaggccg cagcccagat cggggtgcgg ctggagcagc tgtgtcaggc gggtgggcag   3180

tgtgtggatg aagacagctc ccactactgc gtgtgcccag agggccgtac tggtagccac   3240

tgtgagcagg aggtggaccc ctgcttggcc cagccctgcc agcatggggg gacctgccgt   3300

ggctatatgg ggggctacat gtgtgagtgt cttcctggct acaatggtga taactgtgag   3360

gacgacgtgg acgagtgtgc ctcccagccc tgccagcacg gggggttcatg cattgacctc   3420

gtggcccgct atctctgctc ctgtccccca ggaacgctgg gggtgctctg cgagattaat   3480

gaggatgact gcggcccagg cccaccgctg gactcagggc cccggtgcct acacaatggc   3540

acctgcgtgg acctggtggg tggtttccgc tgcacctgtc ccccaggata cactggtttg   3600

cgctgcgagg cagacatcaa tgagtgtcgc tcaggtgcct gccacgcggc acacacccgg   3660

gactgcctgc aggacccagg cggaggtttc cgttgccttt gtcatgctgg cttctcaggt   3720

cctcgctgtc agactgtcct gtctccctgc gagtcccagc catgccagca tggaggccag   3780

tgccgtccta gcccgggtcc tgggggtggg ctgaccttca cctgtcactg tgcccagccg   3840

ttctggggtc cgcgttgcga gcgggtggcg cgctcctgcc gggagctgca gtgcccggtg   3900

ggcgtcccat gccagcagac gccccgcggg ccgcgctgcg cctgcccccc agggttgtcg   3960

ggaccctcct gccgcagctt cccggggtcg ccgccggggg ccagcaacgc cagctgcgcg   4020

gccgcccccct gtctccacgg gggctcctgc cgccccgcgc cgctcgcgcc cttcttccgc   4080

tgcgcttgcg cgcagggctg gaccgggccg cgctgcgagg cgcccgccgc ggcacccgag   4140

gtctcggagg agccgcgaga tctgggcccg ggcgagccca aatcttgtga caaaactcac   4200

acatgcccac cgtgcccagc acctgaactc ctggggggac cgtcagtctt cctcttcccc   4260

ccaaaaccca aggacaccct catgatctcc cggacccctg aggtcacatg cgtggtggtg   4320

gacgtgagcc acgaagaccc tgaggtcaag ttcaactggt acgtggacgg cgtggaggtg   4380

cataatgcca agacaaagcc gcgggaggag cagtacaaca gcacgtaccg tgtggtcagc   4440

gtcctcaccg tcctgcacca ggactggctg aatggcaagg agtacaagtg caaggtctcc   4500

aacaaagccc tcccagcccc catcgagaaa accatctcca aagccaaagg gcagccccga   4560

gaaccacagg tgtacaccct gcccccatcc cgggatgagc tgaccaagaa ccaggtcagc   4620

ctgacctgcc tggtcaaagg cttctatccc agcgacatcg ccgtggagtg ggagagcaat   4680

gggcagccgg agaacaacta caagaccacg cctcccgtgc tggactccga cggctccttc   4740

ttcctctaca gcaagctcac cgtggacaag agcaggtggc agcaggggaa cgtcttctca   4800

tgctccgtga tgcatgaggc tctgcacaac cactacacgc agaagagcct ctccctgtct   4860

ccgggtaaat ga                                                        4872
```

```
<210> SEQ ID NO 32
<211> LENGTH: 1623
<212> TYPE: PRT
<213> ORGANISM: Homo sapiens

<400> SEQUENCE: 32

Met Gly Pro Gly Ala Arg Gly Arg Arg Arg Arg Arg Arg Pro Met Ser
1               5                   10                  15

Pro Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp Gly Ser Pro
        35                  40                  45

Cys Ala Asn Gly Gly Arg Cys Thr Gln Leu Pro Ser Arg Glu Ala Ala
```

-continued

```
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
        355                 360                 365

Asn Pro Val Asn Gly Arg Ala Ile Cys Thr Cys Pro Pro Gly Phe Thr
    370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
    450                 455                 460

Tyr Cys Glu Val Asp Ile Asp Glu Cys Gln Ser Ser Pro Cys Val Asn
465                 470                 475                 480
```

```
Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
    530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
    610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895
```

-continued

```
Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
        915                 920                 925

Ser Pro Ser Ser Cys Phe Asn Gly Gly Thr Cys Val Asp Gly Val Asn
    930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu  Val Asp Trp Cys Ser  Arg Gln Pro
        995                 1000                1005

Cys Gln  Asn Gly Gly Arg Cys  Val Gln Thr Gly Ala  Tyr Cys Leu
    1010                 1015                 1020

Cys Pro  Pro Gly Trp Ser Gly  Arg Leu Cys Asp Ile  Arg Ser Leu
    1025                 1030                 1035

Pro Cys  Arg Glu Ala Ala Ala  Gln Ile Gly Val Arg  Leu Glu Gln
    1040                 1045                 1050

Leu Cys  Gln Ala Gly Gly Gln  Cys Val Asp Glu Asp  Ser Ser His
    1055                 1060                 1065

Tyr Cys  Val Cys Pro Glu Gly  Arg Thr Gly Ser His  Cys Glu Gln
    1070                 1075                 1080

Glu Val  Asp Pro Cys Leu Ala  Gln Pro Cys Gln His  Gly Gly Thr
    1085                 1090                 1095

Cys Arg  Gly Tyr Met Gly Gly  Tyr Met Cys Glu Cys  Leu Pro Gly
    1100                 1105                 1110

Tyr Asn  Gly Asp Asn Cys Glu  Asp Asp Val Asp Glu  Cys Ala Ser
    1115                 1120                 1125

Gln Pro  Cys Gln His Gly Gly  Ser Cys Ile Asp Leu  Val Ala Arg
    1130                 1135                 1140

Tyr Leu  Cys Ser Cys Pro Pro  Gly Thr Leu Gly Val  Leu Cys Glu
    1145                 1150                 1155

Ile Asn  Glu Asp Asp Cys Gly  Pro Gly Pro Pro Leu  Asp Ser Gly
    1160                 1165                 1170

Pro Arg  Cys Leu His Asn Gly  Thr Cys Val Asp Leu  Val Gly Gly
    1175                 1180                 1185

Phe Arg  Cys Thr Cys Pro Pro  Gly Tyr Thr Gly Leu  Arg Cys Glu
    1190                 1195                 1200

Ala Asp  Ile Asn Glu Cys Arg  Ser Gly Ala Cys His  Ala Ala His
    1205                 1210                 1215

Thr Arg  Asp Cys Leu Gln Asp  Pro Gly Gly Gly Phe  Arg Cys Leu
    1220                 1225                 1230

Cys His  Ala Gly Phe Ser Gly  Pro Arg Cys Gln Thr  Val Leu Ser
    1235                 1240                 1245

Pro Cys  Glu Ser Gln Pro Cys  Gln His Gly Gly Gln  Cys Arg Pro
    1250                 1255                 1260

Ser Pro  Gly Pro Gly Gly Gly  Leu Thr Phe Thr Cys  His Cys Ala
    1265                 1270                 1275

Gln Pro  Phe Trp Gly Pro Arg  Cys Glu Arg Val Ala  Arg Ser Cys
    1280                 1285                 1290

Arg Glu  Leu Gln Cys Pro Val  Gly Val Pro Cys Gln  Gln Thr Pro
```

```
    1295                1300                1305

Arg Gly  Pro Arg Cys Ala Cys  Pro Pro Gly Leu Ser  Gly Pro Ser
    1310                1315                1320

Cys Arg  Ser Phe Pro Gly Ser  Pro Pro Gly Ala Ser  Asn Ala Ser
    1325                1330                1335

Cys Ala  Ala Ala Pro Cys Leu  His Gly Gly Ser Cys  Arg Pro Ala
    1340                1345                1350

Pro Leu  Ala Pro Phe Phe Arg  Cys Ala Cys Ala Gln  Gly Trp Thr
    1355                1360                1365

Gly Pro  Arg Cys Glu Ala Pro  Ala Ala Ala Pro Glu  Val Ser Glu
    1370                1375                1380

Glu Pro  Arg Asp Leu Gly Pro  Gly Glu Pro Lys Ser  Cys Asp Lys
    1385                1390                1395

Thr His  Thr Cys Pro Pro Cys  Pro Ala Pro Glu Leu  Leu Gly Gly
    1400                1405                1410

Pro Ser  Val Phe Leu Phe Pro  Pro Lys Pro Lys Asp  Thr Leu Met
    1415                1420                1425

Ile Ser  Arg Thr Pro Glu Val  Thr Cys Val Val Val  Asp Val Ser
    1430                1435                1440

His Glu  Asp Pro Glu Val Lys  Phe Asn Trp Tyr Val  Asp Gly Val
    1445                1450                1455

Glu Val  His Asn Ala Lys Thr  Lys Pro Arg Glu Glu  Gln Tyr Asn
    1460                1465                1470

Ser Thr  Tyr Arg Val Val Ser  Val Leu Thr Val Leu  His Gln Asp
    1475                1480                1485

Trp Leu  Asn Gly Lys Glu Tyr  Lys Cys Lys Val Ser  Asn Lys Ala
    1490                1495                1500

Leu Pro  Ala Pro Ile Glu Lys  Thr Ile Ser Lys Ala  Lys Gly Gln
    1505                1510                1515

Pro Arg  Glu Pro Gln Val Tyr  Thr Leu Pro Pro Ser  Arg Asp Glu
    1520                1525                1530

Leu Thr  Lys Asn Gln Val Ser  Leu Thr Cys Leu Val  Lys Gly Phe
    1535                1540                1545

Tyr Pro  Ser Asp Ile Ala Val  Glu Trp Glu Ser Asn  Gly Gln Pro
    1550                1555                1560

Glu Asn  Asn Tyr Lys Thr Thr  Pro Pro Val Leu Asp  Ser Asp Gly
    1565                1570                1575

Ser Phe  Phe Leu Tyr Ser Lys  Leu Thr Val Asp Lys  Ser Arg Trp
    1580                1585                1590

Gln Gln  Gly Asn Val Phe Ser  Cys Ser Val Met His  Glu Ala Leu
    1595                1600                1605

His Asn  His Tyr Thr Gln Lys  Ser Leu Ser Leu Ser  Pro Gly Lys
    1610                1615                1620


<210> SEQ ID NO 33
<211> LENGTH: 1605
<212> TYPE: PRT
<213> ORGANISM: Homo sapiens

<400> SEQUENCE: 33

Met Trp Gly Trp Lys Cys Leu Leu Phe Trp Ala Val Leu Val Thr Ala
1               5                   10                  15

Thr Leu Cys Thr Ala Arg Pro Pro Cys Leu Asp Gly Ser Pro Cys Ala
            20                  25                  30
```

-continued

```
Asn Gly Gly Arg Cys Thr Gln Leu Pro Ser Arg Glu Ala Ala Cys Leu
        35                  40                  45

Cys Pro Pro Gly Trp Val Gly Glu Arg Cys Gln Leu Glu Asp Pro Cys
    50                  55                  60

His Ser Gly Pro Cys Ala Gly Arg Gly Val Cys Gln Ser Ser Val Val
65                  70                  75                  80

Ala Gly Thr Ala Arg Phe Ser Cys Arg Cys Pro Arg Gly Phe Arg Gly
                85                  90                  95

Pro Asp Cys Ser Leu Pro Asp Pro Cys Leu Ser Ser Pro Cys Ala His
            100                 105                 110

Gly Ala Arg Cys Ser Val Gly Pro Asp Gly Arg Phe Leu Cys Ser Cys
        115                 120                 125

Pro Pro Gly Tyr Gln Gly Arg Ser Cys Arg Ser Asp Val Asp Glu Cys
    130                 135                 140

Arg Val Gly Glu Pro Cys Arg His Gly Gly Thr Cys Leu Asn Thr Pro
145                 150                 155                 160

Gly Ser Phe Arg Cys Gln Cys Pro Ala Gly Tyr Thr Gly Pro Leu Cys
                165                 170                 175

Glu Asn Pro Ala Val Pro Cys Ala Pro Ser Pro Cys Arg Asn Gly Gly
            180                 185                 190

Thr Cys Arg Gln Ser Gly Asp Leu Thr Tyr Asp Cys Ala Cys Leu Pro
        195                 200                 205

Gly Phe Glu Gly Gln Asn Cys Glu Val Asn Val Asp Asp Cys Pro Gly
    210                 215                 220

His Arg Cys Leu Asn Gly Gly Thr Cys Val Asp Gly Val Asn Thr Tyr
225                 230                 235                 240

Asn Cys Gln Cys Pro Pro Glu Trp Thr Gly Gln Phe Cys Thr Glu Asp
                245                 250                 255

Val Asp Glu Cys Gln Leu Gln Pro Asn Ala Cys His Asn Gly Gly Thr
            260                 265                 270

Cys Phe Asn Thr Leu Gly Gly His Ser Cys Val Cys Val Asn Gly Trp
        275                 280                 285

Thr Gly Glu Ser Cys Ser Gln Asn Ile Asp Asp Cys Ala Thr Ala Val
    290                 295                 300

Cys Phe His Gly Ala Thr Cys His Asp Arg Val Ala Ser Phe Tyr Cys
305                 310                 315                 320

Ala Cys Pro Met Gly Lys Thr Gly Leu Leu Cys His Leu Asp Asp Ala
                325                 330                 335

Cys Val Ser Asn Pro Cys His Glu Asp Ala Ile Cys Asp Thr Asn Pro
            340                 345                 350

Val Asn Gly Arg Ala Ile Cys Thr Cys Pro Pro Gly Phe Thr Gly Gly
        355                 360                 365

Ala Cys Asp Gln Asp Val Asp Glu Cys Ser Ile Gly Ala Asn Pro Cys
    370                 375                 380

Glu His Leu Gly Arg Cys Val Asn Thr Gln Gly Ser Phe Leu Cys Gln
385                 390                 395                 400

Cys Gly Arg Gly Tyr Thr Gly Pro Arg Cys Glu Thr Asp Val Asn Glu
                405                 410                 415

Cys Leu Ser Gly Pro Cys Arg Asn Gln Ala Thr Cys Leu Asp Arg Ile
            420                 425                 430

Gly Gln Phe Thr Cys Ile Cys Met Ala Gly Phe Thr Gly Thr Tyr Cys
        435                 440                 445

Glu Val Asp Ile Asp Glu Cys Gln Ser Ser Pro Cys Val Asn Gly Gly
```

```
    450                 455                 460

Val Cys Lys Asp Arg Val Asn Gly Phe Ser Cys Thr Cys Pro Ser Gly
465                 470                 475                 480

Phe Ser Gly Ser Thr Cys Gln Leu Asp Val Asp Glu Cys Ala Ser Thr
                485                 490                 495

Pro Cys Arg Asn Gly Ala Lys Cys Val Asp Gln Pro Asp Gly Tyr Glu
            500                 505                 510

Cys Arg Cys Ala Glu Gly Phe Glu Gly Thr Leu Cys Asp Arg Asn Val
        515                 520                 525

Asp Asp Cys Ser Pro Asp Pro Cys His His Gly Arg Cys Val Asp Gly
    530                 535                 540

Ile Ala Ser Phe Ser Cys Ala Cys Ala Pro Gly Tyr Thr Gly Thr Arg
545                 550                 555                 560

Cys Glu Ser Gln Val Asp Glu Cys Arg Ser Gln Pro Cys Arg His Gly
                565                 570                 575

Gly Lys Cys Leu Asp Leu Val Asp Lys Tyr Leu Cys Arg Cys Pro Ser
            580                 585                 590

Gly Thr Thr Gly Val Asn Cys Glu Val Asn Ile Asp Asp Cys Ala Ser
        595                 600                 605

Asn Pro Cys Thr Phe Gly Val Cys Arg Asp Gly Ile Asn Arg Tyr Asp
    610                 615                 620

Cys Val Cys Gln Pro Gly Phe Thr Gly Pro Leu Cys Asn Val Glu Ile
625                 630                 635                 640

Asn Glu Cys Ala Ser Ser Pro Cys Gly Glu Gly Gly Ser Cys Val Asp
                645                 650                 655

Gly Glu Asn Gly Phe Arg Cys Leu Cys Pro Pro Gly Ser Leu Pro Pro
            660                 665                 670

Leu Cys Leu Pro Pro Ser His Pro Cys Ala His Glu Pro Cys Ser His
        675                 680                 685

Gly Ile Cys Tyr Asp Ala Pro Gly Gly Phe Arg Cys Val Cys Glu Pro
    690                 695                 700

Gly Trp Ser Gly Pro Arg Cys Ser Gln Ser Leu Ala Arg Asp Ala Cys
705                 710                 715                 720

Glu Ser Gln Pro Cys Arg Ala Gly Gly Thr Cys Ser Ser Asp Gly Met
                725                 730                 735

Gly Phe His Cys Thr Cys Pro Pro Gly Val Gln Gly Arg Gln Cys Glu
            740                 745                 750

Leu Leu Ser Pro Cys Thr Pro Asn Pro Cys Glu His Gly Gly Arg Cys
        755                 760                 765

Glu Ser Ala Pro Gly Gln Leu Pro Val Cys Ser Cys Pro Gln Gly Trp
    770                 775                 780

Gln Gly Pro Arg Cys Gln Gln Asp Val Asp Glu Cys Ala Gly Pro Ala
785                 790                 795                 800

Pro Cys Gly Pro His Gly Ile Cys Thr Asn Leu Ala Gly Ser Phe Ser
                805                 810                 815

Cys Thr Cys His Gly Gly Tyr Thr Gly Pro Ser Cys Asp Gln Asp Ile
            820                 825                 830

Asn Asp Cys Asp Pro Asn Pro Cys Leu Asn Gly Gly Ser Cys Gln Asp
        835                 840                 845

Gly Val Gly Ser Phe Ser Cys Ser Cys Leu Pro Gly Phe Ala Gly Pro
    850                 855                 860

Arg Cys Ala Arg Asp Val Asp Glu Cys Leu Ser Asn Pro Cys Gly Pro
865                 870                 875                 880
```

```
Gly Thr Cys Thr Asp His Val Ala Ser Phe Thr Cys Thr Cys Pro Pro
                885                 890                 895

Gly Tyr Gly Gly Phe His Cys Glu Gln Asp Leu Pro Asp Cys Ser Pro
            900                 905                 910

Ser Ser Cys Phe Asn Gly Gly Thr Cys Val Asp Gly Val Asn Ser Phe
        915                 920                 925

Ser Cys Leu Cys Arg Pro Gly Tyr Thr Gly Ala His Cys Gln His Glu
    930                 935                 940

Ala Asp Pro Cys Leu Ser Arg Pro Cys Leu His Gly Gly Val Cys Ser
945                 950                 955                 960

Ala Ala His Pro Gly Phe Arg Cys Thr Cys Leu Glu Ser Phe Thr Gly
                965                 970                 975

Pro Gln Cys Gln Thr Leu Val Asp Trp Cys Ser Arg Gln Pro Cys Gln
            980                 985                 990

Asn Gly Gly Arg Cys Val Gln Thr  Gly Ala Tyr Cys Leu  Cys Pro Pro
        995                 1000                1005

Gly Trp  Ser Gly Arg Leu Cys  Asp Ile Arg Ser Leu  Pro Cys Arg
    1010                1015                1020

Glu Ala  Ala Ala Gln Ile Gly  Val Arg Leu Glu Gln  Leu Cys Gln
    1025                1030                1035

Ala Gly  Gly Gln Cys Val Asp  Glu Asp Ser Ser His  Tyr Cys Val
    1040                1045                1050

Cys Pro  Glu Gly Arg Thr Gly  Ser His Cys Glu Gln  Glu Val Asp
    1055                1060                1065

Pro Cys  Leu Ala Gln Pro Cys  Gln His Gly Gly Thr  Cys Arg Gly
    1070                1075                1080

Tyr Met  Gly Gly Tyr Met Cys  Glu Cys Leu Pro Gly  Tyr Asn Gly
    1085                1090                1095

Asp Asn  Cys Glu Asp Asp Val  Asp Glu Cys Ala Ser  Gln Pro Cys
    1100                1105                1110

Gln His  Gly Gly Ser Cys Ile  Asp Leu Val Ala Arg  Tyr Leu Cys
    1115                1120                1125

Ser Cys  Pro Pro Gly Thr Leu  Gly Val Leu Cys Glu  Ile Asn Glu
    1130                1135                1140

Asp Asp  Cys Gly Pro Gly Pro  Pro Leu Asp Ser Gly  Pro Arg Cys
    1145                1150                1155

Leu His  Asn Gly Thr Cys Val  Asp Leu Val Gly Gly  Phe Arg Cys
    1160                1165                1170

Thr Cys  Pro Pro Gly Tyr Thr  Gly Leu Arg Cys Glu  Ala Asp Ile
    1175                1180                1185

Asn Glu  Cys Arg Ser Gly Ala  Cys His Ala Ala His  Thr Arg Asp
    1190                1195                1200

Cys Leu  Gln Asp Pro Gly Gly  Gly Phe Arg Cys Leu  Cys His Ala
    1205                1210                1215

Gly Phe  Ser Gly Pro Arg Cys  Gln Thr Val Leu Ser  Pro Cys Glu
    1220                1225                1230

Ser Gln  Pro Cys Gln His Gly  Gly Gln Cys Arg Pro  Ser Pro Gly
    1235                1240                1245

Pro Gly  Gly Gly Leu Thr Phe  Thr Cys His Cys Ala  Gln Pro Phe
    1250                1255                1260

Trp Gly  Pro Arg Cys Glu Arg  Val Ala Arg Ser Cys  Arg Glu Leu
    1265                1270                1275
```

```
Gln Cys  Pro Val Gly Val Pro  Cys Gln Gln Thr Pro  Arg Gly Pro
    1280                 1285                 1290

Arg Cys  Ala Cys Pro Pro Gly  Leu Ser Gly Pro Ser  Cys Arg Ser
    1295                 1300                 1305

Phe Pro  Gly Ser Pro Pro Gly  Ala Ser Asn Ala Ser  Cys Ala Ala
    1310                 1315                 1320

Ala Pro  Cys Leu His Gly Gly  Ser Cys Arg Pro Ala  Pro Leu Ala
    1325                 1330                 1335

Pro Phe  Phe Arg Cys Ala Cys  Ala Gln Gly Trp Thr  Gly Pro Arg
    1340                 1345                 1350

Cys Glu  Ala Pro Ala Ala Ala  Pro Glu Val Ser Glu  Glu Pro Arg
    1355                 1360                 1365

Asp Leu  Gly Pro Gly Glu Pro  Lys Ser Cys Asp Lys  Thr His Thr
    1370                 1375                 1380

Cys Pro  Pro Cys Pro Ala Pro  Glu Leu Leu Gly Gly  Pro Ser Val
    1385                 1390                 1395

Phe Leu  Phe Pro Pro Lys Pro  Lys Asp Thr Leu Met  Ile Ser Arg
    1400                 1405                 1410

Thr Pro  Glu Val Thr Cys Val  Val Val Asp Val Ser  His Glu Asp
    1415                 1420                 1425

Pro Glu  Val Lys Phe Asn Trp  Tyr Val Asp Gly Val  Glu Val His
    1430                 1435                 1440

Asn Ala  Lys Thr Lys Pro Arg  Glu Glu Gln Tyr Asn  Ser Thr Tyr
    1445                 1450                 1455

Arg Val  Val Ser Val Leu Thr  Val Leu His Gln Asp  Trp Leu Asn
    1460                 1465                 1470

Gly Lys  Glu Tyr Lys Cys Lys  Val Ser Asn Lys Ala  Leu Pro Ala
    1475                 1480                 1485

Pro Ile  Glu Lys Thr Ile Ser  Lys Ala Lys Gly Gln  Pro Arg Glu
    1490                 1495                 1500

Pro Gln  Val Tyr Thr Leu Pro  Pro Ser Arg Asp Glu  Leu Thr Lys
    1505                 1510                 1515

Asn Gln  Val Ser Leu Thr Cys  Leu Val Lys Gly Phe  Tyr Pro Ser
    1520                 1525                 1530

Asp Ile  Ala Val Glu Trp Glu  Ser Asn Gly Gln Pro  Glu Asn Asn
    1535                 1540                 1545

Tyr Lys  Thr Thr Pro Pro Val  Leu Asp Ser Asp Gly  Ser Phe Phe
    1550                 1555                 1560

Leu Tyr  Ser Lys Leu Thr Val  Asp Lys Ser Arg Trp  Gln Gln Gly
    1565                 1570                 1575

Asn Val  Phe Ser Cys Ser Val  Met His Glu Ala Leu  His Asn His
    1580                 1585                 1590

Tyr Thr  Gln Lys Ser Leu Ser  Leu Ser Pro Gly Lys
    1595                 1600                 1605


<210> SEQ ID NO 34
<211> LENGTH: 4818
<212> TYPE: DNA
<213> ORGANISM: Homo sapiens

<400> SEQUENCE: 34

atgtggggct ggaagtgcct cctcttctgg gctgtgctgg tcacagccac tctctgcact      60

gccaggccac cttgcctgga cggaagcccg tgtgcaaatg gaggtcgttg cacccagctg     120

ccctcccggg aggctgcctg cctgtgcccg cctggctggg tgggtgagcg gtgtcagctg     180
```

```
gaggacccct gtcactcagg cccctgtgct ggccgtggtg tctgccagag ttcagtggtg    240
gctggcaccg cccgattctc atgccggtgc ccccgtggct tccgaggccc tgactgctcc    300
ctgccagatc cctgcctcag cagcccttgt gcccacggtg cccgctgctc agtggggccc    360
gatggacgct tcctctgctc ctgcccacct ggctaccagg gccgcagctg ccgaagcgac    420
gtggatgagt gccgggtggg tgagccctgc cgccatggtg gcacctgcct caacacacct    480
ggctccttcc gctgccagtg tccagctggc tacacagggc cactatgtga gaaccccgcg    540
gtgccctgtg cgccctcacc atgccgtaac gggggcacct gcaggcagag tggcgacctc    600
acttacgact gtgcctgtct tcctgggttt gagggtcaga attgtgaagt gaacgtggac    660
gactgtccag gacaccgatg tctcaatggg gggacatgcg tggatggcgt caacacctat    720
aactgccagt gccctcctga gtggacaggc cagttctgca cggaggacgt ggatgagtgt    780
cagctgcagc ccaacgcctg ccacaatggg ggtacctgct tcaacacgct gggtggccac    840
agctgcgtgt gtgtcaatgg ctggacaggc gagagctgca gtcagaatat cgatgactgt    900
gccacagccg tgtgcttcca tggggccacc tgccatgacc gcgtggcttc tttctactgt    960
gcctgcccca tgggcaagac tggcctcctg tgtcacctgg atgacgcctg tgtcagcaac   1020
ccctgccacg aggatgctat ctgtgacaca aatccggtga acggccgggc catttgcacc   1080
tgtcctcccg gcttcacggg tggggcatgt gaccaggatg tggacgagtg ctctatcggc   1140
gccaacccct gcgagcactt gggcaggtgc gtgaacacgc agggctcctt cctgtgccag   1200
tgcggtcgtg gctacactgg acctcgctgt gagaccgatg tcaacgagtg tctgtcgggg   1260
ccctgccgaa accaggccac gtgcctcgac cgcataggcc agttcacctg tatctgtatg   1320
gcaggcttca caggaaccta ttgcgaggtg gacattgacg agtgtcagag tagcccctgt   1380
gtcaacggtg gggtctgcaa ggaccgagtc aatggcttca gctgcacctg cccctcgggc   1440
ttcagcggct ccacgtgtca gctggacgtg gacgaatgcg ccagcacgcc ctgcaggaat   1500
ggcgccaaat gcgtggacca gcccgatggc tacgagtgcc gctgtgccga gggctttgag   1560
ggcacgctgt gtgatcgcaa cgtggacgac tgctcccctg acccatgcca ccatggtcgc   1620
tgcgtggatg gcatcgccag cttctcatgt gcctgtgctc ctggctacac gggcacacgc   1680
tgcgagagcc aggtggacga atgccgcagc cagccctgcc gccatggcgg caaatgccta   1740
gacctggtgg acaagtacct ctgccgctgc ccttctggga ccacaggtgt gaactgcgaa   1800
gtgaacattg acgactgtgc cagcaacccc tgcacctttg gagtctgccg tgatggcatc   1860
aaccgctacg actgtgtctg ccaacctggc ttcacagggc ccctttgtaa cgtggagatc   1920
aatgagtgtg cttccagccc atgcggcgag ggaggttcct gtgtggatgg ggaaaatggc   1980
ttccgctgcc tctgcccgcc tggctccttg cccccactct gcctcccccc gagccatccc   2040
tgtgcccatg agccctgcag tcacggcatc tgctatgatg cacctggcgg gttccgctgt   2100
gtgtgtgagc ctggctggag tggcccccgc tgcagccaga gcctggcccg agacgcctgt   2160
gagtcccagc cgtgcagggc cggtgggaca tgcagcagcg atggaatggg tttccactgc   2220
acctgcccgc ctggtgtcca gggacgtcag tgtgaactcc tctccccctg caccccgaac   2280
ccctgtgagc atgggggccg ctgcgagtct gcccctggcc agctgcctgt ctgctcctgc   2340
ccccagggct ggcaaggccc acgatgccag caggatgtgg acgagtgtgc tggccccgca   2400
ccctgtggcc ctcatggtat ctgcaccaac ctggcaggga gtttcagctg cacctgccat   2460
ggagggtaca ctggcccttc ctgtgatcag gacatcaatg actgtgaccc caacccatgc   2520
```

-continued

```
ctgaacggtg gctcgtgcca agacggcgtg ggctcctttt cctgctcctg cctccctggt   2580
ttcgccggcc cacgatgcgc ccgcgatgtg gatgagtgcc tgagcaaccc ctgcggcccg   2640
ggcacctgta ccgaccacgt ggcctccttc acctgcacct gcccgccagg ctacggaggc   2700
ttccactgcg aacaggacct gcccgactgc agccccagct cctgcttcaa tggcgggacc   2760
tgtgtggacg gcgtgaactc gttcagctgc ctgtgccgtc ccggctacac aggagcccac   2820
tgccaacatg aggcagaccc ctgcctctcg cggccctgcc tacacggggg cgtctgcagc   2880
gccgcccacc ctggcttccg ctgcacctgc ctcgagagct tcacgggccc gcagtgccag   2940
acgctggtgg attggtgcag ccgccagcct tgtcaaaacg gggtcgctg cgtccagact   3000
ggggcctatt gcctttgtcc ccctggatgg agcggacgcc tctgtgacat ccgaagcttg   3060
ccctgcaggg aggccgcagc ccagatcggg gtgcggctgg agcagctgtg tcaggcgggt   3120
gggcagtgtg tggatgaaga cagctcccac tactgcgtgt gcccagaggg ccgtactggt   3180
agccactgtg agcaggaggt ggacccctgc ttggcccagc cctgccagca tgggggggacc   3240
tgccgtggct atatgggggg ctacatgtgt gagtgtcttc ctggctacaa tggtgataac   3300
tgtgaggacg acgtggacga gtgtgcctcc cagccctgcc agcacggggg ttcatgcatt   3360
gacctcgtgg cccgctatct ctgctcctgt cccccaggaa cgctgggggt gctctgcgag   3420
attaatgagg atgactgcgg cccaggccca ccgctggact cagggccccg gtgcctacac   3480
aatggcacct gcgtggacct ggtgggtggt ttccgctgca cctgtccccc aggatacact   3540
ggtttgcgct gcgaggcaga catcaatgag tgtcgctcag gtgcctgcca cgcggcacac   3600
acccgggact gcctgcagga cccaggcgga ggtttccgtt gcctttgtca tgctggcttc   3660
tcaggtcctc gctgtcagac tgtcctgtct ccctgcgagt cccagccatg ccagcatgga   3720
ggccagtgcc gtcctagccc gggtcctggg ggtgggctga ccttcacctg tcactgtgcc   3780
cagccgttct ggggtccgcg ttgcgagcgg gtggcgcgct cctgccggga gctgcagtgc   3840
ccggtgggcg tcccatgcca gcagacgccc cgcgggccgc gctgcgcctg ccccccaggg   3900
ttgtcgggac cctcctgccg cagcttcccg gggtcgccgc cgggggccag caacgccagc   3960
tgcgcggccg ccccctgtct ccacgggggc tcctgccgcc ccgcgccgct cgcgcccttc   4020
ttccgctgcg cttgcgcgca gggctggacc gggccgcgct gcgaggcgcc cgccgcggca   4080
cccgaggtct cggaggagcc gcgagatctg ggcccgggcg agcccaaatc ttgtgacaaa   4140
actcacacat gcccaccgtg cccagcacct gaactcctgg ggggaccgtc agtcttcctc   4200
ttccccccaa aacccaagga caccctcatg atctcccgga cccctgaggt cacatgcgtg   4260
gtggtggacg tgagccacga agaccctgag gtcaagttca actggtacgt ggacggcgtg   4320
gaggtgcata atgccaagac aaagccgcgg gaggagcagt acaacagcac gtaccgtgtg   4380
gtcagcgtcc tcaccgtcct gcaccaggac tggctgaatg gcaaggagta caagtgcaag   4440
gtctccaaca aagccctccc agcccccatc gagaaaacca tctccaaagc caaagggcag   4500
ccccgagaac cacaggtgta caccctgccc ccatcccggg atgagctgac caagaaccag   4560
gtcagcctga cctgcctggt caaaggcttc tatcccagcg acatcgccgt ggagtgggag   4620
agcaatgggc agccggagaa caactacaag accacgcctc ccgtgctgga ctccgacggc   4680
tccttcttcc tctacagcaa gctcaccgtg gacaagagca ggtggcagca ggggaacgtc   4740
ttctcatgct ccgtgatgca tgaggctctg cacaaccact acacgcagaa gagcctctcc   4800
ctgtctccgg gtaaatga                                                 4818
```